United States Patent [19]

Dobrusin et al.

[11] Patent Number: 5,556,874
[45] Date of Patent: Sep. 17, 1996

[54] 2-THIOINDOLES (SELENOINDOLES) AND RELATED DISULFIDES (SELENIDES) WHICH INHIBIT PROTEIN TYROSINE KINASES AND WHICH HAVE ANTITUMOR PROPERTIES

[75] Inventors: Ellen M. Dobrusin; Howard D. H. Showalter, both of Ann Arbor, Mich.; William A. Denny, Pakuranga, New Zealand; Brian D. Palmer, Glendene, New Zealand; Gordon W. Rewcastle, Manurewa, New Zealand; Moana Tercel, Forrest Hill, New Zealand; Andrew M. Thompson, Mount Eden, New Zealand

[73] Assignee: Warner Lambert Company, Ann Arbor, Mich.

[21] Appl. No.: 438,616

[22] Filed: May 10, 1995

Related U.S. Application Data

[60] Division of Ser. No. 94,792, Aug. 9, 1993, Pat. No. 5,464,861, which is a continuation-in-part of Ser. No. 926,015, Aug. 6, 1992, abandoned.

[51] Int. Cl.[6] .................. A61K 31/40; C07D 209/10
[52] U.S. Cl. .................. 514/414; 514/339; 514/365; 514/369; 514/372; 514/397; 514/418; 514/419; 546/256; 546/269.7; 546/274.4; 546/277.7; 546/270.7; 546/113; 548/206; 548/214; 548/181; 548/460; 548/467; 548/468; 548/485; 548/486; 548/312.1
[58] Field of Search .................. 548/206, 214, 548/181, 336, 460, 467, 468, 485, 486; 514/365, 369, 372, 397, 414, 418, 419, 339; 546/273

[56] References Cited

U.S. PATENT DOCUMENTS 4,997,954  3/1991  Fortunak ................ 548/486
5,137,909  8/1992  Miura et al. ............ 514/418

FOREIGN PATENT DOCUMENTS 895875  3/1972  Canada ................ 548/486

OTHER PUBLICATIONS

CA 895875-S, Mar. 1972, 2-Mercapto- . . . CPDS, FR-022947, 1989.
Acta Chem. Scand., vol. 22, No. 6, pp. 1883–1887, 1968.
Acta Chem. Scand., vol. 17, No. 1, pp. 268–270, 1963.
Aust. J. Chem., vol. 20, pp. 359–364, 1967.
CA 105 = 172217d Studies . . . acid. Barton et al., p. 723, 1986.
CA 112 = 158892h Reaction . . . bromide. Crich et al., p. 781, 1990.
Tetrahedron, vol. 42, No. 21, p. 5879–5886, Takase et al., 1986.
Hino et al., "Chem. Pharm. Bull." 21, 2739–2748 (1973).
Kobayashi et al., "Yakugaku Zasshi" 89, 58–63 (1969).
Takase et al., "Tetrahedron", 42, 5879 (1986).
Wieland et al., "Annalen", 587, 146 (1954).
Palmisano et al., "Tet Lett" 31, 7229 (1990).
CA91=5064n Cyclization . . . halides. Kost et al., p. 475, 1979.
CA105=152874n Thermal . . . indoline–2–thiones. Baudin et al., p. 678, 1986.
CA114=121939u Synthesis . . . triazines. Nesterova et al., p. 755, 1991.

*Primary Examiner*—Joseph McKane
*Attorney, Agent, or Firm*—Merchant, Gould, Smith, Edell, Welter & Schmidt

[57] ABSTRACT

2-Thioindoles (2-selenoindoles) and analogous 2-indolinethione (2-indolineselenone) and polysulfide (selenide) compounds, salts thereof, methods of production, intermediates in their production, pharmaceutical compositions containing said compounds, and methods for inhibiting protein kinase dependent disease in a mammal or treating aberrant cell growth in a mammal, using said compositions, are disclosed.

34 Claims, No Drawings

2-THIOINDOLES (SELENOINDOLES) AND RELATED DISULFIDES (SELENIDES) WHICH INHIBIT PROTEIN TYROSINE KINASES AND WHICH HAVE ANTITUMOR PROPERTIES

CROSS-REFERENCE TO RELATED APPLICATIONS

This is a Divisional of application Ser. No. 08/094,792, filed Aug. 9, 1993, now U.S. Pat. No. 5,464,861 which application is a continuation-in-part of application Ser. No. 07/926,015 filed Aug. 6, 1992, now abandoned.

FIELD OF INVENTION

The present invention relates to substituted 2-thioindoles (selenoindoles) and other related compounds, which we have unexpectedly found to be potent inhibitors of the epidermal growth factor receptor tyrosine kinase (EGF-TK) and other protein tyrosine kinases, and which show antitumor activity. The invention also relates to use of the compounds as inhibitors of protein tyrosine kinases and as antitumor agents.

BACKGROUND OF THE INVENTION

Protein phosphorylation is a critical mechanism for regulating protein function in the signal transduction pathway in normal and transformed cells. Protein tyrosine kinases (PTK) are an important class of phosphorylating enzymes which mediate this signalling and thereby regulate cell growth and proliferation. PTKs catalyze the transfer of the terminal phosphate from ATP to the phenol of tyrosine in substrate proteins. Some growth factor receptors, protooncogenes and oncogene products possess PTK activity. The overexpression or inappropriate expression of normal or mutant kinases can result in the loss of growth control and the unregulated cell proliferation associated with malignancy. Small molecules which selectively inhibit these enzymes are, therefore, of therapeutic interest as mediators of cell growth and as antitumor agents.

In some growth factor dependent tumors, the growth factor signal transduction pathway employs the intrinsic tyrosine kinase activity of the growth factor receptor for autophosphorylation and the phosphorylation of specific cellular proteins involved in mitogenesis and cell proliferation. Specific inhibitors of PTKs have been identified previously. It has been previously demonstrated that by uncoupling the PTK from the signal transduction pathway, inhibitors of the growth factor receptor tyrosine kinases result therapeutically in antitumor activity. This antitumor activity has been demonstrated both in vitro and in vivo. Most known tyrosine kinase inhibitors are styrene-like small molecules in which the aromatic ring is hydroxylated, resembling tyrosine itself.

For example, the EGF-TK inhibitor erbstatin is reported to inhibit the growth of human epidermoid carcinoma A431 cells with an $IC_{50}$=3.6 μg/mL (*J. Antibiot.* 1986;39:170). Erbstatin also inhibits the growth of the human mammary carcinoma MCF-7 and some esophageal tumors in nude mice in a dose-dependent manner (*Eur. J. Cancer* 1990;26(6):722 and Japanese Patent 03,109,323). Another class of PTK inhibitor called the tyrphostins also potently inhibited the EGF-dependent growth of A431 cells in vitro (*J. Med. Chem.* 1989;32:2344; *J. Med. Chem.* 1991;34:1896). The antitumor activity of two tyrphostins has been verified in vivo in nude mice bearing human squamous cell carcinoma MH-85 (*Cancer Res.* 1991;51:4430). In vitro and in vivo antitumor activity against A431 tumors has also been reported for a series of sulfonylbenzoyl nitrostyrenes (*J. Med. Chem.* 1991;34:2328) as TK inhibitors (*J. Med. Chem.* 1991;34:2328 and *Helv. Chim. Acta* 1992;75:696).

SUMMARY AND DETAILED DESCRIPTION

In one aspect, the invention relates to 2-thioindole (selenoindoles) and other related compounds that are potent inhibitors of epidermal growth factor receptor tyrosine kinase and other protein tyrosine kinases, and which have antitumor activity. Thus, the compounds are useful in dosage form as inhibitors of protein tyrosine kinases and as antitumor agents.

More particularly, the invention comprises 2-thioindole, 2-indolinethione, polysulfide, 2-selenoindole, 2-indolineselenone, and selenide compounds represented by the general Formulas I, IV, and XXXII

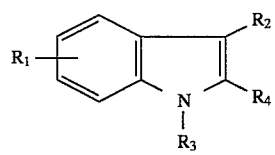

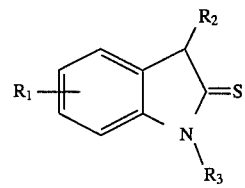

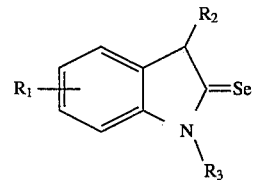

and pharmaceutically acceptable salts thereof, wherein $R_1$ is a member selected from H, halogen, R, OH, OCOR, OR, $CF_3$, $NO_2$, $NH_2$, NHR, COOH, CONHR, $(CH_2)_nOH$, $(CH_2)_nOR$, $(CH_2)_nNH_2$, $(CH_2)_nNHR$, and $(CH_2)_nNRR$, and further represents replacement in the ring of 1 or 2 ring methine (—CH=) atoms with aza (—N=) atoms;

$R_2$ is a member selected from $C_{2-4}$ alkyl, $(CH_2)_nCOOH$, $(CH_2)_nCOOR$, $(CH_2)_nCOR$, $(CH_2)_nSO_2R$, $(CH_2)_nSO_2NRR$, $(CH_2)_nSO_2NHR$,

CH=CHCOOH,

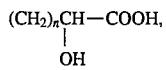

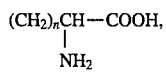

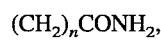

$(CH_2)_nCONHR$,
$(CH_2)_nCONRR$,
$(CH_2)_nCONHCH_2Ph$,
CONHR,
CONRR,
CONHPh,
COY,
COPhCOOH,
COPhCOOR,
$(CH_2)_nCONHPh$,
$(CH_2)_nCONHPhR$,
$SO_2Y$;

n is an integer from 1 to 4;
R is lower alkyl, preferably $C_{1-4}$ alkyl;
$R_3$ is a member selected from H, lower alkyl, and benzyl;
Y represents a benzene, pyridine, thiophene, furan, thiazole, or imidazole ring optionally substituted with a lower alkyl, COOH, OH, OCOR, $NH_2$, CONHR, CONRR, OR, or NHR group; and
$R_4$ represents SH, $S_oX$, $S_oQ$, SeH, $Se_oX$, and $Se_oQ$, where o is 1, 2, or 3, X is a member selected from H, lower alkyl, benzyl, and benzene, pyridine, thiophene, furan, thiazole, and imidazole rings, and Q is another 2-thioindolyl or 2-selenoindolyl moiety of Formula I provided that the group does not comprise compounds having the names 2-(2-thioxo-3-indolinyl)acetic acid,
2-(1-methyl-2-thioxo-3-indolinyl)acetic acid,
methyl 2-(2-thioxo-3-indolinyl)acetate,
ethyl 2-(1-methyl-2-thioxo-3-indolinyl)acetate,
bis[methylindolinyl-3-acetate-(2)]disulfide,
bis[indolyl-3-acetic acid-(2)]disulfide,
bis[methylindolyl-3-acetate-(2)]trisulfide, and
bis[1-methylindolyl-3-acetic acid-(2)]disulfide.

In another aspect, the invention relates to indolinethione compounds of the above Formula IV which exist as tautomers of compounds of Formula I wherein $R_4$ represents SH or indolineselenone compounds of the above Formula XXXII which exist as tautomers of compounds of Formula I wherein $R_4$ represents SeH. The invention comprises the thione or selenone compounds in their racemic and optical isomer forms. The thione or selenone compounds produced in the (±) form can be resolved as their (+) and (−) enantiomorphic optical isomers by per se art-recognized conventional means such as fractional crystallization of salts formed from optically active acids, separation of the isomers by chiral chromatography, or the chiral catalytic reduction of precursors.

In another aspect, the invention relates to pharmaceutical compositions useful for inhibition of protein tyrosine kinases and for antitumor activity containing as an active agent in a pharmaceutically acceptable carrier a therapeutically effective amount of a compound selected from 2-thioindole, 2-indolinethione, polysulfide, 2-selenoindole, 2-indolineselenone or selenide compounds represented by the above Formulas I, IV, and XXXII and pharmaceutically acceptable salts thereof, wherein $R_1$ is a member selected from H, halogen, R, OH, OCOR, OR, $CF_3$, $NO_2$, $NH_2$, NHR, COOH, CONHR, $(CH_2)_nOH$, $(CH_2)_nOR$, $(CH_2)_nNH_2$, $(CH_2)_nNHR$, and $(CH_2)_nNRR$, and further represents replacement in the ring of 1 or 2 ring methine (—CH=) atoms with aza (—N=) atoms;

$R_2$ is a member selected from
lower alkyl, preferably $C_{1-4}$ alkyl,
$(CH_2)_nCOOH$,
$(CH_2)_nCOOR$,
$(CH_2)_nCOR$,
$(CH_2)_nSO_2R$,
$(CH_2)_nSO_2NRR$,
$(CH_2)_nSO_2NHR$,
CH=CHCOOH, $$(CH_2)_n\underset{OH}{CH}-COOH,$$

$$(CH_2)_n\underset{NH_2}{CH}-COOH,$$

$(CH_2)_nCONH_2$,
$(CH_2)_nCONHR$,
$(CH_2)_nCONRR$,
$(CH_2)_nCONHCH_2Ph$,
CONHR,
CONRR,
CONHPh,
COY,
COPhCOOH,
COPhCOOR,
$(CH_2)_nCONHPh$,
$(CH_2)_nCONHPhR$,
$SO_2Y$;

n is an integer from 1 to 4;
R is lower alkyl, preferably $C_{1-4}$ alkyl;
$R_3$ is a member selected from H, lower alkyl and benzyl;
Y represents a benzene, pyridine, thiophene, furan, thiazole, or imidazole ring optionally substituted with a lower alkyl, COOH, OH, OCOR, $NH_2$, CONHR, CONRR, OR, or NHR group; and
$R_4$ represents SH, $S_oX$, $S_oQ$, SeH, $Se_oX$, and $Se_oQ$, where o is 1, 2, or 3, X is a member selected from H, lower alkyl, benzyl, and benzene, pyridine, thiophene, furan, thiazole, and imidazole rings, and Q is another 2-thioindolyl or 2-selenoindolyl moiety of Formula I.

The invention comprises salt compounds formed by the basic or acidic thioindole compounds of the invention which form pharmaceutically acceptable salts with both organic and inorganic acids and/or organic and inorganic bases. Examples of suitable acids for salt formation are hydrochloric, sulfuric, phosphoric, acetic, citric, oxalic, malonic, salicylic, malic, fumaric, succinic, ascorbic, maleic, methanesulfonic, isethionic, and the like. Examples of suitable bases for salt formation are sodium and potassium carbonate, sodium and potassium hydroxide, ammonia, triethylamine, triethanolamine, and the like.

The compounds of Formulas I, IV, and XXXII can be prepared by the processes described in the following Reaction Schemes 1–11.

SCHEME 1

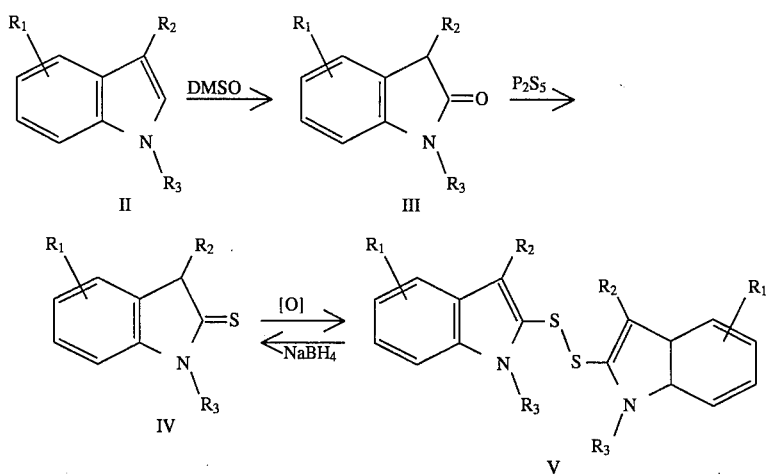

In Scheme 1, $R_1$–$R_3$ are as designated for Formula I. Oxidation of 3-substituted indoles II in DMSO/HCl gives good yields of 3-substituted indolin-2-ones III which are thiated (preferably with $P_2S_5$ and $NaHCO_3$ or $Na_2CO_3$) to yield 3-substituted 2-indolinethiones IV. These compounds can be converted to the corresponding disulfides V by treatment with mild oxidizing agents (e.g., $FeCl_3$), and also undergo spontaneous oxidation to V in solution in air.

tures of dimeric sulfides VI, where n=1–3. These can be separated by chromatography, or more conveniently reduced to 2-indolinethiones IV with a mild reducing agent (preferably $NaBH_4$).

SCHEME 2

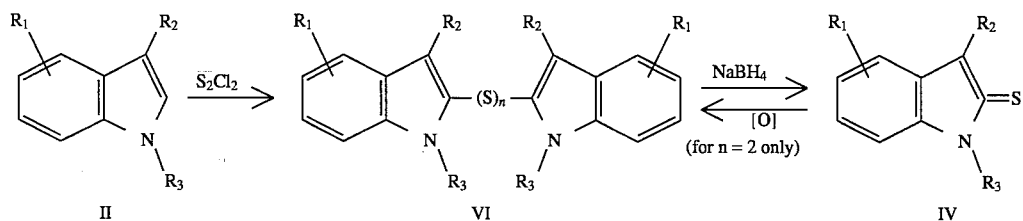

In Scheme 2, $R_1$–$R_3$ are as designated for Formula I. Treatment of 3-substituted indoles II with $S_2Cl_2$ gives mix-

SCHEME 3

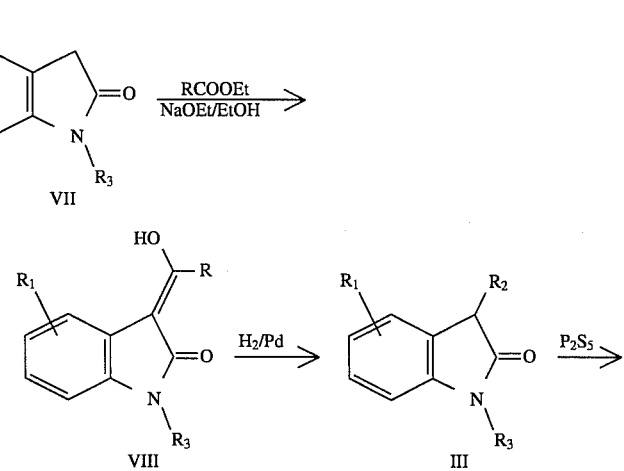

-continued
SCHEME 3

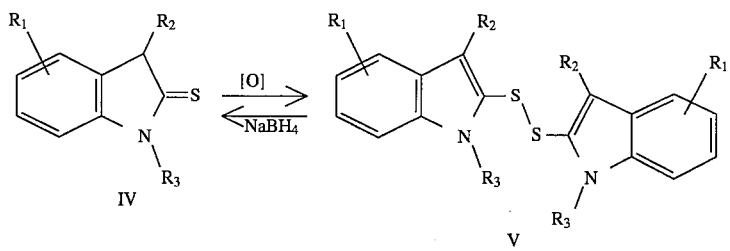

In Scheme 3, $R_1$–$R_3$ are as designated for Formula I, and R represents $(CH_2)_n COOH$, $(CH_2)_n COOX$, $(CH_2)_n CONHX$, $(CH_2)_n SO_2 X$, or $(CH_2)_n SO_2 NX$, where n is from 0 to 4, and X is as designated for Formula I. Treatment of 2-indolinones VII with diesters gives moderate yields of the isatylidene compounds VIII, which can be hydrogenated under acidic conditions to the 3-substituted indolin-2-ones III. Treatment of these as in Scheme 1 gives the desired compounds.

the N-protecting group and electrophile (Katritzky, Fan, Akutagawa, Wang, *Heterocycles* 1990;30:407). 2-Indolinones VII are thiated (preferably with $P_2S_5$ and $NaHCO_3$ or $Na_2CO_3$) to yield 2-indolinethiones IX. These compounds are deprotonated (typically with NaH in THF), and treated with an isocyanate to give 3-substituted 2-indolinethiones IV (where $R_2$=CONHX). These compounds can be converted to the corresponding disulfides V as described in

SCHEME 4

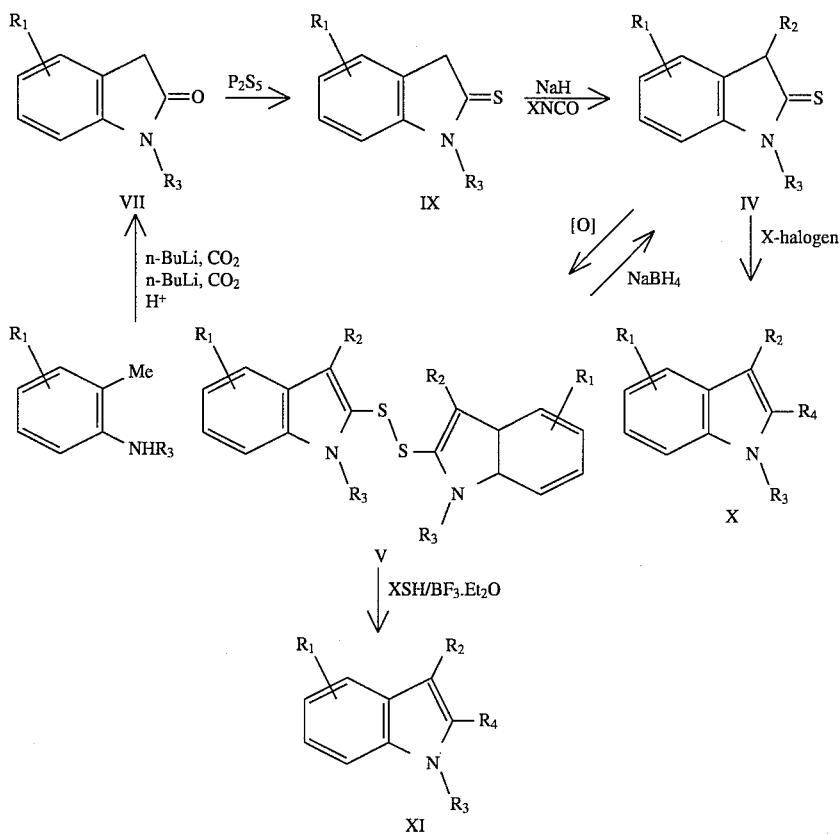

In Scheme 4, $R_1$–$R_4$, R and X are as designated for Formula I (except that X is not H). The ring-substituted oxindoles can be prepared by lithiation of the appropriately substituted ortho-toluidine derivatives, using $CO_2$ as both the N-protecting group and electrophile (Katritzky, Fan, Akutagawa, Wang, *Heterocycles* 1990;30:407). 2-Indolinones VII are thiated (preferably with $P_2S_5$ and $NaHCO_3$ or $Na_2CO_3$) to yield 2-indolinethiones IX. These compounds are deprotonated (typically with NaH in THF), and treated with an isocyanate to give 3-substituted 2-indolinethiones IV (where $R_2$=CONHX). These compounds can be converted to the corresponding disulfides V as described in Scheme 1. The 3-substituted 2-indolinethiones IV can also react with alkylating agents (typically alkyl halides R-halogen) to give (X: where $R_4$=X). Reaction of V with XSH gives mixed disulfides (XI: where $R_4$=SSX).

SCHEME 5

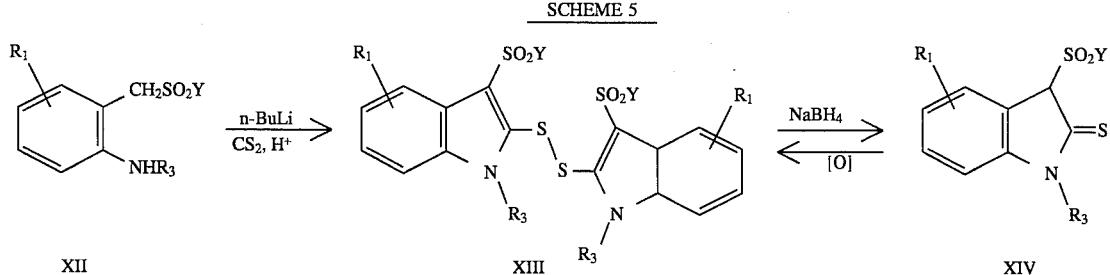

In Scheme 5, $R_1$ and $R_3$ are as designated for Formula I and Y represents lower alkyl or a benzene, pyridine, thiophene, furan, thiazole, or imidazole ring, optionally substituted with a lower alkyl, COOH, OH, $NH_2$, CONHR, OR, O, or NHR group. 2-Sulfonylmethyl anilines XII are treated sequentially with n-butyllithium and $CS_2$, to give the disulfides XIII, which can be reduced to 2-indolinethiones XIV with a mild reducing agent (preferably $NaBH_4$).

SCHEME 6

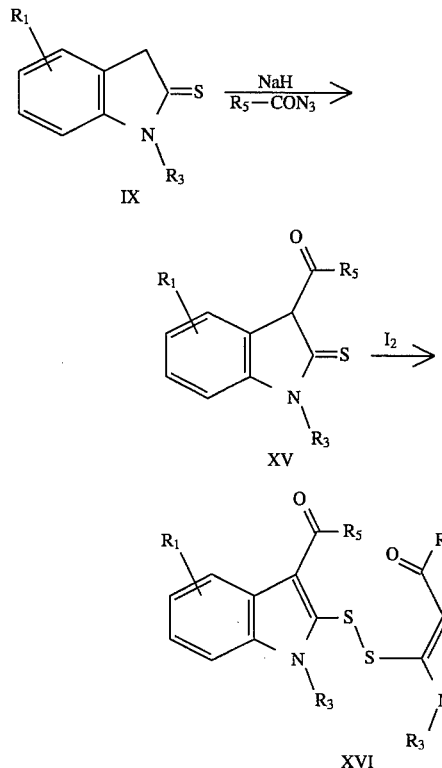

In Scheme 6, $R_1$ and $R_3$ are as designated for Formula I. Deprotonation of substituted 2-indolinethiones IX (typically with NaH in THF), followed by treatment with an acyl azide, gives 3-acyl-substituted 2-indolinethiones XV, where $R_5$ represents H, lower alkyl, benzyl, or a benzene, pyridine, thiophene, furan, thiazole, or imidazole ring optionally substituted with a COOH, OH, $NH_2$, CONHR, OR, NHR, or NRR group. Compounds XV can be converted into the disulfides XVI on mild oxidation (typically by treatment with $I_2$ or $H_2O_2$).

SCHEME 7

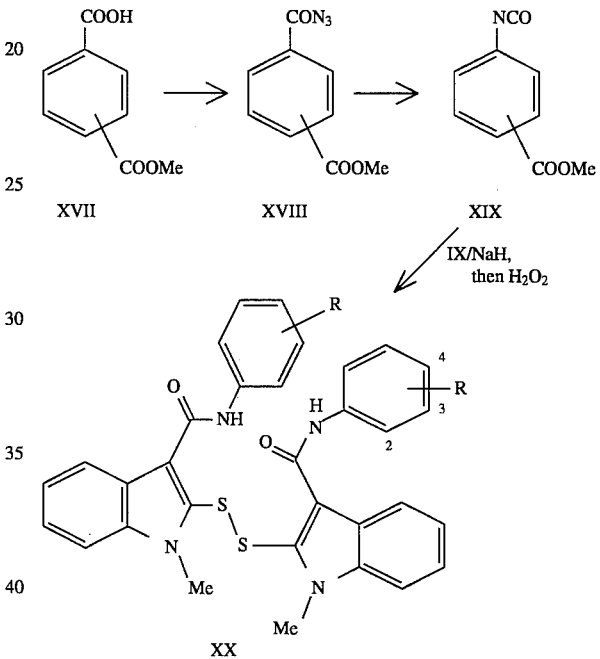

In Scheme 7, R is as designated for Formula I. Substituted aromatic and heteroaromatic acids (e.g., XVII) are converted to the corresponding acid chlorides (preferably with $SOCl_2$), and then to the corresponding acyl azides (e.g., XVIII) with $NaN_3$. Rearrangement to give the isocyanates (e.g., XIX) is carried out in an inert solvent (preferably toluene or xylene). These isocyanates (e.g., XIX) are converted to the disulfides (XX) by reaction with the sodium salt of 1-methyl- 2-indolinethiones as outlined in Scheme 4. In suitable cases, hydrolysis of esters (XX; R=COOMe) with a mild base (preferably $K_2CO_3$) gives the corresponding acids (XX; R=COOH).

SCHEME 8

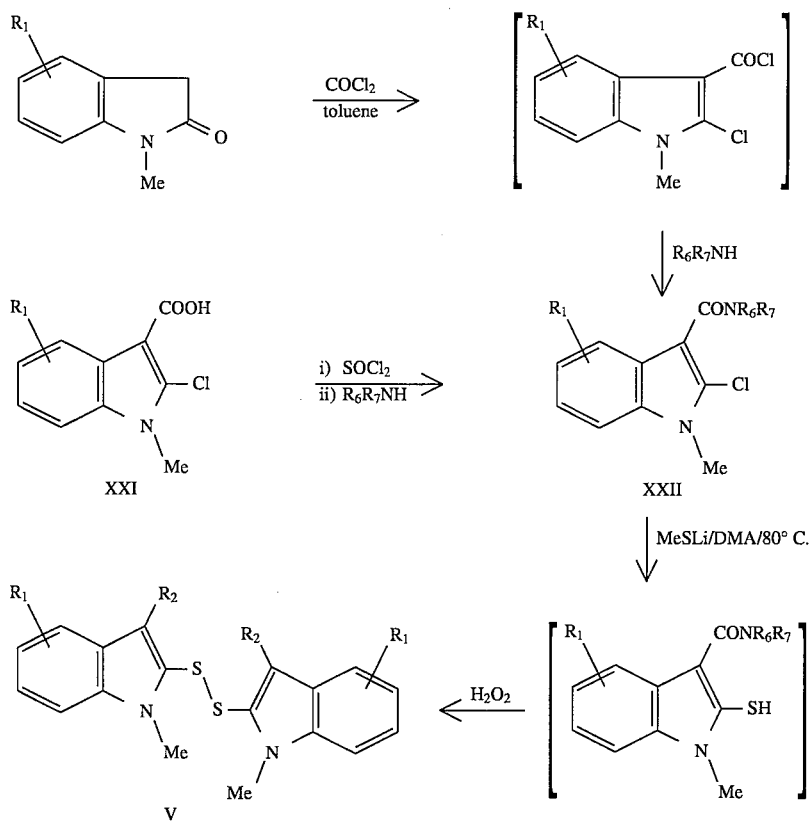

In Scheme 8, $R_1$ and $R_2$ are as designated for Formula I, and $R_6$ and $R_7$ are individually H, lower alkyl, benzyl, or a benzene ring optionally substituted with up to two of the groups COOH, OH, $NH_2$, CONHR, OR, NHR, or NRR. 2-Chloro-1-methylindole-3-carbonyl chloride, prepared either from indolin-2-one and $COCl_2$ or from 2-chloro-1-methylindole-3-carboxylic acid (XXI) and $SOCl_2$, is reacted with amines $HNR_6R_7$ or their salts, in an inert solvent (preferably 1,2-dichloroethane or $CH_2Cl_2$) and a base, if necessary, to give the amides (XXII). These compounds are heated with MeSLi in polar aprotic solvents (preferably dimethylacetamide) in an inert atmosphere to give intermediate thiol carboxamides, which are oxidized, (preferably with $H_2O_2$) to give the desired disulfides (V).

SCHEME 9

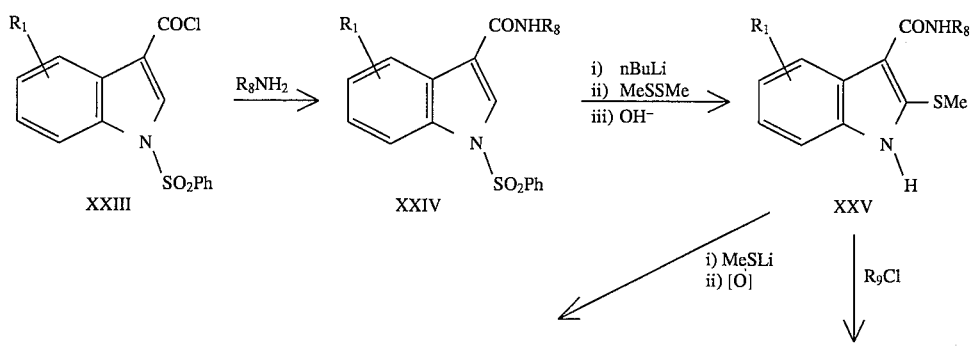

-continued
SCHEME 9

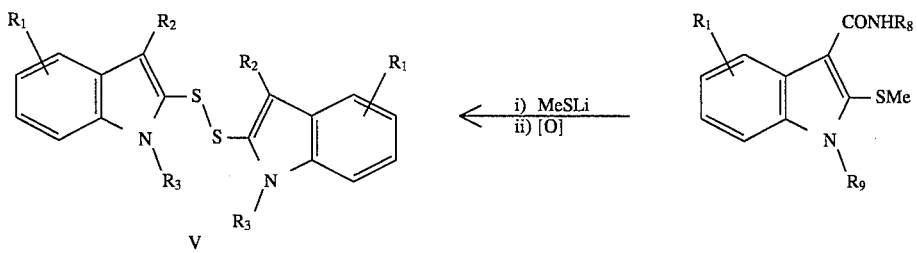

In Scheme 9, $R_1$, $R_2$, $R_3$, and R are as designated for Formula I. Reaction of acid chloride (XXIII) with amines gives amides (XXIV), where $R_8$ represents H, lower alkyl, benzyl, or a benzene ring optionally substituted with up to two of the groups COOH, OH, $NH_2$, CONHR, OR, NHR, or NRR. Compounds (XXIV) can be converted to 2-thioindoles (XXV) by lithiation and quenching with methyl sulfide, followed by base hydrolysis (preferably with $K_2CO_3$). The 2-thioindoles (XXV) can be converted to the desired disulfides (V) by dealkylation (preferably with lithium thiomethoxide) and mild oxidation (preferably with $I_2$ or $H_2O_2$). Compounds (XXV) can also be alkylated with an alkyl halide (e.g., $R_9Cl$), where $R_9$ represents lower alkyl, benzyl, or benzyl optionally substituted with up to two of the groups COOH, OH, $NH_2$, CONHR, OR, NHR, or NRR, and a base (preferably $K_2CO_3$).

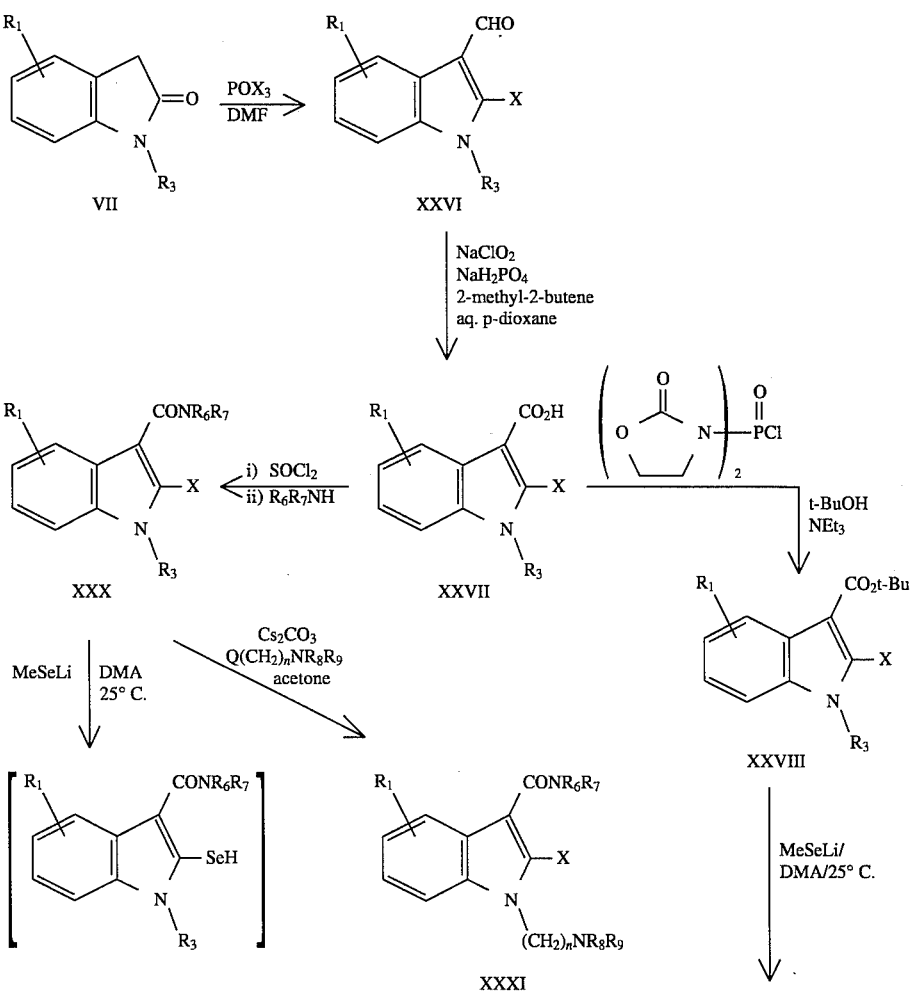

-continued
SCHEME 10

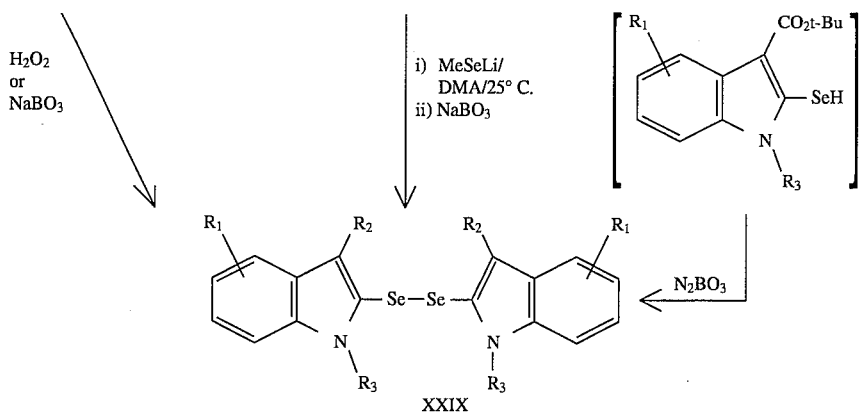

In Scheme 10, $R_1$ is as designated for Formula I and $R_6$ and $R_7$ are individually $H_1$ lower alkyl, benzyl, or a benzene ring optionally substituted with up to two of the groups COOH, OH, $NH_2$, CONHR, OR, NHR, or NRR. $R_3$ is H or lower alkyl, and X=any halogen, preferably bromine or chlorine. Substituted 2-halo-3-indole carboxylic acids XXVII, prepared by oxidation of corresponding substituted 3-carboxaldehydes, are reacted with amines $HNR_6R_7$ or their salts in an inert solvent (preferably 1,2-dichloroethane or $CH_2Cl_2$) and a base, if necessary, to give the amides XXX. These compounds are reacted with MeSeLi in polar aprotic solvents (preferably dimethylacetamide) to give intermediate selenol carboxamides, which are oxidized with $H_2O_2$ or $NaBO_4$ to give the desired diselenides XXIX. Alternatively, intermediate XXX, where $R_3$=H, can be reacted with a haloalkyl amine, or its salt, where Q=Cl, Br, I (preferably Cl) and $R_8$, $R_9$ are as defined in Formula I, but preferably $R_8$ and $R_9$ are H, alkyl, cycloalkyl, and n=1–4 in a polar solvent (preferably acetone) and anhydrous metal carbonate (preferably cesium carbonate) to give intermediate XXXI which is converted to diselenide XXIX as described above for intermediate XXX. Additionally, intermediate acid XXVII can be converted to the substituted 2-halo-3-indole carboxylic acid tertiary butyl ester XXVIII, which can be further reacted with MeSeLi as described above for intermediate XXX to give the target substituted diselenide XXIX where $R_2$=COO-tertiarybutyl.

SCHEME 11

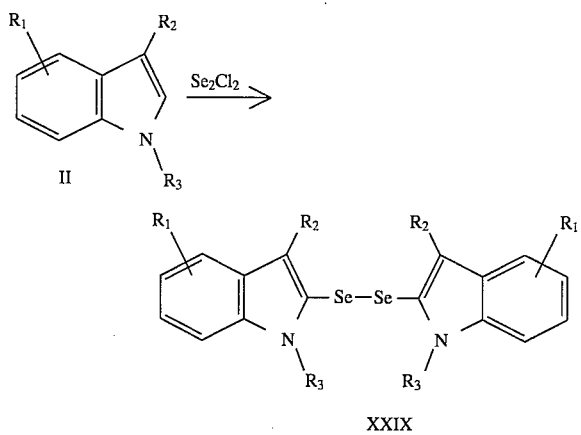

In Scheme 11, $R_1$–$R_3$ are as designated for Formula I. Treatment of 3-substituted indoles II with $Se_2Cl_2$ gives the diselenide XXIX.

As indicated, the compounds of this invention that are basic can form acidic salts and those that are acidic can form basic salts. All such salts are within the scope of this invention and they can be prepared by conventional methods. For example, they can be prepared simply be contacting the acidic and basic entities, usually in a stoichiometric ratio, in either an aqueous, nonaqueous or partially aqueous medium, as appropriate. The salts are recovered either by filtration, by precipitation followed by filtration, by evaporation of the solvent, or in the case of aqueous solutions, by lyophilization, as appropriate.

The compounds of this invention are readily adapted to therapeutic use for the control of tyrosine kinase dependent diseases in mammals. Tyrosine kinase dependent diseases comprise hyperproliferative disorders which are initiated and/or maintained by aberrant tyrosine kinase enzyme activity. Tyrosine kinase inhibitors can therefore have beneficial therapeutic effects against aberrant cell growth disorders such as various cancers, atherosclerosis, angiogenesis (tumor growth/metastasis, diabetic retinopathy, for example), viral diseases (HIV infections, for example), and the like.

Tyrosine kinase dependent diseases further comprise cardiovascular diseases which are related to aberrant tyrosine kinase enzyme activity. Tyrosine kinase inhibitors can therefore have beneficial therapeutic effects against such cardiovascular diseases as restenosis. It should be understood that restenosis is an example of a cardiovascular disease which is dependent upon tyrosine kinase; one skilled in the art, however, will be aware of other examples of cardiovascular diseases which are dependent upon tyrosine kinase.

The compounds are administered either orally or parenterally, or topically as eye drops, in dosages ranging from about 0.1 to 10 mg/kg of body weight per day in single or divided doses. Of course, in particular situations, at the discretion of the attending physician, doses outside of this range will be used.

The compounds of this invention can be administered in a side variety of different dosage forms, i.e., they may be combined with various pharmaceutically acceptable inert carriers in the form of tablets, capsules, lozenges, troches, hard candies, powders, sprays, elixirs, syrups, injectable or eye drop solution, and the like. Such carriers include solid diluents or fillers, sterile aqueous media, and various nontoxic organic solvents.

For purposes of oral administration, tablets containing various excipients such as sodium citrate, calcium carbonate, and calcium phosphate are employed along with various disintegrants such as starch and preferably potato or tapioca starch, alginic acid, and certain complex silicates, together with binding agents such as polyvinylpyrrolidone, sucrose, gelatin, and acacia. Additionally, lubrication agents such as magnesium stearate, sodium lauryl sulfate, and talc are often very useful for tableting purposes. Solid compositions of similar type are also employed as fillers in soft- and hard-filled gelatin capsules; preferred materials in this connection also include lactose or milk sugar as well as high molecular weight polyethylene glycols. When aqueous suspensions and/or elixirs are desired for oral administration, the essential active ingredient therein can be combined with various sweetening agents, flavoring agents, coloring agents, emulsifying agents, and/or suspending agents as well as such diluents as water, ethanol, propylene glycol, glycerin, and various like combinations thereof.

For purposes of parenteral administration, solutions in sesame or peanut oil or in aqueous propylene glycol can be employed, as well as sterile aqueous solutions of the corresponding water soluble, alkali metal, or alkaline earth metal salts previously enumerated. Such aqueous solution should be suitably buffered, if necessary, and the liquid diluent first rendered isotonic with sufficient saline or glucose. These particular aqueous solutions are suitable for intravenous, intramuscular, subcutaneous and intraperitoneal injection purposes. In this connection, the sterile aqueous media employed are all readily obtainable by standard techniques well known to those skilled in the art.

For purposes of topical administration, dilute sterile, aqueous solutions (usually in about 0.1% to 5% concentration), otherwise similar to the above parenteral solutions, are prepared in containers suitable for dropwise administration to the eye.

In a pharmaceutical composition comprising a compound of Formula I, or a pharmaceutically acceptable salt thereof, the weight ratio of carrier to active ingredient will normally be in the range from 1:4 to 4:1, and preferably 1:2 to 2:1. However, in any given case, the ratio chosen will depend on such factors as the solubility of the active component, the dosage contemplated and the precise route of administration.

The following Table 1 sets out physical data for 137 compounds within the general Formula I, representative of it, and preparable by the processes of the invention.

TABLE 1

Formula A: R1-substituted benzene fused to pyrrole with N-R3, 2-SX, 3-R2
Formula B: dimer linked through S, with R1-benzene, N-R3, 3-R2, X substituent
Formula B1: amide dimer N-CH2Ph with linker to S-X structure

| No. | Formula | R₁ | R₂ | R₃ | X | mp (°C.) | Molecular Formula | Analysis[a] |
|---|---|---|---|---|---|---|---|---|
| 1 | A | H | CH₂COOH | H | | | | known[d] |
| 2 | A | H | CH₂COOH | Me | | 166–168 | C₁₀H₉NO₂S | known[d] |
| 3 | A | H | CH₂COOMe | H | | 150–153 | C₁₁H₁₁NO₂S | C, H, N, S[e] |
| 4 | A | H | CH₂COOMe | Me | | 150–152 | C₁₁H₁₁NO₂S | C, H, N, S |
| 5 | A | H | CH₂COOEt | H | | 68–70 | C₁₂H₁₃NO₂S | C, H, N, S |
| 6 | A | H | CH₂CONHCH₂Ph | H | | 47–48 | C₁₃H₁₅NO₂S | C, H, N, S[e] |
| 7 | A | H | (CH₂)₂COOH | H | | 193–195 | C₁₇H₁₀N₂OS | C, H, N, S |
| 8 | A | H | (CH₂)₂COOH | Me | | 170–173 | C₁₁H₁₁NO₂S | C, H, N, S |
| 9 | A | H | (CH₂)₂COOMe | H | | 126–128.5 | C₁₂H₁₃NO₂S·0.25H₂O | C, H, N, S |
| 10 | A | H | (CH₂)₂COOMe | Me | | 95.5–98 | C₁₂H₁₃NO₂S | C, H, N, S |
| 11 | A | H | (CH₂)₂COOEt | H | | oil[b] | C₁₃H₁₅NO₂S | C, H, N, S |
| 12 | A | H | (CH₂)₂COOEt | Me | | 71–73 | C₁₃H₁₅NO₂S | C, H, N, S |
| 13 | A | H | (CH₂)₂CONHCH₂Ph | H | | 61–63 | C₁₄H₁₇NO₂S | C, H, N, S |
| 14 | A | H | (CH₂)₂CONH₂ | Me | | 149.5–151 | C₁₈H₁₈NO₂S·0.5H₂O | C, H, N, S |
| 15 | A | H | (CH₂)₃COOH | H | | 160–163 | C₁₁H₁₂N₂OS | C, H, N, S |
| 16 | A | H | (CH₂)₃COOH | Me | | 132–134 | C₁₂H₁₃NO₂S | C, H, N, S |
| 17 | A | H | (CH₂)₃COOMe | H | | 144–146.5 | C₁₃H₁₅NO₂S·H₂O | C, H, N, S |
| 18 | A | H | (CH₂)₃COOMe | Me | | 109–110 | C₁₃H₁₅NO₂S | C, H, N, S |
| 19 | A | 7-aza | CONHPh | H | | 103–106 | C₁₄H₁₇NO₂S | HRMS |
| 20 | A | 5-Cl | CONHPh | Me | | 162–164 | C₁₅H₁₃N₂O₂S·CH₃OH | C, H, N, S |
| 21 | A | H | CONHPh | Me | | 312–320 | C₁₆H₁₃ClN₂OS | C, H, N, S |
| 22 | A | H | CONHPh | Me | Me | 149–151 | C₁₆H₁₄N₂OS | C, H, N, S |
| 23 | A | H | CONHPh | Me | CH₂Ph | 116–118 | C₁₇H₁₆N₂OS | C, H, N, S |
| 24 | A | H | COPh | Me | | 144–146 | C₂₃H₂₀N₂OS₂ | C, H, N, S |
| 25 | A | H | COPhpCOOH | Me | H | 130–132 | C₁₆H₁₃NOS | C, H, N, S |
| 26 | A | H | COPhpCOOMe | Me | H | 282 (dec) | C₁₇H₁₃NO₃S·0.25H₂O | C, H, N, S |
| 27 | B | H | CH₂COOMe | Me | H | 164–166 | C₁₈H₁₅NO₃S | C, H, N, S[f] |
| 28 | B | H | CH₂COOMe | H | — | 160–162 | C₂₂H₂₀N₂O₄S₂ | C, H, N, S |
| 29 | B | H | CH₂COOH | Me | — | 130–132.5 | C₂₄H₂₄N₂O₄S₂ | C, H, N, S |
| 30 | B | H | CH₂COOH | H | S | 196–199 | C₂₀H₁₆N₂O₄S₃ | known[d] |
| 31 | B | H | CH₂COOH | Me | S | 199–202 | C₂₀H₁₆N₂O₄S₃ | C, H, N, S[f] |
| 32 | B | H | CH₂COOMe | H | — | 130–132 | C₂₂H₂₀N₂O₄S₂ | known[d] |
| 33 | B | H | CH₂COOEt | Me | — | 190–192.5 | C₂₂H₂₀N₂O₄S₂ | C, H, N, S |
|    |   |   |              |    |   | 117–119 | C₂₆H₂₈N₂O₄S₂ |              |

TABLE 1-continued

| No. | Formula | R₁ | R₂ | R₃ | X | mp (°C.) | Molecular Formula | Analysis[a] |
|---|---|---|---|---|---|---|---|---|
| 34 | B | H | CH₂CONHCH₂Ph | H | — | 200.5–203.5 | C₃₄H₃₀N₄O₂S₂ | C, H, N, S |
| 35 | B | H | CH₂CN | H | — | 168.5–169.5 | C₂₀H₁₄N₄S₂ (lit ref)[g] | C, H, N, S |
| 36 | B | H | (CH₂)₂COOH | H | — | 118–120.5 | C₂₂H₂₀N₂O₄S₂·H₂O | C, H, N, S |
| 37 | B | H | (CH₂)₂COOH | Me | — | 158.5–160 | C₂₄H₂₄N₂O₄S₂ | C, H, N, S |
| 38 | B | H | (CH₂)₂COOEt | H | — | 137–139 | C₂₆H₂₈N₂O₄S₂ | C, H, N, S |
| 39 | B | H | (CH₂)₂COOMe | H | — | 162.5–164 | C₂₄H₂₄N₂O₄S₂ | C, H, N, S |
| 40 | B | H | (CH₂)₂COOMe | Me | — | 139–141.5 | C₂₆H₂₈N₂O₄S₂ | C, H, N, S |
| 41 | B | 5-Me | (CH₂)₂COOH | H | — | 91.5–95 | C₂₄H₂₄N₂O₄S₂ | HRMS[c] |
| 42 | B | 5-Me | (CH₂)₂COOEt | H | — | 138.5–139 | C₂₈H₃₂N₂O₄S₂·0.5C₆H₆ | C, H, N, S |
| 43 | B | 6-Me | (CH₂)₂COOH | H | — | 126–128 | C₂₄H₂₄N₂O₄S₂·0.5H₂O | C, H, N, S |
| 44 | B | 6-Me | (CH₂)₂COOEt | H | — | 122–123.5 | C₂₈H₃₂N₂O₄S₂ | C, H, N, S |
| 45 | B | 7-Me | (CH₂)₂COOH | H | — | 172.5–175 | C₂₄H₂₄N₂O₄S₂ | C, H, N |
| 46 | B | 7-Me | (CH₂)₂COOEt | H | — | 120–122.5 | C₂₆H₃₂N₂O₄S₂ | C, H, N, S |
| 47 | B | H | (CH₂)₂CONHCH₂Ph | H | — | 141–144 | C₃₆H₃₄N₄O₂S₂ | C, H, N, S |
| 48 | B | H | (CH₂)₂CN | H | — | 167–169 | C₂₁H₁₆N₄S₂ (lit ref)[g] | |
| 49 | B | H | (CH₂)₂NO₂ | H | — | 153–154 | C₂₀H₁₈N₄O₂S₂·0.5H₂O | C, H, N, S |
| 50 | B | H | (CH₂)₂CONH₂ | H | — | 101 (dec) | C₂₂H₂₂N₄O₂S₂·0.5H₂O | C, H, N, S |
| 51 | B | H | (CH₂)₂CONHMe | H | — | 162.5–164 | C₂₄H₂₄N₄O₂S₂ | C, H, N, S |
| 52 | B | H | (CH₂)₂CONHOMe | H | — | 176–178 | C₂₄H₂₆N₄O₄S₂ | C, H, N, S |
| 53 | B | H | (CH₂)₂CONHMe₂ | H | — | 179–180 | C₂₆H₃₀N₄O₂S₂ | C, H, N, S |
| 54 | B | H | (CH₂)₂CONH(CH₂)₂Ph | H | — | oil | C₃₈H₃₈N₄O₂S₂ | HRFABMS |
| 55 | B | H | (CH₂)₂CONHCH₂Ph{4-COOMe} | H | — | 151–153 | C₃₈H₃₄N₄O₆S₂·H₂O | C, H, N, S |
| 56 | B | H | (CH₂)₂CONHCH₂Ph{4-COOH} | H | — | 135.5–138.5 (dec) | C₃₈H₃₄N₄O₆S₂·0.5H₂O | C, H, N, S |
| 57 | B | H | (CH₂)₂CONHCH₂Ph{3-OH,4-COOMe} | H | — | 183–185 | C₄₀H₃₄N₄O₈S₂·H₂O | C, H, N, S |
| 58 | B | H | (CH₂)₂CONHCH₂Ph{3-OH,4-COOH} | H | — | 160–163.5 (dec) | C₃₈H₃₄N₄O₇S₂·0.5H₂O | C, H, N, S |
| 59 | B | H | (CH₂)₂CONHPh | H | — | 114 (dec) | C₃₀H₃₀N₄O₂S₂·0.5H₂O | C, H, N, S |
| 60 | B | H | NHAc | H | — | 140–144[#] (dec) | C₄₀H₄₀N₆O₆S₂ | C, H, N, S |
| 61 | B1 | H | NHCOCF₃ | H | — | 154.5–157.5[#] (dec) | C₄₀H₃₄F₆N₆O₄S₂·0.5H₂O | C, H, N, S |
| 62 | B1 | H | NH₂ | H | — | 160–164 (dec) | C₃₆H₃₆N₆O₂S₂·0.5H₂O | C, H, N, S |
| 63 | B1 | H | OAc | H | — | 147–150 (dec) | C₄₀H₃₄N₄O₆S₂ | C, H, N, S |
| 64 | B1 | H | OH | H | — | 120–124 (dec) | C₃₆H₃₄N₄O₂S₂ | C, H, N, S |
| 65 | B | H | (CH₂)₃COOH | H | — | 120–125 | C₂₄H₂₄N₂O₄S₂·0.5H₂O | C, H, N, S |
| 66 | B | H | (CH₂)₃COOH | Me | — | 141–143.5 | C₂₆H₂₈N₂O₄S₂·2AcOH | C, H, N, S |
| 67 | B | H | (CH₂)₃COOMe | Me | — | 106.5–109.5 | C₂₈H₃₂N₂O₄S₂ | C, H, N, S |
| 68 | B | H | (CH₂)₃CONHCH₂Ph | H | — | 91–93 | C₃₆H₃₈N₄O₂S₂ | C, H, N, S |
| 69 | B | H | CONHPh | Me | — | 112–113 | C₃₂H₂₆N₄O₂S₂ | C, H, N, S |
| 70 | B | H | CONHPh | Et | — | 98.5–101 | C₃₄H₃₀N₄O₂S₂ | C, H, N, S |
| 71 | B | H | CONHPh | Me | — | 187–188 | C₃₂H₂₆N₄O₂S₂ | C, H, N, S |
| 72 | B | 4-Cl | CONHPh | Me | — | 200–202 | C₃₂H₂₄Cl₂N₄O₂S₂ | C, H, N, S |
| 73 | B | 5-Cl | CONHPh | Me | — | 225–228 | C₃₂H₂₄Cl₂N₄O₂S₂ | C, H, N, S, Cl |
| 74 | B | 7-Cl | CONHPh | Me | — | 214–216 | C₃₂H₂₄Cl₂N₄O₂S₂ | C, H, N, S |
| 75 | B | 4-Me | CONHPh | Me | — | 232–234 | C₃₄H₃₀N₄O₂S₂ | C, H, N, S, Cl |
| 76 | B | 5-Me | CONHPh | Me | — | 237–239 | C₃₄H₃₀N₄O₂S₂ | C, H, N, S |
| 77 | B | 6-Me | CONHPh | Me | — | 231–234 | C₃₄H₃₀N₄O₂S₂ | C, H, N, S |
| 78 | B | 7-Me | CONHPh | Me | — | 192–195 | C₃₄H₃₀N₄O₂S₂ | C, H, N, S |
| 79 | B | 4-OMe | CONHPh | Me | — | 221–223 | C₃₄H₃₀N₄O₄S₂ | C, H, N, S |
| 80 | B | 5-OMe | CONHPh | Me | — | 225–228 | C₃₄H₃₀N₄O₄S₂ | C, H, N, S |
| 81 | B | 6-OMe | CONHPh | Me | — | 161–164 | C₃₄H₃₀N₄O₄S₂ | C, H, N, S |
| 82 | B | 7-OMe | CONHPh | Me | — | 197–200 | C₃₄H₃₀N₄O₄S₂ | C, H, N, S |
| | | | | | | 205–206 | | |

TABLE 1-continued

| No. | Formula | R₁ | R₂ | R₃ | X | mp (°C.) | Molecular Formula | Analysis[a] |
|---|---|---|---|---|---|---|---|---|
| 83 | B | 7-aza | CONHPh | Me | — | 197–198 | $C_{30}H_{24}N_6O_2S_2$ | C, H, N, S |
| 84 | B | 5-CF₃ | CONHPh | Me | — | 214–216 | $C_{34}H_{23}F_6N_4O_2S_2$ | C, H, N, S |
| 85 | B | 6-Cl | CONHPh | Me | — | 243–245 | $C_{32}H_{24}Cl_2N_4O_2S_2$ | C, H, N |
| 86 | B | 5-NO₂ | CONHPh | Me | — | 236–240 | $C_{32}H_{24}N_6O_6S_2 \cdot 2H_2O$ | C, H, N, S |
| 87 | B | 5-F | CONHPh | Me | — | 205–207 | $C_{32}H_{24}F_2N_4O_2S_2$ | C, H, N, S |
| 88 | B | 5-CN | CONHPh | Me | — | 221–224 | $C_{34}H_{24}N_6O_2S_2 \cdot 0.5H_2O$ | C, H, N, S |
| 89 | B | 5-Br | CONHPh | Me | — | 219–221 | $C_{32}H_{24}Br_2N_4O_2S_2$ | C, H, N, S |
| 90 | B | 4-OAc | CONHPh | Me | — | 194 | $C_{36}H_{30}N_4O_6S_2$ | HRFABMS |
| 91 | B | 5-OAc | CONHPh | Me | — | 147–150 | $C_{36}H_{30}N_4O_6S_2 \cdot 0.5H_2O$ | C, H, N, S |
| 92 | B | 5-OH | CONHPh | Me | — | 185–187 | $C_{32}H_{26}N_4O_4S_2 \cdot H_2O$ | C, H, N |
| 93 | B | 6-OAc | CONHPh | Me | — | 219–222 | $C_{36}H_{30}N_4O_6S_2$ | HRMS |
| 94 | B | 6-OH | CONHPh | Me | — | 185–187 | $C_{32}H_{26}N_4O_4S_2$ | C, H, N, S |
| 95 | B | 7-OAc | CONHPh | Me | — | 212–214 | $C_{36}H_{30}N_4O_6S_2 \cdot 0.5H_2O$ | C, H, N, S |
| 96 | B | 7-OH | CONHPh | Me | — | 206–207 | $C_{32}H_{26}N_4O_4S_2$ | C, H, N, S |
| 97 | B | H | CONHMe | Me | — | 162–165 | $C_{22}H_{22}N_4O_2S_2$ | HRMS[c] |
| 98 | B | H | CONHCH₂Ph | H | — | 145–147 | $C_{34}H_{30}N_4O_2S_2$ | C, H, N, S |
| 99 | B | H | SO₂Php-Me | Me | — | 230–233 | $C_{30}H_{24}N_2O_4S_4$ | C, H, N, S |
| 100 | B | H | COPh | Me | — | 199–202 | $C_{32}H_{24}N_2S_2O_2$ | C, H |
| 101 | B | H | COPhpCOOH | Me | — | 241–246 | $C_{34}H_{24}N_2S_2O_6 \cdot 1.5H_2O$ | C, H, N, S |
| 102 | B | H | COPhpCOOMe | Me | — | 200–203 | $C_{36}H_{28}N_2O_6S_2$ | C, H, N, S |
| 103 | B | H | Me | Me | — | 113–115 | $C_{20}H_{20}N_2S_2$ | C, H, N, S |
| 104 | B | H | CONHPh{4-COOMe} | Me | — | 184–186 | $C_{36}H_{30}N_4O_6S_2 \cdot H_2O$ | C, H, N, S |
| 105 | B | H | CONHPh{4-COOH} | Me | — | 221 | $C_{34}H_{26}N_4O_6S_2 \cdot 0.5H_2O$ | C, H, N, S |
| 106 | B | H | CONHPh{3-COOMe} | Me | — | 193–195 | $C_{36}H_{30}N_4O_6S_2$ | C, H, N, S |
| 107 | B | H | CONHPh{3-COOH} | Me | — | 219–220 | $C_{34}H_{26}N_4O_6S_2$ | C, H, N, S |
| 108 | B | H | CONHPh{2-COOMe} | Me | — | 179–181 | $C_{36}H_{30}N_4O_6S_2$ | C, H, N, S |
| 109 | B | H | CONHPh{2-COOH} | Me | — | 184–186 | $C_{34}H_{26}N_4O_6S_2$ | C, H, N, S |
| 110 | B | H | CONHCH₂Ph{4-COOMe} | Me | — | 178–180 | $C_{38}H_{34}N_4O_6S_2$ | C, H, N, S |
| 111 | B | H | CONHCH₂Ph{4-COOH} | Me | — | 178–180 | $C_{36}H_{30}N_4O_6S_2 \cdot 1.5H_2O$ | C, H, N, S |
| 112 | B | H | CONHCH₂COOH | Me | — | 196–198 | $C_{24}H_{22}N_4O_6S_2$ | C, H, N, S |
| 113 | B | H | CON(Me)Ph | Me | — | 158–163 | $C_{34}H_{31}N_4S_2O_2$ | C, H, N, S |
| 114 | B | H | CONHCH₂CH(OH)CH₂OH | Me | — | 198 | $C_{26}H_{30}N_4O_6S_2$ | C, H, N, S |
| 115 | B | H | CONHCH₂CH₂NMe₂ | Me | — | 163.5–165 | $C_{28}H_{36}N_6O_2S_2$ | C, H, N, S |
| 116 | B | H | CONH-4-pyridyl | Me | — | 226–229 | $C_{30}H_{24}N_6O_2S_2$ | C, H, N, S |
| 117 | B | H | CONH-3-pyridyl | Me | — | 257–260 | $C_{30}H_{24}N_6O_2S_2$ | C, H, N, S |
| 118 | B | H | CONH₂ | Me | — | 186–188 | $C_{20}H_{18}N_4O_2S_2 \cdot 0.5H_2O$ | C, H, N, S |
| 119 | B | H | CONMe₂ | Me | — | 96–102 | $C_{24}H_{26}N_4O_2S_2 \cdot 0.5H_2O$ | C, H, N, S |
| 120 | B | H | CN | Me | — | 205–207 | $C_{20}H_{14}N_4S_2$ | C, H, N, S |
| 121 | B | H | COMe | Me | — | 178.5–179.5 | $C_{22}H_{20}N_2O_2S_2 \cdot 0.5H_2O$ | C, H, N, S |
| 122 | B | H | CONH-2-pyridyl | Me | — | 270–272 | $C_{30}H_{24}N_6O_2S_2 \cdot 0.25H_2O$ | C, H, N, S |
| 123 | B | H | CONH-furyl | Me | — | 175–176 | $C_{28}H_{20}N_4O_4S_2$ | C, H, N, S |
| 124 | B | H | CONH-thienyl | Me | — | 183 (DEC) | $C_{28}H_{22}N_4O_4S_0.5H_2O$ | C, H, N |
| 125 | B | H | CONHCH₂Ph | H | — | 203–205 | $C_{32}H_{26}N_4O_2S_2$ | C, H, N, S |
| 126 | B | H | CONHPh | H | — | 220–222.5 | $C_{30}H_{22}N_4O_2S_2$ | C, H, N, S |
| 127 | B | H | CONHMe | H | — | 232–236 | $C_{20}H_{18}N_4O_2S_2$ | C, H, N, S |
| 128 | B | H | CONHPh | (CH₂)₃NMe₂ | — | 165 | $C_{28}H_{36}N_6O_2S_2$ | C, H, N, S |

TABLE 1-continued

| No. | Formula | R₁ | R₂ | R₃ | X | mp (°C.) | Molecular Formula | Analysis[a] |
|---|---|---|---|---|---|---|---|---|
| 129 | D | H | COO$t$-Bu | CH₃ | — | 187–189 | C$_{28}$H$_{32}$N$_2$O$_4$Se$_2$·0.2H$_2$O | C, H, N |
| 130 | D | H | COOH | CH₃ | — | 174 (dec) | C$_{20}$H$_{16}$N$_2$O$_4$Se$_2$·0.1H$_2$O | C, H, N |
| 131 | D | H | CONHMe | CH₃ | — | 225–230 (dec) | C$_{22}$H$_{22}$N$_4$O$_2$Se$_2$·0.9H$_2$O | C, H, N |
| 132 | D | H | CONH(CH$_2$)$_2$NEt$_2$ | CH₃ | — | 160–164 | C$_{32}$H$_{44}$N$_6$O$_2$Se$_2$·2.0HCl·1.7H$_2$O | C, H, N, Cl⁻ |
| 133 | D | H | CONHCH$_3$ | H | — | 272–275 | C$_{20}$H$_{18}$N$_4$O$_2$Se$_2$·0.9H$_2$O | C, H, N |
| 134 | D | H | CONH(CH$_2$)$_2$NEt$_2$ | H | — | 257–259 (dec) | C$_{30}$H$_{40}$N$_6$O$_2$Se$_2$·2.0HCl·1H$_2$O | C, H, N |
| 135 | D | H | CONHCH$_3$ | (CH$_2$)$_2$NEt$_2$ | — | 156–157 | C$_{32}$H$_{44}$N$_6$O$_2$Se$_2$·0.5H$_2$O | C, H, N |
| 136 | D1 | H | NH$_2$[R-(R*,R*)] | H | — | 172–174 | C$_{36}$H$_{36}$N$_6$O$_2$Se$_2$·1.5H$_2$O | C, H, N |
| 137 | D1 | H | NH$_2$[S-(R*,R*)] | H | — | 171 (dec) | | |

Diastereomers
[a]Analyses for all listed elements within ±0.4%
[b]Noncrystalline
[c]High-resolution mass spectrum molecular ion
[d]Wieland T, Wieburg O, Fischer E, Korlein G, Annalen 1954; 587:146
[e]Takase S, Uchida I, Tanaka H, Aoki H, Tetrahedron 1986; 42:5879
[f]Palmisano G, Brenna E, Danieli B, Lesma G, Vodopivec B, Fiori G, Tet. Lett. 1990; 31:7229
[g]Piotrowska H, Serafin B, Wejroch-Matacz K, Rocz. Chem. 1975; 49:635–638.

EXAMPLES

The invention and the best mode for practicing the same are illustrated by the following Examples A–K.

Example A

Preparation of Compounds 15, 17, 65, and 46 of Table 1 by the Method Outlined in Scheme 1

Concentrated HCl (16.6 mL) was added dropwise with stirring, over 10 minutes, to a solution of 4-(3-indolyl)butanoic acid [II: $R_1=R_3=H$, $R_2=(CH_2)_3COOH$] (2.00 g) in DMSO (7.0 mL) at room temperature (method of Savige WE, Fontana A, *J. Chem. Soc. Chem. Commun.* 1976:599). After 15 minutes reaction, the mixture was diluted with water (80 mL) and extracted with EtOAc (4×100 mL). Removal of the solvent gave crude 4-(2-oxo-3-indolinyl)butanoic acid [III: $R_1=R_3=H$, $R_2=(CH_2)_3COOH$] (2.07 g, 96%) as a green-brown solid; mp (water) 169°–171° C. (Hinman RL, Bauman CP, *J. Org. Chem.* 1964;29:1206 record mp 170°–171° C.).

Acetyl chloride (10 mL) was added dropwise with stirring to an ice-cooled solution of the above crude acid [III: $R_1=R_3=H$, $R_2=(CH_2)_3COOH$] (2.05 g) in dry MeOH (50 mL), and the mixture stirred at 20° C. for 18 hours. The solvent was removed, and repeated evaporation from MeOH yielded a brown oil, which was dissolved in $CHCl_3$ (100 mL) and washed with water (2×100 mL). Removal of the solvent gave crude methyl 4-(2-oxo-3-indolinyl)butanoate [III: $R_1=R_3=H$, $R_2=(CH_2)_3COOMe$] (2.20 g) as an oil. A pure sample was obtained by chromatography on silica gel and elution with EtOAc/light petroleum (1:2) as a pale yellow oil.

$^1$H NMR ($CDCl_3$): δ 8.82 (1H, s, NH), 7.24 (1H, d, J=7.7 Hz, ArH), 7.21 (1H, t, J=7.8 Hz, ArH), 7.03 (1H, td, J=7.6, 0.8 Hz, ArH), 6.91 (1H, d, J=7.7 Hz, ArH), 3.65 (3H, s, $COOCH_3$), 3.49 (1H, t, J=6.0 Hz, H-3), 2.34 (2H, t, J=7.5 Hz, $CH_2CO$), 2.00, 1.72 (4H, 2×m, 3-$CH_2CH_2$). $^{13}$C NMR ($CDCl_3$): δ 180.23 (s, CONH), 173.57 (s, $\underline{C}OOCH_3$), 141.54, 129.24 (2×s, Ar), 127.97, 124.11, 122.37, 109.80 (4×d, Ar), 51.53 (q, $COO\underline{C}H_3$), 45.74 (d, C3), 33.83, 29.79, 21.18 (3×t, ($\underline{C}H_3)_3CO$).

Analysis calculated for $C_{13}H_{15}NO_3 \cdot H_2O$ requires: C, 6.45; H, 6.7; N, 5.6%.

Found: C, 64.4; H, 6.5; N, 5.7%.

A solution of the above crude ester [III: $R_1=R_3=H$, $R_2=(CH_2)_3COOMe$] (0.48 g) in dry dioxane (10 mL) was treated with $P_2S_5$ (0.26 g) and $NaHCO_3$ (0.36 g), then the mixture was stirred under nitrogen at 95° C. for 1 hour. The resulting solution was concentrated under reduced pressure, and the residue was diluted with $CH_2Cl_2$ (100 mL) and filtered. The filtrate was washed with water, solvent was removed, and the residue (0.55 g) was chromatographed on silica gel (elution with $CH_2Cl_2$) to give crude methyl 4-(2-thioxo-3-indolinyl)butanoate [IV: $R_1=R_3=H$, $R_2=(CH_2)_3COOMe$] (17) (0.18 g, 35%); mp (benzene-light petroleum) 109°–110° C.

$^1$N NMR ($CDCl_3$): δ 10.59 (1H, s, NH), 7.31 (1H, d, J=7.4 Hz, ArH), 7.27 (1H, td, J=7.7, 0.9 Hz, ArH), 7.14 (1H, td, J=7.5, 0.9 Hz, ArH), 7.02 (1H, d, J=7.7 Hz, ArH), 3.85 (1H, t, J=5.5 Hz, H-3), 3.64 (3H, s, $COOCH_3$), 2.32 (2H, t, J=7.5 Hz, $CH_2CO$), 2.26, 2.15, 1.67, 1.46 (4H, 4×m, 3-$CH_2CH_2$). $^{13}$C NMR ($CDCl_3$): δ 207.80 (s, CSNH), 173.69 (s, $\underline{C}OOCH_3$), 143.27, 133.85 (2×s, ArH), 128.19, 124.17, 124.02, 110.12 (4×d, ArH), 57.36 (d, C-3), 51.61 (q, $COO\underline{C}H_3$), 33.92, 32.76, 20.41 (3×t, ($\underline{C}H_2)_3CO$).

Analysis calculated for $C_{13}N_{15}NO_2S$ requires: C, 62.6; H, 6.1; N, 5.6; S, 12.9%.

Found: C, 62.8; H, 5.9; N, 5.7; S, 12.9%.

A solution of 17 (0.39 g) in MeOH was exposed to air for 13 days, then the solvent was removed. Chromatography of the residue on silica gel (elution with $CH_2Cl_2$) yielded bis[methylindolyl-3-butanoate-(2)]disulfide [V: $R_1=R_3=H$, $R_2=(CH_2)_3COOMe$] (67) (0.31 g, 80%); mp (MeOH-dilute HCl) 91°–93° C.

$^1$N NMR ($CDCl_3$): δ 8.19 (1H, s, NH), 7.57 (1H, d, J=7.9 Hz, ArH), 7.28 (1H, d, J=8.0 Hz, ArH), 7.24 (1H, ddd, J=8.2, 7.1, 1.1 Hz, ArH), 7.12 (1H, ddd, J=8.0, 6.9, 1.4 Hz, ArH), 3.56 (3H, s, $COOCH_3$), 2.67, 2.18 (2×2H, 2×t, J=7.4 Hz, C$\underline{H}_2CH_2\underline{CH}_2CO$), 1.85 (2H, quin, J=7.4 Hz, $CH_2C\underline{H}_2CH_2CO$).

$^{13}$C NMR ($CDCl_3$): δ 174.02 (s, $\underline{C}OOCH_3$), 137.29, 127.49, 125.99 (3×s, ArH), 124.21 (d, ArH), 123.70 (s, ArH), 119.95, 119.88, 111.08 (3×d, ArH), 51.42 (q, $COO\underline{C}H_3$), 33.45, 25.67, 23.95 (3×t, ($\underline{C}H_2)_3CO$).

Analysis calculated for $C_{26}H_{28}N_2O_4S_2$ requires: C, 62.9; H, 5.7; N, 5.7; S, 12.9%.

Found: C, 62.6; H, 6.0; N, 5.5; S, 13.1%.

A mixture of 17 (0.26 g) in MeOH (10 mL) and $K_2CO_3$ (0.55 g) in water (3 mL) was stirred at room temperature for 2 days. $NaBH_4$ (100 mg) was then added, and the mixture stirred for 25 minutes, then diluted with water (100 mL) and extracted with $CH_2Cl_2$ (2×100 mL). The aqueous portion was acidified (to pH 3) with dilute HCl and extracted with EtOAc (3×100 mL). This extract was concentrated under reduced pressure, and the residue was crystallized from $CH_2Cl_2$-light petroleum to give 4-(2-thioxo-3-indolinyl)butanoic acid [IV: $R_1=R_3=H$, $R_2=(CH_2)_3COOH$] (15) (30 mg, 12%); mp 132°–134° C.

$^1$H NMR ($CD_3OD$): δ 7.34 (1H, d, J=7.4 Hz, ArH), 7.26 (1H, td, J=7.7, 1.1 Hz, ArH), 7.12 (1H, td, J=7.5, 0.8 Hz, ArH), 7.00 (1H, d, J=7.8 Hz, ArH), 2.25 (2H, t, J=7.5 Hz, C$\underline{H}_2COOH$), 2.24, 2.10, 1.55, 1.33 (4H, 4×m, 3-$CH_2CH$).

Analysis calculated for $C_{12}H_{13}NO_2S$ requires: C, 61.3; H, 5.6; N, 6.0; S, 13.6%

Found: C, 61.1; H, 6.2; N, 6.1; S, 13.5%.

Similar hydrolysis of 67 (at 30° C. for 6 hours, then 20° C. for 1 day) gave bis[indolyl-3-butanoic acid-(2)]disulfide [V: $R_1=R_3=H$, $R_2=(CH_2)_3COOH$] (65) (30 mg, 20%); mp (aqueous MeOH) 141°–143.5° C.

$^1$H NMR ($CD_3OD$): δ 7.48 (1H, dt, J=8.0, 0.8 Hz, ArH), 7.32 (1H, dt, J=8.2, 0.7 Hz, ArH), 7.16 (1H, ddd, J=8.1, 7.1, 1.1 Hz, ArH), 7.00 (1H, ddd, J=8.0, 7.1, 0.8 Hz, ArH), 2.42 (2H, t, J=7.6 Hz, $CH_2CO$), 1.93 (2H, t, J=7.3 Hz, 3-$CH_2$), 1.58 (2H, quin, J=7.5 Hz, $CH_2C\underline{H}_2CH_2CO$).

$^{13}$C NMR ($CD_3OD$): δ 177.52 (s, COOH), 139.31, 128.69, 126.69, 124.84 (4×s, ArH), 124.67, 120.48, 120.27, 112.34 (4×d, ArH), 34.39, 27.24, 24.82 (3×t, ($\underline{C}H_2)_3COOH$).

Analysis calculated for $C_{24}H_{24}N_2O_4S_2 \cdot H_2O$ requires: C, 60.4; H, 5.2; N, 5.9; S, 13.4%.

Found: C, 60.4; H, 5.4; N, 5.9; S, 13.6%.

Compounds 7, 9, 36 and 39 of Table 1

Similar treatment of methyl 3-(3-indolinyl)propanoic [II: $R_1=R_3=H$, $R_2=(CH_2)_2COOH$] (0.93 g) with DMSO/HCl, followed by esterification with diazomethane and chromatography on silica gel, gave methyl 3-(2-oxo-3-indolyl)propanoate [III: $R_1-R_3=H$, $R_2=(CH_2)_2COOMe$] (0.89 g, 89%)

as a yellow oil (Julian PL, Printy HC, *J. Am. Chem. Soc.* 1953;75:5301–5305 report mp 79°–80° C.).

$^1$H NMR (CDCl$_3$): δ 8.75 (1H, s, NH), 7.22 (2H, m, ArH), 7.03 (1H, ddd, J=7.8, 7.1, 1.1 Hz, ArH), 6.91 (1H, dd, J=7.3, 1.3 Hz, ArH), 3.63 (3H, s, OCH$_3$), 3.54 (1H, t, J=5.8 Hz, H-3), 2.61–2.20 (4H, m, 3-CH$_2$CH$_2$).

Analysis calculated for C$_{12}$H$_{13}$NO$_3$ requires: M+ 219.0895.

HREIMS m/z Found: M+ 219.0898.

Treatment of this ester [III: R$_1$=R$_3$=H, R$_2$=(CH$_2$)$_2$COOMe] (0.89 g) with P$_2$S$_5$ as above, followed by chromatography on silica gel, eluting with EtOAc/light petroleum (3:1), gave an oil (0.44 g). Crystallization from MeOH gave 2,2'-dithiobis[methyl 3-(3-indolyl)propanoate [V: R$_1$=R$_3$=H, R$_2$=(CH$_2$)$_2$COOMe] (39) (61 mg, 6%); mp 162.5°–164° C.

$^1$H NMR (CDCl$_3$): δ 8.21 (1H, s, NH), 7.55 (1H, dd, J=8.0, 0.7 Hz, ArH), 7.25 (2H, m, ArH), 7.12 (1H, ddd, J=8.0, 5.4, 2.6 Hz, ArH), 3.56 (3H, s, OCH$_3$), 2.98, 2.47 (2×2H, 2xt, J=7.9 Hz, 3-CH$_2$CH$_2$).

$^{13}$C NMR (CDCl$_3$): δ 173.38 (s, COOCH$_3$), 137.25, 127.21, 125.80 (3xs, Ar), 124.30 (d, Ar), 122.79 (s, Ar), 120.10, 119.59, 111.21 (3xd, Ar), 51.56 (q, OCH$_3$), 34.97 (t, CH$_2$CO), 20.27 (t, 3-CH$_2$).

Analysis calculated for C$_{24}$H$_{24}$N$_2$O$_4$S$_2$ requires: C, 61.5; H, 5.2; N, 6.0; S, 13.7%.

Found: C, 61.4; H, 5.3; N, 6.1; S, 13.7%.

Crystallization of the mother liquor residue from benzene/light petroleum gave methyl 3-(2-thioxo-3-indolinyl)propanoate [IV: R$_1$=R$_3$=H, R$_2$=(CH$_2$)$_2$COOMe] (9) (0.24 g, 25%); mp (CH$_2$Cl$_2$/light petroleum) 96°–98° C.

$^1$H NMR (CDCl$_3$): δ 9.83 (1H, s, NH), 7.29 (2H, m, ArH), 7.16 (1H, td, J=7.5, 0.9 Hz, ArH), 6.99 (1H, d, J=7.8 Hz, ArH), 3.91 (1H, t, J=5.4 Hz, H-3), 3.60 (3H, s, OCH$_3$), 2.52 (2H, m, 3-CH$_2$), 2.42, 2.11 (2×1H, 2xm, CH$_2$CO).

$^{13}$C NMR (CDCl$_3$): δ 207.26 (s, CSNH), 173.37 (s, COOCH$_3$), 143.24, 133.08 (2xs, Ar), 128.43, 124.35, 124.09, 110.01 (4xd, Ar), 56.45 (d, C-3), 51.68 (q, OCH$_3$), 29.33, 28.19 (2xt, 3-CH$_2$CH$_2$).

Analysis calculated for C$_{12}$H$_{13}$NO$_2$S requires: C, 61.3; H, 5.6; N, 6.0; S, 13.6%.

Found: C, 61.4; H, 5.5; N, 6.0; S, 13.7%.

Hydrolysis of 9 with K$_2$CO$_3$/MeOH/H$_2$O as described above, followed by chromatography on silica gel, reduction with NaBH$_4$ and crystallization from CH$_2$Cl$_2$/isopropyl ether/light petroleum gave 3-(2-thioxo-3-indolinyl)propanoic acid [IV: R$_1$=R$_3$=H, R$_2$=(CH$_2$)$_2$COOH] (7) (25 mg, 22%); mp 170°–173° C.

$^1$H NMR (CD$_3$COCD$_3$): δ 11.48 (1H, s, NH), 7.43 (1H, d, J=7.4 Hz, ArH), 7.30 (1H, t, J=7.7 Hz, ArH), 7.15 (1H, t, J=7.4 Hz, ArH), 7.11 (1H, d, J=7.8 Hz, ArH), 3.90 (1H, t, J=5.3 Hz, H-3), 2.49 (1H, m, CH$_2$CH$_2$CO), 2.37 (2H, m, CH$_2$CH$_2$CO), 2.11 (1H, m, CH$_2$CH$_2$CO).

$^{13}$C NMR (CD$_3$COCD$_3$): δ 208.48 (s, CSNH), 174.14 (s, COOH), 145.18, 134.55 (2xs, Ar), 129.05, 125.08, 124.30, 110.87 (4xd, Ar), 57.18 (d, C-3), 29,86, 29.25 (2xt, CH$_2$CH$_2$COOH).

Analysis calculated for C$_{11}$H$_{11}$NO$_2$S requires: C, 59.71; H, 5.01; N, 6.33%.

Found: C, 59.49; H, 4.97; N, 6.15%.

Aerial oxidation of 7 in MeOH at 20° C. for 12 days, followed by dilution with water, gave bis[indolyl-3-propanoic acid-(2)]disulfide [V: R$_1$=R$_3$=H, R$_2$=(CH$_2$)$_2$COOH] (36) (30 mg, 30%); mp (aqueous MeOH) 118°–120.5° C.

$^1$H NMR (CD$_3$OD): δ 7.47 (1H, dt, J=8.0, 0.8 Hz, ArH), 7.30 (1H, dt, J=8.1, 0.8 Hz, ArH), 7.15 (1H, ddd, J=8.1, 7.1, 1.0 Hz, ArH), 7.00 (1H, ddd, J=8.0, 7.1, 0.9 Hz, ArH), 2.74, 2.2 (2×2H, 2xt, J=8.0 Hz, (CH$_2$)$_2$COOH), $^{13}$C NMR (CD$_3$OD): δ176.95 (s, COOH), 139.26, 128.26 126.65 (3xs, Ar), 124.69 (d, Ar), 123.66 (s, Ar), 120.36, 120.20, 112.41 (3xd, Ar), 36.29, 21.22 (2xt, (CH$_2$)$_2$COOH), Analysis calculated for C$_{22}$H$_{20}$N$_2$O$_4$S$_2$.H$_2$O requires: C, 57.6; H, 4.8; N, 6.1; S, 14.0%.

Found: C, 57.6; H, 5.0; N, 6.1; S, 13.9%.

Compounds 3 and 27 of Table 1

Similar reaction of methyl 2-(2-oxo-3-indolinyl)acetate [III: R$_1$=R$_3$=H, R$_2$=(CH$_2$)$_3$COOMe: Takase S, Uchida I, Tanaka H, Aoki H, *Tetrahedron* 1986;42:5879] (0.13 g) with P$_2$S$_5$ gave methyl 2-(2-thioxo-3-indolinyl)acetate [IV: R$_1$=R$_3$=H, R$_2$=(CH$_2$)$_3$COOMe] (3) (50 mg, 36%); mp (MeOH) 150°–152° C.

$^1$N NMR (CDCl$_3$): δ 10.36 (1H, s, NH), 7.29 (1H, d, J=7.6 Hz, ArH), 7.27 (1H, t, J=7.8 Hz, ArH), 7.11 (1H, t, J=7.6 Hz, ArH), 7.00 (1H, d, J=7.8 Hz, ArH), 4.14 (1H, dd, J=8.4, 4.2 Hz, H-3), 3.72 (3H, s, COOCH$_3$), 3.35 (1H, dd, J=17.0, 4.2 Hz, CH$_2$CO), 2.88 (1H, dd, J=17.0, 8.5 Hz, CH$_2$CO).

$^{13}$C NMR (CDCl$_3$): δ 206.59 (s, CSNH), 171.53 (s, COOCH$_3$), 143.10, 133.53 (2xs, ArH), 128.45, 124.20, 124.12, 110.07 (4xd, ArH), 53.53 (d, C3), 52.02 (q, COOCH$_3$), 37.94 (t, CH$_2$).

Analysis calculated for C$_{11}$H$_{11}$NO$_2$S requires: C, 59.7; H, 5.0; N, 6.3; S, 14.5%.

Found: C, 59.9; H, 5.3; N, 6.4; S, 14.4%.

A solution of 3 (0.10 g) in benzene-light petroleum (1:1, 30 mL) exposed to air for 2 days gave a quantitative yield of bis[methylindolyl-3-acetate-(2)]disulfide [V: R$_1$=R$_3$=H, R$_2$=(CH$_2$)$_3$COOMe] (Compound 27 of Table I); mp (benzene/light petroleum) 160°–162° C.

$^1$N NMR (CDCl$_3$): δ 8.69 (1H, s, NH), 7.52 (1H, dd, J=8.2, 0.6 Hz, ArH), 7.21 (1H, ddd, J=8.2, 6.6, 1.1 Hz, ArH), 7.12 (2H, m, ArH), 3.83 (2H, s, CH$_2$CO), 3.71 (3H, s, COOCH$_3$).

$^{13}$C NMR (CDCl$_3$): δ 172.54 (s, COOCH$_3$), 137.20, 127.19, 127.03 (3xs, ArH), 124.26, 120.31, 119.45 (3xd, ArH), 116.23 (s, ArH), 111.41 (d, ArH), 52.25 (q, OCH$_3$), 30.51 (t, CH$_2$CO).

Analysis calculated for C$_{22}$H$_{20}$N$_2$O$_4$S$_2$ requires: C, 60.0; H, 4.6; N, 6.4; S, 14.6%.

Found: C, 60.0; H, 4.8; N, 6.3; S, 14.4%.

Additional amounts of 27 were also obtained from the mother liquors of the P$_2$S$_5$ reaction.

Compounds 8, 11, 37, and 40 of Table 1

A solution of 18-crown-6 (0.44 g), potassium t-butoxide (2.20 g) and methyl 3-(3-indolyl)propanoate [II: R$_1$=R$_3$=H; R$_2$=(CH$_2$)$_2$COOMe] (3.24 g) in dry benzene (20 mL) was stirred at 20° C. for 15 minutes, then cooled in ice. A solution of CH$_3$I (3.42 g) in benzene (10 mL) was added, then the flask was sealed and the mixture stirred at 20° C. for 1 day (method of Guida WC, Mathre DJ, *J. Org. Chem.* 1980;45:3172). The resulting solution was filtered to remove salts, washing with CH$_2$Cl$_2$, then the combined filtrates washed with water and the solvents removed. Chromatography on silica gel, eluting with CH$_2$Cl$_2$/light petroleum (1:1), gave methyl 3-(1-methyl-3-indolyl)propanoate [II:

R₁=H; R₃=Me; R₂=(CH₂)₂COOMe] (1.90 g, 52%) as a colorless oil (Snyder HR, Eliel EL, *J. Am. Chem. Soc.* 1949;71:663–669 report oil, bp$_{0.25}$ 180°–190° C.).

$^1$H NMR (CDCl₃): δ 7.58 (1H, dt, J=7.7, 0.9 Hz, ArH), 7.28 (1H, dt, J=7.9, 1.3 Hz, ArH), 7.21 (1H, ddd, J=8.1, 6.7, 1.3 Hz, ArH), 7.10 (1H, ddd, J=7.9, 6.5, 1.5 Hz, ArH), 6.86 (1H, s, H-2), 3.73, 3.67 (2×3H, 2×s, NCH₃, OCH₃), 3.09, 2.70 (2×2H, 2×t, J=7.6 Hz, 3-CH₂CH₂).

Analysis calculated for C₁₃H₁₅NO₂ requires: M+ 217.1103.

HREIMS m/z Found: M+ 217.1101.

Oxidation of the ester [II: R₁=H; R₃=Me; R₂=(CH₂)₂COOMe] (1.85 g) with DMSO/HCl as above for 3 hours gave crude 3-(1-methyl-2-oxo-3-indolinyl)propanoic acid [III: R₁=H; R₂=Me; R₃=(CH₂)₂COOH] (2.08 g) as a colorless oil.

$^1$H NMR (CD₃OD): δ 7.31 (2H, m, ArH), 7.09 (1H, td, J=8.0, 1.0 Hz, ArH), 6.98 (1H, d, J=7.6 Hz, ArH), 3.56 (1H, t, J=6.1 Hz, H-3), 3.20 (3H, s, NCH₃), 2.41–2.15 (4H, m, 3-CH₂CH₂).

$^{13}$C NMR (CD₃OD): δ 179.64 (s, COOH), 176.55 (s, CONCH₃), 145.52, 129.73 (2×s, Ar), 129.39, 125.00, 123.93, 109.64 (4×d, Ar), 45.79 (d, C-3), 31.01, 26.91 (2×t, 3-CH₂CH₂), 26.44 (q, NCH₃).

Analysis calculated for C₁₂H₁₃NO₃ requires: M+ 219.0895.

HREIMS m/z Found: M+ 219.0897.

This was esterified with diazomethane as above, then the product chromatographed on silica gel. Elution with EtOAc/ light petroleum (1:2) gave methyl 3-(1-methyl-2-oxo-3-indolinyl)propanoate [III: R₁=H; R₂=Me; R₃=(CH₂)₂COOMe] (1.40 g, 70%) as a colorless oil.

$^1$H NMR (CDCl₃): δ 7.27 (2H, m, ArH), 7.06 (1H, td, J=7.5, 0.8 Hz, ArH), 6.83 (1H, d, J=7.7 Hz, ArH), 3.62 (3H, s, OCH₃), 3.50 (1H, t, J=6.0 Hz, H-3), 3.20 (3H, s, NCH₃), 2.52–2.18 (4H, m, CH₂CH₂).

$^{13}$C NMR (CDCl₃): δ 177 23 (s, CONCH₃), 173.38 (s, COOCH₃), 144.36 (s, Ar), 128.20 (d, Ar), 128.11 (s, Ar), 123.92, 122.48, 108.06 (3×d, Ar), 51.64 (q, OCH₃), 44.36 (d, C-3), 30.12 (t, CH₂OCO), 26.14 (q, NCH₃), 25.64 (t, 3-CH₂).

Analysis calculated for C₁₃H₁₅NO₃ requires: M+ 233.1052.

HREIMS m/z Found: M+ 233.1055.

Treatment of this ester [III: R₁=H; R₂=Me; R₃=(CH₂)₂COOMe] (1.38 g) with P₂S₅ as above followed by chromatography on silica gel, eluting with CH₂CH₂/light petroleum (3:2), gave methyl 3-(1-methyl-2-thioxo-3-indolinyl)propanoate [IV: R₁=H; R₃=Me; R₂=(CH₂)₂COOMe] (11) (1.40 g, 95%); mp (benzene/light petroleum) 71°–73° C.

$^1$H NMR (CDCl₃): δ 7.35 (2H, m, ArH), 7.19 (1H, td, J=7.5, 0.9 Hz, ArH), 7.00 (1H, d, J=7.7 Hz, ArH), 3.92 (1H, t, J=5.4 Hz, H-3), 3.63, 3.58 (2×3H, 2×s, NCH₃, OCH₃), 2.53 (2H, m, 3-CH₂), 2.34, 2.03 (2×1H, 2×m, CH₂CO).

$^{13}$C NMR (CDCl₃): δ 204.77 (s, CSNCH₃), 173.32 (s, COOCH₃), 145.89, 132.37 (2×s, Ar), 128.40, 124.31, 123.99, 109.51 (4×d, Ar), 56.26 (d, C-3), 51.61 (q, OCH₃), 31.35 (q, NCH₃), 29.31, 28.46 (2×t, 3-CH₂CH₂).

Analysis calculated for C₁₃H₁₅NO₂S requires: C, 62.6; H, 6.1; N, 5.6; S, 12.9%.

Found: C, 62.7; H, 6.3; N, 5.7; S, 13.0%.

Oxidation of (11) (0.70 g) with FeCl₃ (0.70 g) in EtOAc/CH₂Cl₂, chromatography of the product on silica gel, and elution with CH₂Cl₂ gave 2,2'-dithiobis[methyl 3-(1-methyl-3-indolyl)propanoate] [V: R₁=H; R₂=Me; R₂=(CH₂)₂COOMe] (40) (0.38 g, 54%); mp (CH₂Cl₂/MeOH) 139°–141.5° C.

$^1$H NMR (CDCl₃): δ 7.49 (1H, d, J=8.0 Hz, ArH), 7.27 (1H, ddd, J-8.3, 6.1, 0.9 Hz, ArH), 7.25 (1H, d, J=8.1 Hz, ArH), 7.09 (1H, ddd, J=8.0, 6.1, 1.9 Hz, ArH), 3.59, 3.53 (2×3H, 2×s, NCH₃, OCH₃), 2.76, 2.21 (2×2H, 2×t, J=7.8 Hz, 3-CH₂CH₂).

$^{13}$C NMR (CDCl₃): δ 173.17 (s, COOCH₃), 138.49, 127.00, 126.09 (3×s, Ar), 124.14 (d, Ar), 123.77 (s, Ar), 119.68, 119.65, 109.87 (3×d, Ar), 51.39 (q, OCH₃), 35.09 (t, CH₂CO), 29.86 (q, NCH₃), 20.50 (t, 3-CH₂).

Analysis calculated for C₂₆H₂₈N₂O₄S₂ requires: C, 62.9; H, 5.7; N, 5.7; S, 12.9%.

Found: C, 62.6; H, 5.6; N, 5.5; S, 13.0%.

A solution of (11) (0.53 g) in EtOH (10 mL) and 2N aqueous NaOH (3 mL) was stirred at 20° C. for 80 minutes. The mixture was then diluted with water (100 mL) and extracted with CH₂Cl₂ (100 mL). The aqueous portion was adjusted to pH 2 with dilute HCl and extracted with EtOAc (3×120 mL). The EtOAc extracts were washed with water (150 mL) and the solvent removed under reduced pressure to give a yellow oil (0.48 g). This was redissolved in MeOH (7 mL) and 2M aqueous NaOH (1 mL) and treated with NaBH (150 mg) for 5 minutes at 20° C. The mixture was then quenched with water and worked up as before to give a pale brown oil (0.46 g). Crystallization from CH/light petroleum gave 3-(1-methyl-2-thioxo-3-indolinyl)propanoic acid [R₁=H; R₂=Me; R₃=(CH₂)₂COOH] (8) (0.32 g, 60%); mp 126°–128.5° C.

$^1$H NMR (CDCl₃): δ 7.35 (2H, m, ArH), 7.18 (1H, td, J=7.5, 0.9 Hz, ArH), 7.00 (1H, d, J=7.8 Hz, ArH), 3.93 (1H, t, J=5.3 Hz, H-3), 3.63 (3H, s, NCH₃), 2.51 (2H, m, 3-CH₂), 2.38 (1H, ddd, J=16.1, 9.3, 6.7 Hz, CHCO), 2.06 (1H, ddd, J=16.0, 9.8, 6.1 Hz, CHCO).

$^{13}$C NMR (CDCl₃): δ 204.61 (s, CSNCH₃), 178.41 (COOH), 145.88, 132.24 (2×s, Ar), 128.50, 124.38, 123.96, 109.57 (4×d, Ar), 56.05 (d, C-3), 31.37 (q, NCH₃), 29.16, 28.16 (2×t, 3-CH₂CH₂).

Analysis calculated for C₁₂H₁₃NO₂S.0.25H₂O requires: C, 60.1; H, 5.6; N, 5.8; S, 13.4%.

Found: C, 60.0; H, 5.6; N, 5.9; S, 13.4%.

Similar hydrolysis of 40 (0.37 g) in EtOH/2M aqueous NaOH for 3 hours at 20° C. gave, after workup, a yellow oil (0.30 g). Crystallization from AcOH gave 2,2'-dithiobis[3-(1-methyl-3-indolyl)propanoic acid] [V: R₁=H; R₂=(CH₂)₂COOH; R₃=Me] (37) (73 mg, 20%); mp 158.5°–160° C.

$^1$H NMR ((CD₃)₂CO): δ 7.59 (1H, d, J=8.1 Hz, ArH), 7.39 (1H, d, J=8.0 Hz, ArH), 7.27 (1H, ddd, J=8.2, 7.1, 0.9 Hz, ArH), 7.07 (1H, ddd, J=8.1, 7.1, 0.8 Hz, ArH), 3.60 (3H, s, NCH₃), 2.79, 2.31 (2×2H, 2×t, J=7.9 Hz, 3-CH₂CH₂).

$^{13}$C NMR ((CD₃)₂CO): δ 173.75 (s, COOH), 139.61, 127.54, 127.06 (3×s, Ar), 125.08 (d, Ar), 125.02 (s, Ar), 120.55, 120.53, 110.03 (3×d, Ar), 35.56 (t, CH₂CO), 30.13 (q, NCH₃), 21.32 (t, 3-CH₂).

Analysis calculated for C₂₄H₂₄N₂O₄S₂ requires: C, 61.5; H, 5.2; N, 6.0; S, 13.7%.

Found: C, 61.5; H, 5.2; N, 6.1; S, 13.6%.

Chromatography of the mother liquors on silica gel, then treatment with NaBH₄ as above and crystallization of the products from CH₂Cl₂/light petroleum also gave 3-(1-methyl-2-thioxo-3-indolinyl)propanoic acid (8) (0.12 g, 32%).

Compounds 16, 18, 66, and 68 of Table 1

N-Alkylation of methyl 4-(3-indolyl)butanoate [II: $R_1=R_3=H$, $R_2=(CH_2)_3COOMe$] (2.14 g), with 18-crown-6 (0.26 g), potassium t-butoxide/$CH_3I$ as above gave methyl 4-(1-methyl-3-indolyl)butanoate [II: $R_1=R_3=H$, $R_2=(CH_2)_3COOMe$, $R_3=Me$] (0.92 g, 40%) as a brown oil, which was used directly.

$^1$H NMR (CDCl$_3$): δ 7.58 (1H, dt, J=7.9, 0.9 Hz, ArH), 7.28 (1H, d, J=8.2 Hz, ArH), 7.21 (1H, ddd, J=8.1, 7.0. 1.1 Hz, ArH), 7.09 (1H, ddd, J=8.0, 7.0, 1.0 Hz, ArH), 6.84 (1H, s, ArH), 3.74 (3H, s, NCH$_3$), 3.66 (3H, s, COOCH$_3$), 2.79, 2.38 (2×2H, 2×t, J=7.4 Hz, C$\underline{H}_2$CH$_2$C$\underline{H}_2$CO), 2.03 (2H, quin, J=7.4 Hz, CH$_2$ C$\underline{H}_2$CH$_2$CO).

$^{13}$C NMR (CDCl$_3$): δ 174.21 (s, $\underline{C}$OOCH$_3$), 137.08, 127.84 (2×s, ArH), 126.34, 121.50, 118.98, 118.62 (4×d, ArH), 114.07 (s, ArH), 109.13 (d, ArH), 51.44 (q, COO$\underline{C}$H$_3$), 33.68 (t, $\underline{C}$H$_2$CO), 32.55 (q, NCH$_3$), 25.58, 24.41 (2×t, 3-CH$_2$CH$_2$).

HREIMS m/z Found: M+ 231.1259.

4-(3-Indolyl)butanoic acid (1.04 g, 52%) was recovered by dissolving the filtered precipitates from the above reaction in water and acidifying; mp 124°–126° C. (Jackson RW, Manske RH, *J. Am. Chem. Soc.* 1930;52:5029 record mp 124° C.).

Reaction of the ester [II: $R_1=R_3=H$, $R_2=(CH_2)_3COOMe$, $R_3=Me$] with DMSO/HCl as above gave crude 4-(1-methyl-2-oxo-3-indolinyl)butanoic acid [III: $R_1=R_3=H$, $R_2=(CH_2)_3COOMe$, $R_3=Me$] (0.84 g, 91% yield) as a brown oil.

$^1$H NMR (CDCl$_3$): δ 7.28 (1H, td, J=7.7, 0.9 Hz, ArH), 7.25 (1H, d, J=7.7 Hz, ArH), 7.06 (1H, td, J=7.5, 0.9 Hz, ArH), 6.83 (1H, d, J=7.8 Hz, ArH), 3.47 (1H, t, J=5.9 Hz, H-3), 3.21 (3H, s, NCH$_3$), 2.37 (2H, t, J=7.4 Hz, CH$_2$CO), 2.00, 1.69 (2×2H, 2×m, 3-CH$_2$CH$_2$).

An ice-cooled solution of the above crude oxoacid [III: $R_1=R_3=H$, $R_2=(CH_2)_3COOMe$, $R_3=Me$] (0.84 g) in ether (10 mL) was treated, dropwise with stirring, with an ethereal solution of diazomethane (from N-nitrosomethylurea, 1.2 g). After 30 minutes at 20° C., the solvent was removed under reduced pressure, and the residue was chromatographed on silica gel (elution with EtOAc/light petroleum (1:2)) to give methyl 4-(1-methyl-2-oxo-3-indolinyl)butanoate [III: $R_1=R_3=H$, $R_2=(CH_2)_3COOMe$, $R_3=Me$] (0.64 g, 72%); mp (EtOAc/light petroleum) 69°–71° C.

$^1$H NMR (CDCl$_3$): δ7.28 (1H, t, J=7.8 Hz, ArH), 7.26 (1H, d, J=7.6 Hz, ArH), 7.05 (1H, td, J=7.6, 0.7 Hz, ArH), 6.82 (1H, d, J=7.7 Hz, ArH), 3.64 (3H, s, COOCH$_3$), 3.44 (1H, t, J=6.0 Hz, H-3), 3.20 (3H, s, NCH$_3$), 2.33 (2H, t, J=7.5 Hz, CH$_2$CO), 1.98, 1.68 (2×2H, 2×m, 3-CH$_2$CH$_2$).

$^{13}$C NMR (CDCl$_3$): δ177.52 (s, CONCH$_3$), 173.59 (s, $\underline{C}$OOCH$_3$), 144.38, 128.71 (2×s, ArH), 128.00, 123.84, 122.40, 108.02 (4×d, ArH), 51.54 (q, COO$\underline{C}$H$_3$), 45.26 (d, C-3), 33.89, 29.98 (2×t, $\underline{C}$H$_2$CH$_2$$\underline{C}$H$_2$CO), 26.15 (q, NCH$_3$), 21.30 (t, 3-CH$_2$$\underline{C}$H$_2$).

Analysis calculated for C$_{14}$H$_{17}$NO$_3$ requires: C, 68.0; H, 6.9; N, 5.7%.

Found: C, 67.9; H, 6.7; N, 5.7%.

The above oxoester [III: $R_1=R_3=H$, $R_2=(CH_2)_3COOMe$, $R_3=Me$] (0.90 g) was treated with P$_2$S$_5$ as above, followed by workup and chromatography on silica gel. Elution with CH$_2$Cl$_2$/light petroleum (3:2) gave methyl 4-(1-methyl-2-thioxo-3-indolyl)butanoate [IV: $R_1=H$, $R_2=(CH_2)_3COOMe$, $R_3=Me$] (18) (1.07 g, 79%); mp (benzene-light petroleum) 103°–106° C.

$^1$H NMR (CDCl$_3$): δ 7.34 (2H, m, ArH), 7.19 (1H, td, J=8.0, 0.9 Hz, ArH), 7.00 (dd, J=8.0. 2.3).

Analysis calculated for C$_{14}$H$_{17}$NO2S requires: C, 63.9; H, 6.5; N, 5.3; S, 12.2%.

Found: C, 64.0; H, 6.4; N, 5.3; S, 12.3%.

A solution of 18 (0.47 g) in EtOAc (7 mL) was stirred with FeCl$_3$ (0.43 g) for 1 hour at 20° C., then worked up and chromatographed on silica gel. Elution with CH$_2$Cl$_2$ gave bis[methyl 1-methylindolyl-3-butanoate-(2)]disulfide [V: $R_1=H$, $R_2=(CH_2)_3COOMe$, $R_3=Me$] (68) (0.40 g, 85%); mp (CH$_2$Cl$_2$/MeOH) 112°–113° C.

$^1$H NMR (CDCl$_3$): δ 7.52 (1H, d, J=8.0 Hz, ArH), 7.28 (1H, ddd, J=8.2, 6.0. 1.0 Hz, ArH), 7.25 (1H, d, J=8.0 Hz, ArH), 7.09 (1H, ddd, J=8.0, 6.0. 1.9 Hz, ArH), 3.59, 3.55 (2×3H, 2×s, NCH$_3$, COOCH$_3$), 2.42, 2.07 (2×2H, 2×t, J=7.4 Hz, C$\underline{H}_2$CH$_2$C$\underline{H}_2$CO), 1.68 (2H, quin, J=7.4 Hz, CH$_2$C$\underline{H}_2$CH$_2$CO).

$^{13}$C NMR (CDCl$_3$): δ173.82 (s, $\underline{C}$OOCH$_3$), 138.47, 127.23, 126.43, 124.74 (4×s, ArH), 124.05, 119.90, 119.49, 109.72 (4×d, ArH), 51.35 (q, COO$\underline{C}$H$_3$), 33.40 (t, $\underline{C}$H$_3$CO), 29.82 (q, NCH$_3$), 25.83, 24.17 (2×t, 3-CH$_2$CH$_2$).

Analysis calculated for C$_{28}$H$_{32}$N$_2$O$_4$S$_2$ requires: C, 64.1; H, 6.1; N, 5.3; S, 12.2%.

Found: C, 63.9; H, 6.4; N, 5.3; S, 12.1%.

Hydrolysis of 18 with EtOH/H$_2$O/NaOH, followed by treatment with NaBH$_4$ and crystallization from CH$_2$Cl$_2$/light petroleum, as above, gave 4-(1-methyl-2-thioxo-3-indolyl) butanoic acid [IV: $R_1=H$, $R_2=(CH_2)_3COOH$, $R_3=Me$] (16) (0.18 g, 44%); mp 144°–146.5° C.

$^1$H NMR (CDCl$_3$): δ 7.34 (2H, m, ArH), 7.18 (1H, t, J=7.6 Hz, ArH), 7.00 (1H, d, J=7.7 Hz, ArH), 3.85 (1H, t, J=5.5 Hz, H-3), 3.63 (3H, s, NCH$_3$), 2.34, 2.07 (2H, t, J=7.6 Hz, CH$_2$CO), 2.28 2.18, 1.59, 1.40 (4×1H, 4×m, 3-CH$_2$CH$_2$).

$^{13}$C NMR (CDCl$_3$): δ 205.31 (s, CSNCH$_3$), 178.62 (s, COOH), 145.81, 133.06 (2×s, Ar), 128.20, 124.30, 123.86, 109.54 (4×d, Ar), 57.14 (d, C-3), 33.77, 33.01 (2×t, 3-CH$_2$CH$_2$CH$_2$), 31.42 (q, NCH$_3$), 20.11 (t, 3-CH$_2$CH$_2$).

Analysis calculated for C$_{13}$H$_{15}$NO$_2$OS.H$_2$O requires: C, 61.6; H, 6.7; N, 5.5; S, 12.7%.

Found: C, 61.9; H, 6.3; N, 5.6; S, 12.8%.

Similar hydrolysis of 68 (0.40 g) gave, after workup, a yellow oil (0.37 g). Chromatography on silica gel, eluting with EtOAc/light petroleum (1:2) containing 1% AcOH, gave an oil (0.25 g). Crystallization from AcOH then gave 2,2'-dithiobis[4 -(1-methyl-3-indolyl)butanoic acid] [V: $R_1=H$, $R_2=(CH_2)_3COOH$, $R_3=Me$] (66) (0.17 g, 42%); mp 106.5°–109.5° C.

$^1$H NMR (CDCl$_3$): δ 7.51 (1H, d, J=8.0 Hz, ArH), 7.27 (2H, m, ArH), 7.08 (1H, ddd, J=8.0, 6.0, 2.0 Hz, ArH), 3.55 (3H, s, NCH$_3$), 2.44 2.12 (2×2H, 2×t, J=7.4 Hz, 3-CH$_2$CH$_2$CH$_2$CO), 1.68 (2H, quintet, J=7.4 Hz, 3-CH$_2$CH$_2$CH$_2$).

$^{13}$C NMR (CDCl$_3$): δ 179.32 (s, COOH), 138.49, 127.49, 126.43, 124.56 (4×s, Ar), 124.14, 119,86, 119.62, 109.79 (4×d, Ar), 33.37 9t, CH$_2$CO), 29.86 (q, NCH$_3$) 25.59, 24.13 (2×t, 3-CH$_2$CH$_2$).

Analysis calculated for C$_{26}$H$_{28}$N$_2$O$_4$S$_2$.2CH$_3$COOH requires: C, 58.4; H, 5.9; N, 4.5; S, 10.4%.

Found: C, 58.4; H, 5.9; N, 4.5; S, 10.6%.

Example B

Preparation of Compounds 1, 29, 30, and 31 of Table 1 by the Method Outlined in Scheme 2

A solution of purified S$_2$Cl$_2$ (0.50 mL) in THF (20 mL) was added dropwise to a stirred, ice-cooled solution of 3-indolylacetic acid [II: $R_1=R_3=H$, $R_2=CH_2COOH$] (2.20 g) in dry THF (30 mL) (method of Wieland T, Wieburg O, Fischer E, Korlein G, *Annalan* 1954;587:146). After 30 minutes at 20° C. the solvent was removed, and the residue was crystallized from aqueous acetic acid to give a yellow solid (1.00 g). Recrystallization of this solid from aqueous MeOH, followed by further crystallization from EtOAc-benzene gave bis[indolyl-3-acetic acid-(2)]trisulfide [VI: $R_1=R_3=H$, $R_2=CH_2COOH$, n=3] (30) as a yellow powder (80 mg, 3%); mp 199°–202° C.

$^1$H NMR (CD$_3$COCD$_3$): δ 10.18 (1H, s, NH), 7.59 (1H, m, ArH), 7.06 (2H, m, ArH), 6.82 (1H, m, ArH), 3.99 (2H, s, CH$_2$CO).

$^{13}$C NMR (CD$_3$COCD$_3$): δ173.30 (s, COOH), 138.82, 128.26, 127.03 (3×s, ArH), 124.76, 120.60, 120.33 (3×d, ArH), 116.97 (s, ArH), 112.16 (d, ArH), 30.89 (t, $\underline{C}$H$_2$CO).

Analysis calculated for C$_{20}$H$_{16}$N$_2$O$_4$S$_3$ requires: C, 54.1; H, 3.6; N, 6.3; S, 21.6%.

Found: C, 54.1; H, 3.8; N, 6.0; S, 21.2%.

The mother liquors from the above aqueous methanol crystallization were evaporated, and the resulting solid was recrystallized from CH$_2$Cl$_2$ to give bis[indolyl-3-acetic acid-(2)]disulfide [[VI: $R_1=R_3=H$, $R_2=CH_2COOH$, n=2] (29) as a yellow solid (0.19 g, 7%); mp 196°–199° C. (Wieland T, Wieburg O, Fischer E, Korlein G, *Annalen* 1954;587:146 record mp 208° C.).

$^1$H NMR (CD$_3$COCD$_3$): δ 10.62 (1H, s, NH), 7.58 (1H, dd, J=8.1, 0.6 Hz, ArH), 7.42 (1H, dt, J=8.2. 0.8 Hz, ArH), 7.23 (1H, ddd, J=8.2, 7.1, 0.9 Hz, ArH), 7.09 (1H, ddd, J=8.0, 7.1, 0.9 Hz, ArH), 3.55 (2H, s, CH$_2$CO).

$^{13}$C NMR (CD$_3$COCD$_3$): δ 172.67 (s, COOH), 138.78, 128.33, 127.86 (3×s, ArH), 124.79, 120.72, 120.56 (3×d, ArH), 117.78 (s, ArH), 112.41 (d, ArH), 30.67 (t, $\underline{C}$H$_2$CO).

Analysis calculated for C$_{20}$H$_{16}$N$_2$O$_4$S$_2$ requires: C, 58.2; H, 3.9; N, 6.8; S, 15.5%.

Found: C, 57.6; H, 4.4; N, 6.6; S, 15.3%.

Methylation of crude 30 with diazomethane as described above, followed by chromatography on silica gel, gave bis[methylindolyl-3-acetate-(2)]trisulfide [VI: $R_1=R_3=H$, $R_2=CH_2COOMe$, n=3] (31) (0.16 g, 47%); mp (CH$_2$Cl$_2$-light petroleum) 130°–132° C. $^1$H NMR (CDCl$_3$): δ 8.76 (1H, s, NH), 7.40 (1H, d, J=8.0 Hz, ArH), 6.99 (1H, ddd, J=8.0, 7.1, 0.9 Hz, ArH), 6.88 (1H, ddd, J=8.2, 7.1, 0.9 Hz, ArH), 6.41 (1H, d, J=8.2 Hz, ArH), 3.93 (2H, s, CH$_2$CO), 3.78 (3H, s, COOCH$_3$).

$^{13}$C NMR (CDCl$_3$): δ172.93 (s, COOCH$_3$), 137.66, 127.02, 125.80 (3×s, ArH), 124.29, 120.06, 118.46 (3×d, ArH), 114.61 (s, ArH), 111.15 (d, ArH), 52.40 (q, COO$\underline{C}$H$_3$), 30.30 (t, $\underline{C}$H$_2$CO).

Analysis calculated for C$_{22}$H$_{20}$N$_2$O$_4$S$_3$ requires: C, 55.9; H, 4.2; N, 5.9; S, 20.3%.

Found: C, 55.6; H, 4.4; N, 5.8; S, 19.9%.

Reduction of 29 with NaBH$_4$/K$_2$CO$_3$/MeOH as above gave 2-(2-thioxo-3-indolinyl)acetic acid [IV: $R_1=R_3=H$; $R_2=CH_2COOH$] (1) (58 mg, 34%); mp (EtOAc/light petroleum) 166°–168° C. (Wieland T, Wieburg O, Fischer E, Korlein G, *Annalen* 1954;587:146 record mp 170°–171° C.).

$^1$H NMR ((CD$_3$)$_2$CO): δ 11.51 (1H, s, NH), 7.39 (1H, d, J=7.9 Hz, ArH), 7.29 (1H, td, J=7.7, 0.8 Hz, ArH), 7.11 (2H, m, ArH), 4.02 (1H, dd, J=3.9, 8.4 Hz, H-3), 3.36 (1H, dd, J=17.2, 3.9 Hz, 3-CH), 2.83 (1H, dd, J=17.2, 8.4 Hz, 3-CH).

Compounds 4 and 28 of Table 1

Methyl 2-(1-methyl-3-indolyl)acetate [II: $R_1=H$; $R_2=CH_2COOMe$; $R_3=Me$] (Guida WC, Mathre DJ, *J. Org. Chem.* 1980;45:3172–3176) (1.18 g) was treated with S$_2$Cl$_2$ (0.25 mL) as above and the product then chromatographed on silica gel. Elution with CH$_2$Cl$_2$/light petroleum (2:1) and CH$_2$Cl$_2$ gave a yellow oil, from which crystallization with EtOAc/light petroleum gave 2,2'-monothiobis[methyl 2-(1-methyl-3-indolyl)acetate] [VI: $R_1=H$, $R_2=CH_2COOMe$; $R_3=Me$; n=1] (0.17 g, 13%); mp 155°–156° C.

$^1$H NMR (CDCl$_3$): 7.54 (1H, d, J=8.0 Hz, ArH), 7.22 (2H, m, ArH), 7.11 (1H, ddd, J=8.0, 4.9, 3.0 Hz, ArH), 3.96 (2H, s, 3-CH$_2$), 3.61 (3H, s, OCH$_3$), 3.48 (3H, s, NCH$_3$).

$^{13}$C NMR (CDCl$_3$): 171.54 (s, COOCH$_3$), 137.80, 126.80, 126.24 (3×s, Ar), 123.03, 119.92, 118.96 (3×d, Ar), 112.95 (s, Ar), 109.37 (d, Ar), 51.85 (q, OCH$_3$), 31.04 (t, 3-CH$_2$), 30.38 (q, NCH$_3$).

Analysis calculated for C$_{24}$H$_{24}$N$_2$O$_4$S requires: C, 66.1; H, 5.5; N, 6.4; S, 7.3%.

Found: C, 65.9; H, 5.6; N, 6.4; S, 7.4%.

Further crystallization of mother liquor fractions from benzene/light petroleum gave 2,2'-dithiobis[methyl 2-(1-methyl-3-indolyl)acetate] [VI: $R_1=H$, $R_2=CH_2COOMe$; $R_3=Me$; n=2] (28) (0.16 g, 13%); mp 130°–132.5° C.

$^1$H NMR (CDCl$_3$): 7.51 (1H, dt, J=8.0, 0.8 Hz, ArH), 7.29 (2H, m, ArH), 7.12 (1H, ddd, J=8.0, 6.0, 2.0 Hz, ArH), 3.57 (3H, s, OCH$_3$), 3.48 (3H, s, NCH$_3$), 3.33 (2H, s, 3-CH$_2$).

$^{13}$C NMR (CDCl$_3$): 171.44 (S, COOCH$_3$), 138.42, 128.13, 126.38 (3×s, Ar), 124.37, 120.13, 120.08 (3×d, Ar), 117.48 (s, Ar), 109.94 (d, Ar), 51.79 (q, OCH$_3$), 30.57 (q, NCH$_3$), 29.96 (t, 3-CH$_2$).

Analysis calculated for C$_{24}$H$_{24}$N$_2$O$_4$S$_2$ requires: C, 61.5; H, 5.1; N, 6.0; S, 13.7%.

Found: C, 61.4; H, 5.2; N, 6.0; S, 13.8%.

The remaining mother liquor was treated successively with NaBH$_4$ and FeCl$_3$ as above, to give an additional 0.36 g (26%) of 28.

Reduction of 28 with NaBH$_4$ as above gave methyl 2-(1-methyl-2-thioxo-3 -indolinyl) acetate [IV: $R_1=H$; $R_2=CH_2COOMe$; $R_3=Me$] (4) (61%); mp (benzene/light petroleum) 68°–70° C.

$^1$H NMR (CDCl$_3$): 7.34 (2H, m, ArH), 7.16 (1H, td, J=7.5, 0.9 Hz, ArH), 7.01 (1H, d, J=7.8 Hz, ArH), 4.15 (1H, dd, J=8.7, 4.1 Hz, H-3), 3.71 (3H, s, OCH$_3$), 3.65 (3H, s, NCH$_3$), 3.40 (1H, dd, J=17.0, 4.1 Hz, 3-CH), 2.83 (1H, dd, J=17.0, 8.7 Hz, 3-CH). $^{13}$C NMR (CDCl$_3$): 204.24 (s, CSNCH$_3$), 171.68 (s, COOCH$_3$), 145.74, 132.95 (2×s, Ar), 128.47, 124.40, 123.96, 109.54 (4×d, Ar), 53.41 (d, C-3), 51.96 (q, OCH$_3$), 38.46 (t, 3-CH$_2$), 31.57 (q, NCH$_3$).

Analysis calculated for Cl$_{12}$H$_{13}$NO$_2$S requires: C, 61.3; H, 5.6; N, 6.0; S, 13.6%.

Found: C, 61.5; H, 5.8; N, 6.2; S, 13.9%.

Compounds 2 and 32 of Table 1

Similar treatment of 1-methyl-3-indolylacetic acid [II: $R_1=H$, $R_2=CH_2COOH$, $R_3=Me$] (Guida WC, Mathre DJ, *J. Org. Chem.* 1980;45:3172; Kaestle KL, Anwer MK, Audhya TK, Goldstein G, *Tetrahedron Lett.*, 1991;32:327) with S$_2$Cl$_2$ followed by chromatography on silica gel gave bis[1-methylindolyl-3-acetic acid-(2)]disulfide [VI: $R_1=R_3=H$, $R_2=CH_2COOH$, n=2] (32) (0.10 g, 8%); mp (Me$_2$CO/light petroleum) 190°–192.5° C. (Wieland T, Wieburg O, Fischer E, Korlein G, *Annalen* 1954;587:146 record mp 190°–191° C.).

$^1$H NMR (CD$_3$COCD$_3$): δ 7.56 (1H, dt, J=8.1, 0.9 Hz, ArH), 7.44 (1H, d, J=8.3 Hz, ArH), 7.31 (1H, ddd, J=8.2, 7.0, 1.2 Hz, ArH), 7.11 (1H, ddd, J=8.0, 7.0, 0.9 Hz, ArH), 3.65 (3H, s, NCH$_3$), 3.23 (2H, s, CH$_2$CO).

$^{13}$C NMR (CD$_3$COCD$_3$): δ 172.21 (s, COOH), 139.52, 128.56, 127.45 (3×s, ArH), 125.21, 120.91, 120.74 (3×d, ArH), 119.38 (s, ArH), 111.04 (d, ArH), 30.81 (t, CH$_2$ CO), 30.31 (q, NCH$_3$).

Analysis calculated for C$_{22}$H$_{20}$N$_2$O$_2$S$_2$ requires: C, 60.0; H, 4.6; N, 6.4; S, 14.5%.

Found: C, 59.4; H, 4.9; N, 6.4; S, 15.0%.

Reduction of 32 with NaBH$_4$/K$_2$CO$_3$/MeOH as above gave 2-(1-methyl-2-thioxo-3-indolinyl)acetic acid [IV: R$_1$=H; R$_2$=CH$_2$COOH; R$_3$=Me] (2) (62 mg, 60%); mp (CH$_2$Cl$_2$/light petroleum) 150°–153° C. (Wieland T, Wieburg O, Fischer E, Korlein G, *Annalen* 1954;587:146 record mp 149°–150° C.).

$^1$H NMR (CDCl$_3$): δ 7.37 (2H, m, ArH), 7.18 (1H, t, J=7.5 Hz, ArH), 7.02 (1H, d, J=7.8 Hz, ArH), 4.14 (1H, dd, J=8.6, 3.9 Hz, H-3), 3.65 (3H, s, NCH$_3$), 3.48 (1H, dd, J=17.5, 4.0 Hz, 3-CH), 2.86 (1H, dd, J=17.5, 8.7 Hz, 3-CH). $^{13}$C NMR (CDCl$_3$): δ 203.88 (s, CSNCH$_3$), 176.31 (s, COOH), 145.67, 132.64 (2×s, Ar), 128.57, 124.52, 124.00, 109.59 (4×d, Ar), 53.07 (d, C-3), 38.33 (t, 3-CH$_2$), 31.59 (q, NCH$_3$).

Compounds 6 and 34 of Table 1

N-Benzyl 3-indolylacetamide [II: R$_1$=R$_3$=H, R$_2$=CH$_2$CONHCH$_2$Ph] (Katritzky AR, *J. Chem. Soc.* 1955:2581) (1.48 g) was treated with S$_2$Cl$_2$ as above, and the product mixture was treated with NaBH$_4$ (ca. 0.7 g) in EtOH (10 mL) for 30 minutes at 20° C., then diluted with water (100 mL), acidified with dilute HCl and extracted in CH$_2$Cl$_2$(2×100 mL) and EtOAc (100 mL). A sample from evaporation of the combined extracts was crystallized from EtOAc-light petroleum to give N-benzyl (2-thioxo-3-indolinyl) acetamide [IV: R$_1$=R$_3$=H, R$_2$=CH$_2$CONHCH$_2$Ph] (6) (0.12 g, 7%); mp 193°–195° C.

$^1$H NMR (CD$_3$SOCD$_3$): δ 12.64 (1H, s, NH), 8.50 (1H, t, J=5.9 Hz, NHCH$_2$), 7.32 (2H, t, J=7.3 Hz, ArH), 7.25 (3H, m, ArH), 7.11 (1H, d, J=7.3 Hz, ArH), 7.00 (1H, t, J=8.0 Hz, ArH), 6.53 (1H, m, ArH), 4.34, 4.28 (2×1H, 2×dd, J=15.3, 5.9 Hz, NHCH$_2$), 4.04 (1H, dd, J=9.5, 4.2 Hz, H-3), 3.10 (1H, dd, J=15.3, 4.2 Hz, CH$_2$CO), 2.47 (1H, dd, J=15.3, 9.5 Hz, CH$_2$CO).

$^{13}$C NMR (CD$_3$SOCD$_3$): δ 206.62 (s, CSNH), 169.41 (s, CONH), 143.97, 139.24, 134.36 (3×s, ArH), 128.22 (2×d, ArH), 127.95 (d, ArH), 127.36 (2×d, ArH), 126.77, 123.91, 123.09, 110.10 (4×d, ArH), 53.94 (d, C-3), 42.27, t, NHCH$_2$), 39.19 (t, CH$_2$CO).

Analysis calculated for C$_{17}$H$_{10}$N$_2$OS requires: C, 68.9; H, 5.4; N, 9.5; S, 10.8%.

Found: C, 68.8; H, 5.8; N, 9.5; S, 10.7%.

The remaining product mixture (1.60 g) was treated with FeCl$_3$ as above then chromatographed on silica gel to give a yellow oil (1.40 g). Crystallization from EtOAc/light petroleum then EtOAc gave 2,2'-dithiobis[N-benzyl 2-(3-indolyl)acetamide] [VI: R$_1$=R$_3$=H; R$_2$=CH$_2$CONHCH$_2$Ph] (34) (0.36 g, 22%); mp 200.5°–203.5° C.

$^1$H NMR (CD$_3$)$_2$SO): δ 11.57 (1H, s, CSNH), 8.45 (1H, t, J=5.9 Hz, NHCH$_2$), 7.53 (1H, d, J=8.0 Hz, ArH), 7.30 (1H, d, J=8.2 Hz, ArH), 7.29–7.14 (6H, m, ArH), 7.01 (1H, t, J=7.5 Hz, ArH), 4.19 (2H, d, J=5.9 Hz, NHCH$_2$), 3.44 (2H, s, 3-CH$_2$).

$^{13}$C NMR (CD$_3$)$_2$SO): δ170.08 (9s, CONH), 139.36, 137.42 (2×s, Ar), 128.12, 127.13 (4×d, Ar), 127.12, 126.82 (2×s, Ar), 126.63, 123.41, 119.67, 119.09 (4×d, Ar), 116.83 (s, Ar), 111.43 (d, Ar), 42.25 (t, NHCH$_2$), 31.73 (t, 3-CH$_2$).

Analysis calculated for C$_{34}$H$_{30}$N$_4$O$_2$S$_2$ requires: C, 62.6; H, 6.1; N, 5.6; S, 12.9%.

Found: C, 62.7; H, 6.3; N, 5.7; S, 13.0%.

Compounds 13 and 47 of Table 1

Esterification of 3-(3-indolyl)propanoic acid [II: R$_1$=R$_2$=H, R$_3$=(CH$_2$)$_2$COOH] (1.50 g) with diazomethane as above gave methyl 3-(3-indolyl)propanoate [II: R$_1$=R$_2$=H, R$_3$=(CH$_2$)$_2$COOMe] (1.62 g, 100%) as a light brown oil. This was stirred with benzylamine (5 mL) at 140° C. for 4 hours (Katritzky AR, *J. Chem. Soc.* 1955:2581–2586) to give, after workup and chromatography on silica, gel, N-benzyl 3-(3-indolyl)propanamide [II: R$_1$=R$_2$=H; R$_3$=(CH$_2$)$_2$CONHCH$_2$Ph] (1.81 g, 88%); mp (EtOAc/light petroleum) 125°–126.5° C.

$^1$H NMR (CDCl$_3$): 8.05 (1H, s, NH), 7.59 (1H, d, J=7.8 Hz, ArH), 7.34 (1H, d, J=7.9 Hz, ArH), 7.24 (3H, m, ArH), 7.18 (1H, dd, J=7.9, 7.2 Hz, ArH), 7.10 (1H, dd, J=7.9, 7.2 Hz, ArH), 7.07 (2H, m, ArH), 6.93 (1H, d, J=1.9 Hz, H-2), 5.64 (1H, t, J=5.7 Hz, NHCH$_2$), 4.35 (2H, d, J=5.7 Hz, 2H, NHCH$_2$), 3.13, 2.59 (2×2H, 2×t, J=7.3 Hz, 3-CH$_2$CH$_2$).

$^{13}$C NMR (CDCl$_3$): 172.54 (s, CONH), 138.20, 136.35 (2×s, Ar), 128.58, 127.66 (4×d, Ar), 127.35 (d, Ar), 127.08 (s, Ar), 122.04, 121.88, 119.35, 118.68 (4×d, Ar), 113.79 (s, Ar), 111.21 (d, Ar), 43.51 (t, NHCH$_2$), 37.42 (t, CH$_2$CO), 21.38 (t, 3-CH$_2$).

Analysis calculated for C$_{18}$H$_{18}$N$_2$O requires: C, 77.7; H, 6.6; N, 10.1%.

Found: C; 77.4; H, 6.5; N, 10.3%.

The above amide [II: R$_1$=R$_2$=H, R$_3$=(CH$_2$)$_2$CONHCH$_2$Ph] (1.74 g) was treated with S$_2$Cl$_2$, and the product mixture was treated successively with NaBH$_4$ and FeCl$_3$ as above, then chromatographed on silica gel. Elution with EtOAc/light petroleum (2:1) gave 2,2'-monothiobis[N-benzyl 3-(3-indolyl)propanamide] [VI: R$_1$=R$_2$=H; R$_3$=(CH$_2$)$_2$CONHCH$_2$Ph; n=1] (0.10 g, 6%); mp (CH$_2$Cl$_2$/light petroleum) 218°–219° C. $^1$H NMR (CD$_3$)$_2$SO): 11.01 (1H, s, CSNH), 8.38 (1H, t, J=5.7 Hz, NHCH$_2$), 7.56 (1H, d, J=7.9 Hz, ArH), 7.26–7.03 (7H, 2×m, ArH), 6.97 (1H, t, J=7.5 Hz, ArH), 4.26 (2H, d, J=5.5 Hz, NHCH$_2$), 3.22, 2.55 (2×2H, 2×t, J=7.6 Hz, 3-CH$_2$CH$_2$).

Analysis calculated for C$_{36}$H$_{34}$N$_4$O$_2$S.H$_2$O requires: C, 72.6; H, 5.9; N, 9.4; S, 5.4%.

Found: C, 72.7; H, 5.9; N, 9.6; S, 5.7%.

Further elution with EtOAc/light petroleum (1:1) gave a yellow oil (1.10 g) from which crystallization with benzene/ CH$_2$Cl$_2$/light petroleum gave 2,2'-dithiobis[N-benzyl 3-(3-indolyl)propanamide] [VI=R$_1$=R$_2$=H, R$_3$=(CH$_2$)$_2$CONHCH$_2$Ph; n=2] (47) (0.73 g, 38%); mp (CH$_2$Cl$_2$/light petroleum) 141°–144° C.

$^1$H NMR (CDCl$_3$): 8.47 (1H, s, CSNH), 7.51 (1H, d, J=7.9 Hz, ArH), 7.27–7.20 (4H, m, ArH), 7.13 (1H, ddd, J=8.2, 7.1, 1.1 Hz, ArH), 7.00 (3H, m, ArH), 5.01 (1H, t, J=5.7 Hz, NHCH$_2$), 4.16 (2H, d, t, J=5.7 Hz, NHCH$_2$), 2.88, 1.87 (2×2H, 2×t, J=7.7 Hz, 3-CH$_2$CH$_2$).

$^{13}$C NMR (CDCl$_3$): 171.93 (s, CONH), 138.30, 137.27 (2×s, Ar), 128.51, 127.78 (4×d, Ar), 127.30 (d, Ar), 127.07, 125.66 (2×s, Ar), 124.43 (d, Ar), 123.93 (s, Ar), 120.18, 119.94, 111.23 (3×d, Ar), 43.39 (t, NHCH$_2$), 37.09 (t, CH$_2$CO), 20.56 (t, 3-CH$_2$).

Analysis calculated for C$_{36}$H$_{34}$N$_4$O$_2$S$_2$ requires: C, 69.9; H, 5.5; N, 9.1; S, 10.3%.

Found: C, 69.7; H, 5.6; N, 9.1; S, 10.5%.

Reduction of 47 with $NaBH_4$ as above gave a quantitative yield of N-benzyl 3-(2-thioxo- 3-indolinyl)propanamide [IV: $R_1=R_3=H$, $R_2=(CH_2)_2CONHCH_2Ph$] (13); mp ($CH_2Cl_2$) 149.5°–151° C.

$^1$H NMR (($CD_3)_2CO$): 11.46 (1H, s, CSNH), 7.45 (1H, t, J=6.0 Hz, $NHCH_2$), 7.42 (1H, d, J=7.9 Hz, ArH), 7.32–7.16 (6H, m, ArH), 7.13 (1H, td, J=7.5, 0.9 Hz, ArH), 7.09 (1H, d, J=7.8 Hz, ArH), 4.37, 4.33 (2×1H, 2×dd, J=15.0, 6.0 Hz, $NHCH_2$), 3.87 (1H, t, J=5.4 Hz, H-3), 2.56, 2.34, 2.04 (4H, 3×m, 3-$CH_2CH_2$). $^{13}$C NMR (($CD_3)_2CO$): 208.79 (s, CSNH), 172.23 (s, CONH), 145.20, 140.69, 134.88 (3×s, Ar), 129.14 (d, 2e, Ar), 128.93 (d, Ar), 128.33 (d, 2e, Ar), 127.62, 125.27, 124.22, 110.78 (4×d, Ar), 57.57 (d, C-3), 43.46 (t, $NHCH_2$), 31.87, 30.09 (2×t, 3-$CH_2CH_2$).

Analysis calculated for $C_{18}H_{18}N_2OS$ requires: C, 67.7; H, 6.0; N, 8.8; S, 10.0%.

Found: C, 67.3; H, 5.9; N, 8.9; S, 10.5%.

Compound 69 of Table 1

3-(3-Indolyl)butanoic acid [II: $R_1=R_3=H$, $R_2=(CH_2)_3COOH$] (1.10 g) was esterified with excess ethereal diazomethane to give methyl 4-(3-indolyl)butanoate [II: $R_1=R_3=H$, $R_2=(CH_2)_3COOMe$] (1.17 g, 100% ); mp 73°–75° C. (Jackson RW, Manske RH, J. Am. Chem. Soc. 1930;52:5029 record mp 73°–74° C.). This was stirred with benzylamine (5 mL) at 150° C. for 4 hours to give, after chromatography on silica gel (eluting with 1:4 EtOAc: $CH_2Cl_2$), N-benzyl-4-(3-indolyl)butanamide [II: $R_1=R_3H$, $R_2=(CH_2)_3CONHCH_2Ph$] (1.43 g, 90%); mp ($CH_2Cl_2$/light petroleum) 123°–124° C.

$^1$H NMR ($CDCl_3$): δ 8.05 (1H, br s, NH), 7.58 (1H, d, J=7.9 Hz, ArH), 7.37–7.23 (6H, m, ArH), 7.18 (1H, ddd, J=8.1, 7.1, 1.0 Hz, ArH), 7.10 (1H, ddd, J=8.0, 7.0, 0.9 Hz, ArH), 6.95 (1H, d, J=1.7 Hz, H-2), 5.68 (1H, br t, J=5.7 Hz, $NHCH_2$), 4.42 (1H, d, J=5.7 Hz, $NHCH_2$), 2.82 (2H, t, J=7.3 Hz, 3-$CH_2$), 2.27 (2H, t, J=7.5 Hz, $CH_2CO$), 2.09 (2H, pentet, J=7.3 Hz, 3-$CHCH_2$).

$^{13}$C NMR ($CDCl_3$): δ 172.79 (s, CONH), 138,35, 136.33 (2×s, Ar), 128.69, 127.84 (2d, 2×2C, Ar), 127.49 (d, Ar), 127.46 (s, Ar), 121.91, 121.50, 119.83, 118.3 (4×d, Ar), 115.57 (s, Ar), 111.10 (d, Ar), 43.58 (t, $NCH_2$), 36.15 (t, $CH_2CO$), 26.06, 24.48 (2×t, 3-$CH_2CH_2$).

Analysis calculated for $C_{19}H_{20}N_2O$ requires: C, 78.1; H, 6.9; N, 9.6%.

Found: C, 77.8; H, 6.8; N, 9.7%.

The above amide (1.38 g) was treated with $S_2Cl_2$ as above, then the product mixture obtained after workup was treated with $NaBH_4$ as described above. The resulting oil was oxidized with 35% $H_2O_2$ (0.50 mL) in MeOH (10 mL) at 20° C. for 20 minutes. Dilution with water, extraction in $CH_2Cl_2$, and evaporation gave an oil which was chromatographed on silica gel. Elution with EtOAc/light petroleum (3:5) gave 2,2'- thiobis[N-benzyl-4-(3-indolyl)butanamide] [VI: n=1; $R_1=R_3=H$, $R_2=(CH_2)_3CONHCH_2Ph$] (0.14 g, 10%); mp ($CH_2Cl_2$/light petroleum) 105.5°–108° C. (dec).

$^1$H NMR ($CDCl_3$): δ 10.25 (1H, s, NH), 7.49 (1H, d, J=8.0 Hz, ArH), 7.35–7.25 (6H, m, ArH), 7.11 (1H, ddd, J=8.2, 7.0, 1.2 Hz, ArH), 7.01 (1H, ddd, J=7.9, 7.0, 0.9 Hz, ArH), 5.75 (1H, t, J=5.6 Hz, $NHCH_2$), 4.38 (2H, d, J=5.7 Hz, $NHCH_2$), 3.07 (2H, t, J=7.8 Hz, 3-$CH_2$), 2.38 (2H, t, J=6.3 Hz, $CH_2CO$), 2.13 (2H, m, 3-$CH_2CH_2$).

$^{13}$C NMR ($CDCl_3$): δ 173.49 (s, CONH), 138.12, 136.97 (2×s, Ar), 128.73, 127.93 (2×d, 2×2C, Ar), 127.56 (d, Ar), 127.48, 124.00 (2×s, Ar), 122.53 (d, Ar), 119.79 (s, Ar), 119.07, 118.60, 111.52 (3×d, Ar), 43.79 (t, $NCH_2$), 35.66 (t, $CH_2CO$), 25.77, 24.38 (2×t, 3-$CH_2CH_2$).

Analysis calculated for $C_{38}H_{38}N_4O_2S$ requires: C, 74.3; H, 6.2; N, 9.1; S, 5.2%.

Found: C, 74.2; H, 6.1; N, 9.1; S, 5.0%.

Elution with EtOAc: light petroleum (1:1) gave 2,2'-dithiobis[N-benzyl-4-(3-indolyl)butanamide] (69) [VI: n=2; $R_1=R_3=H$, $R_2=(CH_2)_3CONHCH_2Ph$] (0.55 g, 36%); mp ($CH_2Cl_2$/benzene) 98.5°–101° C. (dec).

$^1$H NMR (($CD_3)_2CO$): δ 10.48 (1H, s, NH), 7.58 (1H, d, J=8.0 Hz, ArH), 7.38 (1H, d, J=8.2 Hz, ArH), 7.37 (1H, m, $NHCH_2$), 7.30–7.15 (6H, m, ArH), 7.03 (1H, ddd, J=7.9, 7.3, 0.7 Hz, ArH), 4.30 (2H, d, J=6.0 Hz, $NHCH_2$), 2.67 (2H, t, J=7.6 Hz, 3-$CH_2$), 2.09 (2H, t, J=7.5 Hz, $CH_2CO$), 1.84 (2H, pentet, J=7.5 Hz, 3-$CH_2CH_2$).

$^{13}$C NMR (($CD_3)_2CO$): δ 172.93 (s, CONH), 140.80, 138.83 (2×s, Ar), 129.12 (d, 2C, Ar), 128.46 (s, Ar), 128.35 (d, 2C, Ar), 127.58 (d, Ar), 126.71, 124.54, (2×s, Ar), 124.46, 120.60, 120.13, 112.36 (4×d, Ar), 43.43 (t, $NCH_2$), 36.34 (t, $CH_2CO$), 27.75, 24.95 (2×t, 3-$CH_2CH_2$).

Analysis calculated for $C_{38}H_{38}N_4O_2S_2$ requires: C, 70.6; H, 5.9; N,8.7; S, 9.9%.

Found: C, 70.4; H, 6.0; N, 8.8; S, 9.8%.

Compound 35 of Table 1

3-Indolylacetonitrile [II: $R_1=R_3=H$, $R_2=CH_2CN$] (1.00 g) was treated with $S_2Cl_2$ as above, then the product mixture obtained after workup was treated with $NaBH_4$ as described above. Crystallization of the resulting oil from $CH_2Cl_2$ gave 2,2'-thiobis[3-indolylacetonitrile] [VI: n=1; $R_1=R_3=H$, $R_2=CH_2CN$] (0.11 g, 10%); mp 237°–240° C. (Piotrowska H, Serafin B, Wejroch-Matacz K, Rocz. Chem. 1975;49:635 record mp 242°–244° C.).

1H NMR (($CD_3)_2SO$): δ 11.61 (1H, s, NH), 7.65 (1H, d, J=8.0 Hz, ArH), 7.37 (1H, d, J=8.2 Hz, ArH), 7.20 (1H, ddd, J=8.0, 7.1, 0.9 Hz, ArH), 7.10 (1H, ddd, J=8.0, 7.1, 0.8 Hz, ArH), 4.26 (2H, s, 3-$CH_2$).

$^{13}$C NMR: δ 136.52, 125.99, 123.92 (3×s, Ar), 123.25, 119.78 (2×d, Ar), 118.67 (s, Ar), 118.48, 111.60 (2×d, Ar), 108.78 (s, 3-$CH_2CN$), 12.98 (t, 3-$CH_2$).

Analysis calculated for $C_{20}H_{14}N_4S.0.5H_2O$ requires: C, 68.4; H, 4.3; N, 16.0; S, 9.2%.

Found: C, 68.4; H,4.2; N, 16.2; S, 9.1%.

The mother liquor was oxidized with $H_2O_2$ in MeOH as above, then the resulting solid was chromatographed on silica gel, eluting with $CH_2Cl_2$, to give 2,2'-dithiobis[3-indolylacetonitrile] (35) [VI: n=2; $R_1=R_3=H$, $R_2=CH_2CN$] (0.62 g, 52%); mp ($CH_2Cl_2$/MeOH) 168.5°–169.5° C. (Piotrowska H, Serafin B, Wejroch-Matacz K, Rocz. Chem. 1975;49:635 record mp 169°–170° C.).

$^1$H NMR (($CD_3)_2SO$): δ 11.90 (1H, s, NH), 7.67 (1H, d, J=8.1 Hz, ArH), 7.42 (1H, d, J=8.2 Hz, ArH), 7.28 (1H, ddd, J=8.1, 7.1, 1.0 Hz, ArH), 7.14, (1H, ddd, J=8.0, 7.1, 0.8 Hz, ArH), 3.69 (2H, s, 3-$CH_2$).

$^{13}$C NMR: δ 137.28, 126.36, 125.82 (3×s, Ar), 124.26, 120.03, 119.11, (3×d, Ar), 118.10 (s, Ar), 112.03 (d, Ar), 111.66 (s, 3-$CH_2CN$), 12.56 (t, 3-$CH_2$).

Analysis calculated for $C_{20}H_{14}N_4S_2$ requires: C, 64.2; H, 3.7; N, 15.0; S, 17.1%.

Found: C, 64.1; H, 3.9; N, 15.1; S, 17.0%.

Compound 48 of Table 1

3-Indolylpropionitrile [II: $R_1=R_3=H$, $R_2=(CH_2)_2CN$] (Reppe W, Ufer H, German patent 698,273) (1.00 g) was treated with $S_2Cl_2$ as above, then the product mixture obtained after workup was treated successively with $NaBH_4$, then $H_2O_2$ as described above. The resulting oil was chromatographed on silica gel, eluting with $CH_2Cl_2$, to give 2,2'-thiobis[3-indolylpropionitrile] [VI: n=1; $R_1=R_3=H$, $R_2=(CH_2)_2CN$] (43 mg, 4%); mp ($CH_2Cl_2$/light petroleum) 204.5°–207° C. (Piotrowska H, Serafin B, Wejroch-Matacz K, *Rocz. Chem.* 1975;49:635 record mp 198°–200° C.).

$^1$H NMR (($CD_3$)$_2$SO): δ 11.25 (1H, s, NH), 7.61 (1H, d, J=7.9 Hz, ArH), 7.31 (1H, d, J=7.8 Hz, ArH), 7.13 (1H, dd, J=8.0, 7.1 Hz, ArH), 7.02 (1H, dd, J=7.9, 7.1 Hz, ArH), 3.23, 2.71 (2×2H, 2×t, J=7.2 Hz, 3-$CH_2CH_2$).

$^{13}$C NMR: δ 136.65, 126.58, 124.04 (3×s, Ar), 122.65 (d, Ar), 120.36 (s, CN), 119.25, 118.79 (2×d, Ar), 116.32 (s, Ar), 111.31 (d, Ar), 20.60, 17.98 (2×t, 3-$CH_2CH_2$).

Further elution with $CH_2Cl_2$ gave 2,2'-dithiobis[3-indolylpropionitrile] (48) [VI: n=2; $R_1=R_3=H$, $R_2=(CH_2)_2CN$] (0.82 g, 69%); mp ($CH_2Cl_2$) 167°–169° C. (Piotrowska H, Serafin B, Wejroch-Matacz K, *Rocz. Chem.* 1975;49:635 record mp 165°–167° C.).

$^1$H NMR (($CD_3$)$_2$SO): δ 11.71 (1H, s, NH), 7.59 (1H, d, J=8.0 Hz, ArH), 7.38 (1H, dt, J=8.2, 0.8 Hz, ArH), 7.22 (1H, ddd, J=8.2, 7.1, 1.1 Hz, ArH), 7.04 (1H, ddd, J=8.0, 7.1, 0.9 Hz, ArH), 2.57, 2.37 (2×2H, 2×t, J=7.2 Hz, 3-$CH_2CH_2$).

$^{13}$C NMR: δ 137.48, 126.16, 125.59 (3×s, Ar), 123.88 (d, Ar), 120.39, 119.87 (2×s, Ar, CN), 119.45, 111.64 (2×d, Ar), 19.80, 17.97 (2×t, 3-$CH_2CH_2$).

Compound 49 of Table 1

A solution of gramine (8.4 g) and methyl nitroacetate (11.5 g) in xylene (50 mL) was stirred under nitrogen at 90°–100° C. for 5 hours (method of Lyttle DA, Weisblat DI, *J. Am. Chem. Soc.* 1947;69:2118). Evaporation gave an oil which was chromatographed on silica gel, eluting with $CH_2Cl_2$:light petroleum (1:1), to give 3-(2-nitroethyl)indole [II: $R_1=R_3=H$, $R_2=(CH_2)_2NO_2$] (4.44 g, 48%); mp (benzene/light petroleum) 57°–59.5° C. (Somei M, Karasawa Y, Kaneko C, *Heterocycles* 1981;16:941 record mp (MeOH) 54°–55° C.).

$^1$H NMR (CDCl$_3$): δ 8.05 (1H, br s, NH), 7.57 (1H, d, J=7.9 Hz, ArH), 7.37 (1H, dt, J=8.2, 0.8 Hz, ArH), 7.22 (1H, ddd, J=8.1, 7.0, 1.1 Hz, ArH), 7.16 (1H, ddd, J=7.9, 7.1, 0.9 Hz, ArH), 7.04 (1H, d, J=2.4 Hz, H-2), 4.66 (2H, t, J=7.3 Hz, 3-$CH_2CH_2$), 3.49 (2H, td, J=7.3, 0.6 Hz, 3-$CH_2$).

$^{13}$C NMR: δ 136.25, 126.67 (2×s, Ar), 122.56, 122.54, 119.91, 118.13, 111.45 (5×d, Ar), 110.05 (s, Ar), 75.73 (n, 3-$CH_2CH_2$), 23.63 (t, 3-$CH_2$).

The above nitroethyl compound (1.50 g) was treated with $S_2Cl_2$ as above, then the product mixture obtained after workup was treated successively with $NaBH_4$ then $H_2O_2$ as described above. The resulting oil was chromatographed on silica gel, eluting with $CH_2Cl_2$: light petroleum (4:3), to give 2,2'-thiobis[3-(2-nitroethyl)indole] [VI; n=1; $R_1=R_3H$, $R_2=(CH_2)_2NO_2$] (49 mg, 3%); mp ($CH_2Cl_2$/light petroleum) 134.5°–136° C.

$^1$H NMR (($CD_3$)$_2$SO): δ 11.26 (1H, s, NH), 7.59 (1H, d, J=7.9 Hz, ArH), 7.30 (1H, d, J=8.1 Hz, ArH), 7.13 (1H, ddd, J=8.1, 7.1, 0.9 Hz, ArH), 7.02 (1H, ddd, J=7.9, 7.1, 0.8 Hz, ArH), 4.71 (2H, t, J=7.3 Hz, 3-$CH_2CH_2$), 3.57 (2H, t, J=7.3 Hz, 3-$CH_2$).

$^{13}$C NMR: δ 136.59, 126.60, 124.20 (3×s, Ar), 122.56, 119.27, 118.43 (3×d, Ar), 113.37 (s, Ar), 111.24 (d, Ar), 75.11 (t, 3-$CH_2CH_2$, 22.69 (t, 3-$CH_2$).

Analysis calculated for $C_{20}H_{18}N_4O_4S$ requires: C, 58.5; H, 4.4; N, 13.7; S, 7.8%.

Found: C, 58.3; H, 4.7; N, 13.6; S, 8.0%.

Further slution as above gave 2,2'-dithiobis[3-(2-nitroethyl)indole] (49) [VI: n=2; $R_1=R_3=H$, $R_2=(CH_2)_2NO_2$] (1.28 g, 73%); mp ($CH_2Cl_2$/light petroleum) 153°–154° C.

$^1$H NMR (($CD_3$)$_2$SO): δ 11.68 (1H, s, NH), 7.57 (1H, d, J=8.0 Hz, ArH), 7.36 (1H, d, J=8.2 Hz, ArH), 7.21 (1H, ddd, J=8.1, 7.1, 0.9 Hz, ArH), 7.04 (1H, ddd, J=7.9, 7.1, 0.8 Hz, ArH), 4.41 (2H, t, J=7.2 Hz, 3-$CH_2CH_2$), 2.97 (2H, t, J=7.2 Hz, 3-$CH_2$).

$^{13}$C NMR: δ 137.37, 126.18, 125.95 (3×s, Ar), 123.76, 119.50, 119.08 (3×d, Ar), 117.39 (s, Ar), 111.59 (d, Ar), 75.05 (t, 3-$CH_2CH_2$), 22.06 (t, 3-$CH_2$).

Analysis calculated for $C_{20}H_{18}N_4O_4S_2 \cdot 0.5H_2O$ requires: C, 53.2; H, 4.2; N, 12.4; S, 14.2%.

Found: C, 53.4; H, 4.2; N, 12.6; S, 14.0%.

Compounds 14 and 50 of Table 1

DEPC (98%, 1.28 mL) was added to a stirred solution of 3-(3-indolyl)propanoic acid [II: $R_1=R_3=H$, $R_2=(CH_2)_2COOH$] (1.30 g) and triethylamine (1.15 mL) in THF (15 mL) at 0° C. After 5 minutes the solution was saturated with ammonia gas, then the mixture was stirred at 20° C. for 16 hours. The reaction was then quenched with water and extracted with EtOAc. Evaporation gave a solid, which was purified by chromatography on silica gel, eluting with EtOAc, to give 3-(3-indolyl)propanamide [II: $R_1=R_3=H$, $R_2=(CH_2)_2CONH_2$] (1.09 g, 84%); mp (MeOH/water) 134°–136° C. (Crosby DG, Boyd JB, Johnson HE, *J. Org. Chem.* 1960;25:1826 record mp 131.5°–133° C.).

$^1$H NMR (($CD_3$)$_2$CO): δ 9.95 (1H, s, NH), 7.58 (1H, dt, J=8.2, 0.7 Hz, ArH), 7.36 (1H, dt, J=8.1, 0.8 Hz, ArH), 7.13 (1H, m, H-2), 7.08 (1H, ddd, J=8.1, 7.0, 1.1 Hz, ArH), 7.00 (1H, ddd, J=8.0, 7.0, 1.0 Hz, ArH), 6.75, 6.12 (2×H, 2×br s, $CONH_2$), 3.04 (2H, m, 3-$CH_2$), 2.05 (2H, m, 3-$CH_2CH_2$).

$^{13}$C NMR: δ 174.87 (s, $CONH_2$), 137.75, 128.44 (2×s, Ar), 122.80, 122.02 (2×d, Ar), 119.30 (2×d, Ar), 115.67 (s, Ar), 112.08 (d, Ar), 37.05 (t, 3-$CH_2CH_2$), 21.87 (t, 3-$CH_2$).

The above amide (1.03 g) was treated with $S_2Cl_2$ as above, then the product mixture obtained after workup was treated successively with $NaBH_4$ then $H_2O_2$ as described above. The resulting oil was chromatographed on silica gel, eluting with EtOAc:light petroleum (3:1), to give firstly 2,2'-thiobis[3-(3-indolyl)propanamide] [VI: n=1; $R_1=R_3=H$, $R_2=(CH_2)_2CONH_2$] (0.16 g, 14%); mp (EtOAc/light petroleum) 196.5°–197.5° C.

$^1$H NMR (($CD_3$)$_2$SO): δ 11.02 (1H, s, NH), 7.55 (1H, d, J=8.0 Hz, ArH), 7.38 (1H, s, NH), 7.26 (1H, d, J=8.1 Hz, ArH), 7.08 (1H, ddd, J=8.0, 7.1, 0.8 Hz, ArH), 6.98 (1H, dd, J=7.8, 7.1 Hz, ArH), 6.85 (1H, s, NH), 3.16, 2.46 (2×2H, 2×t, J=7.7 Hz, 3-$CH_2CH_2$.

$^{13}$C NMR: δ 174.26 (s, $CONH_2$), 136.77, 126.82, 123.29 (3×s, Ar), 122.09, 118.82, 118.68 (3×d, Ar), 118.43 (s, Ar), 111.12 (d, Ar), 35.94 (t, 3-$CH_2CH_2$), 20.58 (t, 3-$CH_2$).

Analysis calculated for $C_{22}H_{22}N_4O_2S$ requires: C, 65.0; H, 5.4; N, 13.8; S, 7.9%.

Found: C, 64.8; H, 5.7; N, 13.6; S, 7.7%.

Further elution with EtOAc and EtOAc:EtOH (9:1) gave 2,2'-dithiobis[3-(3-indolyl)propanamide] (50) [VI: n=2; $R_1=R_3=H$, $R_2=(CH_2)_2CONH_2$] (0.90 g, 75%) as a yellow oil. A subsample crystallized from MeOH/dilute HCl as a solid which decomposed above 101° C.

$^1$H NMR (CD$_3$)$_2$SO): δ 11.37 (1H, s, NH), 7.55 (1H, d, J=8.0 Hz, ArH), 7.32 (1H, d, J=8.2 Hz, ArH), 7.16 (1H, t,

J=7.6 Hz, ArH), 7.00 (1H, t, J=7.5 Hz, ArH), 6.94, 6.64 (2×1H, 2×s, CONH$_2$), 2.72, 2.14 (2×2H, 2×m, 3-CH$_2$CH$_2$).

$^{13}$C NMR: δ 173.48 (s, CONH$_2$), 137.42, 126.58, 125.09 (3×s, Ar), 123.29 (d, Ar), 122.65 (s, Ar), 119.53, 118.91, 111.46 (3×d, Ar), 36.48 (t, 3-CH$_2$CH$_2$), 20.26 (t, 3-CH$_2$).

Analysis calculated for C$_{22}$H$_{22}$N$_4$O$_2$S$_2$.0.5H$_2$O requires: C, 59.1; H, 5.2; N, 12.5; S, 14.3%.

Found: C, 59.1; H, 5.4; N, 12.2; S, 14.0%.

Reduction of (50) with NaBH$_4$ as above gave a quantitative yield of 3-(2-thioxo-3-indolinyl)propanamide (14) [IV: R$_1$=R$_2$=H, R$_3$=(CH$_2$)$_2$CONH$_2$]; mp (EtOAc) 160°–163° C.

$^1$H NMR ((CD$_3$)$_2$SO): δ 12.63 (1H, s, NH), 7.38 (1H, d, J=7.3 Hz, ArH), 7.27 (1H, t, J=7.6 Hz, ArH), 7.22 (1H, s, NH), 7.12 (1H, t, J=7.5 Hz, ArH), 7.00 (1H, d, J=7.7 Hz, ArH), 6.70 (1H, s, NH), 3.84 (1H, t, J=5.4 Hz, H-3), 2.38 (1H, m, 3-CH$_2$CH$_2$), 2.16–1.96 (2H, m, 3-CH$_2$CH$_2$), 1.77 (1H, ddd, J=14.6, 10.3, 4.2 Hz, 3-CH$_2$CH$_2$).

$^{13}$C NMR: δ 206.83 (s, CSNH), 173.37 (CONH$_2$), 144.11, 133.81 (2×s, Ar), 127.95, 124.11, 123.21, 110.03 (4×d, Ar), 56.35 (d, C-3), 30.12, 28.32 (2×t, 3-CH$_2$CH$_2$).

Analysis calculated for C$_{11}$H$_{12}$N$_2$OS requires: C, 60.0; H, 5.5; N, 12.7; S, 14.6%.

Found: C, 60.0; H, 5.5; N, 12.8; S, 14.3%.

Compound 51 of Table 1

DEPC (98%, 1.08 mL) was added to a stirred solution of 3-(3-indolyl) propanoic acid [II: R$_1$=R$_3$=H, R$_2$=(CH$_2$)$_2$COOH] (1.10 g), triethylamine (1.94 mL) and methylamine hydrochloride (0.47 g) in THF (20 mL) at 0° C., then the mixture was stirred at 20° C. for 20 hours. The reaction was then quenched with water and extracted with EtOAc. Evaporation gave an oil which was purified by chromatography on silica gel. Elution with EtOAc gave firstly foreruns, then N-methyl-3-(3-indolyl)propanamide [II: R$_1$=R$_3$=H, R$_2$=(CH$_2$)$_2$CONHMe] (0.81 g, 69%); mp (CH$_2$Cl$_2$/light petroleum) 97.5°–99° C. (Kononova VV, Vereshchagin AL, Polyachenka VM, Semenov AA, *Khim.-Farm. Zh.* 1978;12:30 record mp 97°–99° C.).

$^1$H NMR ((CD$_3$)$_2$CO): δ 9.97 (1H, s, NH), 7.56 (1H, dd, J=8.0, 0.8 Hz, ArH), 7.36 (1H, dt, J=8.1, 0.8 Hz, ArH), 7.11 (1H, m, H-2), 7.08 (1H, ddd, J=8.1, 7.0, 1.1 Hz, ArH), 6.99 (1H, ddd, J=7.8, 7.0, 1.0 Hz, ArH), 6.99 (1H, br s, NHCH$_3$), 3.04 (2H, td, J=7.7, 0.9 Hz, 3-CH$_2$), 2.68 (3H, d, J=4.7 Hz, NHCH$_3$), 2.51 (2H, t, J=7.7 Hz, 3-CH$_2$CH$_2$).

$^{13}$C NMR: δ 173.30 (s, CONH), 137.73, 128.42 (2×s, Ar), 122.80, 122.01, 119.31 (3×d, Ar), 115.62 (s, Ar), 112.08 (d, Ar), 37.67 (t, 3-CH$_2$CH$_2$), 26.06 (q, NCH$_3$), 22.08 (t, 3-CH$_2$).

The above N-methylpropanamide (0.75 g) was treated with S$_2$Cl$_2$ as above, then the product mixture obtained after workup was treated successively with NaBH$_4$ then H$_2$O$_2$ as described above. The resulting oil was chromatographed on silica gel, eluting with EtOAc, to give firstly 2,2'-thiobis[N-methyl-3-(3-indolyl)propanamide] [VI: n=1; R$_1$=R$_3$=H, R$_2$=(CH$_2$)$_2$CONHMe] (0.13 g, 16%); mp (EtOAc/benzene/light petroleum) 120°–123° C.

$^1$H NMR (CDCl$_3$): δ 10.50 (1H, s, NH), 7.54 (1H, d, J=7.9 Hz, ArH), 7.31 (1H, d, J=8.1 Hz, ArH), 7.14 (1H, ddd, J=8.1, 7.1, 1.0 Hz, ArH), 7.04 (1H, ddd, J=7.9, 7.0, 0.9 Hz, ArH), 5.31 (1H, br d, J=4.9 Hz, NHCH$_3$), 3.47 (2H, m, 3-CH$_2$), 2.80 (2H, m, 3-CH$_2$CH$_2$), 2.60 (3H, d, J=4.9 Hz, NHCH$_3$).

$^{13}$C NMR: δ 174.25 (s, CONH), 137.17, 126.67, 125.39 (3×s, Ar), 122.51, 118.88, 118.58 (3×d, Ar), 117.62 (s, Ar), 111.43 (d, Ar), 36.01 (t, 3-CH$_2$CH$_2$), 26.27 (q, NCH$_3$), 21.02 (t, 3-CH$_2$).

Analysis calculated for C$_{24}$H$_{26}$N$_4$O$_2$S.C$_6$H$_6$ requires: C, 70.3; H, 6.3; N, 10.9; S, 6.3%.

Found: C, 70.1; H, 6.2; N, 11.0; S, 6.0%.

Further elution with EtOAc gave 2,2'-dithiobis[N-methyl-3-(3-indolyl)propanamide] (51) [V: n=2; R$_1$=R$_3$=H, R$_2$=(CH$_2$)$_2$CONHMe] (0.29 g, 34%); mp (EtOAc/benzene/light petroleum) 162.5°–164° C.

$^1$H NMR (CD$_3$CD): δ 7.50 (1H, dt, J=8.1, 0.8 Hz, ArH), 7.33 (1H, dt, J=8.2, 0.8 Hz, ArH), 7.18 (1H, ddd, J=8.1, 7.0, 1.0 Hz, ArH), 7.02 (1H, ddd, J=8.0, 7.1, 0.8 Hz, ArH), 2.71 (2H, m, 3-CH$_2$), 2.49 (3H, s, NCH$_3$), 2.02 (2H, m, 3-CH$_2$CH$_2$).

$^{13}$C NMR: δ 175.76 (s, CONH), 139.27, 128.33, 127.01 (3×s, Ar), 124.80, (d, Ar), 123.92 (s, Ar), 120.48, 120.44, 112.48 (3×d, Ar), 38.44 (t, 3-CH$_2$CH$_2$), 26.32 (q, NCH$_3$), 21.95 (t, 3-CH$_2$).

Analysis calculated for C$_{24}$H$_{26}$N$_4$O$_2$S$_2$ requires: C, 61.8; H, 5.6; N, 12.0; S, 13.7%.

Found: C, 61.7; H, 5.7; N, 12.2; S, 13.7%.

Compound 52 of Table 1

A solution of 3-(3-indolyl)propanoic acid [II: R$_1$=R$_3$=H, R$_2$=(CH$_2$)$_2$COOH] (0.70 g), triethylamine (5 mL) and methoxyamine hydrochloride (0.90 g) in THF (20 mL) was stirred at 20° C. for 3 hours, then cooled to 0° C. DEPC (98%, 0.70 mL) was added, then the mixture was stirred at 20° C. for 18 hours. The reaction was then quenched with water and extracted with EtOAc. Evaporation gave an oil which was purified by chromatography on silica gel. Elution with EtOAc:light petroleum (1:1) gave foreruns, then elution with EtOAc:light petroleum (3:1) gave N-methoxy-3-(3-indolyl)propanamide [II: R$_1$=R$_3$=H, R$_2$=(CH$_2$)$_2$CONHOMe] (0.50 g, 62%); mp (CH$_2$Cl$_2$/light petroleum) 116°–118° C. (Kononova VV, Vereshchagin AL, Polyachenka VM, Semenov AA, *Khim.-Farm. Zh.* 1978;12:30 record mp 114°–115° C.).

$^1$H NMR ((CD$_3$)$_2$SO): δ 10.97, 10.77 (2×1H, 2×s, 2×NH), 7.51 (1H, d, J=7.8 Hz, ArH), 7.32 (1H, d, J=8.1 Hz ArH), 7.09 (1H, s, H-2), 7.06 (1H, td, J=8.0, 1.0 Hz, ArH), 6.97 (1H, td, J=8.0, 0.9 Hz, ArH), 3.55 (3H, s, NHOCH$_3$), 2.91, 2.30 (2×2H, 2×t, J=7.6 Hz, 3-CH$_2$CH$_2$).

$^{13}$C NMR: δ 168.72 (s, CONH), 136.13, 126.87 (2×s, Ar), 122.14, 120.83, 118.21, 118.09 (4×d, Ar), 113.30 (s, Ar), 111.23 (d, Ar), 63.00 (q, OCH$_3$), 33.20 (t, 3-CH$_2$CH$_2$), 20.53 (t, 3-CH$_2$).

The above N-methoxypropanamide (1.00 g) was treated with S$_2$Cl$_2$ as above, then the product mixture obtained after workup was treated successively with NaBH$_4$ then H$_2$O$_2$ as described above. The resulting oil was chromatographed on silica gel, eluting with EtOAc:light petroleum (3:2), to give firstly 2,2'- thiobis[N-methoxy-3-(3-indolyl)propanamide] [VI: n=1; R$_1$=R$_3$=H, R$_2$=(CH$_2$)$_2$CONHOMe] (0.12 g, 11%); mp (EtOAc/light petroleum) 157.5°–158.5° C.

$^1$H NMR ((CD$_3$)$_2$SO): δ 11.02, 10.95 (2×1H, 2×s, 2×NH), 7.53 (1H, d, J=7.9 Hz, ArH), 7.25 (1H, d, J=8.1 Hz, ArH), 7.09 (1H, t, J=7.5 Hz, ArH), 6.99 (1H, t, J=7.4 Hz, ArH), 3.52 (3H, s, NHOCH$_3$), 3.17, 2.31 (2×2H, 2×t, J=7.5 Hz, 3-CH$_2$CH$_2$).

$^{13}$C NMR: δ 168.73 (s, CONH), 136.75, 126.79, 123.29 (3×s, Ar), 122.23 (d, Ar), 118.78 (d, 2C, Ar), 118.00 (s, Ar), 111.08 (d, Ar), 63.04 (q, OCH$_3$), 33.43 (t, 3-CH$_2$CH$_2$), 20.46 (t, 3-CH$_2$).

Analysis calculated for C$_{24}$H$_{26}$N$_4$O$_4$S requires: C, 61.8; H, 5.6; N, 12.0; S, 6.9%.

Found: C, 61.6; H, 5.8; N, 12.2; S, 6.9%.

Elution with EtOAc gave 2,2'-dithiobis[N-methoxy- 3-(3-indolyl)propanamide] (52) [VI: n=2; R$_1$=R$_3$=H, R$_2$=(CH$_2$)$_2$CONHOMe] (0.35 g, 31%); mp (EtOAc/light petroleum) 176°–178° C.

$^1$H NMR ((CD$_3$)$_2$SO): δ 11.39, 10.73 (2×1H, 2×s, 2×NH), 7.51 (1H, d, J=8.0 Hz, ArH), 7.32 (1H, d, J=8.2 Hz, ArH), 7.16 (1H, t, J=7.7 Hz, ArH), 7.00 (1H, t, J=7.5 Hz, ArH), 3.41 (3H, s, NHOCH$_3$), 2.65, 2.01 (2×2H, 2×t, J=7.4 Hz, 3-CH$_2$CH$_2$).

$^{13}$C NMR: δ 168.21 (s, CONH), 137.42, 126.52, 125.16 (3×s, Ar), 123.37 (d, Ar), 122.20 (s, Ar), 119.48, 118.96, 111.48 (3×d, Ar), 62.91 (q, OCH$_3$), 33.79 (t, 3-CH$_2$CH$_2$), 20.09 (t, 3-CH$_2$).

Analysis calculated for C$_{24}$H$_{26}$N$_4$O$_4$S$_2$ requires: C, 57.8; H, 5.2; N, 11.2; S, 12.9%.

Found: C, 57.6; H, 5.4; N, 11.3; S, 12.7%.

Compound 53 of Table 1

DEPC (98%, 1.28 mL) was added to a stirred solution of 3-(3-indolyl)propanoic acid [II: R$_1$=R$_3$=H, R$_2$=(CH$_2$)$_2$COOH] (1.04 g) and triethylamine (1.15 mL) in THF (15 mL) at 0° C. After 5 minutes the solution was saturated with dimethylamine gas, then the mixture was stirred at 20° C. for 16 hours. Workup as above and chromatography on silica gel, eluting with EtOAc, gave N,N-dimethyl 3-(3-indolyl)propanamide [II: R$_1$=R$_3$=H, R$_2$=(CH$_2$)$_2$CONMe$_2$] (0.90 g, 76%); mp (CH$_2$Cl$_2$/light petroleum) 141°–142° C. (Avramenko VG, Suvorov NN, Mashkovskii MD, Mushulov PI, Eryshev BYa, Fedorova VS, Orlova IA, Trubitsyna TK, *Khim.-Farm. Zh.* 1970;4:10 record mp 139°–140.5° C.).

$^1$H NMR (CD$_3$OD): δ 7.53 (1H, dt, J=7.9, 0.9 Hz, ArH), 7.32 (1H, dt, J=8.1, 0.8 Hz, ArH) 7.07 (1H, ddd, J=8.1, 7.0, 1.1 Hz, ArH), 7.04 (s, H-2), 6.99 (1H, ddd, J=7.9, 7.0, 0.9 Hz, ArH), 3.05 (2H, m, 3-CH$_2$), 2.88, 2.86 (2×3H, 2×s, N(CH$_3$)$_2$, 2.73 (2H, m, 3-CH$_2$CH$_2$).

$^{13}$C NMR: δ 175.75 (s, CON(CH$_3$)$_2$), 138.20, 128.59 (2×s, Ar), 123.11, 122.36, 119.61, 119.24 (4×d, Ar), 115.16 (s, Ar), 112.26 (d, Ar), 37.89, 35.82 (2×q, N(CH$_3$)$_2$), 35.30 (t, 3-CH$_2$CH$_2$), 22.32 (t, 3-CH$_2$).

The above dimethylpropanamide (0.82 g) was treated with S$_2$Cl$_2$ as above, then the product mixture obtained after workup was treated successively with NaBH$_4$ then H$_2$O$_2$ as described above. The resulting oil was chromatographed on silica gel, eluting with EtOAc:light petroleum (3:2), to give firstly 2,2'-thiobis-[N,N-dimethyl-3-(3-indolyl)propanamide] [VI: n=1; R$_1$=R$_3$=H, R$_2$=(CH$_2$)$_2$CONHMe$_2$] (0.12 g, 14%); mp (EtOAc/light petroleum) 189°–190° C.

$^1$H NMR (CDCl$_3$): δ 10.72 (br s, 1H, NH), 7.55 (1H, d, J=7.9 Hz, ArH), 7.24 (1H, d, J=8.1 Hz, ArH), 7.10 (ddd, J=8.0, 7.1, 0.9 Hz, 1H, ArH), 7.02 (dd, J=7.9, 7.1 Hz, 1H, ArH), 3.47, 2.97 (2×2H, 2×m, 3-CH$_2$CH$_2$), 2.95, 2.91 (2×3H, 2×s, N(CH$_3$)$_2$).

$^{13}$C NMR: δ 173.36 (s, CON(CH$_3$)$_2$), 137.15, 126.92, 125.55 (3×s, Ar), 122.26, 118.68, 118.58 (3×d, Ar), 118.02 (s, Ar), 111.35 (d, Ar), 37.49, 35.74 (2×q, N(CH$_3$)$_2$), 32.14 (t, 3-CH$_2$CH$_2$), 20.54 (t,3-CH$_2$).

Analysis calculated for C$_{26}$H$_{30}$N$_4$O$_2$S requires: C, 67.5; H, 6.5; N, 12.1; S, 6.9%.

Found: C, 67.4; H, 6.6; N, 12.0; S, 7.2%.

Elution with EtOAc gave 2,2'-dithiobis-[N,N-dimethyl-3-(3-indolyl)propanamide] (53) [VI: n=2; R$_1$=R$_3$=H, R$_2$=(CH$_2$)$_2$CONMe$_2$] (0.49 g, 52%); mp (EtOAc) 179°–180° C.

$^1$H NMR (CD$_3$OD): δ 7.45 (1H, dt, J=8.0, 0.8 Hz, ArH), 7.32 (1H, dt, J=8.2, 0.8 Hz, ArH), 7.17 (1H, ddd, J=8.2, 7.1, 1.1 Hz, ArH), 7.01 (1H, ddd, J=8.0, 7.1, 0.9 Hz, ArH), 2.72 (2H, m, 3-CH$_2$CH$_2$), 2.71, 2.44 (2×3H, 2×s, N(CH$_3$)$_2$), 2.09 (2H, m, 3-CH$_2$CH$_2$).

$^{13}$C NMR: δ 174.68 (s, CON(CH$_3$)$_2$), 139.43, 128.26, 126.61 (3×s, Ar), 124.85 (d, Ar), 123.84 (s, Ar), 120.55, 120.28, 112.51 (3×d, Ar), 37.57 (q, NCH$_3$), 35.69 (t, 3-CH$_2$CH$_2$), 35.60 (q, NCH$_3$), 21.49 (t, 3-CH$_2$).

Analysis calculated for C$_{26}$H$_{30}$N$_4$O$_2$S$_2$ requires: C, 63.2; H, 6.1; N, 11.3; S, 13.0%.

Found: C, 63.2; H, 6.2; N, 11.3; S, 13.1%.

Compound 54 of Table 1

DEPC (98%, 0.69 mL) was added to a stirred solution of 3-(3-indolyl)propanoic acid [II: R$_1$=R$_3$=H, R$_2$=(CH$_2$)$_2$COOH] (0.70 g) and phenethylamine (1.1 mL) in THF (15 mL) at 0° C., then the mixture was stirred at 20° C. for 3 hours. Workup and chromatography on silica gel, eluting with EtOAc/light petroleum (1:1) gave N-(2-phenylethyl)-3-(3-indolyl)propanamide [II: R$_1$=R$_3$=H, R$_2$=(CH$_2$)$_2$CONH(CH$_2$)$_2$Ph] (0.58 g, 54%); mp (EtOAc/ light petroleum) 88°–89° C.

$^1$H NMR (CDCl$_3$): δ 8.02 (1H, br s, NH), 7.58 (1H, d, J=7.9 Hz, ArH), 7.36 (1H, d, J=8.1 Hz, ArH) 7.24–7.15 (4H, m, ArH), 7.12 (1H, ddd, J=7.9, 7.0, 0.8 Hz, ArH), 6.99 (2H, dd, J=7.4, 1.7 Hz, ArH), 6.95 (1H, d, J=2.2 Hz, H-2), 5.34 (1H, br t, J=6.0 Hz, NHCH$_2$), 3.44 (2H, q, J=6.6 Hz, NHCH$_2$), 3.09 (2H, t, J=7.3 Hz, 3-CH$_2$), 2.66 (2H, t, J=6.9 Hz, NHCH$_2$CH$_2$), 2.52 (2H, t, J=7.3 Hz, 3-CHCH$_2$).

$^{13}$C NMR: δ 172.64 (s, CONH), 138.90, 136.38 (2×s, Ar), 128.71, 128.58 (2×d, 2×2C, Ar), 127.13 (s, Ar), 126.41, 122.10, 121.77, 119.37, 118.72 (5×d, Ar), 114.95 (s, Ar), 111.23 (d, Ar), 40.48, 37.42, 35.62 (3×t, 3-CH$_2$CH$_2$CONH(CH$_2$)$_2$), 21.35 (t, 3-CH$_2$).

Analysis calculated for C$_{19}$H$_{20}$N$_2$O requires: C, 78.1; H, 6.9; N, 9.6%.

Found: C, 77.9; H, 7.0; N, 9.6%.

The above phenylethylpropanamide (0.53 g) was treated with S$_2$Cl$_2$ as above, then the product mixture obtained after workup was treated successively with NaBH$_4$ then H$_2$O$_2$ as described above. The resulting oil was chromatographed on silica gel, eluting with EtOAc:light petroleum (1:2), to give firstly 2,2'-thiobis[N-(2-phenylethyl)-3-(3-indolyl)propanamide] [VI: n=1; R$_1$=R$_3$=H, R$_2$=(CH$_2$)$_2$CONH(CH$_2$)$_2$Ph] (0.13 g, 23%); mp (EtOAc/light petroleum) 120°–121.5° C.

$^1$H NMR (CDCl$_3$): δ 10.69 (1H, s, NH), 7.55 (1H, d, J=7.9 Hz, ArH), 7.35 (1H, d, J=8.2 Hz, ArH), 7.17 (1H, ddd, J=8.1, 7.1, 1.0 Hz, ArH), 7.08 (1H, ddd, J=8.0, 0.9 Hz, ArH), 7.02 (1H, t, J=7.4 Hz, ArH), 6.93 (2H, t, J=7.4 Hz, ArH), 6.33 (2H, d, J=7.2 Hz, ArH), 5.26 (1H, t, J=5.9 Hz, NHCH$_2$), 3.51 (2H, m, 3-CH$_2$), 3.14 (2H, q, J=6.6 Hz, NHCH$_2$), 2.77 (2H, m, 3-CH$_2$CH$_2$), 1.92 (2H, t, J=6.8 Hz, NHCH$_2$CH$_2$).

$^{13}$C NMR: δ 173.62 (s, CONH), 138.20, 137.33 (2×s, Ar), 128.40, 128.36 (2×d, 2×2C, Ar), 126.76 (s, Ar), 126.16 (d, Ar), 125.51 (s, Ar), 122.78, 119.17, 118.70 (3×d, Ar), 117.57 (s, Ar), 111.70 (d, Ar), 40.49, 36.43, 35.46 (3×t, 3-CH$_2$CH$_2$CONH(CH$_2$)$_2$), 21.35 (t, 3-CH$_2$).

Analysis calculated for $C_{38}H_{38}N_4O_2S$ requires: C, 74.2; H, 6.2; N, 9.1; S, 5.2%.

Found: C, 74.4; H, 6.4; N, 9.0; S, 5.2.%

Elution with EtOAc: light petroleum (2:3) gave 2,2'-dithiobis[N-(2-phenylethyl)-3-(3-indolyl)propanamide] (54) [VI: n=2; $R_1=R_3=H$, $R_2=(CH_2)_2CONH(CH_2)_2Ph$] (0.36 g, 61%) as an oil.

$^1$H NMR (CDCl$_3$): δ 8.42 (1H, s, NH), 7.51 (1H, d, J=8.0 Hz, ArH), 7.32–7.16 (5H, m, ArH), 7.04 (3H, m, ArH), 4.63 (1H, t, J=5.9 Hz, NHCH$_2$), 3.23 (2H, q, J=6.7 Hz, NHCH$_2$), 2.85 (t, J=7.8 Hz, 3-CH$_2$), 2.59 (2H, t, J=7.0 Hz, NHCH$_2$CH$_2$), 1.81 (2H, t, J=7.8 Hz, 3-CH$_2$CH$_2$).

$^{13}$C NMR: δ 171.95 (s, CONH), 139.15, 137.23 (2×s, Ar), 128.87, 128.55 (2×d, 2×2C, Ar), 127.02 (s, Ar), 126.39 (d, Ar), 125.50 (s, Ar), 124.33 (d, Ar), 123.98 (s, Ar), 120.11, 119.88, 111.17 (3×d, Ar), 40.62, 37.37, 35.58 (3×t, 3-CH$_2$CH$_2$CONH(CH$_2$)$_2$), 20.64 (t, 3-CH$_2$).

HRFABMS m/z calculated for $C_{38}H_{39}N_4O_2S_2$: 647.2514 (MH$^+$)

Found: 647.2471.

Compounds 55 and 56 of Table 1

A solution of 3-(3-indolyl)propanoic acid [II: $R_1=R_3=H$, $R_2=(CH_2)_2COOH$] (0.80 g), triethylamine (10 mL) and methyl 4-(aminomethyl)benzoate hydrochloride (Nair MG, Baugh CM, *J. Org. Chem.* 1973;38:2185) (1.29 g) in THF (20 mL) was stirred at 20° C. for 15 minutes, then cooled to 0° C. DEPC (98%, 1.00 mL) was added, then the mixture was stirred at 20° C. for 18 hours. Workup and chromatography on silica gel, eluting with EtOAc:light petroleum (5:3) gave N-(4-methoxycarbonylbenzyl)-3-(3-indolyl)propanamide [II: $R_1=R_3=H$, $R_2=(CH_2)_2CONHCH_2Ph\{4\text{-COOMe}\}$] (1.10 g, 77%); mp (CH$_2$Cl$_2$/light petroleum)130°–132° C.

$^1$H NMR (CDCl$_3$): δ 8.08 (1H, s, NH), 7.88 (2H, d, J=8.2 Hz, ArH), 7.60 (1H, d, J=7.8 Hz, ArH), 7.36 (1H, d, J=8.1 Hz, ArH), 7.19 (1H, ddd, J=8.1, 7.1, 0.9 Hz, ArH), 7.11 (1H, ddd, J=7.9, 7.2, 0.7 Hz, ArH), 7.06 (2H, d, J=8.2 Hz, ArH), 6.94 (1H, d, J=2.3 Hz, H-2), 5.74 (1H, br t, J=5.9 Hz, NHCH$_2$), 4.38 (2H, d, J=5.9 Hz, NHCH$_2$), 3.90 (3H, s, OCH$_3$), 3.15, 2.63 (2×2H, 2×t, J=7.2 Hz, 3-CH$_2$CH$_2$).

$^{13}$C NMR: δ 172.68 (s, CONH), 166.87 (s, COOCH$_3$), 143.50, 136.37 (2×s, Ar), 129.80 (2×d, Ar), 129.10 (s, Ar), 127.28 (2×d, Ar), 127.03 (s, Ar), 122.11, 121.92, 119.41, 118.64 (4×d, Ar), 114.66 (s, Ar), 111.27 (d, Ar), 52.09 (q, OCH$_3$), 43.05 (t, NHCH$_2$), 37.37 (t, 3-CH$_2$CH$_2$), 21.39 (t, 3-CH$_2$).

Analysis calculated for $C_{20}H_{20}N_2O_3$ requires: C, 71.4; H, 6.0; N, 8.3%.

Found: C, 71.1; H, 5.7; N, 8.4%.

The above methoxycarbonylbenzylpropanamide (1.08 g) was treated with S$_2$Cl$_2$ as above, then the product mixture obtained after workup was treated successively with NaBH$_4$ then H$_2$O$_2$ as described above. The resulting oil was chromatographed on silica gel, eluting with EtOAc:light petroleum (2:3), to give firstly 2,2'-thiobis[N-(4-methoxycarbonylbenzyl)-3-(3-indolyl)propanamide] [VI: n=1; $R_1=R_3=H$, $R_2=(CH_2)_2CONHCH_2Ph\{4\text{-COOMe}\}$] (0.18 g, 16% ); mp (MeOH/dilute HCl) 101°–104.5° C. (dec).

$^1$H NMR (CDCl$_3$): δ 10.28 (1H, s, NH), 7.47 (1H, d, J=7.7 Hz, ArH), 7.45 (2H, d, J=8.4 Hz, ArH), 7.05 (1H, d, J=8.0 Hz, ArH), 6.97 (1H, ddd, J=8.0, 6.9, 1.1 Hz, ArH), 6.91 (1H, ddd, J=7.9, 6.8, 1.1 Hz, ArH), 6.61 (2H, d, J=8.3 Hz, ArH), 6.34 (1H, br t, J=5.8 Hz, NHCH$_2$), 4.40 (2H, d, J=5.9 Hz, NHCH$_2$), 3.79 (3H, s, OCH$_3$) 3.54, 2.97 (2×2H, 2×m, 3-CH$_2$CH$_2$).

$^{13}$C NMR: δ 174.37 (s, CONH), 166.75 (s, COOCH$_3$), 142.31, 137.15 (2×s, Ar), 129.35 (d, 2C, Ar), 128.39, 126.52 (2×s, Ar), 126.24 (d, 2C, Ar), 125.30 (s, Ar), 122.65, 118.87, 118.49 (3×d, Ar), 117.92 (s, Ar), 111.31 (d, Ar), 51.95 (q, OCH$_3$), 43.22 (t, NHCH$_2$), 36.34 (t, 3-CH$_2$CH$_2$), 21.17 (t, 3-CH$_2$).

Analysis calculated for $C_{40}H_{38}N_4O_6S \cdot 0.5H_2O$ requires: C, 67.5; H, 5.5; N, 7.9%.

Found: C, 67.4; H, 5.4; N, 8.1%.

Elution with EtOAc:light petroleum (1:1) gave 2,2'-dithiobis[N-(4-methoxycarbonylbenzyl)-3-(3-indolyl)propanamide] (55) [VI: n=2; $R_1=R_3=H$, $R_2=(CH_2)_2CONHCH_2Ph\{4\text{-COOMe}\}$] (0.50 g, 42%); mp (EtOAc/light petroleum) 151°–153° C.

$^1$H NMR ((CD$_3$)$_2$SO): δ 11.42 (1H, s, NH), 8.06 (1H, t, J=5.7 Hz, NHCH$_2$), 7.81 (2H, d, J=8.2 Hz, ArH), 7.55 (1H, d, J=8.0 Hz, ArH), 7.34 (1H, d, J=8.2 Hz, ArH), 7.17 (1H, t, J=7.6 Hz, ArH), 7.11 (2H, d, J=8.1 Hz, ArH), 6.99 (1H, t, J=7.5 Hz, ArH), 4.19 (2H, d, J=5.8 Hz, NHCH$_2$), 3.84 (3H, s, OCH$_3$), 2.73, 2.24 (2×2H, 2×t, J=7.5 Hz, 3-CH$_2$CH$_2$).

$^{13}$C NMR: δ 171.48 (s, CONH), 166.00 (s, COOCH$_3$), 145.01, 137.37 (2×s, Ar), 128.98 (d, 2C, Ar), 127.84 (s, Ar), 127.01 (d, 2C, Ar), 126.53, 125.21 (2×s, Ar), 123.24 (d, Ar), 122.39 (s, Ar), 119.57, 118.86, 111.38 (3×d, Ar), 51.93 (q, OCH$_3$), 41.62 (t, NHCH$_2$), 36.65 (t, 3-CH$_2$CH$_2$), 20.38 (t, 3-CH$_2$).

Analysis calculated for $C_{40}H_{38}N_4O_6S_2$ requires: C, 65.4; H, 5.2; N, 7.6; S, 8.7%.

Found: C, 65.5; H, 5.5; N, 7.3; S, 8.8%.

Hydrolysis of 55 (0.24 g) with K$_2$CO$_3$ in MeOH/water at 30° C. for 1 day, then 50° C. for 1 hour, under nitrogen as above gave an oil. Chromatography on silica gel, eluting with EtOAc:light petroleum (1:1) containing 1% AcOH, gave 2,2'-dithiobis[N-(4-carboxybenzyl)-3-(3-indolyl)propanamide] (56) [VI: n=2; $R_1=R_3=H$, $R_2=(CH_2)_2CONHCH_2Ph\{4\text{-COOH}\}$] (60 mg, 26%); mp (MeOH/dilute HCl) 135.5°–138.5° C. (decomposed).

$^1$H NMR (CD$_3$)$_2$SO): δ 11.41 (1H, s, NH), 8.03 (1H, t, J=5.8 Hz, NHCH$_2$), 7.79 (2H, d, J=8.2 Hz, ArH), 7.55 (1H, d, J=8.0 Hz, ArH), 7.33 (1H, d, J=8.2 Hz, ArH), 7.16 (1H, t, J=7.6 Hz, ArH), 7.09 (2H, d, J=8.1 Hz, ArH), 6.99 (1H, t, J=7.5 Hz, ArH), 4.18 (2H, d, J=5.8 Hz, NHCH$_2$), 2.73, 2.23 (2×2H, 2×t, J=7.5 Hz, 3-CH$_2$CH$_2$).

$^{13}$C NMR: δ 171.44 (s, CONH), 167.10 (s, COOH), 144.46, 137.37 (2×s, Ar), 129.14 (d, 2C, Ar), 129.05 (s, Ar), 126.87 (d, 2C, Ar), 126.53, 125.18 (2×s, Ar), 123.23 (d, Ar), 122.40 (s, Ar), 119.58, 118.85, 111.37 (3×d, Ar), 41.65 (t, NHCH$_2$), 36.42 (t, 3-CHCH$_2$), 20.37 (t, 3-CH$_2$).

Analysis calculated for $C_{38}H_{34}N_4O_6S_2 \cdot H_2O$ requires: C, 63.0; H, 5.0; N, 7.7; S, 8.8%.

Found: C, 62.5; H, 5.2; N, 8.2; S, 8.8%.

Compounds 57 and 58 of Table 1

A stirred solution of methyl 2-acetoxy-4-bromomethylbenzoate (Regnier G, Canevari R, Le Douarec J-C, *Bull. Soc. Chim. Fr.* 1966;2821) (10.7 g) and hexamethylenetetramine (17.1 g) in CHCl$_3$ (150 mL) was refluxed for 5 hours, then the solvent was removed (method of Meindl W, v Angerer E, Ruckdeschel G, Schonenberger H, *Arch. Pharm. (Weinheim)* 1982;315:941). The residue was stirred with MeOH (60 mL) and concentrated HCl (30 mL) at 20° C. for 10 minutes, then the solvent removed. Treatment of the solid residue twice more with HCl/MeOH and evaporation gave a solid, which was washed with $CH_2Cl_2$, then treated with saturated $KHCO_3$ solution. The base was extracted with EtOAc and $CH_2Cl_2$, then the solvents removed. The crude hydrochloride salt (5.30 g, 70% pure) was precipitated from an ethereal solution of the base upon the addition of HCl gas. A subsample of the above crude base was purified by chromatography on silica gel, eluting with EtOAc/light petroleum (1:2). Acidification of a solution of the purified base gave pure methyl 4-(aminomethyl)-2-hydroxybenzoate hydrochloride; mp ($CH_2Cl_2$/light petroleum) 225°–227° C.

$^1$H NMR $(CD_3)_2SO)$: δ 10.56 (1H, s, OH), 8.58 (3H, br s, $NH_3^+$), 7.78 (1H, d, J=8.1 Hz, H-6), 7.14 (1H, s, H-3), 7.05 (1H, d, J=8.1 Hz, H-5), 4.01 (2H, br s, 4-$CH_2$), 3.88 (3H, s, $OCH_3$).

$^{13}$C NMR: δ 168.81 (s, $\underline{C}OOCH_3$), 159.80 (s, C-2), 141.84 (s, C-4), 130.25 (d, C-6), 119.61 (d, C-5), 117.48 (d, C-3), 112.90 (s, C-1), 52.53 (q, $OCH_3$), 41.63 (t, 4-$CH_2$).

Analysis calculated for $C_9H_{11}NO_3$·HCl·0.5$H_2O$ requires: C, 47.7; H, 5.8; N, 6.2; Cl, 15.7%.

Found: C, 47.9; H, 5.8; N, 6.3; Cl, 15.9%.

A solution of 3-(3-indolyl)propanoic acid [II: $R_1=R_3=H$, $R_2=(CH_2)_2COOH$] (1.50 g), triethylamine (10 mL) and crude methyl 4-(aminomethyl)-2-hydroxybenzoate hydrochloride (3.46 g) in DMF (20 mL) was stirred at 20° C. for 10 minutes, then cooled to 0° C. DEPC (98%, 1.47 mL) was added, then the mixture was stirred at 20° C. for 17 hours. Workup and chromatography on silica gel, eluting with EtOAc:light petroleum (1:1) gave N-(3-hydroxy-4-methoxycarbonylbenzyl)- 3-(3-indolyl)propanamide [II: $R_1=R_3=H$, $R_2=(CH_2)_2CONHCH_2Ph\{3\text{-OH, 4-COOMe}\}$] (1.40 g, 50%); mp (EtOAc/light petroleum) 132°–133° C.

$^1$H NMR $((CD_3)_2SO)$: δ 10.76 (1H, br s, NH), 10.50 (1H, s, OH), 8.41 (1H, t, J=5.8 Hz, N$\underline{H}$C$H_2$), 7.70 (1H, d, J=8.1 Hz, ArH), 7.54 (1H, d, J=7.8 Hz, ArH), 7.33 (1H, d, J=8.1 Hz, ArH), 7.10 (1H, d, J=2.2 Hz, H-2), 7.06 (1H, ddd, J=8.0, 7.1, 0.9 Hz, ArH), 6.97 (1H, ddd, J=7.8, 7.0, 0.8 Hz, ArH), 6.83 (1H, d, J=1.4 Hz, ArH), 6.74 (1H, dd, J=8.2, 1.4 Hz, ArH), 4.27 (2H, d, J=6.0 Hz, NHC$\underline{H}_2$), 3.88 (3H, s, $OCH_3$), 2.96, 2.54 (2×2H, 2×t, J=7.7 Hz, 3-$CH_2CH_2$).

$^{13}$C NMR: δ 172.05 (s, CONH), 169.14 (s, $\underline{C}OOCH_3$), 160.10, 148.27, 136.22 (3×s, Ar), 129.92 (d, Ar), 126.98 (s, Ar), 122.14, 120.84, 118.30, 118.12, 118.09, 115.41 (6×d, Ar), 113.68 (s, Ar), 111.27 (d, Ar), 111.20 (s, Ar), 52.34 (q, $OCH_3$), 41.67 (t, NH$CH_2$), 36.23 (t, 3-$CH_2\underline{C}H_2$), 21.00 (t, 3-$CH_2$).

Analysis calculated for $C_{20}H_{20}N_2O_4$ requires: C, 68.2; H, 5.7; N, 8.0%.

Found: C, 68.3; H, 5.9; N, 8.0%.

A solution of acetyl chloride (0.42 mL) in THF (5 mL) was added to a stirred solution of the above propanamide (1.22 g) and triethylamine (1.00 mL) in THF (15 mL) at 0° C., then the mixture was stirred at 20° C. for 18 hours. The reaction was then quenched with water (100 mL) and extracted with EtOAc (3×100 mL). Evaporation and chromatography on silica gel, eluting with EtOAc:light petroleum (2:1) gave N-(3-acetoxy-4-methoxycarbonylbenzyl)-3-(3-indolyl)propanamide [II: $R_1=R_3=H$, $R_2=(CH_2)_2CONHCH_2Ph\{3\text{-OAc, 4-COOMe}\}$] (1.28 g, 94%) as an oil.

$^1$H NMR $(CDCl_3)$: δ 8.18 (1H, br s, NH), 7.87 (1H, d, J=8.1 Hz, ArH), 7.57 (1H, d, J=8.0 Hz, ArH), 7.31 (1H, dt, J=8.1, 0.8 Hz, ArH), 7.17 (1H, ddd, J=8.1, 7.0, 1.1 Hz, ArH), 7.09 (1H, ddd, J=7.9, 7.0, 0.9 Hz, ArH), 6.97 (1H, dd, J=8.1, 1.6 Hz, ArH), 6.84 (1H, d, J=1.5 Hz, ArH), 6.77 (1H, d, J=2.3 Hz, H-2), 5.67 (1H, br t, J=5.8 Hz, N$\underline{H}$C$H_2$), 4.31 (2H, d, J=6.0 Hz, NHC$\underline{H}_2$), 3.87 (3H, s, $COOCH_3$), 3.11, 2.58 (2×2H, 2×t, J=6.9 Hz, 3-$CH_2CH_2$), 2.36 (3H, s, $OCOCH_3$).

$^{13}$C NMR: δ 172.84 (S, CONH), 170.14 (s, O$\underline{C}OCH_3$), 164.64 (s, $\underline{C}OOCH_3$), 150.82, 145.26, 136.33 (3×s, Ar), 132.04 (d, Ar), 126.85 (s, Ar), 125.42, 122.93, 122.31, 121.95 (4×d, Ar), 121.87 (s, Ar), 119.28, 118.52 (2×d, Ar), 114.08 (s, Ar), 111.36 (d, Ar), 52.23 (q, $OCH_3$), 42.62 (t, NH$CH_2$), 37.32 (t, 3-$CH_2CH_2$), 21.46 (t, 3-$CH_2$), 21.06 (q, OCO$\underline{C}H_3$).

HREIMS m/z calculated for $C_{22}H_{22}N_2O_5$: 394.1529 ($M^+$).

Found: 394.1526.

The above O-acetate (1.47 g) was treated with $S_2Cl_2$ as above, then the product mixture obtained after workup was treated successively with $NaBH_4$ then $H_2O_2$ as described above. Hydrolysis of the resulting oil with excess $KHCO_3$ in MeOH/water at 20° C. for 1 hour (to remove the acetate group) gave an oil which was purified by chromatography on silica gel. Elution with EtOAc:light petroleum (1:2) gave firstly 2,2'-thiobis[N-(3-hydroxy-4-methoxycarbonylbenzyl)-3-(3-indolyl)propanamide] [VI: n=1; $R_1=R_3=H$, $R_2=(CH_2)_2CONHCH_2Ph\{3\text{-OAc, 4-COOMe}\}$] (0.12 g, 9%); mp (MeOH/dilute HCl) 109°–112° C. (decomposed).

$^1$H NMR $(CDCl_3)$: δ 10.50 (1H, s, OH), 10.17 (1H, s, NH), 7.49 (1H, d, J=7.9 Hz, ArH), 7.31 (1H, d, J=8.2 Hz, ArH), 7.19 (1H, d, J=8.1 Hz, ArH), 7.07 (1H, ddd, J=8.0, 7.1, 0.8 Hz, ArH), 6.97 (1H, ddd, J=7.8, 7.2, 0.6 Hz, ArH), 6.32 (1H, d, J=1.1 Hz, ArH), 5.98 (1H, dd, J=8.2, 1.5 Hz, ArH), 5.72 (1H, t, J=5.7 Hz, N$\underline{H}$C$H_2$), 4.22 (2H, d, J=5.7 Hz, NHC$\underline{H}_2$), 3.86 (3H, s, $OCH_3$), 3.50, 2.88 (2×2H, 2×m, 3-$CH_2CH_2$).

$^{13}$C NMR: δ 173.77 (s, CONH), 170.06 (s, $\underline{C}OOCH_3$), 161.36, 145.57, 137.16 (3×s, Ar), 130.02 (d, Ar), 126.62, 125.16 (2×s, Ar), 122.69, 119.13, 118.43 (3×d, Ar), 117.65 (s, Ar), 117.40, 115.51, 111.53 (3×d, Ar), 111.07 (s, Ar), 52.18 (q, $OCH_3$), 43.19 (t, NH$CH_2$), 36.32 (t, 3-$CH_2\underline{C}H_2$), 21.22 (t, 3-$CH_2$).

Analysis calculated for $C_{40}H_{38}N_4O_8S$ requires: C, 65.4; H, 5.2; N, 7.6; S, 4.4%.

Found: C, 65.2; H, 5.1; N, 7.4; S, 4.4%.

Elution with EtOAc:light petroleum (2:3) gave 2,2'-dithiobis[N-(3-hydroxy-4-methoxycarbonylbenzyl)-3-(3-indolyl)propanamide] (57) [V: n=2; $R_1=R_3=H$, $R_2=(CH_2)_2CONHCH_2Ph\{3\text{-OH, 4-COOMe}\}$] (0.38 g, 27%); mp (MeOH) 183°–185° C.

$^1$H NMR $(CDCl_3)$: δ 10.80 (1H, s, OH), 8.65 (1H, s, NH), 7.67 (1H, d, J=8.1 Hz, ArH), 7.52 (1H, d, J=8.0 Hz, ArH), 7.27 (1H, d, J=7.7 Hz, ArH), 7.15 (1H, ddd, J=8.1, 7.2, 0.9 Hz, ArH), 7.01 (1H, ddd, J=7.9, 7.2, 0.7 Hz, ArH), 6.55 (1H, d, J=1.5 Hz, ArH), 6.52 (1H, dd, J=8.2, 1.5 Hz, ArH), 5.10 (1H, t, J=5.9 Hz, N$\underline{H}$C$H_2$), 4.13 (2H, d, J=6.0 Hz, NHC$\underline{H}_2$), 3.94 (3H, s, $OCH_3$), 2.88, 1.94 (2×2H, 2×t, J=7.7 Hz, 3-$CH_2CH_2$).

$^{13}$C NMR: δ 172.12 (s, CONH), 170.39 (s, $\underline{C}OOCH_3$), 161.55, 146.95, 137.29 (3×s, Ar), 130.09 (d, Ar), 127.01, 125.87 (2×s, Ar), 124.39 (d, Ar), 123.79 (s, Ar), 120.16, 119.86, 118.34, 115.69, 111.37 (5×d, Ar), 111.20 (s, Ar), 52.31 (q, $OCH_3$), 42.82 (t, NH$CH_2$), 37.09 (t, 3-$CH_2CH_2$), 20.54 (t, 3-$CH_2$).

Analysis calculated for $C_{40}H_{38}N_4O_8S_2$ requires: C, 62.7; H, 5.0; N, 7.3; S, 8.4%.

Found: C, 62.5; H, 4.9; N, 7.3; S, 8.4%.

Hydrolysis of 57 (0.28 g) with $K_2CO_3$ in MeOH/water at 50° C. for 5 hours, under nitrogen as above, gave an oil.

Chromatography on silica gel, eluting with EtOAc:light petroleum (1:1) containing 1% AcOH, gave 2,2'-dithiobis[N-(4-carboxy-3-hydroxybenzyl)-3-(3-indolyl)propanamide] (58) [VI: n=2; $R_1=R_3=H$, $R_2=(CH_2)_2CONHCH_2Ph\{3-OH, 4-COOH\}$] (72 mg, 27%) mp (MeOH/dilute HCl) 160°–163.5° C. (dec).

$^1$H NMR $(CD_3)_2SO$): δ 11.39 (1H, s, NH), 8.03 (1H, t, J=5.9 Hz, NH$CH_2$), 7.65 (1H, d, J=8.1 Hz, ArH), 7.54 (1H, d, J=8.0 Hz, ArH), 7.32 (1H, d, J=8.2 Hz, ArH), 7.16 (1H, ddd, J=8.1, 7.1, 1.0 Hz, ArH), 6.99 (1H, ddd, J=7.8, 7.1, 0.7 Hz, ArH), 6.72 (1H, d, J=1.3 Hz, ArH), 6.57 (1H, dd, J=8.2, 1.4 Hz, ArH), 4.13 (2H, d, J=5.9 Hz, NH$CH_2$), 2.75, 2.24 (2×2H, 2×t, J=7.8 Hz, 3-$CH_2CH_2$).

$^{13}$C NMR: δ 171.70 (s, CONH), 171.47 (s, COOH), 161.04, 147.83, 137.37 (3×s, Ar), 130.08 (d, Ar), 126.51, 125.11 (2×s, Ar), 123.25 (d, Ar), 122.42 (s, Ar), 119.49, 118.86, 117.73, 115.09, 111.41 (5×d, Ar), 111.21 (s, Ar), 41.67 (t, NH$CH_2$), 36.63 (t, 3-$CH_2CH_2$), 20.41 (t, 3-$CH_2$).

Analysis calculated for $C_{38}H_{34}N_4O_8S_2.H_2O$ requires: C, 60.3; H, 4.8; N, 7.4; S, 8.5%.

Found: C, 60.2; H, 4.9; N, 7.1; S, 8.5%.

Compound 59 of Table 1

3-(3-Indolyl)propanoic acid [II: $R_1=R_3=H$, $R_2=(CH_2)_2COOH$] (0.95 g) was treated with $S_2Cl_2$ as above, then the product mixture obtained after workup was treated successively with $NaBH_4$ then $H_2O_2$ as described above, to give crude 2,2'-dithiobis[3-(3-indolyl)propanoic acid] [VI: n=2; $R_1=R_3=H$, $R_2=(CH_2)_2COOH$] (1.12 g) as an oil. DEPC (98%, 1.00 mL) was added to a stirred solution of this oil, triethylamine (0.84 mL) and aniline (1.55 mL) in THF (15 mL) at 0° C., then the mixture was stirred at 20° C. for 1 day. Dilute KOH (0.1M, 100 mL) was added and the mixture stirred for 30 minutes (in an attempt to cleave the DEPC adduct and reform the disulfide), then the mixture extracted with $CH_2Cl_2$ (3×100 mL). Evaporation gave an oil which was partly purified by chromatography on silica gel, eluting with EtOAc/light petroleum (2:1). The yellow disulfide was further purified by chromatography on fresh silica gel, eluting with $CH_2Cl_2$, then $CHCl_3$:EtOH (99:1), to give 2,2'-dithiobis[N-phenyl-3-(3-indolyl)propanamide] (59) [VI: n=2; $R_1=R_3=H$, $R_2=(CH_2)_2CONHPh$] (0.23 g, 16% overall); mp ($CH_2Cl_2$/benzene) 181°–182.5° C. (an analytical sample recrystallized from $CH_2Cl_2$/light petroleum decomposed above 114° C.).

$^1$H NMR ($(CD_3)_2CO$): δ 10.52 (1H, s, NH), 8.88 (1H, s, NHPh), 7.64 (1H, d, J=8.0 Hz, ArH), 7.56 (2H, dd, J=7.5, 0.9 Hz, ArH), 7.37 (1H, d, J=8.2 Hz, ArH), 7.24 (2H, dd, J=8.4, 7.5 Hz, ArH(Ph)), 7.16 (1H, ddd, J=8.1, 7.1, 1.1 Hz, ArH), 7.02 (2H, m, ArH), 3.04, 2.54 (2×2H, 2×m, 3-$CH_2CH_2$).

$^{13}$C NMR: δ 171.48 (s, CONH), 140.24, 138.80 (2×s, Ar), 129.37 (2×d, Ar), 128.17, 126.81 (2×s, Ar) 124.57, 124.02 (2×d, Ar), 123.86 (s, Ar), 120.62, 120.36 (2×d, Ar), 120.23 (2×br d, Ar), 112.38 (d, Ar), 38.97 (t, 3-$CH_2CH_2$) 21.39 (t, 3-$CH_2$).

Analysis calculated for $C_{34}H_{30}N_4O_2S_2.0.5H_2O$ requires: C, 68.1; H, 5.2; N, 9.4; S, 10.7%.

Found: C, 68.3; H, 5.1; N, 9.3; S, 10.9%.

Compound 60 of Table 1

DEPC (98%, 0.72 mL) was added to a stirred solution of DL-N-acetyltryptophan (1.00 g) and benzylamine (2.0 mL) in DMF (10 mL) at 0° C., then the mixture was stirred at 20° C. for 16 hours. The reaction was then quenched with water and extracted with EtOAc. Evaporation gave an oil which was chromatographed on silica gel. Elution with $CH_2Cl_2$ and EtOAc gave firstly foreruns, then DL-α-acetylamino-N-benzyl-3-(3-indolyl)propanamide [II: $R_1=R_3=H$, $R_2=CH_2CH(NHAc)CONHCH_2Ph$] (0.82 g, 60%); mp ($CH_2Cl_2$/light petroleum) 169°–170° C.

$^1$H NMR ($(CD_3)_2SO$): δ 10.80 (1H, s, NH), 8.47 (1H, br t, J=5.8 Hz, NH$CH_2$), 8.08 (1H, d, J=8.1 Hz, CHN$H$), 7.61 (1H, d, J=7.8 Hz, ArH), 7.33 (1H, d, J=8.1 Hz, ArH), 7.26 (2H, dt, J=7.1, 1.5 Hz, ArH), 7.20 (1H, dt, J=7.2, 1.5 Hz, ArH), 7.13 (1H, m, H-2), 7.12 (2H, d, J=7.2 Hz, ArH), 7.06 (1H, ddd, J=7.9, 7.1, 0.9 Hz, ArH), 6.97 (1H, ddd, J=7.9, 7.0, 0.9 Hz, ArH), 4.57 (1H, td, J=8.3, 5.7 Hz, 3-$CH_2CH$), 4.28, 4.24 (2×1H, 2×dd, J=15.9, 5.9 Hz, NH$CH_2$), 3.13 (1H, dd, J=14.4, 5.6 Hz, 3-CH), 2.93 (1H, dd, J=14.4, 8.6 Hz, 3-CH), 1.80 (3H, s, $COCH_3$).

$^{13}$C NMR: δ 171.59 (s, $COCH_3$), 169.02 (s, CONH), 139.18, 135.99 (2×s, Ar), 128.06 (d, 2C, Ar), 127.21 (s, Ar), 126.87 (d, 2C, Ar), 126.49, 123.47, 120.75, 118.39, 118.10, 111.17 (6×d, Ar), 110.11 (s, Ar), 53.53 (d, CH), 41.91 (t, NH$CH_2$), 27.92 (t, 3-$CH_2$), 22.50 (q, $CH_3$).

Analysis calculated for $C_{20}H_{21}N_3O_2$ requires: C, 71.6; H, 6.3; N, 12.5%.

Found: C, 71.5; H, 6.4; N, 12.6%.

Acidification of the aqueous portion with dilute HCl, extraction with EtOAc and evaporation gave N-acetyltryptophan (0.30 g, 30%); mp (EtOAc/light petroleum) 204°–206° C.

The above α-acetamide (1.25 g) was treated with $S_2Cl_2$ as above, then the product mixture obtained after workup was treated successively with $NaBH_4$ then $H_2O_2$ as described above. The resulting oil was chromatographed on silica gel, eluting with $CH_2Cl_2$: EtOAc (2:1) to give firstly 2,2'-thiobis[α-acetylamino-N-benzyl-3-(3-indolyl)propanamide] [VI: n=1; $R_1=R_3=H$, $R_2=CH_2CH(NHAc)CONHCH_2Ph$] (0.30 g, 23%) as a mixture of diastereoisomers; mp (EtOAc/light petroleum) 190°–194° C.

$^1$H NMR ($(CD_3)_2SO$): δ 10.97, 10.94 (2×1H, 2×s, NH), 8.50, 8.48 (2×1H, 2×br t, J=5.8 Hz, NH$CH_2$), 8.17, 8.15 (2×1H, d, J=8.4 Hz, CHN$H$), 7.63 (2×1H, d, J=7.7 Hz, ArH), 7.3–6.9 (2×8H, m, ArH), 4.75 (2×1H, m, 3-$CH_2CH$), 4.27, 4.19 (4×1H, 2×dd, J=16.1, 5.7 Hz, NH$CH_2$), 3.44 (2×1H, m, 3-CH), 3.18 (2×1H, m, 3-CH), 1.79 (2×3H, 2×s, $COCH_3$).

$^{13}$C NMR: δ 171.20, 171.18 (2×s, $C$O$CH_3$), 169.13 (s, 2C, CONH), 138.83, 138.79 (2×s, Ar), 136.66 (s, 2C, Ar), 128.03, 128.01 (2×d, 2×2C, Ar), 127.42 (s, 2C, Ar), 126.96, 126.91 (2d, 2×2C, Ar), 126.51, 126.48 (2×d, Ar), 124.58, 124.55 (2×s, Ar), 121.97 (d, 2×2C, Ar), 119.02, 118.98 (2×d, Ar), 118.66 (d, 2C, Ar), 115.01, 114.94 (2×s, Ar), 110.79 (d, 2C, Ar), 53.66, 53.59 (2×d, 3-$CH_2CH$), 42.13 (t, 2C, NH$CH_2$), 28.14, 28.07 (2×t, 3-$CH_2$), 22.52 (q, 2C, $CH_3$).

Analysis calculated for $C_{40}H_{40}N_6O_4S.0.5H_2O$ requires: C, 67.7; H, 5.8; N, 11.9; S, 4.5%.

Found: C, 67.7; H, 5.8; N, 11.9; S, 5.1%.

Elution with $CH_2Cl_2$:EtOAc (1:2) gave 2,2'-dithiobis[α-acetylamino-N-benzyl-3-(3-indolyl)propanamide] (60) [VI: n=2; $R_1=R_3=H$, $R_2=CH_2CH(NHAc)CONHCH_2Ph$] (0.84 g, 62%) as a yellow oil (a mixture of diastereoisomers). Crystallizations from $CH_2Cl_2$/light petroleum gave a single pair of diastereoisomers; mp 140°–144° C. (dec).

$^1$H NMR ($CDCl_3$): δ 9.16 (1H, s, NH), 7.51 (1H, d, J=8.1 Hz, ArH), 7.2–7.0 (6H, m, ArH), 6.89 (2H, m, ArH), 6.76 (1H, d, J=7.2 Hz, CHN$H$), 6.16 (1H, t, J=5.8 Hz, N$H$CH$_2$), 4.64 (1H, q, J=7.2 Hz, 3-$CH_2CH$), 4.20, 4.12 (2×1H, 2×dd, J=14.8, 5.9 Hz, NH$CH_2$), 3.13 (1H, dd, J=14.0, 7.1

Hz, 3-CH), 2.96 (1H, dd, J=14.0, 7.3 Hz, 3-CH), 1.84 (3H, s, COCH$_3$).

Analysis calculated for C$_{40}$H$_{40}$N$_6$O$_4$S$_2$.0.5H$_2$O requires: C, 64.8; H, 5.5; N, 11.3; S, 8.6%.

Found: C, 65.0; H, 5.4; N, 11.3; S, 8.8%.

Crystallizations from EtOAc/light petroleum gave the other pair of diastereoisomers of 60; mp 154.5°–157.5° C (dec).

$^1$H NMR (CDCl$_3$): δ 9.27 (1H, s, NH), 7.42 (1H, d, J=8.0 Hz, ArH), 7.28–7.12 (6H, m, ArH), 7.04 (1H, dd, J=7.8, 7.0 Hz, ArH), 6.75 (2H, m, ArH), 6.45 (1H, br d, J=7.1 Hz, CHNH), 5.90 (1H, br s, NHCH$_2$), 4.41 (1H, q, J=7.4 Hz, 3-CH$_2$CH), 4.17 (1H, dd, J=14.8, 6.0 Hz, NHCH), 4.08 (1H, dd, J=14.8, 5.0 Hz, NHCH), 2.99 (1H, dd, J=14.0, 6.9 Hz, 3-CH), 2.93 (1H, dd, J=13.9, 7.6 Hz, 3-CH), 1.82 (3H, s, COCH$_3$).

$^{13}$C NMR: δ 170.74 (s, COCH$_3$), 169.92 (s, CONH), 137.42, 137.28 (2×s, Ar), 128.58 (d, 2C, Ar) 127.59 (s, Ar), 127.51 (d, 2C, Ar), 127.40 (d, Ar), 126.26 (s, Ar), 124.39, 120.37, 119.51 (3×d, Ar), 118.96 (s, Ar), 111.51 (d, Ar), 54.63 (d, 3-CH$_2$CH), 43.70 (t, NHCH$_2$), 28.87 (t, 3-CH$_2$), 23.23 (q, CH$_3$).

Analysis calculated for C$_{40}$H$_{40}$N$_6$O$_4$S$_2$ requires: C, 65.6; H, 5.5; N, 11.5; S, 8.7%.

Found: C, 65.4; H, 5.6; N, 11.5; S, 8.7%.

In DMSO solution, both pure diastereomers reverted to a 1:1 mixture of diastereoisomers by disulfide exchange within 3 minutes.

Compounds 61 and 62 of Table 1

Ethyl trifluoroacetate (1.7 mL) was added to a stirred solution of DL-tryptophan (2.3 g) and triethylamine (1.6 mL) in DMF (5 mL), then the flask was sealed and purged with nitrogen, and the mixture stirred at 20° C. for 1 day (method of Curphey TJ, *J. Org. Chem.* 1979;44:2805). Excess reagents were removed under vacuum, then triethylamine (1.9 mL) and DMF (10 mL) were added, and the mixture cooled to 0° C. DEPC (98%, 2.0 mL) was added, followed by benzylamine (1.72 mL), then the mixture was stirred under nitrogen at 20° C. for 1 day. The resulting solution was diluted with water (100 mL) and extracted with EtOAc (3×100 mL). Evaporation gave an oil which was purified by chromatography on silica gel, eluting with EtOAc:light petroleum (1:1), to give DL-N-benzyl-α-trifluoroacetylamino-3-(3-indolyl)propanamide [II: R$_1$=R$_3$=H, R$_2$=CH$_2$CH(NHCOCF$_3$)CONHCH$_2$Ph] (2.21 g, 50%); mp (EtOAc/light petroleum) 181°–183° C.

$^1$H NMR ((CD$_3$)$_2$SO): δ 10.84 (1H, s, NH), 9.65 (1H, br s, CHNH), 8.79 (1H, t, J=5.5 Hz, NHCH$_2$), 7.67 (1H, d, J=7.8 Hz, ArH), 7.34 (1H, d, J=8.0 Hz, ArH), 7.30 (2H, t, J=7.2 Hz, ArH), 7.23 (1H, t, J=7.3 Hz, ArH), 7.18 (2H, d, J=7.5 Hz, ArH), 7.15 (1H, d, J=2.2 Hz, H-2), 7.07 (1H, ddd, J=8.0, 7.1, 0.9 Hz, ArH), 6.98 (1H, dd, J=7.8, 7.0 Hz, ArH), 4.63 (1H, br m, 3-CH$_2$CH), 4.32 (2H, d, J=5.8 Hz, NHCH$_2$), 3.25 (1H, dd, J=14.5, 5.0 Hz, 3-CH), 3.12 (1H, dd, J=14.5, 9.9 Hz, 3-CH).

$^{13}$C NMR: δ 169.89 (s, CONH), 156.14, (q, J$_{CF}$=36.5 Hz, COCF$_3$), 138.92, 135.97 (2×s, Ar), 128.17, 126.95 (2×d, 2×2C, Ar), 126.95 (s, Ar) 126.68, 123.77, 120.86, 118.36, 118.17 (5×d, Ar), 115.69 (q, J$_{CF}$=288 Hz, CF$_3$), 111.24 (d, Ar), 109.41 (s, Ar), 54.24 (d, 3-CH$_2$CH), 42.11 (t, NHCH$_2$), 27.08 (t, 3-CH$_2$).

Analysis calculated for C$_{20}$H$_{18}$F$_3$N$_3$O$_2$ requires: C, 61.7; H, 4.6; N, 10.8%.

Found: C, 61.9; H, 4.9; N, 10.9%.

Acidification of the aqueous portion with dilute HCl, then extraction with EtOAc (3×100 mL) and evaporation gave DL-α-trifluoroacetylamino-3-(3-indolyl)propanoic acid [II: R$_1$=R$_3$=H, R$_2$=CH$_2$CH(NHCOCF$_3$)COOH] (0.72 g, 21%); mp (water) 155°–157° C. (Weygand F, Geiger R, *Chem. Ber.* 1956;89:647 record mp 162°–163° C.).

$^1$H NMR ((CD$_3$)$_2$SO): δ 10.86 (1H, br s, NH), 9.75 (1H, br d, J=8.0 Hz, CHNH), 7.55 (1H, d, J=7.8 Hz, ArH), 7.34 (1H, d, J=8.1 Hz, ArH), 7.14 (1H, d, J=2.3 Hz, H-2), 7.07 (1H, ddd, J=8.0, 7.1, 0.9 Hz, ArH), 6.99 (1H, ddd, J=7.9, 7.0, 0.9 Hz, ArH), 4.51 (1H, ddd, J=10.2, 8.0, 4.2 Hz, 3-CH$_2$CH), 3.32 (1H, dd, J=14.8, 4.3 Hz, 3-CH), 3.17 (1H, dd, J=14.8, 10.3 Hz, 3-CH).

$^{13}$C NMR: δ 171.64 (s, COOH), 156.23 (q, J$_{CF}$=36.5 Hz, COCF$_3$), 136.01, 126.85 (2×s, Ar), 123.45, 120.93, 118.35, 117.90 (4×d, Ar), 117.09, 115.66 (q, J$_{CF}$=288 Hz, CF$_3$), 111.36 (d, Ar), 109.56 (s, Ar), 53.58 (d, 3-CH$_2$CH), 25.88 (t, 3-CH$_2$).

The above α-trifluoroacetamide (2.15 g) was treated with S$_2$Cl$_2$ as above, then the product mixture obtained after workup was chromatographed directly on silica gel. Elution with CH$_2$Cl$_2$ and CH$_2$Cl$_2$:EtOAc (19:1) gave foreruns, including mono- and trisulfides, then 2,2'-dithiobis[N-benzyl-α-trifluoroacetylamino-3-(3-indolyl)propanamide] (61) [VI: n=2; R$_1$=R$_3$=H, R$_2$=CH$_2$CH(NHCOCF$_3$)CONHCH$_2$Ph] (1.01 g, 44%) as a yellow oil (a mixture of diastereoisomers). A subsample crystallized from EtOH was a single pair of diastereoisomers; mp 160°–164° C. (decomposed). $^1$H NMR (CDCl$_3$): δ 8.76 (1H, s, NH), 7.57 (1H, d, J=8.0 Hz, CHNH), 7.43 (1H, d, J=7.9 Hz, ArH), 7.3–7.0 (6H, m, ArH), 6.75 (2H, m, ArH), 5.49 (1H, t, J=5.2 Hz, NHCH$_2$), 4.26 (1H, td, J=7.9, 6.4 Hz, 3-CH$_2$CH), 4.14 (1H, dd, J=14.8, 5.8 Hz, NHCH$_2$), 4.00 (1H, dd, J=14.5, 4.9 Hz, NHCH$_2$) 2.99 (1H, dd, J=14.0, 8.4 Hz, 3-CH), 2.77 (1H, dd, J=14.0, 5.9 Hz, 3-CH).

$^{13}$C NMR: δ 168.87 (s, CONH), 156.81 (q, J$_{CF}$=36.5 Hz, COCF$_3$), 137.25, 136.61 (2×s, Ar), 128.73 (d, 2C, Ar), 127.71 (d, 3C, Ar), 126.96, 126.11 (2×s, Ar), 124.97, 120.95, 119.25 (3×d, Ar), 118.14 (s, Ar), 115.62 (q, J$_{CF}$=288 Hz, CF$_3$), 111.49 (d, Ar), 54.67 (d, 3-CH$_2$CH), 44.02 (t, NHCH$_2$), 28.22 (t, 3-CH$_2$).

Analysis calculated for C$_{40}$H$_{34}$F$_6$N$_6$O$_4$.0.5H$_2$O requires: C, 56.5; H, 4.1; N, 9.9; S, 7.5%.

Found: C, 56.6; H, 4.3; N, 9.8; S, 7.6%.

The trifluoroacetamide disulfide (61) (0.80 g) was treated with excess NaBH$_4$ at 20° C. as above, then the resulting oil was chromatographed on alumina. Elution with CHCl$_3$:EtOH (99:1) gave foreruns, then elution with CHCl$_3$:EtOH (98:2) gave 2,2'-dithiobis[α-amino-N-benzyl-3-(3-indolyl)propanamide] (62) [VI: n=2; R$_1$=R$_3$=H, R$_2$=CH$_2$CH(NH$_2$)CONHCH$_2$Ph] (0.14 g, 22%); mp (CH$_2$Cl$_2$/light petroleum) 147°–150° C. (decomposed).

$^1$H NMR ((CD$_3$)$_2$SO): δ 11.56 (1H, s, NH), 8.18 (1H, t, J=5.8 Hz, NHCH$_2$), 7.61 (1H, d, J=7.8 Hz, ArH), 7.36 (1H, d, J=8.1 Hz, ArH), 7.33–6.95 (7H, m, ArH), 4.23, 4.13 (2×1H, 2×dd, J=15.2, 5.8 Hz, NHCH$_2$), 3.41 (1H, br m, 3-CH$_2$CH), 2.93 (1H, dd, J=13.7, 4.9 Hz, 3-CH), 2.64 (1H, br m, 3-CH), 1.7 (2H, br s, NH$_2$).

$^{13}$C NMR: δ 174.12 (s, CONH), 139.13, 137.38 (2×s, Ar), 128.06, 127.02 (2×d, 2×2C, Ar), 126.95, 126.71 (2×s, Ar), 126.51, 123.19, 119.62 (3×d, Ar), 119.18 (s, Ar), 118.87, 111.39 (2×d, Ar), 55.57 (d, 3-CH$_2$CH), 41.90 (t, NHCH$_2$), 30.58 (t, 3-CH$_2$).

Analysis calculated for $C_{36}H_{36}N_6O_2S_2 \cdot 0.5H_2O$ requires: C, 65.8; H, 5.6; N, 12.8%.

Found: C, 65.8; H, 5.8; N, 12.6%.

Compound 63 of Table 1

Acetyl chloride (0.50 mL, 7.0 mmol) was added to a stirred solution of DL-3-(3-indolyl)lactic acid (1.00 g, 14.3 mmol) and $Et_3N$ (2 mL, 14.3 mmol) in THF (5 mL) at 0° C. The mixture was stirred at 0° C. for 7 hours, then at 20° C. for 15 hours, quenched with water (100 mL), acidified with dilute HCl (to pH 2), then extracted with EtOAc (3×100 mL). Evaporation gave crude (ca. 90% pure) DL-α-acetoxy-3-(3-indolyl)propanoic acid [II: $R_1=R_3=H$, $R_2=CH_2CH(OAc)COOH$] (1.30 g) as an oil which was used directly.

$^1H$ NMR (($CD_3$)$_2$SO): δ 10.88 (1H, s, NH), 7.54 (1H, d, J=7.8 Hz, ArH), 7.33 (1H, d, J=8.0 Hz, ArH), 7.17 (1H, br s, H-2), 7.06 (1H, dd, J=8.0, 7.1 Hz, ArH), 6.99 (1H, t, J=7.4 Hz, ArH), 5.06 (1H, dd, J=7.3, 4.9 Hz, 3-CH$_2$C$\underline{H}$), 3.22 (1H, dd, J=15.1, 4.5 Hz, 3-CH), 3.16 (1H, dd, J=15.0, 7.7 Hz, 3-CH), 2.00 (3H, s, COCH$_3$).

$^{13}C$ NMR: δ 170.87, 169.96 (2×s, COOH, OCOCH$_3$), 136.04, 127.28 (2×s, Ar), 123.84, 120.94, 118.43, 118.33, 111.39 (5×d, Ar), 108.90 (s, Ar), 72.70 (d, 3-CH$_2$$\underline{C}$H), 26.75 (t, 3-CH$_2$), 20.54 (q, CH$_3$).

HREIMS m/z calculated for $C_{13}H_{13}NO_4$: 247.0845 (M$^+$). Found: 247.0848.

The above α-O-acetate (1.30 g of 90%, 4.4 mmol) and $Et_3N$ (0.88 mL, 6.3 mmol) in DMF (10 mL) at 0° C. was treated sequentially with DEPC (0.91 mL of 98%, 5.9 mmol) and benzylamine (0.69 mL, 6.3 mmol), and the mixture was stirred under nitrogen at 20° C. for 18 hours. Workup and chromatography on silica gel, eluting with EtOAc/light petroleum (1:2 then 1:1) gave DL-α-acetoxy-N-benzyl-3-(3-indolyl)propanamide [II: $R_1=R_3=H$, $R_2=CH_2CH(OAc)CONHCH_2Ph$] (0.29 g, 18%) as an oil.

$^1H$ NMR (CDCl$_3$): δ 8.05 (1H, s, NH), 7.60 (1H, d, J=7.9 Hz, ArH), 7.37 (1H, dt, J=8.1, 0.9 Hz, ArH), 7.26–7.21 (3H, m, ArH), 7.20 (1H, ddd, J=8.1, 7.0, 1.1 Hz, ArH), 7.12 (1H, ddd, J=8.0, 7.0, 1.0 Hz, ArH), 6.97 (1H, d, J=2.4 Hz, H-2), 6.94 (2H, m, ArH), 6.07 (1H, t, J=5.8 Hz, N$\underline{H}$CH$_2$), 5.47 (1H, t, J=5.4 Hz, 3-CH$_2$C$\underline{H}$), 4.38 (1H, dd, J=14.9, 6.1 Hz, NHC$\underline{H}$), 4.29 (1H, dd, J=14.9, 5.5 Hz, NHC$\underline{H}$), 3.41 (2H, d, J=5.5 Hz, 3-CH$_2$), 2.06 (3H, s, COCH$_3$).

$^{13}C$ NMR: δ 169.63, 169.33 (2×s, CONH, OCOCH$_3$), 137.56, 136.05 (2×s, Ar), 128.55 (d, 2C, Ar), 127.75 (s, Ar), 127.60 (d, 2C, Ar), 127.40, 123.43, 122.08, 119.61, 118.92, 111.13 (6×d, Ar), 109.83 (s, Ar), 74.56 (d, 3-CH$_2$$\underline{C}$H), 43.12 (t, NHCH$_2$), 27.42 (t, 3-CH$_2$), 21.09 (q, CH$_3$).

HREIMS m/z calculated for $C_{20}H_{20}N_2O_3$: 336.1474 (M$^+$). Found: 336.1471.

Unreacted α-acetoxy-3-(3-indolyl)propanoic acid (0.68 g, 52%) was also recovered.

Alternative Preparation of Above Acetoxypropanamide

A solution of $SnCl_4$ (5.4 mL, 46 mmol) in $CCl_4$ (50 mL) was added dropwise to a stirred solution of indole (5.4 g, 46 mmol) and N-benzyl-2,3-epoxypropanamide (Dolzani L, Tamaro M, Monti-Bragadin C, Cavicchionz G, Vecchiati G, D'Angeli F, *Mutation Res.* 1986;172:37) (14 g of 85%, 67 mmol) in $CCl_4$ (100 mL) at −5° C. (method of Entzeroth M, Kunczik T, Jaenicke L, *Liebig's Ann. Chim.* 1983:226). The mixture was stirred at 20° C. for 16 hours, then diluted with $CHCl_3$ (100 mL) and 10% $NaHCO_3$ (250 mL) and stirred vigorously for 4 hours. The aqueous portion was separated and extracted with $CH_2Cl_2$ (2×100 mL), and the combined organic extracts were washed with water, dried, and the solvents removed. The resulting oil was chromatographed on silica gel, eluting with $CH_2Cl_2$/light petroleum (1:1) to yield unreacted indole (1.27 g, 24%). Elution with $CH_2Cl_2$ gave mixtures, then $CH_2Cl_2$/EtOAc (4:1) gave a crude product. This was crystallized successively from $CH_2Cl_2$/light petroleum, then $CH_2Cl_2$/benzene/light petroleum to give DL-N-benzyl-α-hydroxy-3-(3-indolyl)propanamide [II: $R_1=R_3=H$, $R_2=CH_2CH(OH)CONHCH_2Ph$] (0.70 g, 5%); mp 127°–128.5° C.

$^1H$ NMR (($CD_3$)$_2$SO): δ 10.79 (1H, s, NH), 8.20 (1H, t, J=6.2 Hz, N$\underline{H}$CH$_2$), 7.56 (1H, d, J=7.8 Hz, ArH), 7.34 (1H, d, J=8.1 Hz, ArH), 7.24 (2H, m, ArH), 7.19 (1H, m, ArH), 7.12 (1H, d, J=2.3 Hz, H-2), 7.10 (1H, m, ArH), 7.05 (1H, ddd, J=8.0, 7.0, 1.0 Hz, ArH), 6.96 (1H, ddd, J=7.9, 7.0, 0.9 Hz, ArH), 5.54 (1H, d, J=5.7 Hz, OH), 4.26 (2H, d, J=6.2 Hz, NHCH$_2$), 4.19 (1H, ddd, J=7.5, 5.7, 4.3 Hz, 3-CH$_2$C$\underline{H}$), 3.14 (1H, dd, J=14.5, 4.1 Hz, 3-CH), 2.91 (1H, dd, J=14.5, 7.6 Hz, 3-CH).

$^{13}C$ NMR: δ 173.59 (s, CONH), 139.40, 135,93 (2×s, Ar), 128.00 (d, 2C, Ar), 127.60 (s, Ar), 126.95 (d, 2C, Ar), 126.42, 123.58, 120.56, 118.60, 117.97, 111.05 (6×d, Ar), 110.53 (s, Ar), 71.86 (d, 3-CH$_2$$\underline{C}$H), 41.60 (t, NHCH$_2$), 30.33 (t, 3-CH$_2$).

Analysis calculated for $C_{18}H_{18}N_2O_2 \cdot 0.25H_2O$ requires: C, 72.4; H, 6.2; N, 9.4%.

Found: C, 72.4; H, 6.0; N, 9.3%.

This α-hydroxypropanamide (0.62 g, 2.1 mmol) was stirred with pyridine (1.5 mL, 18.5 mmol) and $Ac_2O$ (1.7 mL, 18.0 mmol) at 20° C. for 17 hours. The mixture was partitioned between water and $CH_2Cl_2$, and worked up to give a quantitative yield of DL-α-acetoxy-N-benzyl-3-(3-indolyl)propanamide [II: $R_1=R_3=H$, $R_2=CH_2CH(OAc)CONHCH_2Ph$].

This compound (1.07 g) was treated with $S_2Cl_2$ as above, and the resulting product mixture chromatographed on silica gel, eluting with $CH_2Cl_2$/EtOAc (19:1), to give firstly 2,2'-thiobis-[α-acetoxy-N-benzyl-3-(3-indolyl)propanamide] [VI: n=1, $R_1=R_3=H$, $R_2=CH_2CH(OAc)CONHCH_2Ph$] (0.19 g, 17%) as a mixture of diastereoisomers; mp (MeOH/dilute HCl) 105°–109° C.

$^1H$ NMR (CDCl$_3$): δ 10.09, 10.06 (2×1H, 2×s, NH), 7.61, 7.60 (2×1H, 2×d, J=7.9 Hz, ArH), 7.24 (2×1H, d, J=8.2 Hz, ArH), 7.14–7.00 (2×5H, m, ArH), 6.78, 6.70 (2×2H, 2×m, ArH), 6.27, 6.26 (2×1H, 2×t, J=5.8 Hz, N$\underline{H}$CH$_2$), 5.72 (1H, dd, J=7.0, 6.0 Hz, 3-CH$_2$C$\underline{H}$), 5.69 (1H, t, J=6.1 Hz, 3-CH$_2$C$\underline{H}$), 4.30, 4.27 (2×1H, 2×dd, J=15.0, 5.8 Hz, NHC$\underline{H}$), 4.23, 4.21 (2×1H, 2×dd, J=15.0, 5.4 Hz, NHC$\underline{H}$), 3.67 (1H, dd, J=14.5, 7.0 Hz, 3-CH), 3.65 (1H, dd, J=14.7, 5.8 Hz, 3-CH), 3.60 (1H, dd, J=14.7, 6.3 Hz, 3-CH), 3.53 (1H, dd, J=14.5, 6.0 Hz, 3-CH) 2.12, 2.11 (2×3H, 2×s, COCH$_3$).

$^{13}C$ NMR (CDCl$_3$): δ 169.87, 169.73 (2×s, 2×2C, COCH$_3$, CONH), 137.09, 137.03, 136.70, 136.65 (4×s, Ar), 128.60, 128.56 (2×d, 2×2C, Ar), 127.48, 127.44 (2×d, Ar), 127.43, 127.39 (2×s, Ar), 127.31, 127.28 (2×d, 2×2C, Ar), 125.47, 125.40 (2×s, Ar), 122.95, 122.93 (2×d, Ar), 119.64 (d, 2C, Ar), 119.07, 118.88 (2×d, Ar), 113.92, 113.70 (2×s, Ar), 111.32 (d, 2C, Ar), 73.99, 73.77 (2×d, 3-CH$_2$$\underline{C}$H), 43.31 (t, 2C, NHCH$_2$), 28.00 (t, 2C, 3-CH$_2$), 21.19, 21.13 (2×q, CH$_3$).

Analysis calculated for $C_{40}H_{38}N_4O_2S$ requires: C, 68.4; H, 5.4; N, 8.0; S, 4.6%.

Found: C, 68.2; H, 5.6; N, 8.0; S, 4.8%.

Elution with $CH_2Cl_2/EtOAc$ (9:1) gave 2,2'-dithiobis[α-acetoxy-N-benzyl-3-(3-indolyl)propanamide] (63) [VI: n=2, $R_1=R_3=H$ $R_2=CH_2CH(OAc)CONHCH_2Ph$] (0.76 g, 65%) as a yellow oil (mixture of diastereoisomers). A subsample crystallized from $CH_2Cl_2$/dilute HCl as a single pair of diastereoisomers; mp 120°–124° C. (dec).

$^1$H NMR (CDCl$_3$): δ 8.64 (1H, s NH) 7.60 (1H d J=7.9 Hz, ArH), 7.27–7.15 (4H, m, ArH), 7.12, 7.11 (2×1H, 2×t, J=8.1 Hz, ArH), 6.91 (2H, m, ArH), 6.12 (1H, t, J=5.6 Hz, N$\underline{H}$CH$_2$), 5.41 (1H, t, J=6.2 Hz, 3-CH$_2$C$\underline{H}$), 4.30, 4.24 (2×1H, 2×dd, J=14.8, 5.71 Hz, NHC$\underline{H}_2$), 3.31 (1H, dd, J=14.5, 5.8 Hz, 3-CH), 3.17 (1H, dd, J=14.5, 6.6 Hz, 3-CH), 1.99 (3H, s, COCH$_3$).

$^{13}$C NMR (CDCl$_3$): δ 169.65, 168.96 (2×s, CONH, $\underline{C}$OCH$_3$), 137.50, 137.05 (2×s, Ar), 128.63 (d, 2C, Ar), 127.81 (s, Ar), 127.68 (d, 2C, Ar), 127.49 (d, Ar), 126.85 (s, Ar), 124.30, 120.30, 120.03 (3×d, Ar), 117.87 (s, Ar), 111.33 (d, Ar), 74.06 (d, 3-CH$_2$$\underline{C}$H), 43.30 (t, NHCH$_2$), 27.45 (t, 3-CH$_2$), 21.18 (q, CH$_3$).

Analysis calculated for $C_{40}H_{38}N_4O_2S_2$ requires: C, 65.4; H, 5.2; N, 7.6; S, 8.7%.

Found: C, 65.2; H, 5.2, N, 7.8; S, 8.8%.

Compound 64 of Table 1

Hydrolysis of 63 with excess KHCO$_3$ in aqueous MeOH at 20° C. for 2 hours gave 2,2'-dithiobis[α-hydroxy-N-(phenylmethyl)- 1H-indole-3-propanamide] (64) [II: $R_1=R_3=H$, $R_2=Ch_2CH(OH)COOH$] as an oil (mixture of diastereomers) in essentially quantitative yield. Crystallization from $CH_2Cl_2$/light petroleum gave a single pair of diastereomers (66% yield); mp 120°–125° C.

$^1$H NMR (CDCl$_3$): δ 7.61 (1H, d, J=8.0 Hz, ArH), 7.33–7.17 (5H, m, ArH), 7.12 (2H, dd, J=7.8, 1.5 Hz, ArH), 7.09 (1H, ddd, J=8.1, 5.4, 2.7 Hz, ArH), 6.80 (1H, t, J=5.8 Hz, NHCH$_2$), 4.33, 4.27 (2×1H, 2×dd, J=14.8, 5.9 Hz, NHCH$_2$), 3.78 (1H, ddd, J=9.5, 5.4, 3.4 Hz, 3-CH$_2$CH), 3.30 (1H, d, J=5.4 Hz, OH), 3.24 (1H, dd, J=14.4, 3.4 Hz, 3-CH), 2.88 (1H, dd, J=14.3, 9.5 Hz, 3-CH).

Analysis calculated for $C_{36}H_{34}N_4O_4S_2$ requires: C, 66.1; H, 5.3; N, 8.6; S, 9.6%.

Found: C, 66.5; H, 5.2; N, 8.6; S, 9.8%

Example C

Preparation of Compounds 5 and 33 of Table 1 by the Method Outlined in Scheme 3

1-Methyl-2-indolinone [VII: $R_1=H$, $R_3=Me$] was condensed with diethyl oxalate in NaOEt/EtOH, to give ethyl 1-methyl isatylidenehydroxyacetate [VIII: $R_1=H$, $R_3=Me$, R=COOEt] (82% yield); mp 62°–64° C. (according to the method of Porter JC, Robinson R, Wyler M, *J. Chem. Soc.* 1941:620, who report mp 81° C.). The above acetate [VIII: $R_1=H$, $R_3=Me$, R=COOEt] (2.30 g) was hydrogenated in glacial AcOH (150 mL) containing concentrated H$_2$SO$_4$ (1 mL) and 5% Pd/C catalyst (5 g) for 1 day. The reaction mixture was filtered onto NaOAc (4 g) and the solvent removed under reduced pressure. The residue was partitioned between CH$_2$Cl$_2$ and water, then the aqueous phase re-extracted with CH$_2$Cl$_2$. The CH$_2$Cl$_2$ extracts were combined, washed with water, the solvent removed, and the residue was chromatographed on silica gel. Elution with CH$_2$Cl$_2$ gave ethyl 2-(1-methyl-2-oxo-3-indolinyl)acetate [III: $R_1=H$, $R_2=CH_2COOEt$, $R_3=Me$] as an oil (1.23 g, 57%).

$^1$H NMR (CDCl$_3$): δ 7.29 (1H, t, J=7.7 Hz, ArH), 7.26 (1H, d, J=7.5 Hz, ArH), 7.03 (1H, t, J=7.5 Hz, ArH), 6.84 (1H, d, J=7.7 Hz, ArH), 4.15, 4.11 (2×1H, 2×dq, J=10.8, 7.1 Hz, COOCH$_2$), 3.79 (1H, dd, J=8.0, 4.4 Hz, H-3), 3.23 (3H, s, NCH$_3$), 3.07 (1H dd, J=16.8, 4.4 Hz, CH$_2$CO), 2.78 (1H, dd, J=16.8, 8.1 Hz, CH$_2$CO), 1.20 (3H, t, J=7.1 Hz, OCH$_2$C$\underline{H}_3$).

$^{13}$C NMR (CDCl$_3$): δ 176.72 (s, $\underline{C}$ONCH$_3$), 171.02 ($\underline{C}$OOCH$_2$) 144.35 (s, ArH), 128.27 (d, ArH), 128.18 (s, ArH), 123.80, 122.45, 108.01 (3×d, ArH), 60.85 (t, OCH$_2$), 41.83 (d, C-3), 34.94 (t, $\underline{C}$H$_2$CO), 26.28 (q, NCH$_3$), 14.05 (q, OCH$_2$$\underline{C}$H$_3$).

The above oxoacetate [III: $R_1=H$, $R_2=CH_2COOEt$, $R_3=Me$] was treated with P$_2$S$_5$ as described in Example A, then chromatographed on silica gel, with CH$_2$Cl$_2$/light petroleum (3:2) eluting ethyl 2-(1-methyl-2-thioxo-3-indolinyl)acetate [IV: $R_1=H$, $R_2=CH_2COOEt$, $R_3=Me$] (5) (90% yield); mp (benzene/light petroleum) 47°–48° C.

$^1$H NMR (CDCl$_3$): δ 7.35 (2H, m, ArH), 7.16 (1H, td, J=7.5, 0.8 Hz, ArH), 7.01 (1H, dd, J=7.7, 1.0 Hz, ArH), 4.15 (2H, q, J=7.1 Hz, COOCH$_2$), 4.14 (1H, m, H-3), 3.65 (3H, s, NCH$_3$), 3.39 (1H, dd, J=17.0, 4.1 Hz, CH$_2$CO), 2.83 (1H, dd, J=17.0, 8.6 Hz, CH$_2$CO), 1.22 (3H, t, J=7.1 Hz, OCH$_2$C$\underline{H}_3$).

$^{13}$C NMR (CDCl$_3$): δ 204.35 (s, $\underline{C}$SNCH$_3$), 171.11 (s, $\underline{C}$OOCH$_2$), 145.73, 133.01 (2×s, ArH), 128.39, 124.34, 123.94, 109.46 (4×d, ArH), 60.85 (t, OCH$_2$), 53.44 (d, C-3), 38.66 (t, $\underline{C}$H$_2$CO), 31.52 (q, NCH$_3$), 14.13 (q, OCH$_2$$\underline{C}$H$_3$).

Analysis calculated for $C_{13}H_{15}NO_2S$ requires: C, 62.7; H, 6.0; N, 5.6; S, 12.9%.

Found: C, 62.5; H, 6.2; N, 5.6; S, 12.8%.

A solution of crude 5 in EtOH was exposed to air for 2 weeks, during which time bis[ethyl 1-methylindolyl-3-acetate-(2)]disulfide [V: $R_1=H$, $R_2=CH_2COOEt$, $R_3=Me$] (33) slowly separated as yellow needles (0.18 g, 26%); mp 117°–119° C.

$^1$H NMR (CDCl$_3$): δ 7.53 (1H, dt, J=8.0, 0.8 Hz, ArH), 7.30 (1H, ddd, J=8.3, 6.3, 1.1 Hz, ArH), 7.27 (1H, ddd, J=8.1, 1.6, 0.7 Hz, ArH), 7.12 (1H, ddd, J=8.0, 6.2, 1.8 Hz, ArH), 3.96 (2H, q, J=7.1 Hz, COOCH$_2$), 3.54 (3H, s, NCH$_3$), 3.38 (2H, s, CH$_2$CO), 1.14 (3H, t, J=7.1 Hz, OCH$_2$C$\underline{H}_3$).

$^{13}$C NMR (CDCl$_3$): δ 171.06 (s, $\underline{C}$OOCH$_2$), 138.45, 128.42, 126.47 (3×s, ArH), 124.33, 120.20, 120.07 (3×d, ArH), 117.59 (s, ArH), 109.93 (d, ArH), 60.70 (t, OCH$_2$), 30.99 (t, $\underline{C}$H$_2$CO), 29.97 (q, NCH$_3$), 14.13 (q, OCH$_2$$\underline{C}$H$_3$).

Analysis calculated for $C_{26}H_{28}N_2O_4S_2$ requires: C, 62.9; H, 5.7; N, 5.7; S, 12.9%.

Found: C, 62.7; H, 5.6; N, 5.6; S, 13.0%.

Compounds 10 and 38 of Table 1

Similar reactions on 2-indolinone [VII: $R_1=R_3=H$], using diethyl malonate, gave ethyl 3-(2-oxo-3-indolinyl)propanoate [III: $R_1=R_3=H$, $R_2=(CH_2)_2COOE$] (Julian PL, Printy HC, *J. Am. Chem. Soc.* 1953;75:5301). Reaction of this with P$_2$S$_5$ as described in Example A, followed by chromatography on silica gel, elution with CH$_2$Cl$_2$, and crystallization from benzene/light petroleum over 2 days, gave bis[ethyl indolyl-3-propanoate-(2)]disulfide [V: $R_1=R_3=H$, $R_2=(CH_2)_2COOEt$] (38) (18% yield); mp 137°–139° C.

¹H NMR (CDCl₃): δ 8.25 (1H, s, NH), 7.55 (1H, d, J=8.0 Hz, ArH), 7.22 (2H, m, ArH), 7.11 (1H, ddd, J=8.0, 5.0, 3.0 Hz, ArH), 4.02 (2H, q, J=7.1 Hz, COOCH₂), 2.98, 2.46 (2×2H, 2×t, J=7.9 Hz, CH₂CH₂CO), 1.16 (3H, t, J=7.1 Hz, OCH₂CH₃).

¹³C NMR (CDCl₃): δ 173.03 (s, $\underline{C}$OOCH₂), 137.26, 127.22, 125.83 (3×s, ArH), 124.26 (d, ArH), 122.81 (s, ArH), 120.03, 119.63, 111.19 (3×d, ArH), 60.41 (t, COO$\underline{C}$H₂), 35.20 (t, CH₂CO), 20.26 (t, 3-CH₂), 14.14 (q, OCH₂$\underline{C}$H₃).

Analysis calculated for C₂₆H₂₈N₂O₄S₂ requires: C, 62.9; H, 5.7; N, 5.6; S, 12.9%.

Found: C, 63.3; H, 5.9; N, 5.7; S, 13.0%.

Treatment of the mother liquors with NaBH₄ gave ethyl 3-(2-thioxo-3-indolinyl)propanoate [IV: R₁=R₃=H, R₂=(CH₂)₂COOEt] (10) (56% yield) as an oil.

¹H NMR (CDCl₃): δ 10.40 (1H, s, NH), 7.31 (1H, d, J=7.4 Hz, ArH), 7.27 (1H, td, J=7.8, 0.7 Hz, ArH), 7.14 (1H, td, J=7.5, 0.7 Hz, ArH), 7.01 (1H, d, J=7.8 Hz, ArH), 4.07, 4.03 (2×1H, 2×dq, J=10.8, 7.1 Hz, COOCH₂), 3.91 (1H, t, J=5.4 Hz, H-3), 2.52 (2H, m, C$\underline{H}$₂CH₂CO), 2.41 (1H, ddd, J=15.8, 9.9, 5.9 Hz, CH₂CO), 2.10 (1H, ddd, J=15.8, 9.1, 6.7 Hz, CH₂CO), 1.20 (3H, t, J=7.1 Hz, OCH₂C$\underline{H}$₃).

¹³C NMR (CDCl₃): δ 207.31 (s, CSNH), 172.96 (s, $\underline{C}$OOCH₂), 143.31, 133.15 (2×s, ArH), 128.40, 124.34, 124.07, 110.04 (4×d, ArH), 60.55 (t, OCH₂), 56.44 (d, C-3), 29.56, 28.16 (2×t, (CH₂)₂CO), 14.15 (q, OCH₂CH₃).

Analysis calculated for C₁₃H₁₅NO₂S requires: C, 62.6; H, 6.1; N, 5.6; S, 12.9%.

Found: C, 62.3; H, 5.9; N, 5.6; S, 12.6%.

Compounds 12 of Table 1

Similar treatment of 1-methyl-2-indolinone, using diethyl malonate, and subsequent thiation, gave ethyl 3-(1-methyl-2-thioxo-3-indolinyl)propanoate [IV: R₁=H, R₂=(CH₂)₂COOEt, R₃=Me] (12); mp (benzene/light petroleum) 61°–63° C.

¹H NMR (CDCl₃): δ 7.35 (2H, m, ArH), 7.20 (1H, t, J=7.5 Hz, ArH), 7.00 (1H, d, J=7.8 Hz, ArH), 4.05, 4.02 (2×1H, 2×dq, J=10.8, 7.1 Hz, COOCH₂), 3.92 (1H, t, J=5.4 Hz, H-3), 3.63 (3H, s, NCH₃), 2.53 (2H, td, J=8.0, 5.4 Hz, CH₂CH₂CO), 2.32, 2.01 (2×1H, 2×td, J=16.0, 8.0 Hz, CH₂CH₂CO), 1.19 (3H, t, J=7.1 Hz, CH₂C$\underline{H}$₃).

¹³C NMR (CDCl₃): δ 204.85 (s, $\underline{C}$SNCH₃), 172.87 (s, $\underline{C}$OOCH₂), 145.89, 132.44 (2×s, ArH), 128.37, 124.30, 124.00, 109.49 (4×d, ArH), 60.43 (t, OCH₂), 56.29 (d, C3), 31.35 (q, NCH₃), 29.53, 28.46 (2×t, CH₃CH₂CO), 14.15 (q, OCH₂$\underline{C}$H₃).

Analysis calculated for C₁₄H₁₇NO₂S requires: C, 63.9; H, 6.5; N, 5.3; S, 12.2%.

Found: C, 64.1; H, 6.7; N, 5.4; S, 12.0%.

Compounds 41 and 42 of Table 1

Similar treatment of 5-methyl-2-indolinone [VII: R₁=5-Me, R₃=H] gave bis[ethyl 5-methylindolyl-3-propanoate-(2)]disulfide [V: R₁=5-Me, R₂=(CH₂)₂COOEt, R₃=H] (42) as a yellow solid; mp (benzene/petroleum ether) 138.5°–139° C.

¹H NMR (CDCl₃): 8.10 (1H, s, NH), 7.32 (1H, d, J=0.6 Hz, H-4), 7.15 (1H, d, J=8.3 Hz, H-7), 7.06 (1H, dd, J=8.3, 1.4 Hz, H-6), 4.03 (2H, q, J=7.2 Hz, C$\underline{H}$₂CH₃), 3.02–2.85 (2H, m, CH₂CH₂CO₂), 2.51–2.36 (2H, m, CH₂CH₂CO₂), 2.43 (3H, s, ArCH₃), 1.18 (3H, t, J=7.2 Hz, CH₂C$\underline{H}$₃).

¹³C NMR (CDCl₃): δ 173.1 (CO₂Et), 135.6, 129.3, 127.4, 125.9, 122.3 (C-2,3,5,8,9), 126.0, 119.1, 110.9 (C-4,6,7), 60.4 (O$\underline{C}$H₂CH₃), 35.2 ($\underline{C}$H₂CH₂CO2), 21.5 (ArCH₃), 20.3 (CH₂$\underline{C}$H₂CO2), 14.1 (OCH₂$\underline{C}$H₃).

Analysis calculated for C₂₈H₃₂N₂O₄S₂.0.5C₆H₆ requires: C, 66.1; H, 6.3; N, 5.0; S, 11.4%.

Found: C, 66.2; H, 6.4; N, 5.0; S, 11.7%.

Ester hydrolysis of 42 as above gave bis[5-methylindolyl-3-propanoic acid-(2)]disulfide [V: R₁=5-Me, R₂=(CH)₂CO₂H, R₃=H] (41) as orange-brown prisms; mp (CH₂Cl₂/petroleum ether) 91.5°–95° C.

¹H NMR (CDCl₃): δ 7.98 (1H, s, NH), 7.33 (1H, s, H-4), 7.14 (1H, d, J=8.4 Hz, H-7), 7.07 (1H, dd, J=8.4, 1.3 Hz, H-6), 2.98 (2H, t, J=7.5 Hz, CH₂CH₂CO₂), 2.56 (2H, t, J=7.5 Hz, CH₂CH₂CO₂), 2.43 (3H, s, ArCH₃).

HREIMS m/z calculated for C₂₄H₂₄N₂O₄S₂ requires: 235.06670.

Found: m/z 235.06639.

Compounds 43 and 44 of Table 1

Similar treatment of 6-methyl-2-indolinone [VII: R₁=6-Me, R₃=H] gave bis[ethyl 6-methylindolyl-3-propanoate-(2)]disulfide [V: R₁=6-Me, R₂=(CH₂)₂COOEt, R₃=H] (44) as a yellow solid; mp 122°–123.5° C.

¹H NMR (CDCl₃): δ 8.06 (1H, s, NH), 7.43 (1H, d, J=8.2 Hz, H-4), 7.03–7.00 (1H, m, H-7), 6.97–6.92 (1H, m, H-5), 4.02 (2H, q, J=7.2 Hz, C$\underline{H}$₂CH₃), 2.98–2.91 (2H, m, CH₂CH₂CO), 2.48–2.42 (2H, m, CH₂CH₂CO), 2.44 (3H, s, ArHMe), 1.17 (3H, t, J=7.2 Hz, CH₂C$\underline{H}$₃).

¹³C NMR (CDCl₃): δ 173.0 (CO₂Et), 137.7, 134.3, 125.2, 125.0, 122.9 (C-2,3,6,8,9), 121.9, 119.3 (C-4,5,7), 60.3 (O$\underline{C}$H₂CH₃), 35.2 ($\underline{C}$H₂CH₂CO₂), 21.8 (ArCH₃), 20.3 (CH₂$\underline{C}$H₂CO₂), 14.1 (OCH₂$\underline{C}$H₃).

Analysis calculated for C₂₈H₃₂N₂O₄S₂ requires: C, 64.1; H, 6.2; N, 5.3; S, 12.2%.

Found: C, 64.1; H, 6.2; N, 5.4; S, 12.0%.

Ester hydrolysis of the above as above gave bis[methylindolyl-3-propanoate-(2)]disulfide [V: R₁=6-Me, R₂=(CH₂)₂COOEt, R₃=H] (43) as yellow microcrystals; mp (CH₂Cl₂/petroleum ether) 126°–128° C.

¹H NMR ((CD3)₂CO): δ 10.34 (1H, br s, NH), 7.49 (1H, d, J=8.2 Hz, H-4), 7.19 (H, s, H-7), 6.19 (1H, dd, J=8.2, 1.2 Hz, H-5), 2.97–2.90 (2H, m, CHCH₂CO₂), 2.49–2.43 (2H, m, CH₂CH₂CO₂), 2.42 (3H, s, ArCH₃).

Analysis calculated for C₂₄H₂₄N₂O₄S₂.H₂O requires: C, 60.4; H, 5.9; N, 5.9%.

Found: C, 60.2; H, 5.3; N, 5.9%.

Compounds 45 and 46 of Table 1

Similar treatment of 7-methyl-2-indolinone [VII: R₁=7-Me, R₃=H] gave bis[ethyl 7-methylindolyl-3-propanoate-(2)]disulfide [V: R₁=7-Me, R₂=(CH₂)₂COOEt, R₃=H] (46) as a yellow solid; mp (benzene/petroleum ether) 120°–122.5° C.

¹H NMR (CDCl₃): δ 8.23 (1H, s, NH), 7.38 (1H, d, J=7.4 Hz, ArH), 7.00 (1H, t, J=7.3 Hz, H-5), 6.94 (1H, d, J=6.3 Hz, ArH), 4.02 (2H, q, J=7.2 Hz, C$\underline{H}$₂CH₃), 3.16 (2H, t, J=7.5 Hz, CH₂CH₂CO₂), 2.71 (2H, t, J=7.5 Hz, CH₂CH₂CO₂), 1.96 (3H, S, ArCH₃), 1.23 (3H, t, J=7.2 Hz, CH₂C$\underline{H}$₃).

¹³C NMR (CDCl₃): δ 173.6 (CO₂Et), 136.9, 127.0, 124.8, 122.9, 121.0 (C-2,3,7,8,9) 124.3, 120.0, 117.0 (C-4,5,6), 60.6 (O$\underline{C}$H₂CH₃), 35.3 ($\underline{C}$H₂CH₂CO₂), 20.9 (CH₂$\underline{C}$H₂CO₂), 16.0 (ArCH₃), 14.1 (OCH₂$\underline{C}$H₃).

Analysis calculated for $C_{28}H_{32}N_2O_4S_2$ requires: C, 64.1; H, 6.2; N, 5.3; S, 12.2%.

Found: C, 64.2; H, 6.4; N, 5.4; S, 12.0%.

Ester hydrolysis of 46 as above gave bis[7-methylindolyl-3-propanoic acid-(2)]disulfide [V: $R_1$=7-Me, $R_2$=$(CH_2)_2CO_2H$, $R_3$=H] (45) as green needles; mp (AcOH/petroleum ether) 172.5°–175° C.

$^1$H NMR ($(CD3)_2CO$): δ 10.37 (1H, br s, NH), 7.45 (1H, d, J=7.0 Hz, ArH), 7.03–6.95 (2H, m, ArH), 3.01–2.94 (2H, m, $CH_2CH_2CO_2$), 2.50–2.42 (2H, m, $CH_2CH_2CO_2$), 2.49 (3H, s, ArCH$_3$).

Analysis calculated for $C_{24}H_{24}N_2O_4S_2$ requires: C, 61.5; H, 5.2; N, 6.0%.

Found: C, 61.3; H, 5.1; N, 6.0%.

Example D

Preparation of Compounds 21–23 and 70 of Table 1 by the Method Outlined in Scheme 4

Powdered $Na_2CO_3$ (0.70 g, 6.61 mmol) was added to a suspension of $P_2S_5$ (2.93 g, 6.61 mmol) in THF (40 mL) and the mixture was stirred vigorously at 20° C. until homogeneous, and gas evolution had ceased (15 minutes). A solution of 1-methyl -2-indolinone [VII: $R_1$=$R_3$=Me] (0.80 g, 5.50 mmol) in THF (10 mL) was added and stirring was continued for 18 hours. After pouring into brine, the mixture was extracted into EtOAc, worked up, and chromatographed on silica. Elution with EtOAc/petroleum ether (1:4) gave 1-methyl-2-indolinethione [IX: $R_1$=$R_3$=Me] (0.71 g, 87%); mp 108°–109° C. (Hino T, Tsuneoka K, Nakagawa M, Akaboshi S, *Chem. Pharm. Bull.* 1969;17:550 record 109°–111° C.).

A solution of the above 1-methyl-2-indolinethione (4.1 g) in THF (150 mL) was treated dropwise over 15 minutes with an ice-cooled suspension of NaH (57%, 1.4 g) in THF (100 mL). The mixture was stirred for 30 minutes, then a solution of phenyl isocyanate (3.5 g) in THF (50 mL) was added, and stirring continued for 3 hours at 20° C. The solvent was removed under vacuum, then the residue decomposed with ice-HCl, and extracted in $CH_2Cl_2$. Removal of the solvent gave an oil (6.0 g), which crystallized from ether. Two recrystallizations from THF-ether gave N-phenyl (1-methyl-2-thioxo-3-indolinyl) carboxamide [IV: $R_1$=H, $R_2$=CONHPh, $R_3$=Me] (21) (2.8 g, 39%) as a pale yellow solid; mp 149°–151° C.

$^1$H NMR (CDCl$_3$): δ 10.36 (1H, s, NH), 7.87 (1H, d, J=7.4 Hz, ArH), 7.60 (2H, d, J=7.9 Hz, ArH), 7.41 (2H, t, J=7.5 Hz, ArH), 7.31 (2H, m, ArH), 7.11 (1H, t, J=7.3 Hz, ArH), 7.03 (1H, d, J=7.8 Hz, ArH), 3.73 (3H, s, NCH$_3$).

Analysis calculated for $C_{16}H_{14}N_2OS$ requires: C, 68.1; H, 5.1; N, 9.9; S, 11.4%.

Found: C, 67.8; H, 5.1; N, 9.8; S, 11.4%.

A solution of 21 (200 mg) in $CH_2Cl_2$/MeOH (2:1) (30 mL) was stirred at 20° C. for 5 days, then the solvents were removed under reduced pressure. Chromatography on silica gel, eluting with $CH_2Cl_2$ then CHCl$_3$/EtOH (99:1), gave bis[N-phenyl 1-methylindolyl-3-carboxamide-(2)]disulfide [V: $R_1$=H, $R_2$=CONHPh, $R_3$=Me] (70) (0.19 g, 95%); mp (benzene) 187°–188° C.

$^1$H NMR (CDCl$_3$): δ 8.21 (1H, s, NH), 8.01 (1H, d, J=8.1 Hz, ArH), 7.19 (1H, ddd, J=8.1, 7.1, 0.9 Hz, ArH), 7.13 (4H, d, J=4.3 Hz, Ph), 7.09 (1H, ddd, J=8.1, 7.1, 0.9 Hz, ArH), 7.05 (1H, d, J=8.1 Hz, ArH), 6.98 (1H, quin, J=4.3 Hz, Ph), 3.77 (3H, s, NCH$_3$).

$^{13}$C NMR (CDCl$_3$): δ 161.57 (CO), 138.55, 137.95 (2×s), 128.64 (d), 127.41, 126.07 (2×s), 125.55, 122.28, 122.00 (4×d), 119.76 (s), 119.27, 110.14 (2×d), 30.33 (NCH$_3$).

Analysis calculated for $C_{32}H_{26}N_4O_2S_2$ requires: C, 68.3; H, 4.6; N, 10.0; S, 11.4%.

Found: C, 68.9; H, 4.9; N, 9.6; S, 11.1%.

A solution of 21 (200 mg) in Me$_2$CO (20 mL) was treated with $K_2CO_3$ (0.12 g) and methyl iodide (0.14 g) and the mixture stirred at 20° C. for 1 hour. $CH_2Cl_2$ (100 mL) was added, then the solution filtered and the solvents removed, to yield a brown oil (0.26 g). Chromatography on silica gel, eluting with $CH_2Cl_2$, gave N-phenyl (1-methyl -2-methylthio-3-indolyl)carboxamide as an oil [X: $R_1$=H, $R_2$=CONHPh, $R_3$=Me, R4=SMe] (22) (200 mg, 95%), which crystallized from MeOH/$CH_2Cl_2$ as a white solid; mp 116°–118° C.

$^1$H NMR (CDCl$_3$): δ 9.99 (1H, s, NH), 8.58 (1H, d, J=8.0 Hz, ArH), 7.75 (2H, d, J=7.6 Hz, ArH), 7.38 (4H, m, ArH), 7.29 (1H, quin, J=4.3 Hz, ArH), 7.12 (1H, t, J=7.4 Hz, ArH), 3.95 (3H, s, NCH$_3$), 2.47 (3H, s, SCH$_3$).

$^{13}$C NMR (CDCl$_3$): δ 162.59 (s, CONH), 138.80, 137.46, 131.43 (3×s, ArH), 129.03 (2×d, ArH), 127.35 (s, ArH), 124.14, 123.67, 123.02, 122.24 (4×d, ArH), 119.86 (2×d, ArH), 114.04 (s, ArH), 109.69 (d, ArH), 30.23 (q, NCH$_3$), 20.50 (q, SCH$_3$).

Analysis calculated for $C_{17}H_{16}N_2OS$ requires: C, 68.9; H, 5.4; N, 9.5; S, 10.8%.

Found: C, 68.6; H, 5.5; N, 9.4; S, 10.8%.

Benzyl mercaptan (0.02 mL, 0.178 mmol) was added to a suspension of 70 (50 mg, 89 mmol) and BF3-etherate (1 drop) in $CH_2Cl_2$ (1 mL). After stirring at 20° C. for 3 hours, the homogeneous mixture was poured into saturated aqueous NaHCO3, diluted with $CH_2Cl_2$ and worked up, and the residue was chromatographed on silica gel. Elution with $CH_2Cl_2$/petroleum ether (1:1) gave foreruns, and elution with $CH_2Cl_2$ elute benzyl [N-phenyl 1-methylindolyl-3-carboxamide-(2)]disulfide [XI: $R_1$=H, $R_2$=CONHPh, $R_3$=Me, $R_4$=S$_2$CH$_2$Ph] (23) (39 mg, 54%); mp (CHCl$_3$/petroleum ether) 146°–148° C.

$^1$H NMR: δ 8.95 (1H, br s, CONH), 8.47 (1H, dd, J=7.7, 1.3 Hz, ArH-4), 7.66 (2H, dd, J=7.5, 1.2 Hz, Ph), 7.40–7.07 (11H, m, ArH-5, -6, -7 and Ph), 3.90 (3H, s, NMe).

$^{13}$C NMR: δ 162.31 (CONHPh), 138.31 (s), 138.04 (s), 135.13 (s), 130.00 (s), 129.15, 129.06, 128.69, 127.83, 126.83 (s), 124.79, 123.94, 122.80, 122.36, 119.90, 109.92, 42.51 (CH$_2$Ph), 30.73 (NCH$_3$).

Analysis calculated for $C_{23}H_{20}N_2S_2O$ requires: C, 68.3; H, 5.0; N, 6.9; S, 15.9%.

Found: C, 68.4; H, 5.1; N, 6.9; S, 16.0%

Compound 71 of Table 1

Similarly was prepared, from 1-ethyl-2-indolinethione (Kendall JD, Ficken GE, British Patent 829,584, *Chem. Abstr.* 1960;54:12847h) and phenyl isocyanate, bis[N-phenyl 1-ethylindolyl-3-carboxamide-(2)]disulfide [V: $R_1$=H, $R_2$=CONHPh, $R_3$=Et] (71) (25% yield); mp 200°–202° C.

$^1$H NMR (CDCl$_3$): δ 8.22 (1H, br, CONH), 7.98 (1H, d, J=8.1 Hz, H-4), 7.18 (1H, t, J=8.0 Hz, H-6), 7.11–7.04 (6H, m, H-5 and Ph), 6.95 (1H, dd, J=8.0, 1.0 Hz, H-7), 4.32 (2H, q, J=7.0 Hz, NC$\underline{H}_2$CH$_3$), 1.36 (3H, t, J=7.0 Hz, NCH$_2$C$\underline{H}_3$).

$^{13}$C NMR: δ 161.73 (CONH), 137.91 (s), 137.44 (s), 128.55, 128.55, 128.35 (2s), 126.33 (s), 125.41, 123.47, 122.12, 122.07, 119.37, 110.19 (C-7), 38.86 (NCH$_2$CH$_3$), 15.23 (NCH$_2$CH$_3$).

Analysis calculated for C$_{34}$H$_{30}$N$_4$S$_2$O$_2$ requires: C, 69.1; H, 5.1; N, 9.5; S, 10.8%.

Found: C, 68.9; H, 5.4; N, 9.5; S, 10.4%.

Compound 72 of Table 1

Similarly was prepared 4-chloro-1-methyl-2-indolinethione [IX: R$_1$=4-Cl, R$_3$=Me] (92% yield); mp 147.5°–149.5° C.

$^1$H NMR (CDCl$_3$): δ 7.29 (1H, t, J=8.0 Hz, H-6), 7.13 (1H, d, J=8.0 Hz, H-5), 6.86 (1H, d, J=8.0 Hz, H-7), 4.09 (2H, s, H-3), 3.60 (3H, s, NCH$_3$).

$^{13}$C NMR: δ 200.75 (C-2), 147.65 (s), 130.04 (s), 129.52, 127.44 (s), 124.34, 107.81 (C-7), 48.42 (C-3), 31.55 (NCH$_3$).

Analysis calculated for C$_9$H$_8$ClNS requires: C, 54.7; H, 4.1; N, 7.1; S, 16.2%.

Found: C, 54.5; H, 4.3; N, 7.1; S, 16.0%.

Reaction of this with phenyl isocyanate as above gave bis[N-phenyl 4-chloro-1-methylindolyl-3-carboxamide-(2)]disulfide [V: R$_1$=4-Cl, R$_2$=CONHPh, R$_3$=Me] (72) (21% yield); mp 225°–228° C.

$^1$H NMR (CDCl$_3$): δ 8.38 (1H, br, NH), 7.49 (1H, dd, J=7.9, 1.5 Hz, H-5), 7.12 (1H, t, J=7.9 Hz, H-6), 7.08–7.05 (4H, m, CONHPh), 6.98 (1H, dd, J=7.9, 1.5 Hz, H-7), 6.96 (1H, m, CONHPh), 3.77 (3H, S, N—CH$_3$).

Analysis calculated for C$_{32}$H$_{24}$Cl$_2$N$_4$O$_2$S$_2$ requires: C, 60.8; H, 3.8; N, 8.9; Cl, 11.2%.

Found: C, 60.7; H, 4.1; N, 8.7; Cl, 11.8%.

Compound 73 of Table 1

Similarly was prepared, from 5-chloro-1-methyl-2-indolinethione [IX: R$_1$=5-Cl, R$_3$=Me]; mp 163°–165° C. (Baudin J-B, Julia SA, Lorne R, *Bull. Soc. Chim. Fr.* 1987:181–188 records mp 153°–155° C.) and phenyl isocyanate, bis[N-phenyl 5-chloro-1-methylindolyl-3-carboxamide-(2)]disulfide [V: R$_1$=5-Cl, R$_2$=CONHPh, R$_3$=Me] (73) (27% yield); mp 214°–216° C.

$^1$H NMR (CDCl$_3$): δ 8.14 (1H, br, CONH), 7.94 (1H, d, J=1.8 Hz, H-4), 7.12 (4H, br, ArH), 7.07 (1H, d, J=8.4 Hz, ArH), 7.01 (1H, m, ArH), 6.90 (1H, d, J=8.9 Hz, ArH), 3.76 (3H, s, NCH$_3$).

$^{13}$C NMR: δ 161.06 (CONH), 137.72 (s), 136.81 (s), 128.73, 128.44 (s), 128.25 (s), 126.58 (s), 126.11, 123.76, 121.27, 119.71 (s), 118.80, 111.16 (C-7), 30.53 (NCH$_3$).

Analysis calculated for C$_{32}$H$_{24}$Cl$_2$N$_4$O$_2$S$_2$ requires: C, 60.8; H, 3.8; N, 8.9; S, 10.2%.

Found: C, 60.6; H, 4.0; N, 8.9; S, 10.2%.

NaBH$_4$ (14 mg, 0.38 mmol) was added to a stirred suspension of the above compound (0.12 g, 0.19 mmol) in MeOH (5 mL). After 15 minutes, the solution was concentrated to dryness and the residue was partitioned between EtOAc and water. The organic solution was worked up to give a solid which was recrystallized from degassed CHCl$_3$/benzene at −5° C. to give N-phenyl 5-chloro-1-methyl-2-thioxoindole -3-carboxamide (20) [IV: R$_1$=5-Cl, R$_2$=CONHPh, R$_3$=Me] as coarse needles (86% yield); mp 312°–320° C. (dec).

$^1$H NMR ((CD$_3$)$_2$SO): δ 12.84 (1H, s, SH), 8.09 (1H, d, J=2.2 Hz, H-4), 7.70 (2H, d, J=8.5 Hz, H-2',6'), 7.27 (2H, dd, J=8.5, 8.2 Hz, H-3',5'), 7.07 (1H, d, J=8.4 Hz, H-7), 6.92 (1H, t, J=8.2 Hz, H-4'), 6.86 (1H, dd, J=8.4, 2.2 Hz, H-6), 3.64 (3H, s, N—CH$_3$).

$^{13}$C NMR: δ 164.73 (CONH), 140.81 (s), 135.17 (s), 130.29 (s), 128.55 (d), 123.93 (s), 121.01 (d), 118.20 (d), 117.65 (d), 117.30 (d), 107.97 (d), 104.40 (s), 29.18 (N—CH$_3$).

Analysis calculated for C$_{16}$H$_{13}$ClN$_2$OS requires: M+ 318.0408, 316.0437.

Found: M+ (mass spectrum) 318.0414, 316.0431.

Compound 74 of Table 1

Similarly was prepared, from 7-chloro-1-methyl-2-indolinethione [IX: R$_1$=7-Cl, R$_3$=Me]; mp 126°–128° C. (Inoue S, Uematsu T, Karo T, Ueda K, *Pestic. Sci.* 1985;16:589–598 records mp 125°–127° C.) and phenyl isocyanate, bis[N-phenyl-7-chloro-1-methylindolyl-3-carboxamide-(2)]disulfide [V: R$_1$=7-Cl, R$_2$=CONHPh, R$_3$=Me] (74) (27% yield); mp 232°–234° C.

$^1$H NMR (CDCl$_3$): δ 8.15 (1H, br, CONH), 7.85 (1H, d, J=8.0 Hz, H-4), 7.19–7.05 (5H, m, ArH), 7.00 (1H, t, J=6.6 Hz, ArH), 6.90 (1H, t, J=7.8 Hz, ArH), 4.25 (3H, s, N—CH$_3$).

Analysis calculated for C$_{32}$H$_{24}$Cl$_2$N$_4$O$_2$S$_2$ requires: C, 60.8; H, 3.8; N, 8.9%.

Found: C, 60.4; H, 4.0; N, 8.8%.

Compound 75 of Table 1

1,4-Dimethyl-2-indolinethione [IX: R$_1$=4-Me, R$_3$=Me] (81%); mp 160°–162° C.

Analysis calculated for C$_{10}$H$_{11}$NS requires: C, 67.8; H, 6.3; N, 7.9; S, 18.1%

Found: C, 68.0; H, 6.4; N, 8.0; S, 18.3% was prepared by the method given for Compound 77 (below).

Reaction of this with phenyl isocyanate gave bis[N-phenyl 1,4-dimethylindolyl-3-carboxamide-(2)]disulfide [V: R$_1$=4-CH$_3$, R$_2$=CONHPh, R$_3$=Me] (75); mp 237°–239° C.

$^1$H NMR (CDCl$_3$): δ 8.30 (1H, br s, CONH), 7.14 (1H, dd, J=7.3, 7.3 hz, H-6), 7.04–6.86 (7H, m, H-5,7 and CONH Ph), 3.69 (3H, s, NCH$_3$), 2.47 (3H, s, 4-CH$_3$).

$^{13}$C NMR (CDCl$_3$): δ 164.57 (CONHPh), 138.59, 137.62, 131.51 (3×s), 128.62 (d), 127.23 (s), 125.11 (d), 124.15 (s), 123.94, 122.62 (2×d), 122.10 (s), 119.61, 107.91 (2×s), 30.26 (NCH$_3$), 19.66 (4-CH$_3$).

Analysis calculated for C$_{34}$H$_{30}$N$_4$O$_2$S$_2$ requires: C, 69.1; H, 5.1; N, 9.5; S, 10.9%.

Found: C, 69.1; H, 5.1; N, 9.7; S, 11.0%.

Compound 76 of Table 1

1,5-Dimethyl-2-indolinethione [IX: R$_1$=5-Me, R$_3$=Me]; mp 143°–145° C. (*Bull. Fr.* 1987:181 reports mp 132°–133° C.) was prepared by the method given for Compound 77 (below). Reaction of this with phenyl isocyanate gave bis [N-phenyl 1,5-dimethylindolyl-3-carboxamide-(2)]disulfide [V: R$_1$=5-CH$_3$, R$_2$=CONHPh, R$_3$=Me] (76); mp 231°–234° C.

$^1$H NMR (CDCl$_3$): δ 8.24 (1H, br s, CONH), 7.78 (1H, br, H-4), 7.19–7.13 (4H, m, CONHPh), 7.05–6.90 (3H, m, H-6,7 and CONHPh), 3.71 (3H, s, NCH$_3$), 2.36 (3H, s, 5-CH$_3$).

$^{13}$C NMR (CDCl$_3$): δ 161.75 (CONH), 138.00, 137.10, 131.77, 129.01 (4×s), 128.53, 127.37 (2×d), 126.35 (s), 123.40, 121.33, 119.85, 109.85 (4×d), 30.32 (NCH$_3$), 21.57 (5-CH$_3$).

Analysis calculated for C$_{34}$H$_{30}$N$_4$O$_2$S$_2$ requires: C, 69.1; H, 5.1; N, 9.5; S, 10.9%.

Found: C, 69.4; H, 5.2; N, 9.6; S, 11.2%.

Compound 77 of Table 1

A mixture of 2,5-dimethylaniline (27.4 g, 0.2 mol) and benzotriazole (23.8 g, 0.2 mol) in EtOH (300 mL) was stirred at 20° C. as 37% aqueous formaldehyde (16.1 g, 0.2 mol) was added gradually. After 30 minutes, the white solid which precipitated was collected and washed with EtOH to give N-(1-benzotriazolylmethyl)-2,5-dimethylaniline (33.9 g, 67% yield); mp (EtOH) 147°–149° C.

$^1$H NMR (CDCl$_3$): δ 6.85–8.10 (7H, m, ArH), 6.56 (minor isomer) and 6.13 (major isomer) (2H, 2×m, CH$_2$), 5.08 (minor) and 4.70 (major) (1H, 2×m, NH), 2.24 (3H, s, CH$_3$), and 2.12 (3H, s, CH$_3$).

Analysis calculated for C$_{15}$H$_{16}$N$_4$ requires: C, 70.6; H, 5.9; N, 23.5%.

Found: C, 71.5; H, 6.3; N, 22.1%.

A suspension of this compound (33 g, 0.13 mol) and NaBH$_4$ (5 g) in dioxane (400 mL) was heated under reflux for 5 hours, and the solution was concentrated. After cooling, water was added and the resulting mixture was extracted with EtOAc. The organic layer was washed twice with aqueous K$_2$CO$_3$ and water, and dried (Na$_2$SO$_4$). Removal of the solvent gave N,2,5-trimethylaniline (17.6 g, 99% yield) as an oil, which was used directly.

$^1$H NMR (CDCl$_3$): δ 6.93 (1H, d, J=7.4 Hz, H-3), 6.49 (1H, d, J=7.6 Hz, H-4), 6.44 (1H, s, H-6), 3.72, (1H, s, NH), 2.88 (3H, s, NCH$_3$), 2.31 (3H, s, CH$_3$), and 2.09 (3H, s, CH$_3$).

A solution of 2,4,6-trimethylaniline (6.86 g, 5 mmol) in dry THF (100 mL) under an atmosphere of N$_2$ was cooled to −78° C. and n-butyllithium (21 mL, 2.5M solution in hexanes) was added dropwise. The mixture was allowed to warm to 0° C., and dry CO$_2$ gas was bubbled in for 2–3 minutes. The excess CO$_2$ was removed under vacuum, and after the addition of further THF to replace that lost by evaporation, the solution was recooled to −78° C. n-Butyllithium (22 mL, 2.5M solution in hexanes) was again added dropwise, and the temperature was then allowed to rise slowly to −10° C. where a deep red colored solution was obtained. After a further 30 minutes at that temperature, the mixture was again recooled to −78° C. and CO$_2$ gas was bubbled in until the red color disappeared. The reaction mixture was allowed to warm to 20° C., and after removal of the solvent, 0.1M HCL (50 mL) was added to initiate both deprotection of the nitrogen and ring-closure. The resulting mixture was extracted with EtOAc, and this was then washed successively with 0.1M HCl, water, and dilute aqueous Na$_2$CO$_3$. After drying (Na$_2$SO$_4$), the solvent was removed under vacuum, to leave an oil which was purified by chromatography on Al$_2$O$_3$ to give 1,6-dimethyl-2-indolinone (3.37 g, 42% yield) [VII: R$_1$=6-Me; R$_3$=Me]; mp (hexane) 94.5°–96° C.

$^1$H NMR (CDCl$_3$): δ 7.11 (2H, d, J=7.5 Hz, H-4), 6.85 (2H, d, J=7.5 Hz, H-5), 6.65 (1H, s, H-7), 3.47 (2H, s, CH$_2$), 3.19 (3H, s, 1-CH$_3$), and 2.38 (3H, s, 6-CH$_3$).

Analysis calculated for C$_{10}$H$_{11}$NO requires: C, 74.5; H, 6.9; N, 8.7%.

Found: C, 74.5; H, 6.6; N, 8.7%.

Thiation of this with P$_2$S$_5$ as above gave 1,6-dimethyl-2-indolinethione [IX: R$_1$=6-Me, R$_3$=Me]; mp 141°–143° C.

Analysis calculated for C$_{10}$H$_{11}$NS requires: C, 67.8; H, 6.3; N, 7.9; S, 18.1%.

Found: C, 67.6; H, 6.5; N, 8.2; S, 18.0%.

This was reacted with phenyl isocyanate as above to give bis[N-phenyl 1,6-dimethylindolyl-3-carboxamide-(2)]disulfide [V: R$_1$=6-CH$_3$, R$_2$=CONHPh, R$_3$=Me] (77); mp 192°–195° C.

$^1$H NMR (CDCl$_3$): δ 8.16 (1H, br s, CONH), 7.85 (1H, d, J=8.3 Hz, H-4), 7.10 (4H, br, CONHPh), 6.98 (1H, m, CONH Ph), 6.87 (1H, d, J=8.3 Hz, H-5), 6.73 (1H, br, H-7), 3.71 (3H, s, NCH$_3$), 2.35 (3H, s, 6-CH$_3$).

$^{13}$C NMR (CDCl$_3$): δ 161.49 (CONH), 139.05, 137.98, 135.63 (3×s), 128.44 (d), 126.10 (s), 124.28 (d), 124.06 (s), 123.17, 121.61, 119.21, 109.85 (4×d), 30.17 (NCH$_3$), 21.98 (6-CH$_3$).

Analysis calculated for C$_{34}$H$_{30}$N$_4$O$_2$S$_2$ requires: C, 69.1; H, 5.1; N, 9.5; S, 10.9%.

Found: C, 68.9; H, 5.2; N, 9.6; S, 11.0%.

Compound 78 of Table 1

Similarly was prepared 1,7-dimethyl-2-indolinethione [IX: R$_1$=7-Me, R$_3$=Me]; mp 138°–9° C.

Analysis calculated for C$_{10}$H$_{11}$NS requires: C, 67.8; H. 6.3; N, 7.9; S, 18.1%.

Found: C, 67.6; H, 6.2; N, 8.0; S, 18.1%.

Reaction of this with phenyl isocyanate gave bis[N-phenyl 1,7-dimethylindolyl-3-carboxamide-(2)]disulfide [V: R$_1$=7-CH$_3$, R$_2$=CONHPh, R$_3$=Me] (78); mp 221°–223° C.

$^1$H NMR (CDCl$_3$): δ 8.11 (1H, br s, CONH), 7.83 (1H, J=8.1 Hz, H-4), 7.15–7.07 (4H, m, CONHPh), 6.99 (1H, m, CONHPh), 6.94 (1H, dd, J=8.1, 8.1 Hz, H-5), 6.85 (1H, d, J=8.1 Hz, H-6), 4.07 (3H, s, NCH$_3$), 2.44 (3H, s, 7-CH$_3$).

$^{13}$C NMR (CDCl$_3$): δ 161.67 (CONH), 137.95, 137.86 (2×s), 128.55, 128.31 (2×d), 126.85 (s), 123.57, 122.10 (2×d), 121.77 (s), 119.72, 119.21 (2×d), 33.36 (NCH$_3$), 20.23 (7-CH$_3$).

Analysis calculated for C$_{34}$H$_{30}$N$_4$O$_2$S$_2$ requires: C, 69.1; H, 5.1; N, 9.5; S, 10.9%.

Found: C, 69.1; H, 5.2; N, 9.7; S, 11.0%.

Compound 79 of Table 1

Similarly was prepared, from 4-methoxy-1-methyl-2-indolinethione [IX: R$_1$=4-OMe, R$_3$=Me]; mp 141°–144° C. (U.S. Pat. No. 5,030,646 records mp 126°–128° C.) and phenyl isocyanate, bis[N-phenyl 4-methoxy-1-methylindolyl-3-carboxamide-(2)]disulfide [V: R$_1$=4-OCH$_3$, R$_2$=CONHPh, R$_3$=Me] (79); mp 225°–228° C.

$^1$H NMR (CDCl$_3$): δ 8.85 (1H, br s, CONH), 7.25–7.06 (5H, m, H-6 and CONHPh), 6.98 (1H, m, CONHPh), 6.82 (1H, d, J=8.3 Hz, H-7), 6.36 (1H, d, J=7.8 Hz, H-5), 3.76 (3H, s, OCH$_3$), 3.69 (3H, s, NCH$_3$).

$^{13}$C NMR (CDCl$_3$): 162.36 (CONH), 152.70, 139.39, 138.73, 130.20 (4×s), 128.54, 125.39, 123.08 (3×s), 130.20 (s), 128.54, 125.39, 123.08 (3×d), 19.96 (s), 119.19 (d), 114.66 (s), 103.67, 101.55 (2×d), 22.58 (OCH$_3$), 30.48 (NCH$_3$).

Analysis calculated for C$_{34}$H$_{30}$N$_4$O$_4$S$_2$ requires: C, 65.6; H, 4.9; N, 9.0; S, 10.3%.

Found: C, 65.7; H, 4.9; N, 9.2; S, 10.2%.

Compound 80 of Table 1

Similarly was prepared, from 5-methoxyl-1-methyl- 2-indolinethione [IX: $R_1$=5-OMe, $R_3$=Me]; mp 148°–150° C. (U.S. Pat. No. 5,030,646 records mp 142°–144° C.) and phenyl isocyanate, bis[N-phenyl 5-methoxy-1-methylindolyl-3-carboxamide-(2)]disulfide [V: $R_1$=5-OCH$_3$, $R_2$=CONHPh, $R_3$=Me] (80); mp 161°–164° C.

$^1$H NMR (CDCl$_3$): δ 8.41 (1H, br s, CONH), 7.55 (d, J=1.8 Hz, H-4), 7.18 (4H, m, CONHPh), 7.00 (2H, m, H-6 and CONHPh), 6.89 (1H, d, J=7.4 Hz, H-7), 3.82 (3H, s, OCH$_3$), 3.68 (3H, s, NCH$_3$).

$^{13}$C NMR (CDCl$_3$): δ 161.80 (CONH), 155.94, 137.87, 134.07 (3×s), 128.71, 123.68, 119.50, 117.48, 111.10, 102.29 (6×d), 55.63 (OCH$_3$), 30.47 (NCH$_3$).

Analysis calculated for C$_{34}$H$_{30}$N$_4$O$_4$S$_2$ requires: C, 65.6; H, 4.9; N, 9.0; S, 10.3%.

Found: C, 65.3; H, 5.1; N, 9.2; S, 10.4%.

Compound 81 of Table 1

Similarly was prepared, from 6-methoxy-1-methyl-2-indolinethione [IX: $R_1$=6-OMe, $R_3$=Me]; mp 133°–136° C. (U.S. Pat. No. 5,030,646 records mp 135°–136° C.) and phenyl isocyanate, bis[N-phenyl 6-methoxy-1-methylindolyl-3-carboxamide-(2)]disulfide [V: $R_1$=6-OCH$_3$, $R_2$=CONHPh, $R_3$=Me] (81); mp 197°–200° C.

$^1$H NMR (CDCl$_3$): δ 8.19 (1H, br s, CONH), 7.91 (1H, d, J=8.9 Hz, H-4), 7.12 (4H, br, CONHPh), 6.97 (1H, m, CONHPh), 6.71 (1H, d, J=8.9 Hz, H-5), 6.25 (1H, br, H-7), 3.74 (3H, s, OCH$_3$), 3.70 (3H, s, NCH$_3$).

$^{13}$C NMR (CDCl$_3$): δ 161.37 (CONH), 158.75, 139.82, 138.04, 128.65 (4×s), 128.50, 123.30, 123.12, (3×d), 120.64, 120.26 (2×s), 119.10, 113.22, 98.02 (3×d), 55.26 (OCH$_3$), 30.21 (NCH$_3$).

Analysis calculated for C$_{34}$H$_{30}$N$_4$O$_4$S$_2$ requires: C, 65.6; H, 4.9; N, 9.0; S, 10.3%.

Found: C, 65.5; H, 4.8; N, 9.2; S, 10.4%.

Compound 82 of Table 1

Similarly was prepared, from 7-methoxy-1-methyl-2-indolinethione [IX: $R_1$=7-OMe, $R_3$=Me]; mp 124°–126° C. (U.S. Pat. No. 5,030,646 records mp 114°–116° C.) and phenyl isocyanate, bis[N-phenyl 7-methoxy-1-methylindolyl-3-carboxamide-(2)]disulfide [V: $R_1$=7-OCH$_3$, $R_2$=CONHPh, $R_3$=Me] (82); mp 205°–208° C.

$^1$H NMR (CDCl$_3$): δ 8.14 (1H, br s, CONH), 7.57 (1H, d, J=8.2 Hz, H-4), 7.13 (4H, m, CONHPh), 6.96 (1H, m, CPNHPh), 6.93 (1H, dd, J=8.2, 8.2 Hz, H-5), 6.48 (1H, d, J=8.2 Hz, H-6), 4.12 (3H, s, OCH$_3$), 3.73 (3H, s, NCH$_3$).

$^{13}$C NMR (CDCl$_3$): δ 161.72 (CONH), 147.12, 137.99, 129.08 (3×s), 128.45 (d), 128.01 (s), 123.27, 122.35, 119.33, 114.13, 105.35 (5×d), 55.22 (OCH$_3$), 33.73 (NCH$_3$).

Analysis calculated for C$_{34}$H$_{30}$N$_4$O$_4$S$_2$ requires: C, 65.6; H, 4.9; N, 9.0; S, 10.3%.

Found: C, 64.9; H, 5.0; N, 9.0; S, 10.4%.

Compound 84 of Table 1

A solution of 3-(methylthio)-5-(trifluoromethyl)oxindole (Gassman PG, Cue BW, Luh T-Y, *J. Org. Chem.* 1977;42:1344–1348) (10 g, 40 mmol) in AcOH (100 mL) was heated under reflux with Zn dust (13.3 g, 0.2 mol) for 1 hour. The mixture was cooled and filtered, and the precipitate was washed with AcOH. The combined filtrates were evaporated under reduced pressure, and the residue was diluted with 1M aqueous ammonia to give 5-trifluoromethyloxindole [VII: $R_1$=5-CF$_3$, $R_3$=H] (7.22 g, 90%); mp (aqueous EtOH) 188.5°–191° C. (lit. [Hardtmann GE, U.S. Pat. No. 4,160,032; *Chem. Abstr.* 1979;91:P107890w]; mp 188°–189° C.).

$^1$H NMR (CDCl$_3$): δ 8.74 (1H, s, NH), 7.52 (1H, d, J=8.2 Hz, H-6), 7.49 (1H, s, H-4), 6.97 (1H, d, J=8.2 Hz, H-7), 3.61 (2H, s, CH$_2$).

A suspension of the above oxindole (5.03 g, 25 mmol) in water (100 mL) containing NaOH (1.5 g) was treated with Me$_2$SO$_4$ (4.7 g, 37 mmol). The mixture was warmed to 100° C. for 10 minutes, cooled, a further portion of Me$_2$SO$_4$ and NaOH added, and warmed again briefly. After thorough cooling, the solid was collected and chromatographed on alumina. Elution with CH$_2$Cl$_2$/hexane (7:3) gave 1-methyl-5-(trifluoromethyl)oxindole [VII: $R_1$=5-CF$_3$, $R_3$=Me] (3.5 g, 65%); mp (hexane) 127.5°–129° C.

$^1$H NMR (CDCl$_3$): δ 7.58 (1H, d, J=8.2 Hz, H-6), 7.50 (1H, s, H-4), 6.89 (1H, d, J=8.2 Hz, H-7), 3.58 (2H, s, CH$_2$), 3.25 (3H, s, CH$_3$).

Analysis calculated for C$_{10}$H$_8$F$_3$NO requires: C, 55.8; H, 3.8; N. 6.5%.

Found: C, 55.5; H, 3.8; N, 6.5%.

Reaction of this compound with P$_2$S$_5$ as above gave 1-methyl -5-(trifluoromethyl)-2-indolinethione [IX: $R_1$=5-CF$_3$, $R_3$=Me] (96% yield); mp 124.5°–126° C.

$^1$H NMR (CDCl$_3$): δ 7.63 (1H, dd, J=8.3, 0.8 Hz, H-6), 7.54 (1H, d, J=0.8 Hz, H-4), 7.03 (1H, d, J=8.3 Hz, H-7), 4.15 (2H, s, C-3), 3.64 (3H, s, N—CH$_3$).

$^{13}$C NMR: δ 202.28 (C-2), 149.34 (s), 129.60 (s), 126.54 (J=32.5 Hz, C-5), 125.9 (J=4.0 Hz), 124.21 (J=271.9 Hz) (CF$_3$), 121.00 (J=3.8 Hz), 109.28 (d), 48.75 (C-3), 31.35 (N—CH$_3$).

Analysis calculated for (C$_{10}$H$_8$F$_3$NS) requires: C, 51.9; H, 3.5;N, 6.3; S, 14.1%.

Found: C, 52.0; H, 3.7; N, 6.3; S, 14.1%.

Reaction of this with phenyl isocyanate as above gave 2,2-dithiobis[N-phenyl-1-methyl-5-(trifluoromethyl)indolyl- 3-carboxamide] (84) [V: $R_1$=5-CF$_3$, $R_2$=CONHPh, $R_3$=Me] (71% yield); mp 214°–216° C.

$^1$H NMR ((CD$_3$)$_2$SO): δ 9.53 (1H, s, CONH), 8.14 (1H, br s, H-4), 7.59 (1H, d, J=8.8 Hz, H-7), 7.53 (1H, dd, J=8.8, 1.5 Hz, H-6), 7.12–7.09 (4H, m, ArH), 6.97 (1H, m, ArH), 3.76 (3H, s, N—CH$_3$).

$^{13}$C NMR: δ 160.49 (CONH), 138.93 (s), 138.21 (s), 131.76 (s), 128.19 (d), 124.96 (J=271.6 Hz, CF$_3$), 124.60 (d), 119.21 (s), 119.09 (d), 118.57 (J=4.1 Hz), 30.46 (N—CH$_3$).

Analysis calculated for C$_{34}$H$_{24}$F$_6$N$_4$O$_2$S$_2$ requires: C, 58.4; H, 3.5; N, 8.0; S, 9.2%.

Found: C, 58.5; H, 3.8; N, 7.9; S, 9.3%.

Compound 85 of Table 1

Methylation of 6-chlorooxindole [VII: $R_1$=6-Cl, $R_3$=H] (Quallich GJ, Morrissey PM, *Synthesis* 1993: 51–53) with Me$_2$SO$_4$/NaOH as above gave 6-chloro-1-methyloxindole [VII: $R_1$=6-Cl, $R_3$=CH$_3$]; mp (aqueous EtOH) 119.5°–123° C.

$^1$H NMR (CDCl$_3$): δ 7.15 (1H, d, J=7.8 Hz, H-4), 7.01 (1H, dd, J=7.8, 1.8 Hz, H-5), 6.82 (1H, d, J=1.7 Hz, H-7), 3.49 (2H, s, CH$_2$), 3.19 (3H, s, CH$_3$).

Analysis calculated for $C_9H_8ClNO$ requires: C, 59.5; H, 4.4; N, 7.7%.

Found: C, 59.6; H, 4.6; N, 7.6%.

Reaction of this with $P_2S_5$ as above gave 6-chloro-1-methyl-2-indolinethione [IX: $R_1$=6-Cl, $R_3$=Me] (87% yield); mp (EtOAc/petroleum ether) 162°–165° C.

$^1$H NMR (CDCl$_3$): δ 7.20 (1H, d, J=7.9 Hz, H-4), 7.13 (1H, dd, J=7.9, 1.7 Hz, H-5), 6.96 (1H, d, J=1.7 Hz, H-7), 4.06 (2H, s, H-3), 3.59 (3H, s, N—CH$_3$).

$^{13}$C NMR: δ 202.00 (C-2), 147.76 (s), 133.98 (s), 127.35 (s), 124.64 (d), 124.06 (d), 110.20 (d), 48.59 (C-3), 31.29 (N—CH$_3$).

Analysis calculated for $C_9H_8ClN_2SO$ requires: C, 54.7; H, 4.1; N, 7.1; S, 16.23.

Found: C, 54.8; H, 4.1; N, 7.0; S, 16.3%.

Reaction of this with phenyl isocyanate as above gave bis[N-phenyl 6-chloro-1-methylindolyl-3-carboxamide-(2)] disulfide (85) [V: $R_1$=6-Cl, $R_2$=CONHPh, $R_3$=Me] (61% yield); mp 243°–245° C.

$^1$H NMR ((CD$_3$)$_2$SO): δ 9.43 (1H, br, CONH), 7.77 (1H, d, J=8.6 Hz, H-4), 7.46 (1H, d, J=1.4 Hz, H-7), 7.19–7.09 (5H, m, ArH), 7.01 (1H, m, ArH), 3.67 (3H, s, N—CH$_3$).

$^{13}$C NMR: δ 160.66 (CONH), 138.29 (s), 138.04 (s), 129.87 (s), 129.41 (s), 128.15 (d), 123.94 (e), 122.91 (d), 122.37 (d), 121.70 (d), 119.20 (s), 119.12 (d), 110.69 (d), 30.22 (N—CH$_3$).

Analysis calculated for $C_{32}H_{24}Cl_2N_4O_2S_2$ requires: C, 60.9; H, 3.8; N, 8.9; S, 10.2%.

Found: C, 60.9; H, 4.0; N, 8.7; S, 10.2%.

Compound 86 of Table 1

Similarly was prepared, from 1-methyl-5-nitro-2-oxindole (Robinson R, Wyler M, *J. Chem. Soc.* 1941: 620–624), 1-methyl-5-nitro-2-indolinethione IX: $R_1$=5-NO$_2$, $R_3$=Me] (68% yield); mp (EtOAc/light petroleum) >330° C.

$^1$H NMR ((CD$_3$)$_2$SO): δ 8.28 (1H, dd, J=8.7, 1.7 Hz, H-6), 8.17 (1H, d, J=1.7 Hz, H-4), 7.41 (1H, d, J=8.7 Hz, H-7), 4.26 (2H, s, H-3), 3.60 (3H, s, N—CH$_3$).

$^{13}$C NMR: δ 203.48 (C-2), 151.49 (s), 143.81 (s), 130.53 (s), 124.80 (d), 119.00 (d), 110.24 (d), 48.45 (C-3), 31.34 (N—CH$_3$).

Analysis calculated for $C_9H_8N_2SO_2$ requires: M+208.0306.

Found: M+208.0311 (mass spectrum).

Reaction of this with phenyl isocyanate as above gave 2,2'-dithiobis[N-phenyl-1-methyl-5-nitroindolyl-3-carboxamide] (86) [V: $R_1$=5-NO$_2$, $R_2$=CONHPh, $R_3$=Me] (52% yield); mp 236°–240° C. (dec).

$^1$H NMR ((CD$_3$)$_2$CO): δ 9.68 (1H, br, CONH), 8.64 (1H, d, J=1.6 Hz, H-4), 8.07 (1H, dd, J=8.8, 1.6 Hz, H-6), 7.56 (1H, d, J=8.8 Hz, H-7), 7.18–7.08 (4H, m, ArH), 6.98 (1H, t, J=6.8 Hz, ArH), 3.79 (3H, s, N—CH$_3$).

$^{13}$C NMR: δ 160.04 (CONH) 141.96 (s), 140.17 (s), 138.22 (s) 128.24 (d) 124.35 (s) 123.09 (d), 120.25 (s), 118.90 (d), 117.76 (d), 111.64 (d), 370.70 (N—CH$_3$).

Analysis calculated for $C_{32}H_{24}N_6O_6S_2 \cdot 0.2H_2O$ requires: C, 55.8; H, 4.1; N, 12.2%.

Found: C, 55.5; H, 3.9; N, 12.0%.

Analysis calculated for $C_{32}H_{25}N_6SO_2O_6$ requires: [M+H]$^+$653.1277.

Found: [M+H]$^+$653.1275 (FAB mass spectrum).

Compound 87 of Table 1

Similarly was prepared, from 5-fluoro-1-methyloxindole (Wiseman EH, Chiaini J, McManus JM, *J. Med. Chem.* 1973;16:131–134), 5-fluoro-1-methyl-2-indolinethione [IX: $R_1$=5-F, $R_3$=Me] (93% yield); mp 155°–157° C.

$^1$H NMR (CDCl$_3$): δ 7.11–6.99 (2H, m, H-4,6), 6.88 (1H, dd, J=9.3, 4.2 Hz, H-7), 4.09 (2H, s, H-3), 3.61 (3H, s, N—CH$_3$).

$^{13}$C NMR: δ 200.61 (C-2), 160.49 (J=243.6 Hz, C-5), 142.76 (s), 130.80 (J=8.6 Hz, C-3a), 114.48 (J=24.1 Hz), 112.13 (J=25.1 Hz), 109.94 (J=8.6 Hz), 48.96 (J=1.8 Hz, C-3), 31.38 (N—CH$_3$).

Analysis calculated for $C_9H_8FNS$ requires: C, 59.7; H, 4,5; N, 7.7; S, 17.7%.

Found: C, 59.7; H, 4.6; N, 7.8; S, 17.4%.

Reaction of this with phenyl isocyanate as above gave 2,2'-dithiobis[N-phenyl-5-fluoro-1-methylindolyl-3-carboxamide] (87) [V: $R_1$=5-F, $R_2$=CONHPh, $R_3$=Me]) (74% yield); mp 205°–207° C.

$^1$H NMR (CDCl$_3$): δ 8.17 (1H, br, CONH), 7.64 (1H, dd, J=9.4, 2.0 Hz, H-4), 7.17 (4H, br d, ArH), 7.00 (1H, m, ArH), 6.95–6.88 (2H, m, ArH), 3.78 (3H, s, N—CH$_3$).

$^{13}$C NMR: δ 161.17 (CONH), 158.97 (J=239.4 Hz, C-5), 138.02 (s), 135.71 (s), 128.69 (d), 123.69 (d), 118.87 (d), 114.66 (J=27.1 Hz), 111.14 (J=10.0 Hz), 106.92 (J=25.5 Hz), 30.61 (N—CH$_3$).

Analysis calculated for $C_{32}H_{24}F_2N_4O_2S_2$ requires: C, 64.2; H, 4.0; N, 9.4; S, 10.7%.

Found: C, 63.9; H, 4.2; N, 9.3; S, 10.7%.

Compound 88 of Table 1

Reduction of 5-cyano-3-methylthiooxindole (Gassman PG, Cue BW, Luh T-Y, *J. Org. Chem.* 1977;42:1344–1348) with Zn/AcOH as above gave 5-cyanooxindole [VII: $R_1$=5-CN; $R_3$=H] (89% yield); mp (aqueous EtOH) 249° C. (dec) (lit. [Gassman PG, Gilbert DP, Luh T-Y, *JOC* 1977;42:1340–1344]; mp 249°–251° C.). Methylation of this with Me$_2$SO$_4$/NaOH as above gave 5-cyano-1-methyloxindole [VII: $R_1$=5-CN, $R_3$=H] (53% yield); mp (hexane) 201°–203° C.

$^1$H NMR (CDCl$_3$): δ 7.63 (1H, dd, J=8.1, 1.1 Hz, H-6), 7.51 (1H, d, J=1.1 Hz, H-4), 6.90 (1H, d, J=8.1 Hz, H-7), 3.57 (2H, s, CH$_2$), 3.25 (3H, s, CH$_3$).

Analysis calculated for $C_{10}H_8N_2O$ requires: C, 69.8; H, 4.7; N, 16.3%.

Found: C, 70.2; H, 4.64; N, 16.7%.

Reaction of the above compound with $P_2S_5$ gave 5-cyano-1-methyl-2-indolinethione [IX: $R_1$=5-CN, $R_3$=Me] (41% yield); mp 185°–187° C.

$^1$H NMR ((CD$_3$)$_2$SO): δ 7.87 (1H, br d, J=8.3 Hz, H-6), 7.76 (1H, br s, H-4), 7.41 (1H, d, J=8.3 Hz, H-7), 4.22 (2H, s, H-3), 3.58 (3H, s, N—CH$_3$).

$^{13}$C NMR: δ 202.34 (C-2), 149.78 (s), 133.05 (d), 130.42 (s), 126.92 (d), 119.05 (s), 110.98 (d), 48.20 (C-3), 31.11 (N—CH$_3$).

Analysis calculated for $C_{10}H_8N_2S \cdot 0.5H_2O$ requires: C, 60.7; H, 4.6; N, 14.2%.

Found: C, 61.3; H, 4.1; N, 14.4%.

Reaction of this with phenyl isocyanate as above gave 2,2'-dithiobis[N-phenyl-5-cyano-1-methylindolyl-3-carboxamide] (88) [V: $R_1$=5-CN, $R_2$=CONHPh, $R_3$=Me] (47% yield); mp 221°–224° C.

¹H NMR ((CD₃)₂SO): δ 9.51 (1H, s, CONH), 8.18 (1H, br s, H-4), 7.60–7.48 (2H, m, H-6,7), 7.20–7.06 (4H, m, ArH), 7.00 (1H, br s, ArH), 3.75 (3H, s, N—CH₃).

¹³C NMR: δ 160.21 (CONH), 138.97 (s), 138.26 (s), 132.74 (C-5), 128.77 (s), 128.27 (d), 126.52 (d), 124.72 (s), 123.14 (d), 119.80 (s), 119.11 (d), 118.87 (s), 112.29 (d), 103.53 (CN), 30.46 (N—CH₃).

Analysis calculated for $C_{34}H_{24}N_6O_2S_2 \cdot 0.5H_2O$ requires: C, 65.7; H, 4.1; N, 13.5; S, 10.3%.

Found: C, 65.6; H, 4.0; N, 13.5; S, 10.6%.

Compound 89 of Table 1

Similarly was prepared, from 5-bromo-1-methyl-2-indolinethione [IX: $R_1$=5-Br, $R_3$=Me]; mp 137°–139° C., (Baudin J-B, Julia SA, Lorne R, *Bull. Soc. Chim. France* 1987:181 records mp 126°–127° C.) and phenyl isocyanate as above, 2,2'-dithiobis[N-phenyl-5-bromo-1-methylindolyl-3-carboxamide] (89) [V: $R_1$=5-Br, $R_2$=CONHPh, $R_3$=Me] (68% yield); mp 219°–221° C.

¹H NMR (CDCl₃): δ 8.14 (1H, br, CONH), 8.10 (1H, d, J=1.6 Hz, H-4), 7.21–7.12 (5H, m, ArH), 7.01 (1H, m, ArH), 6.83 (1H, br d, J=8.2 Hz, ArH), 3.73 (3H, s, N—CH₃).

¹³C NMR: δ 161.04 (CONH), 137.68 (s), 137.00 (s), 128.75 (d), 128.60 (d) 127.13 (s), 124.29 (d), 123.78 (d), 118.82 (d), 115.92 (s), 111.46 (d), 30.48 (N—CH₃).

Analysis calculated for $C_{32}H_{24}Br_2N_4O_2S_2$ requires: C, 53.3; H, 3.4; N, 7.8; S, 8.9%.

Found: C, 53.1; H, 3.5; N, 7.7; S, 8.9%.

Compound 90 of Table 1

A solution of 4-methoxy-1-methyl-2-oxindole [VII: $R_1$=4-OMe, $R_3$=Me] (1.20 g, 6.77 mmol) in 48% HBr/ glacial AcOH (40 mL) was heated under reflux for 6 hours, then poured into water. The precipitate of crude phenol was filtered off, washed well with water and dried, then acetylated with Ac₂O/pyridine for 1 hour at 20° C. Solvents were removed under reduced pressure, and the residue was partitioned between EtOAc and 3N HCl. Chromatography of the organic residue on silica gel, eluting with EtOAc/ petroleum ether gave 4-acetoxy-1-methyl-2-oxindole [VII: $R_1$=4-OAc, $R_3$=Me] (75% yield); mp 109°–111° C.

¹H NMR (CDCl₃): δ 7.30 (1H, dd, J=8.2, 7.7 Hz, H-6), 6.78 (1H, d, J=8.2 Hz, H-7), 6.71 (1H, d, J=7.7 Hz, H-5), 3.41 (2H, s, H-3), 3.22 (3H, s, N—CH₃), 2.32 (3H, s, OCOCH₃).

¹³C NMR: δ 174.26 (C-2), 168.30 (OCOCH₃), 164.71 (s), 146.58 (s), 129.12, 116.62 (s), 115.83 (d), 105.90 (d), 33.74 (C-3), 26.51 (N-CH₃), 20.83 (COOCH₃).

Analysis calculated for $C_{11}H_{11}NO_3$ requires: C, 64.4; H, 5.4; N, 6.8%.

Found: C, 64.3; H, 5.4; N, 7.0%.

Reaction of this with P₂S₅ as above gave 4-acetoxy-1-methyl-2-indolinethione [IX: $R_1$=4-OAc, $R_3$=Me] (94% yield); mp 156° C.

¹H NMR (CDCl₃): δ 7.35 (1H, dd, J=8.2, 7.9 Hz, H-6), 6.90 (1H, d, J=8.2 Hz, H-7), 6.86 (1H, d, J=7.9 Hz, H-5), 4.00 (2H, s, H-3), 3.61 (3H, s, N—CH₃), 2.32 (3H, s, OCOCH₃).

¹³C NMR: δ 200.75 (C-2), 168.14 (OCOCH₃), 148.30 (s), 146.27 (s), 129.44 (d), 121.18 (s), 117.69 (d), 107.32 (d), 47.09 (C-3), 31.57 (N—CH₃), 20.81 (COOCH₃).

Analysis calculated for $C_{11}H_{11}NO_2S$ requires: C, 59.7; H, 5.0; N, 6.3; S, 14.5%.

Found: C, 59.4; H, 5.2; N, 6.6; S, 14.5%.

Reaction with phenyl isocyanate as above gave 2,2'-dithiobis[N-phenyl 4-acetoxy-1-methylindolyl-3-carboxamide] (90) [V: $R_1$=4-OAc, $R_2$=CONHPh, $R_3$=Me] (31%); mp 194° C.

¹H NMR ((CD₃)₂SO): δ 9.92 (1H, s, CONH), 7.34–7.27 (4H, m, H-5,7,2',6'), 7.14 (2H, dd, J=7.8, 7.6 Hz, H-3',5'), 6.98 (1H, t, J=7.8 Hz, H-5'), 6.89 (1H, dd, J=8.0, 7.8 Hz, H-5), 3.66 (3H, s, NCH₃), 1.95 (3H, s, OCH₃).

¹³C NMR: δ 168.57 (CONHPh), 162.09 (OCOCH₃), 142.91 (s), 139.20 (s), 138.75 (s), 129.01 (s), 128.38 (d), 124.56 (d), 123.14 (d), 119.23 (s), 118.38 (d), 117.70 (s), 113.94 (d), 108.70 (d), 30.39 (N—CH₃), 20.32 (COOCH₃).

Analysis calculated for $C_{36}H_{30}N_4O_6S_2$ requires: 679.1685.

Found: [M+H]⁺ 679.1705 (FABMS).

Compound 91 of Table 1

Similar demethylation/acetylation of 5-methoxy-1-methyl-2-oxindole [VII: $R_1$=5-OMe, $R_3$=Me] gave 5-acetoxy-1-methyl-2-oxindole [VII: $R_1$=5-OAc, $R_3$=Me] (70% yield); mp (EtOAc/petroleum ether) 104°–106° C.

¹H NMR (CDCl₃): δ 7.01 (1H, br s, H-4), 7.00 (1H, dd, J=9.1, 2.4 Hz, H-6), 3.53 (2H, s, H-3), 3.20 (3H, s, N—CH₃), 2.30 (3H, s, OCOCH₃).

¹³C NMR: δ 174.79 (C-2), 169.96 (OCOCH₃), 146.08 (s), 142.96 (s), 125.50 (s), 120.84 (d), 118.54 (d), 108.25 (d), 35.89 (C-3), 26.30 (N—CH₃), 21.04 (OCOCH₃).

Analysis calculated for $C_{11}H_{11}NO_3$ requires: C, 64.4; H, 5.4; N, 6.8%.

Found: C, 64.4; H, 5.4; N, 6.8%.

Reaction of this with P₂S₅ as above gave 5-acetoxy-1-methyl-2-indolinethione [IX: $R_1$=5-OAc, $R_3$=Me] (86% yield); mp 134°–135.5° C.

¹H NMR (CDCl₃): δ 7.06 (2H, br s, H-4,6), 6.93 (1H, d, J=8.6 Hz, H-7), 4.08 (2H, s, H-3), 3.60 (3H, s, N—CH₃), 2.31 (3H, s, OCOCH₃).

¹³C NMR: δ 200.86 (C-2), 169.62 (OCOCH₃) 147.62 (s), 144.14 (s), 130.10 (s), 120.97 (d), 117.99 (d), 109.62 (d), 48.79 (C-3), 31.24 (N—CH₃), 20.94 (OCOCH₃).

Analysis calculated for $C_{11}H_{11}NO_2S$ requires: C, 59.7; H, 5.0; N, 6.3; S, 14.5%.

Found: C, 59.6; H, 5.2; N, 6.2; S, 14.6%.

Reaction with phenyl isocyanate as above gave 2,2'-dithiobis[N-phenyl-5-acetoxy-1-methylindolyl-3-carboxamide] (91) [V: $R_1$=5-OAc, $R_2$=CONHPh, $R_3$=Me], (45% yield); mp 147°–150° C.

¹H NMR ((CD₃)₂SO): δ 9.60 (1H, br, CONH), 7.54 (1H, d, J=1.9 Hz, H-4), 7.42 (1H, d, J=8.9 Hz, H-7), 7.23 (2H, d, J=7.8 Hz, H-2',6') 7.17 (2H, dd, J=7.8, 7.1 Hz, H-3', 5') 7.06 (1H, dd, J=8.9, 1.9 Hz, H-6), 6.98 (1H, t, J=7.1 Hz, H-4), 3.66 (3H, s, NCH₃), 2.29 (3H, s, OCOCH₃).

¹³H NMR: δ 169.52 (CONH), 161.18 (OCOCH₃), 145.27 (s), 138.49 (s), 135.41 (s), 128.31 (d), 125.46 (s), 122.94 (d), 119.15 (d), 112.82 (d), 111.43 (d), 30.26, (N—CH₃), 20.80 (OCOCH₃).

Analysis calculated for $C_{36}H_{30}N_4O_6S_2 \cdot 0.5H_2O$ requires: C, 62.9; H, 4.5; N, 8.2; S, 9.3%.

Found: C, 63.1; H, 4.6; N, 8.2; S, 9.5%.

Compound 92 of Table 1

A stirred suspension of the 5-acetoxydisulfide (91) (0.25 g, 0.37 mmol) in MeOH (15 mL) was treated with NaBH₄

(0.05 g, 1.32 mmol) at 20° C. for 10 minutes. Aqueous 3N KOH (2 mL) was then added, and after a further 15 minutes the solution was diluted with water and extracted with $CH_2Cl_2$. The resulting oil was immediately dissolved in MeOH (3 mL) and mixed with $H_2O_2$ (0.10 mL of 35%). The solution was chilled at −30° C. for 48 hours and then filtered to yield 2,2'-dithiobis(N-phenyl-5-hydroxy-1-methylindole-3-carboxamide) (92) [V: $R_1$=5-OH, $R_2$=CONHPh, $R_3$=Me] (41 mg, 19%); mp 185°–187° C.

$^1$H NMR (($CD_3$)$_2$SO): δ 9.50 (1H, s, CONH), 9.15 (1H, br, OH), 7.32 (2H, d, J=7.8 Hz, H-2',6'), 7.27 (1H, d, J=8.9 Hz, H-7), 7.19 (1H, d, J=2.3 Hz, H-4), 7.18 (2H, dd, J=7.8, 7.4 Hz, H-3',5'), 6.99 (1H, t, J=7.4 Hz, H-4'), 6.83 (1H, dd, J=8.9, 2.3 Hz, H-6), 3.51 (3H, s, N—$CH_3$).

Analysis calculated for $C_{32}H_{26}N_4O_4S_2.H_2O$ requires: C, 64.6; H, 4.4; N, 9.4%.

Found: C, 62.7; H, 4.6; N, 9.1%.

Compound 93 of Table 1

Similar demethylation/acetylation of 6-methoxy-1-methyl-2-oxindole [VII: $R_1$=6-OMe, $R_3$=Me] gave 6-acetoxy-1-methyl-2-oxindole [VII: $R_1$=6-OAc, $R_3$=Me] (81% yield); mp 119°–121° C.

$^1$H NMR (CDCl$_3$): δ 7.22 (1H, d, J=7.9 Hz, H-4), 6.74 (1H, dd, J=7.9, 2.1 Hz, H-5), 6.59 (1H, d, J=2.1 Hz, H-7), 3.49 (2H, s, H-3), 3.18 (3H, s, N—$CH_3$), 2.31 (3H, s, OCO$CH_3$).

$^{13}$C NMR: δ 175.28 (C-2), 169.57 (O$C$OCH$_3$), 150.74 (s), 146.23 (s), 124.83 (d), 121.81 (s), 115.00 (d), 102.68 (d), 35.33 (C-3), 26.27 (N—$CH_3$), 21.09 (OCO$C$H$_3$).

Analysis calculated for $C_{11}H_{11}NO_3$ requires: C, 64.4; H, 5.4; N, 6.8%.

Found: C, 64.5; H, 5.5; N, 6.9%.

Reaction of this with $P_2S_5$ as above gave 6-acetoxy-1-methyl-2-indolinethione [IX: $R_1$=6-OAc, $R_3$=Me] (91% yield); mp 131°–133° C.

$^1$H NMR: δ (CDCl$_3$) 7.27 (1H, d, J=8.0 Hz, H-4), 6.87 (1H, dd, J=8.0, 1.9 Hz, H-5), 6.75 (1H, d, J=1.9 Hz, H-7), 4.08 (2H, s, H-3), 3.58 (s, N—$CH_3$), 2.33 (3H, s, OCO$CH_3$).

$^{13}$C NMR: δ 202.18 (C-2), 169.44 (O$C$OCH$_3$), 150.80 (s), 147.57 (s), 126.38 (s), 124.32 (d), 117.05 (d), 104.06 (d), 48.62 (C-3), 31.33 (N—$CH_3$), 21.09 (OCO$C$H$_3$).

Analysis calculated for $C_{11}H_{11}NO_2S$ requires: C, 59.7; H, 5.0; N, 6.3; S, 14.5%.

Found: C, 59.4; H, 5.2; N, 6.1; S, 14.3%.

Reaction with phenyl isocyanate as above gave 2,2'-dithiobis[N-phenyl-6-acetoxy-1-methylindolyl-3-carboxamide] (93) [V: $R_1$=6-OAc, $R_2$=CONHPh, $R_3$=Me] (53%); mp 219°–222° C.

$^1$H NMR (($CD_3$)$_2$SO): δ 9.71 (1H, br s, CONH), 7.78 (1H, d, J=8.7 Hz, H-4), 7.27 (3H, m, H-2',6'), 7.18 (2H, dd, J=8.2, 7.3 Hz, H-3',5'), 6.99 (1H, t, J=7.3 Hz, H-4'), 6.95 (1H, dd, J=8.7, 1.8 Hz, H-5), 3.60 (3H, s, NCH$_3$), 2.32 (3H, s, OCOCH$_3$).

$^{13}$C NMR: δ 169.31 ($C$ONHPh), 161.23 (O$C$OCH$_3$), 147.99 (s), 138.54 (s), 137.66 (s), 128.29 (d), 123.13 (s), 122.98 (d), 121.48 (d), 119.38 (d), 118.73 (s), 116.34 (d), 103.76 (d), 30.17 (N—$CH_3$), 20.81 (OCO$C$H$_3$).

Analysis calculated for $C_{36}H_{30}N_4O_6S_2$ requires: C, 63.7; H, 4.5; N, 8.3; S, 9.4%.

Found: C, 63.7; H, 4.4; N, 8.2; S, 9.8%.

Compound 94 of Table 1

Similar treatment of the 6-acetoxydisulfide (93) gave 2,2'-dithiobis (6-hydroxy-1-methyl-N-phenyl-1H-indole-3-carboxamide) (94) [V: $R_1$=6-OH, $R_2$=CONHPh, $R_3$=Me]; mp 185°–187° C. (dec).

$^1$H NMR (($CD_3$)$_2$SO): δ 10.01, 9.43 (2H, 2s, OH and CONH), 7.76 (1H, d, J=7.9 Hz, H-4), 7.35 (2H, d, J=7.6 Hz, H-2',6'), 7.31 (1H, d, J=2.2 Hz, H-7), 7.10 (2H, dd, J=7.6, 7.4 Hz, H-3',5'), 6.95 (1H, t, J=7.4 Hz, H-4'), 6.71 (1H, dd, J=7.9, 2.2 Hz, H-5), 3.58 (3H, s, NCH$_3$).

Analysis calculated for $C_{32}H_{26}N_4O_4S_2$ requires: 595.1474.

Found: [M+H$^+$ 595.1483 (FABMS).

Compound 95 of Table 1

Similar demethylation/acetylation of 7-methoxy-1-methyl-2-oxindole [VII: $R_1$=7-OMe, $R_3$=Me] gave 7-acetoxy-1-methyl-2-oxindole [VII: $R_1$=7-OAc, $R_3$=Me] (68% yield); mp 95°–97° C.

$^1$H NMR (CDCl$_3$): δ 7.12 (1H, dd, J=7.1, 1.0 Hz, H-6), 7.01 (1H, dd, J=8.4, 7.1 Hz, H-5), 6.96 (1H, dd, J=8.4, 1.0 Hz, H-4), 3.54 (2H, s, H-3), 3.34 (3H, s, N—$CH_3$), 2.35 (3H, s, OCOCH$_3$).

$^{13}$C NMR: δ 174.88 (C-2), 169.57 (O$C$OCH$_3$), 136.11 (s), 134.24 (s), 126.73 (s), 123.02 (d), 122.60 (d), 122.18 (d), 35.68 (C-3), 28.17 (N—$CH_3$), 20.89 (OCO$C$H$_3$).

Analysis is calculated for $C_{11}H_{11}NO_3$ requires: C, 64.4; H, 5.4; N, 6.8%.

Found: C, 64.5; H, 5.5; N, 6.7%.

Reaction of this with $P_2S_5$ as above gave 7-acetoxy-1-methyl-2-indolinethione [IX: $R_1$=7-OAc, $R_3$=Me] (85% yield); mp 133°–135° C.

$^1$H NMR (CDCl$_3$): δ 7.17 (1H, d, J=7.9 Hz, H-6), 7.14 (1H, dd, J=8.0, 7.9 Hz, H-5), 7.01 (1H, d, J=8.0 Hz, H-4), 4.13 (2H, s, H-3), 3.78 (3H, s, N—$CH_3$), 2.39 (3H, s, OCOCH$_3$).

$^{13}$C NMR: δ 202.00 (C-2), 169.22 (O$C$OCH$_3$), 137.53 (s), 134.33 (s), 131.42 (s), 124.78 (d), 123.23 (d), 121.69 (d), 49.20 (C-3), 33.67 (N—$CH_3$), 20.97 (OCO$C$H$_3$).

Analysis calculated for $C_{11}H_{11}NO_2S$ requires: C, 59.7; H, 5.0; N, 6.3; S, 14.5%.

Found: C, 59.4; H, 5.2; N, 6.2; S, 14.2%.

Reaction with phenyl isocyanate as above gave 2,2'-dithiobis[N-phenyl-7-acetoxy-1-methylindolyl-3-carboxamide] (95) [V: $R_1$=7-OAc, $R_2$=CONHPh, $R_3$=Me]; mp 212°–214.5° C.

$^1$H NMR (($CD_3$)$_2$SO): δ 10.28 (1H, br, CONH), 7.72 (1H, d, J=7.8 Hz, H-4), 7.44 (2H, d, J=7.8 Hz, H-2',6') 7.23 (2H, dd, J=8.1, 7.8 Hz, H-3', 5'), 7.11 (1H, dd, J=7.8, 7.7 Hz, H-5), 7.01 (2H, m, H-6, H-4'), 3.68 (3H, s, N—$CH_3$), 2.35 (3H, s, OCOCH$_3$).

$^{13}$C NMR: δ 169.49 (CONHPh), 161.36 (OCOCH$_3$), 138.75 (s), 135.92 (s), 129.43 (s), 128.80 (s), 128.43 (d), 128.0 (s), 123.13 (d), 121.21 (d), 119.35 (d), 118.50 (d), 118.16 (d), 31.84 (OCOCH$_3$), 20.68 (N—$CH_3$).

Analysis calculated for $C_{36}H_{30}N_4O_6S_2.0.5H_2O$ requires: C, 62.9; H, 4.5; N, 8.2; S, 9.3%.

Found: C, 62.9; H, 4.5; N, 7.8; S, 9.6%.

Compound 96 of Table 1

Reaction of 96 as above with NaBH$_4$ followed by 3N KOH gave, after reoxidation, 2,2'-dithiobis(N-phenyl-7-hydroxy-1-methylindole-3-carboxamide) (96) [V: $R_1$=7-OH, $R_2$=CONHPh, $R_3$=Me] (81% yield); mp 207° C. (dec).

¹H NMR ((CD₃)₂SO): δ 9.94, 9.63 (each 1H, 2s, CONH and ArOH), 7.33 (1H, d, J=8.0 Hz, H-2',6'), 7.23 (1H, d, J=8.0 Hz, H-4), 7.18 (2H, dd, J=8.0, 8.0 Hz, H-3',5'), 6.99 (1H, t, J=8.0 Hz, H-4'), 6.91 (1H, dd, J=8.0, 7.5 Hz, H-5), 6.65 (1H, d, J=7.5 Hz, H-6), 3.89 (3H, s, N—CH₃).

¹³C NMR: δ 161.89 (CONH), 144.46 (s), 138.72 (s), 128.30 (d), 127.74 (s), 127.57 (s), 122.98 (d), 121.76 (d), 119.46 (d), 119.36 (s), 119.32 (s), 111.57 (d), 108.85 (d), 32.84 (N—CH₃).

Analysis calculated for $C_{32}H_{26}N_4O_4S_2$ requires: C, 64.3; H, 4.4; N, 9.4; S, 10.8%.

Found: C, 64.2; H, 4.4; N, 9.3; S, 10.9%.;

Compound 97 of Table 1

Similarly was prepared, from 1-methyl -2-indolinethione and methyl isocyanate, bis[N-methyl 1-methylindolyl-3-carboxamide-(2)]-disulfide [V: $R_1$=H, $R_2$=CONHMe, $R_3$=Me] (97) (18% yield); mp 162°–165° C.

¹H NMR (CDCl₃): δ 8.07 (1H, d, J=8.0 Hz, H-4), 7.40–7.20 (3H, m, H-5, H-6, H-7), 6.31 (1H, br, CONH), 3.82 (3H, s, NCH₃), 2.13 (3H, d, J=5.0 Hz, CONHC$\underline{H}$₃).

¹³C NMR (CDCl₃): δ 173.29 (CONH), 128.34 (s), 125.28, 122.31, 122.02, 120.0 (s), 116.5 (s), 113.2 (s), 110.06, 30.26 (N—CH₃), 25.68 (CONHCH₃).

Alternate Preparation of Compound 97 of Table 1

A mixture of 20 g (136 mmol) of 1-methyl-2-indolinone and 250 mL of dichloroethane was sealed in a 500 mL stainless steel autoclave. The reactor was cooled to less than −10° C. and 60 g of phosgene was distilled into the vessel. The reactor was sealed and heated to 80° C. while rocking. After 1 hour, the reactor was cooled to room temperature, vented, and purged with nitrogen. The reactor was opened and the solution was rinsed out with fresh dichloromethane. The dichloroethane solution from the rinsed reactor was concentrated to a purple solid. The solid was dissolved into 300 mL of dichloromethane and the solution was cooled in an ice bath. Into the cold solution was bubbled anhydrated methylamine at a moderate rate over a 50-minute period. The mixture was washed with water (2×300 mL) and brine, dried (Na₂SO₄), and concentrated to ca. 150 mL. The solution was purified by flash silica gel chromatography (7.5×13 cm bed) eluting with 1.6 L dichloromethane, 2 L 2%, then 2 L 5% acetone/dichloromethane, with 500 mL fractions collected. Impure early product fractions were combined, concentrated, and recrystallized from 40 mL ethanol/12 mL pet ether to give 3.04 g of 2-chloro-1-methylindole-3-N-methylcarboxamide [XXII: $R_6$=H, $R_7$=CH₃]; mp 148°–151° C. Pure product fractions were combined and concentrated to give 16.41 g of additional product as a pale yellow solid; mp 150°–151° C. Total yield=19.45 g (64%).

Reaction of 9.30 g (41.8 mmol) of the above carboxamide was carried out with 129.5 mmol of MeSLi in 36 mL of DMA. After heating at 60° C. for 7 hours, the clear amber solution was cooled in an ice bath and treated slowly with 150 mL of 5% aqueous HCl. The resultant suspension was diluted with ca. 150 mL of dichloromethane, and the mixture was stirred for 1 hour. The layers were separated, and the aqueous phase was extracted twice more. The combined organic extracts were washed with water (3×200 mL), then brine, dried MgSO₄, and concentrated to a residue that was pumped at 0.05 mm for 1 hour to leave 12.5 g of an orange solid. The solid was suspended into 100 mL of HOAc and 50 mL of water, and with vigorous stirring the suspension was treated with 12.85 g of sodium perborate. The thick suspension was stirred for ca. 30 minutes, then filtered using 10% methanol in water to aid in the transfer. The solids were washed well with water, then with ether, and air dried. Further drying at 200 mm/65° C./overnight over P₂O₅ afforded 6.38 g (70%) of pure bis[N-methyl 1-methylindolyl-3-carboxamide-(2)]disulfide (97) [V: $R_2$=CONHCH₃]; mp 186°–187° C.

Compound 98 of Table 1

Similarly was prepared, from 1'-methyl-2-indolinethione and benzyl isocyanate, bis[N-benzyl 1-methylindolyl-3-carboxamide-(2)]disulfide [V: $R_1$=H, $R_2$=CONHCH₂Ph, $R_3$=Me] (98) (0.12 g, 22%); mp 145°–147° C.

¹H NMR (CDCl₃): δ 8.13 (1H, d, J=8.1 Hz, H-4), 7.38 (1H, t, J=7.4 Hz, H-6), 7.31–7.20 (6H, m, H-5 and CH₂P$\underline{h}$), 7.11 (1H, d, J=7.4 Hz, H-7), 6.60 (1H, br, CONH), 3.75 (2H, br, COC$\underline{H}$₂Ph), 3.64 (3H, s, N—CH₃).

¹³C NMR (CDCl₃): δ 163.42 ($\underline{C}$ONH), 138.37 (s), 128.59, 128.54 (s), 127.63 (s), 127.52, 127.40 (s), 127.20, 126.40 (s), 125.39, 122.52, 122.32, 110.30 (C-7), 42.94 (CH₂Ph), 30.24 (N—CH₃).

Analysis calculated for $C_{34}H_{30}N_4O_2S_2$ requires: C, 69.1; H, 5.2; N, 9.5; S, 10.8%.

Found: C, 68.6; H, 5.3; N, 9.5; S, 10.6%.

Example E

Preparation of Compounds 19 and 83 of Table 1 by the Method of Scheme 4

A mixture of 2-amino-3-methylpyridine (43.28 g, 0.4 mol) and benzotriazole (47.65 g, 0.4 mol) in EtOH (500 mL) was treated over 5 minutes with formaldehyde (32.2 g of 37% solution, 0.4 mol). The mixture was stirred at 20° C. overnight, then cooled and filtered to give 2-[(1-benzotriazolyl)methyl]-3-methyl pyridine (30 g, 31%). A sample was crystallized from EtOH; mp 175°–177° C.

¹H NMR (CDCl₃): δ 8.10 (1H, d, J=5 Hz, H-8), 8.10 and 8.00 (2H, 2d, J=8 Hz, H-4',7'), 7.45 and 7.33 (2H, 2t, J=8 Hz, H-5',6'), 7.25 (1H, d, J=7 Hz, H-4), 6.54 (1H, dd, J=7.5 Hz, H-5), 6.47 (2H, d, J=7 Hz, CH₂), 5.38 (1H, t, J=7 Hz, NH), 2.07 (3H, s, CH₃).

Crude 2-[(1-benzotriazolyl)methyl]-3-methylpyridine (30 g, 125 mmol) was suspended in dioxan (400 mL) and treated with NaBH₄ (5 g, 130 mmol). The mixture was heated under reflux for 8 hours, then the majority of the solvent was removed under reduced pressure. The residue was partitioned between toluene and water, and the organic layer was washed successively with dilute NaOH solution and water, and dried. Removal of the solvent gave 2.-methylamino-3-methylpyridine as an oil (12.8 g, 84%).

¹H NMR (CDCl₃): δ 8.04 (1H, d, J=5.1 Hz, H, H-6), 7.19 (1H, d, J=7.1 Hz, H-4), 6.50 (1H, dd, J=7.1, 5.1 Hz, 5-H), 4.15 (1H, m, NH), 3.03 (3H, d, J=4.5 Hz, CH₃N), 2.06 (3H, s, CH₃).

¹³C NMR (CDCl₃): δ 157.3 (C-2), 145.0 (C-8), 136.1 (C-4), 116.4 (C-3), 111.9 (C-5), 28.3 (CH₂) and 16.5 (CH₃).

A solution of the above pyridine (6.1 g, 50 mmol) in dry THF (150 mL) was cooled to −78° C. under dry N₂, and n-BuLi (19.6 mL of a 2.5M solution in hexanes, 50 mmol) was added dropwise, followed by t-BuLi (32 mL of a 1.7M in pentane, 55 mmol). The resulting mixture was allowed to warm to −20° C. and maintained at that temperature for 30 minutes before being recooled to −78° C. and treated with dry $CO_2$ gas until the mixture was decolorized. After warming to 20° C., the mixture was acidified with dilute HCl, and the solvent was removed under reduced pressure. The residue was dissolved in EtOH (100 mL) containing p-TsOH (100 mg), heated under reflux for 3 hours to effect ring closure, and neutralized with aqueous ammonia. Solvent was then removed, and the residue was worked up in EtOAc to give an oil, which was extracted with hot hexane, charcoaled, and filtered through celite. Concentration of the solution and cooled, gave 1-methyl-7-aza-2-indolinone (1,3-dihydro-1-methyl-2H-pyrrolo-( 2,3-bipyridin-2-one) [VII: $R_1$=7-aza, $R_3$=Me] (1.2 g, 15%); mp (hexane) 94°–96° C.

$^1$H NMR ($CDCl_3$): δ 8.15 (1H, d, J=5.3 Hz, H-8), 7.48 (1H, d, J=7.2 Hz, H-4), 8.94 (1H, dd, J=7.2, 5.3 Hz, H-5), 3.53 (2H, s, $CH_2$), 3.29 (3H, s, $CH_3$).

$^{13}$C NMR ($CDCl_3$): δ 174.1 (C-2), 158.1 (C-7a), 146.6 (C-8), 131.3 (C-4), 119.0 (C-3a), 117.8 (C-5), 34.6 ($CH_2$), 25.1 ($CH_3$).

$P_2S_5$ (3.80 g, 8.10 mmol) was added to a vigorously stirred suspension of $Na_2CO_3$ (0.88 g, 8.10 mmol) in THF (30 mL). After the mixture had become homogeneous (ca. 15 minutes), a solution of 1-methyl-7-aza-2-indolinone [VII: $R_1$=7-aza, $R_3$=Me] (1.00 g) in THF (10 mL) was added and stirring was continued for 18 hours at 20° C. Solvent was removed under reduced pressure, and the residue was partitioned between EtOAc and water. Workup of the organic layer, and chromatography of the residue on silica gel (elution with EtOAc/petroleum ether (1:5)) gave 1-methyl-7-aza-2-indolinethione [IX: $R_1$=7-aza, $R_3$=Me] (0.81 g, 73%); mp (EtOAc/petroleum ether) 130°–133° C.

$^1$H NMR ($CDCl_3$): δ 8.28 (1H, dd, J=5.2, 0.6 Hz, H-6), 7.57 (1H, dd, J=7.3, 0.6 Hz, H-4), 7.07 (1H, dd, J=7.3, 5.2 Hz, H-5), 4.06 (2H, s, H-3), 3.66 (3H, s, N—$CH_3$).

$^{13}$C NMR: δ 201.70 (C-2), 159.21 (s), 147.22 (d), 131.39 (d), 123.20 (s), 119.34 (d), 46.98 (C-3), 30.02 (N—$CH_3$).

Analysis calculated for $C_8H_8N_2S$ requires: C, 58.5; H, 4.9; N, 17.1; S, 19.5%.

Found: C, 58.3; H, 4.9; N, 17.0; S, 19.8%.

A solution of the above thione (0.70 g, 4.26 mmol) in THF (5 mL) was added dropwise over 5 minutes under $N_2$ to an ice-cooled suspension of NaH (0.2 g of a 60% w/w dispersion in oil, 6.11 mmol). After gas evolution had ceased (5 minutes), phenyl isocyanate (0.47 mL, 4.25 mmol) was added, and stirring was continued for 1 hour at 20° C. Aqueous 1N HCl was then added, and the mixture was extracted with EtOAc. The organic layer was worked up, and the residue was chromatographed on silica gel. Elution with EtOAc/petroleum ether (1:1) and EtOAc gave foreruns, while elution with EtOAc/MeOH (10:1) gave N-phenyl (1-methyl-7-aza-2-thioxo-3-indolinyl) carboxamide (19) [IV: $R_1$=7-aza, $R_2$=CONHPh, $R_3$=Me] as a fluorescent green solid (0.67 g, 55% yield); mp (after trituration with MeOH) 162°–164° C. (dec).

$^1$H NMR (($CD_3$)$_2$SO): δ 12.46 (1H, s, CONH), 8.68 (1H, dd, J=7.7, 1.0 Hz, H-6), 8.02 (1H, d, J=6.0 Hz, H-4), 7.72 (2H, d, J=8.4 Hz, ArH), 7.36–7.29 (4H, m, ArH), 7.01 (1H, t, J=7.3 Hz, ArH), 3.80 (3H, s, N—$CH_3$).

$^{13}$C NMR: δ 66.96 (C-2), 163.59 (CONH), 140.77 (s), 139.81 (s), 129.29 (d), 128.85 (d), 127.21 (s), 126.84 (d), 122.16 (d), 118.65 (d), 115.92 (d), 48.57 (C-3), 29.18 (N—$CH_3$).

Analysis calculated for $C_{15}H_{13}N_3O_2S.CH_3OH$ requires: C, 60.9; H, 5.4; N, 13.3; S, 10.2%.

Found: C, 60.6; H, 5.4; N, 13.4; S, 10.3%.

A solution of sodium perborate (0.50 g, 5.00 mmol) in water (25 mL) was added to a vigorously stirred suspension of the above 7-aza compound (19) (0.50 g, 176 mmol) in glacial AcOH (50 mL). After 1 hour the solid was filtered off, washed sequentially with water and $Et_2O$, and dried to give 2,2'-dithiobis[N-phenyl-1-methyl-7-azaindolyl-3-carboxamide] [V: $R_1$=7-aza, $R_2$=CONHPh, $R_3$=Me] (83) (100%); mp 197°–198° C.

$^1$H NMR (($CD_3$)$_2$SO): δ 9.49 (1H, s, CONH), 8.36 (1H, dd, J=4.5, 1.5 Hz, H-6), 8.14 (1H, dd, J=7.9, 1.5 Hz, H-4), 7.19 (1H, dd, J=7.9, 4.5 Hz, H-5), 7.16–7.09 (4H, m, ArH), 6.98 (1H, m, ArH), 3.75 (3H, s, N—$CH_3$).

$^{13}$C NMR: δ 160.42 (CONH), 147.58 (s), 145.99 (d), 138.29 (s), 129.86 (s), 129.62 (d), 128.25 (d), 123.05 (d), 119.23 (d), 118.09 (s), 117.76 (d), 117.57 (s), 28.61 (N—$CH_3$).

Analysis calculated for $C_{30}H_{24}N_6O_2S_2.2.5H_2O$ requires: C, 59.1; H, 4.8; N, 13.8; S, 10.5%.

Found: C, 59.1; H, 4.2; N, 13.8; S, 10.5%.

Example F

Preparation of Compound 99 of Table 1 by the Method Outlined in Scheme 5

A solution of 2-[(4-methylphenylsulfonyl)methyl]-aniline [XII: $R_1$=H, $R_2$=Me, X=4-methylphenyl](Le Corre M, Hercouet A, Le Stanc Y, Le Baron Tetrahedron 1985;22:5313) in dry THF (60 mL), under $N_2$, was cooled to −78° C. and n-butyllithium (9.6 mL, 2.5M solution in hexanes) was added dropwise. The mixture was allowed to warm to −10° C. to give a deep red colored solution which was recooled to −78° C. after 30 minutes. $CS_2$ (3 mL, 5 mmol) was added rapidly, and the mixture was allowed to warm slowly to 20° C. The solvent was removed under vacuum and the residue was diluted with water, and acidified with 2M HCl. After stirring at 20° C. for 3 hours, the solution was extracted with EtOAc and dried ($Na_2SO_4$). The solvent was removed, and chromatography of the residue on $SiO_2$ ($CH_2Cl$/EtOAc, 9:1) gave bis[3-(4-methylphenylsulfonyl)-2-indolyl]disulfide [XIII: $R_1$=H, $R_2$=Me, X=4-methylphenyl] (99) (0.2 g, 7% yield); mp (benzene) 230°–233° C.

$^1$H NMR ($CDCl_3$): δ 8.06 (1H, m, NH), 7.91 (3H, m, H-4, H-2, and H-4'), 7.45 (1H, m, H-6), 7.21 (4H, m, H-5, H-7, H-3', and H-5'), 2.33 (3H, s, $CH_3$).

$^{13}$C NMR ($CDCl_3$): δ 144.1, 140.0, 136.6, 134.0, 129.9 (CH), 126.4 (CH), 125.4, 124.5 (CH), 122.8 (CH), 119.1 (CH), 115.1, 112.2 (CH), and 21.5 ($CH_3$).

Analysis calculated for $C_{30}H_{24}N_2O_4S_4.0.2(C_6H_6)$ requires: C, 60.4; H, 4.1; N, 5.5; S, 20.7%.

Found: C, 60.7; H, 4.4; N, 4.9; S, 21.1%.

Example G

Preparation of Compounds 24 and 100 of Table 1 by the Method Outlined in Scheme 6

A stirred solution of benzoyl chloride (from benzoic acid, 0.45 g, 3.68 mmol) in $Me_2CO$ (20 mL) was treated dropwise at 0° C. with a solution of $NaN_3$ (0.26 g, 3.98 mmol) in water (2 mL). After 15 minutes the solution was partitioned between water, and benzene, and the organic layer was washed well with $NaHCO_3$ and worked up to give crude phenacyl azide, which was used directly.

A solution of 1-methyl-2-indolinethione (0.50 g, 3.06 mmol) in dry THF (3 mL) was added dropwise at 20° C. under $N_2$ to a stirred suspension of NaH (0.13 g of a 60% w/w suspension in mineral oil, 3.37 mmol) in THF (2 mL). After gas evolution had ceased (5 minutes), a solution of the above phenacyl azide in THF (2 mL) was added dropwise, and the mixture was stirred at 20° C. for 1 hour, then poured into 6N HCl and extracted with EtOAc. The residue from the organic layer was chromatographed on silica gel. Elution with $CH_2Cl_2$/petroleum ether (3:7) gave foreruns, and elution with $CH_2Cl_2$/petroleum ether (2:3) gave 3-benzoyl-1-methyl-2-indolinethione [XV: $R_1$=H, $R_3$=Me, $R_5$=C6H5] (24) (0.31 g, 38%); mp (trituration from MeOH) 132°–134° C.

$^1$H NMR (CDCl$_3$): δ 15.83 (1H, s, SH), 7.68–7.53 (5H, m, COPh), 7.21 (1H, dd, J=8.1, 7.3 Hz, H-5), 7.11 (1H, d, J=8.1 Hz, H-4), 6.90 (1H, dd, J=8.0, 7.3 Hz, H-6), 6.76 (1H, d, J=8.0 Hz, H-7), 3.74 (3H, S, NCH$_3$).

$^{13}$C NMR (CDCl$_3$): δ 181.71 (COPh), 175.09 (C-2), 141.42 (s), 134.87 (s), 131.29, 128.85, 128.37, 125.64 (4×d), 125.22 (s), 122.81, 120.31 (2×d), 111.77 (s), 109.129 (d), 29.57 (NCH$_3$).

Analysis calculated for $C_{16}H_{13}NOS$ requires: C, 71.9; H, 4.9; N, 5.2; S, 12.0%.

Found: C; 71.6; H, 5.1; N, 6.2; S, 13.9%.

A solution of 24 (0.10 g, 0.37 mmol) in $CH_2Cl_2$ (20 mL) was treated dropwise at 20° C. with a solution of $I_2$ (0.50 g) in $CH_2Cl_2$ (5 mL), until TLC indicated complete conversion (ca. 2 hours). The solution was concentrated to ca. 1 mL and chromatographed directly on silica gel. Elution with $CH_2Cl_2$ gave traces of $I_2$ and starting material, and further elution with $CH_2Cl_2$/MeOH (19:1) gave bis[3-benzoyl-1-methylindole-( 2)]disulfide [XVI: $R_1$=H, $R_3$=Me, $R_5$=C$_6$H$_5$] (100) (0.06 g, 61%); mp (CHCl$_3$/petroleum ether) 199°–202° C.

$^1$H NMR (CD$_3$SOCD$_3$): δ 7.56 (1H, d, J=8.4 Hz, H-4), 7.50 (1H, d, J=8.1 Hz, H-7), 7.46 (dd, J=8.1, 7.4 Hz, H-6), 7.35 (1H, dd, J=8.4, 7.4 Hz, H-5), 7.19 (3H, m, H-2',4',6'), 6.92 (2H, d, J=7.1 Hz, H-3',5'), 3.48 (3H, s, NCH$_3$).

$^{13}$C NMR (CD$_3$SOCD$_3$): δ 190.20 (COPh), 140.05, 138.03, 132.75 (3×s), 131.60, 128.48, 127.88 (3×d), 126.00 (s), 124,78, 122.27 (2×d), 122.03 (s), 121.03, 111.20 (2×d), 30.37 (NCH$_3$).

Analysis calculated for $C_{32}H_{24}N_2O_2S_2$ requires: C, 69.8; H, 4.8; N, 5.1; S, 11.6%.

Found: C, 70.3; H, 4.7; N, 5.2; S, 11.3%.

Compounds 25, 26, 101, and 102 of Table 1

Similar treatment of 1-methyl-2-indolinethione with 4-carbomethoxybenzoyl azide gave 3-(4'-carbomethoxybenzoyl)- 1-methyl -2-indolinethione [XV: $R_1$=H, $R_3$=Me, $R_5$=4-MeOOCC$_6$H$_4$] (26) (68%); mp 164°–166° C.

$^1$H NMR (CDCl$_3$): δ 15.85 (1H, s, SH), 8.23 (2H, d, J=8.3 Hz, H-3',5'), 7.76 (2H, d, J=8.3 Hz, H-2',6'), 7.23 (1H, dd, J=8.0, 7.6 Hz, H-5'), 7.12 (1H, d, J=7.6 Hz, H-4), 6.90 (1H, dd, J=8.0, 7.9 Hz, H-6), 6.69 (1H, d, J=7.9 Hz, H-7), 3.99 (3H, s, COOCH$_3$), 3.74 (3H, s, NCH$_3$).

$^{13}$C NMR (CDCl$_3$): δ 182.07 (COAr), 173.27 (C-2), 166.31 (COOCH$_3$), 141.59, 138.92, 132.51 (3×s), 130.11, 128.54, 126.04 (3×d), 124.76 (s), 123.00, 120.26 (2×d), 119.95 (s), 109.28 (d), 52.50 (COOCH$_3$), 29.61 (NCH$_3$).

Analysis calculated for $C_{18}H_{15}NO_3S$ requires: C, 66.4; H, 4.7; N, 4.3; S, 9.8%.

Found: C, 66.5; H, 4.7; N, 4.6; S, 9.8%.

Oxidation of 26 with $I_2$/$CH_2Cl_2$ as above gave bis[3-(4'-carbomethoxybenzoyl)-1-methylindole-(2)]disulfide [XVI: $R_1$=H, $R_3$=Me, $R_5$=4-MeOOCC$_6$H$_4$] (102); mp (CHCl$_3$/petroleum ether) 200°–203° C.

$^1$H NMR (CD$_3$SOCD$_3$): δ 7.74 (2H, d, J=8.4 Hz, H-3',5'), 7.67 (1H, d, J=8.0 Hz, H-4), 7.64 (1H, d, J=8.4 Hz, H-7), 7.44 (1H, dd, J=8.4, 8.0 Hz, H-6), 7.27 (1H, dd, J=8.0, 8.0 Hz, H-5), 6.99 (2H, d, J=8.4 Hz, H-2',6'), 3.91 (3H, s, COOCH$_3$), 3.51 (3H, s, NCH$_3$).

$^{13}$C NMR (CD$_3$SOCD$_3$): δ 189.31 (COAr), 165.56 (COOCH$_3$), 143.77, 137.98, 133.31, 131.61 (4×s), 128.50, 128.33 (2×d), 125.87 (s), 124.99, 122.62 (2×d), 121.27 (s), 121.09, 111.22 (2×d), 52.34 (COOCH$_3$), 30.33 (NCH$_3$).

Analysis calculated for $C_{36}H_{28}N_2O_6S_2$ requires: C, 66.6; H, 4.4; N, 4.3; S, 9.9%.

Found: C, 66.2; H, 4.8; N, 4.4; S, 9.9%.

A suspension of 26 (0.1 g, 0.31 mmol) in MeOH (5 mL) containing 3N NaOH (2 mL) was stirred at 20° C. for 3 hours, then concentrated to dryness. The residue was dissolved in water and acidified (concentrated HCl) to give 3-(4'-carboxybenzoyl)-1-methyl-2-indolinethione [XV: $R_1$=H, $R_3$=Me, $R_5$=4-HOOCC$_6$H$_4$] (25) (100%); mp 282° C. (dec).

$^1$H NMR (CD$_3$SOCD$_3$/CD$_3$COCD$_3$): δ 15.90 (0.3H, br, SH), 13.00 (1H, br s, COOH), 8.26 (2H, d, J=8.2 Hz, H-3',5'), 8.10 (0.6H, s, SH), 7.85 (2H, d, J=8.2 Hz, H-2',6'), 7.40 (1H, d, J=8.0 Hz, H-4), 7.29 (1H, dd, J=8.0, 8.0 Hz, H-5), 6.98 (1H, dd, J=8.0, 7.5 Hz, H-6), 6.68 (1H, d, J=7.5 Hz, H-7), 3.77 (3H, s, NCH$_3$).

$^{13}$C NMR CD$_3$SOCD$_3$/CD$_3$COCD$_3$): δ 167.57, 167.50 ( COAr and COOH), 142.40, 135.64, 134.55 (3×s), 130.86, 130.18, 129.13, 126.93 (4×d), 125.17 (s), 123.81, 120.68 (2×d), 112.39 (s), 110.82 (d), 29.94 (NCH$_3$).

Analysis calculated for $C_{17}H_{13}NSO_3.H_2O$ requires: C, 64.6; H, 4.3; N, 4.4; S, 10.1%.

Found: C, 64.6; H, 4.4; N, 4.0; S, 9.6%.

Similar hydrolysis of 102 gave bis[3 -(4'-carboxybenzoyl)-1-methylindole-(2)]disulfide [XVI: $R_1$=H, $R_3$=Me, $R_5$=4-HOOCC$_6$H$_4$] (101); mp (CHCl$_3$/petroleum ether) 241°–246° C.

$^1$H NMR (CD$_3$SOCD$_3$): δ 12.62 (1H, br, COOH), 7.89 (3H, m, H-4 and H-3',5'), 7.74 (1H, d, J=8.5 Hz, H-7), 7.58 (3H, m, H-6 and H-2',6'), 7.36 (1H, m, H-5), 3.66 (3H, s, NCH$_3$).

Analysis calculated for $C_{34}H_{24}N_2O_6S_2.0.5.H_2O$ requires: C, 63.1; H, 4.2%.

Found: C, 63.1; H, 5.3%.

Example H

Preparation of Compounds 104 and 105 of Table 1 by the Method Outlined in Scheme 7

A solution of monomethyl terephthalate [XVII: 4-COOMe] (1.32 g, 7.33 mmol) and DMF (1 drop) in SOCl$_2$ (30 mL) was heated under reflux for 45 minutes, before concentration to dryness under reduced pressure. The residue was dissolved in benzene and evaporated to dryness again. The crude acid chloride was dissolved in dry Me$_2$CO (20 mL), cooled to 0° C., and treated with a solution of NaN$_3$ (0.52 g, 8.00 mmol) in water (3 mL). After 20 minutes the solution was diluted with water, extracted with CH$_2$Cl$_2$, and worked up to give the crude acyl azide [XVIII: 4-COOMe], which was immediately dissolved in dry toluene (25 mL) and heated under reflux under N$_2$ for 2 hours. Concentration to dryness under reduced pressure afforded the isocyanate [XIX: 4-COOMe] which was used directly.

A solution of 1-methyl-2-indolinethione [IV: $R_1$, $R_2$=H, $R_3$=$CH_3$] (1.00 g, 6.13 mmol) in THF (2 mL) was added under $N_2$ to a suspension of NaH (0.26 g of 60% w/w dispersion in mineral oil, 6.50 mmol) in THF (15 mL). After gas evolution had ceased (5 minutes), a solution of the above crude isocyanate in THF (10 mL) was added, and the solution was stirred at 20° C. for a further 1 hour. The mixture was acidified with 3N HCl, extracted with EtOAc and worked up to give an oily solid. Chromatography on silica gel, eluting with EtOAc, afforded a greenish solid. This was dissolved in MeOH and treated with 30% $H_2O_2$ (0.20 mL), and the resulting yellow precipitate was filtered off and washed well with MeOH to give 2,2'-dithiobis[N-(4'-carbomethoxy)phenyl-1-methylindolyl-3-carboxamide] (104) [XX: R=4-COOMe] (0.74 g, 35%); mp 184°–186° C.

$^1$H NMR (($CD_3$)$_2$SO): δ 9.87 (1H, br, CONH), 7.80 (1H, d, J=8.0 Hz, H-4), 7.74 (2H, d, J=8.7 Hz, H-2',6'), 7.37 (1H, d, J 8.3 Hz, H-7), 7.32 (2H, d, J=8.7 Hz, H-3',5') 7.26 (1H, dd, J=8.3, 7.6 Hz, H-6), 7.15 (1H, dd, J=8.0, 7.6 Hz, H-5), 3.84 (3H, s, $CO_2CH_3$), 3.66 (3H, s, N—$CH_3$).

$^{13}$C NMR: δ 165.79 (COOCH$_3$), 161.56 (CONH), 143.01 (s), 137.68 (s), 129.79 (d), 125.41 (s), 124.35 (d), 123.37 (s), 121.40 (d), 120.82 (d), 119.90 (s), 118.33 (s), 117.93 (s), 110.74 (d), 51.74 (COOCH$_3$), 30.04 (N—CH$_3$).

Analysis calculated for $C_{36}H_{30}N_4O_6S_2.H_2O$ requires: C, 62.1; H, 4.6; N, 8.1; S, 9.2%.

Found: C, 62.2; H, 4.6; N, 8.0; S, 9.2%.

A suspension of (104) (0.23 g, 0.34 mmol) in MeOH (40 mL) was treated with 3N KOH (15 mL) and stirred at 20° C. for 90 minutes. The resulting solution was filtered, acidified, and the resulting precipitate collected and re-dissolved in $CH_2Cl_2$ (10 mL) containing MeOH (1 mL). $H_2O_2$ (0.20 mL of 30%) was added, and after 1 hour the solvents were removed under reduced pressure. The residue was triturated with MeOH to give 2,2'-dithiobis[N-(4'-carboxy)phenyl-1-methylindolyl-3-carboxamide] (105) [XX: R=4-COOH] (100% yield); mp 221° C. (dec).

$^1$H NMR (($CD_3$)$_2$SO): δ 12.63 (1H, br, COOH), 9.78 (1H, s, CONH), 7.80 (1H, d, J=8.0 Hz, H-4), 7.72 (2H, d, J=8.7 Hz, H-3',5'), 7.39 (1H, d, J=8.4 Hz, H-7), 7.30 (2H, d, J=8.7 Hz, H-2',6'), 7.28 (t, J=8.4, 7.7 Hz, H-6), 7.16 (1H, t, J=8.0, 7.7 Hz, H-5), 3.66 (3H, s, N—CH$_3$).

$^{13}$C NMR: δ 166.95 (COOH), 161.58 (CONH), 142.67 (s), 137.78 (s), 129.99 (d), 129.81 (s), 125.41 (s), 124.72 (s), 124.54 (d), 121.50 (d), 120.93 (d), 118.39 (d), 110.89 (d), 30.12 (N—CH$_3$).

Analysis calculated for $C_{34}H_{26}N_4O_6S_2.0.5H_2O$ requires: C, 61.9; H, 4.1; N, 8.5; S, 9.7%.

Found: C, 61.6; H, 4.2; N, 8.4; S, 9.9%.

Compounds 106 and 107 of Table 1

Similar treatment of 1-methyl -2-indolinethione [IV: $R_1$, $R_2$=H, $R_3$=$CH_3$] with the isocyanate [XIX: 3-COOMe] derived from monomethyl isophthalate gave 2,2'-dithiobis [N-(3'-carbomethoxy)phenyl-1-methylindolyl-3-carboxamide] (106) [XX: R=3-COOMe] (57% yield); mp 193°–195° C.

$^1$H NMR (($CD_3$)$_2$SO): δ 9.67 (1H, s, CONH), 7.96 (1H, br s, H-2'), 7.79 (1H, d, J=8.0 Hz, H-4), 7.56 (1H, d, J=7.7 Hz, H-6'), 7.45 (1H, d, J=8.2 Hz, H-7), 7.34 (1H, d, J=8.3 Hz, H-4'), 7.28 (1H, dd, J=8.3, 7.7 Hz, H-5'), 7.21 (1H, dd, J=8.2, 7.7 Hz, H-6), 7.10 (1H, dd, J=8.0, 7.7 Hz, H-5), 3.88 (3H, s, COOCH$_3$), 3.66 (3H, s, N—CH$_3$).

$^{13}$C NMR: δ 166.04 (COOCH$_3$), 161.48 (CONH), 138.89 (s), 137.63 (s), 129.77 (s), 129.54 (s), 128.62 (d), 125.21 (s), 124.39 (d), 123.51 (s), 121.28 (d), 120.83 (d), 119.50 (d), 118.31 (s), 110.64 (d), 51.99 (COOCH$_3$), 30.02 (N—CH$_3$).

Analysis calculated for $C_{36}H_{30}N_4O_6S_2$ requires: C, 63.7; H, 4.5; N, 8.3; S, 9.5%.

Found: C, 63.9; H, 4.6; N, 8.4; S, 9.6%.

Hydrolysis of the ester (106) as above, followed by re-oxidation with $H_2O_2$/MeOH, gave 2,2'-dithiobis[N-(3-carboxy)phenyl-1-methylindolyl-3-carboxamide] (107) [XX: R=3-COOH] (97% yield); mp 219°–220° C.

$^1$H NMR (($CD_3$)$_2$SO): δ 12.68 (1H, br, COOH), 9.69 (1H, s, CONH), 7.98 (1H, br s, H-2'), 7.80 (1H, d, J=8.0 Hz, H-4), 7.56 (1H, d, J=7.7 Hz, H-6'), 7.43 (1H, d, J=8.2 Hz, H-7), 7.36 (1H, d, J=8.3, 7.7 Hz, H-4'), 7.24 (2H, m, H-5',6), 7.11 (1H, t, J=8.0, 7.7 Hz, H-5), 3.66 (3H, s, N—CH$_3$).

$^{13}$C NMR: δ 167.10 (COOH), 161.53 (CONH), 138.77 (s), 137.62 (s), 130.92 (s), 129.47 (s), 128.44 (d), 125.18 (s), 124.45 (d), 123.75 (d), 123.31 (d), 121.32 (d), 120.81 (d), 119.91 (d), 118.51 (s), 110.67 (d), 30.01 (N—CH$_3$).

Analysis calculated for $C_{34}H_{26}N_4O_6S_2.0.5H_2O$ requires: C, 61.9; H, 4.1; N, 8.5; S, 9.7%.

Found: C, 61.7; H, 4.3; N, 8.8; S, 9.7%.

Compounds 108 & 109 of Table 1

Similar treatment of 1-methyl -2-indolinethione [IV: $R_1$, $R_2$=H, $R_3$=$CH_3$] with the isocyanate [XIX: 2-COOMe] derived from monomethyl phthalate gave 2,2'-dithiobis[N-(2-carbomethoxy)phenyl-1-methylindolyl- 3-carboxamide] (108) [XX: R=2-COOMe] (61% yield); mp 179°–181° C.

$^1$H NMR (($CD_3$)$_2$SO): δ 10.82 (1H, s, CONH), 7.89 (2H, 2×d, J=8.3, 8.0 Hz, H-3',6'), 7.74 (1H, d, J=8.3 Hz, H-4), 7.32 (2H, m, H-7,4'), 7.20 (1H, dd, J=8.1, 7.5 Hz, H-6), 7.12 (1H, dd, J=8.3, 7.5 Hz, H-5), 6.97 (1H, m, H-5'), 3.84 (3H, s, COOCH$_3$), 3.68 (3H, s, N—CH$_3$).

Analysis calculated for $C_{36}H_{30}N_4O_6S_2.0.5H_2O$ requires: C, 62.9; H, 4.5; N, 8.2; S, 9.3%.

Found: C, 62.8; H, 4.5; N, 8.1; S, 9.3%.

Hydrolysis of the ester (108) as above, followed by re-oxidation with $H_2O_2$/MeOH, gave 2,2'-dithiobis[N- (2'-carboxy)phenyl-1-methylindolyl-3-carboxamide] (109) [XX: R=2-COOH] (91% yield); mp 184°–186° C.

$^1$H NMR (($CD_3$)$_2$SO): δ 13.33 (1H, br, COOH), 11.31 (1H, s, CONH), 7.95 (1H, d, J=8.1 Hz, H-6'), 7.90 (1H, d, J=7.9 Hz, H-3'), 7.83 (1H, d, J=8.3 Hz, H-4), 7.30 (2H, m, H-7,4'), 7.19 (1H, dd, J=8.0, 7.5 Hz, H-6), 7.08 (1H, dd, J=8.3, 7.5 Hz, H-5), 7.02 (1H, dd, J=8.1, 7.8 Hz, H-5'), 3.67 (3H, s, N—CH$_3$).

$^{13}$C NMR: δ 169.16 (COOH), 160.71 (CONH), 140.55 (s), 137.78 (s), 133.31 (d), 130.50 (d), 129.30 (s), 125.01 (s), 124.50 (d), 121.79 (d), 121.47 (d), 121.05 (d), 120.28 (d), 118.21 (s), 115.91 (s), 110.68 (d), 29.93 (N—CH$_3$).

Analysis calculated for $C_{34}H_{26}N_4O_6S_2.2H_2O$ requires: C, 59.5; H, 4.4; N, 8.2; S, 9.3%.

Found: C, 59.3; H, 4.3; N, 8.3; S, 9.6%.

Compound 110 of Table 1

Similar treatment of 1-methyl -2-indolinethione [IV: $R_1$, $R_2$=H, $R_3$=$CH_3$] with the isocyanate derived from 4-(carbomethoxy)phenylacetic acid gave 2,2'-dithiobis[N-(4'-carbomethoxy)benzyl 1-methylindolyl-3-carboxamide] (110) [V: $R_1$=H, $R_2$=CONHCH$_2$Ph{4-COOMe}, $R_3$=Me] (38% yield); mp 178°–180° C.

$^1$H NMR ((CD$_3$)$_2$SO): δ 8.18 (1H, br, CONH), 7.88 (1H, d, J=8.1 Hz, H-4), 7.82 (2H, d, J=7.9 Hz, C-2',6'), 7.55 (1H, d, J=8.3 Hz, H-7), 7.35 (1H, dd, J=8.3, 7.7 Hz, H-6), 7.28 (2H, d, J=7.9 Hz, C-3',5'), 7.20 (1H, dd, J=8.1, 7.7 Hz, H-5), 4.06 (2H, d, J=5.1 Hz, CONHC$\underline{H}_2$), 3.83 (3H, s, COOCH$_3$), 3.61 (3H, s, N—CH$_3$).

$^{13}$C NMR: δ 165.98 ($\underline{C}$OOCH$_3$), 163.17 (CONH), 145.10 (s), 137.61 (s), 129.06 (d), 129.00 (s), 127.85 (s), 126.95 (d), 125.37 (s), 124.31 (d), 121.22 (d), 121.09 (d), 117.89 (s), 110.78 (d), 51.89 (COO$\underline{C}$H$_3$), 41.90 (CH$_2$Ar), 29.94 (N—CH$_3$).

Analysis calculated for $C_{38}H_{34}N_4O_6S_2$.0.5H$_2$O requires: C, 63.8; H, 4.9; N, 7.8; S, 8.9%.

Found: C, 63.7; H, 4.8; N, 7.8; S, 9.1%.

Example I

Preparation of Compound 111 of Table 1 by the Method Outlined in Scheme 8.

A solution of 2-chloro-1-methyl indole-3-carboxylic acid [XXI] (Marchetti L, Andreani A, *Ann. Chim.* (*Rome*) 1973;63:681) (0.95 g, 4.52 mmol) and SOCl$_2$ (0.99 mL, 13 mmol) in 1,2-dichloroethane (100 mL) containing DMF (1 drop) was heated under reflux under N$_2$ for 2 hours, then concentrated to dryness. The residue was dissolved in CH$_2$Cl$_2$ (50 mL) and treated with a slurry of methyl 4-(aminomethyl)benzoate hydrochloride (Nair MG, Baugh CM, *J. Org. Chem.* 1973;38:2185) (1.00 g, 4.98 mmol) and Et$_3$N (1.58 mL, 11 mmol) in CH$_2$Cl$_2$ (50 mL). After vigorous stirring at 20° C. for 24 hours, the mixture was washed with water and the organic portion worked up to give N-(4'-carbomethoxy)benzyl 2-chloro-1-methylindole-3-carboxamide [XXII: $R_6$=H, $R_7$=CH$_2$Ph{4-COOMe}] (1.40 g, 86%) which crystallized from aqueous acetone; mp 108°–110° C. $^1$H NMR ((CD$_3$)$_2$SO): δ 8.38 (1H, t, J=5.8 Hz, CON$\underline{H}$CH$_2$), 7.95 (2H, d, J=7.9 Hz, H-2',6'), 7.91 (1H, d, J=7.8 Hz, H-4), 7.56 (1H, d, J=7.9 Hz, H-7), 7.52 (2H, d, J=7.9 Hz, H-3',5'), 7.29 (1H, dd, J=7.9, 7.1 Hz, H-6), 7.19 (1H, dd, J=7.8, 7.1 Hz, H-5), 4.60 (2H, d, J=5.8 Hz, CONHC$\underline{H}_2$), 3.84 (3H, s, COOCH$_3$), 3.79 (3H, s, N—CH$_3$).

$^{13}$C NMR: δ 166.09 ($\underline{C}$OOCH$_3$), 162.77 (CONH), 145.65 (s), 135.00 (s), 129.18 (d), 129.14 (d), 127.94 (s), 127.34 (d), 127.25 (d), 126.34 (s), 124.77 (s), 122.57 (d), 121.19 (d), 119.97 (d), 110.21 (s), 107.111 (d), 51.95 (COO$\underline{C}$H$_3$), 42.15 (CH$_2$), 29.97 (N—CH$_3$).

Analysis calculated for $C_{19}H_{17}ClN_2O_3$ requires: C, 64.0; H, 4.8; N, 7.9; Cl, 9.9%.

Found: C, 64.0; H, 4.8; N, 7.6; Cl, 9.8%.

A solution of the above carboxamide (1.00 g, 2.80 mmol) in DMA (10 mL) was added under N$_2$ to a stirred suspension of MeSLi (1.06 g, 19 mmol) in DMA (25 mL). After warming at 80° C. for 6 hours, the mixture was acidified with 3N HCl, extracted with CH$_2$Cl$_2$, and worked up to give a yellow oil. Traces of DMA were removed under high vacuum, and the residue was dissolved in MeOH (20 mL) and treated dropwise with H$_2$O$_2$ (0.60 mL of 30% solution). After chilling at −30° C. overnight, the precipitate was filtered off, washed well with MeOH, and dried to give 2,2'-dithiobis[N-(4'-carboxy)benzyl 1-methylindol-3-carboxamide] (111) [V: $R_1$=H, $R_2$=CONHCH$_2$Ph{4-COOH}, $R_3$=Me] (0.68 g, 72%); mp 178°–180° C.

$^1$H NMR ((CD$_3$)$_2$SO): δ 12.86 (1H, br, COOH), 8.13 (1H, t, J=5.8 Hz, CON$\underline{H}$CH$_2$), 7.92–7.80 (3H, m, H-4,2',6'), 7.56 (1H, d, J=8.3 Hz, H-7), 7.37 (1H, t, J=8.3, 7.8 Hz, H-6), 7.27 (2H, d, J=8.3 Hz, H-3',5'), 7.20 (1H, dd, J=8.1, 7.8 Hz, H-5), 4.02 (2H, d, J=5.8 Hz, CONHC$\underline{H}_2$), 3.62 (3H, s, N—CH$_3$).

$^{13}$C NMR: δ 167.08 (COOH), 163.08 (CONH), 144.51 (s), 137.64 (s), 130.38 (s), 129.25 (d), 129.04 (s), 126.85 (d), 125.25 (s), 124.44 (d), 121.23 (d), 121.10 (d). 118.33 (e), 110.87 (d), 41.92 (CH$_2$), 29.94 (N—CH$_3$).

Analysis calculated for $C_{36}H_{30}N_4O_6S_2$.1.5H$_2$O requires: C, 61.3; H, 4.7; N, 7.9; S, 9.1%.

Found: C, 61.1; H, 4.8; N, 8.3; S, 9.0%.

Compound 112 of Table 1

Similar reaction of 2-chloro-1-methylindole-3-carboxylic acid [XXI] with SOCl$_2$ and glycine methyl ester hydrochloride gave N-carbomethoxymethyl 2-chloro-1-methylindole-3-carboxamide [XXII: $R_6$=H, $R_7$-CH$_2$COOMe] (78% yield); mp (CHCl$_3$/light petroleum) 102.5°–104° C.

$^1$H NMR (CDCl$_3$): δ 8.26 (1H, d, J=8.1 Hz, H-4), 7.30–7.23 (3H, m, H -5,6,7), 6.96 (1H, br, CONH ), 4.32 (2H, d, J=5.0 Hz, C$\underline{H}_2$NHCO), 3.81 (3H, s, COOCH$_3$), 3.75 (3H, s, N—CH$_3$).

$^{13}$C NMR: δ 170.91 ($\underline{C}$OOCH$_3$), 163.48 (CONH), 135.45 (s), 126.90 (s), 125.93 (8), 123.24 (d), 122.25 (d), 121.30 (d), 109.26 (d), 106.32 (s), 52.41 (COO$\underline{C}$H$_3$), 41.38 (C$\underline{H}_2$COOMe), 30.11 (N—CH$_3$).

Analysis calculated for $C_{13}H_{13}ClN_2O_3$ requires: C, 55.6; H, 4.7; N, 10.0%.

Found: C, 55.3; H, 4.8; N, 10.2%.

Treatment of this with MeSLi as above gave 2,2'-dithiobis [N-carboxymethyl 1-methylindolyl-3-carboxamide] (112) [V: $R_1$=H, $R_2$=CONHCH$_2$COOH, $R_3$=Me] (56% yield); mp 197° C. (dec).

$^1$H NMR ((CD$_3$)$_2$SO): δ 7.98 (1H, d, J=8.1 Hz, H-4), 7.59 (1H, br, CONH), 7.55 (1H, d, J=8.4 Hz, H -7), 7.35 (1H, dd, J=8.4, 7.5 Hz, H-6), 7.20 (1M, dd, J=8.1, 7.5 Hz, H-5), 3.68 (3H, s, N—CH$_3$), 3.20 (2H, d, J=5.2 Hz, C$\underline{H}_2$COOH).

$^{13}$C NMR: δ 171.02 (COOH), 162.57 (CONH), 137.60 (s), 125.36 (s), 124.30 (d), 121.27 (d), 121.11 (d), 117.69 (s), 110.65 (d), 40.35 (CH$_2$), 29.87 (N—CH$_3$).

Analysis calculated for $C_{24}H_{22}N_4O_6S_2$.H$_2$O requires: C, 52.9; H, 4.4: N, 10.3; S, 11.8%.

Found: C, 52.5; H, 4.5; N, 10.0; S, 11.2%.

Compound 113 of Table 1

Similar reaction of 2-chloro-1-methylindole-3-carboxylic acid [XXI] with SOCl$_2$ and N-methylaniline gave N-methyl-N-phenyl 2-chloro-1-methylindole-3-carboxamide [XXII: $R_6$=Me; $R_7$=Ph] (67% yield); mp (Me$_2$CO/water) 163° C.

$^1$H NMR ((CD$_3$)$_2$SO): δ 7.47 (1H, d, J=7.6 Hz, H-4), 7.41 (1H, d, J=8.3 Hz, H-7), 7.22–7.00 (7H, m, ArH), 3.63 (3H, s, N—CH$_3$), 3.42 (3H, s, N—CH$_3$).

$^{13}$C NMR: δ 164.33 (CONMePh), 143.88 (s), 134.69 (s), 128.50 (d), 125.90 (d), 125.70 (d), 124.86 (s), 124.21 (s), 122.24 (d), 120.71 (d), 118.94 (d), 110.06 (d), 108.80(s), 37.40 (N—CH$_3$), 29.77 (N—CH$_3$).

Analysis calculated for $C_{17}H_{15}ClN_2O$ requires: C, 68.3; H, 5.1; N, 9.4; Cl, 11.9%.

Found: C, 68.4; H, 5.1; N, 9.3; Cl, 12.1%.

Treatment of this with MeSLi as above gave 2,2'-dithiobis[N-methyl-N-phenyl-1-methylindolyl-3-carboxamide] (113) [V: $R_1$=H, $R_2$=CON(Me)Ph, $R_3$=Me] (53% yield), mp 158°–163° C.

$^1$H NMR ((CD$_3$)$_2$SO): δ 7.80 (1H, d, J=7.5 Hz, H-4), 7.57 (1H, d, J=7.8 Hz, H-7), 7.33–6.99 (7H, m, ArH), 3.86 (3H, s, N—CH$_3$), 3.33 (3H, s, N—CH$_3$).

$^{13}$C NMR: δ 164.14 (CONMePh), 137.59 (s), 129.94 (s), 124.21 (s), 123.73 (s), 123.24 (d), 122.34 (d), 120.25 (d), 119.56 (d), 118.79 (d), 115.43 (s), 110.27 (d), 39.68 (N—CH$_3$), 30.99 (N—CH$_3$).

Analysis calculated for C$_{34}$H$_{31}$N$_4$S$_2$O$_2$ requires: [M+H]$^+$ 591.3447.

Found: [M+H]$^+$ 591.3441 (FAB mass spectrum).

Analysis calculated for C$_{34}$H$_{30}$N$_4$S$_2$O$_2$ requires: C, 69.1; H, 5.1; N, 9.5; S, 10.9%.

Found: C, 69.2; H, 5.2; N, 9.6; S, 10.6%.

Compound 114 of Table 1

Similar reaction of 2-chloro-1-methylindole-3-carboxylic acid [XXI] with SOCl$_2$ and 3-aminopropane-1,2-diol gave N-(2,3-dihydroxypropyl)-2-chloro-1-methylindole-3-carboxamide [XXII: $R_6$=H;, $R_7$=CH$_2$CH(OH)CH$_2$OH] (46%) as an oil.

$^1$H NMR ((CD$_3$)$_2$SO/D$_2$O): δ 7.94 (1H, d, J=7.0 Hz, H-4), 7.53 (1H, d, J=7.2 Hz, H-7), 7.38–7.19 (2H, m, H-5,6), 3.78 (3H, s, N—CH$_3$), 3.68–3.26 (5H, m, C$\underline{H}_2$CHOHC$\underline{H}_2$OH).

$^{13}$C NMR: δ 162.72 (CONH), 134.94 (s), 125.94 (s), 124.79 (s), 122.52 (d), 121.15 (d), 120.05 (d), 110.17 (d), 107.09 (d), 70.17 (CHOH), 63.90 (CH$_2$OH), 42.34 (CONHC$\underline{H}_2$), 29.97 (N—CH$_3$).

Analysis calculated for C$_{13}$H$_{15}$ClN$_2$O$_3$ requires: M$^+$ 284.0742, 282.0771.

Found: M$^+$ 284.0744, 282.0763 (mass spectrum).

Treatment of this with MeSLi as above gave 2,2'-dithiobis[N-(2,3-dihydroxypropyl)-1-methylindolyl- 3-carboxamide] (114) [V: $R_1$=H, $R_2$=CONHCH$_2$CH(OH)CH$_2$OH, $R_3$=Me] (71% yield) as a yellow foam; mp 198° C. (dec.).

$^1$H NMR ((CD$_3$)$_2$SO/D$_2$O): δ 7.89 (1H, d, J=8.1 Hz, H-4), 7.56 (1H, d, J=8.4 Hz, H-7), 7.42 (1H, dd, J=8.4, 7.3 Hz, H-6), 7.27 (1H, dd, J=8.0, 7.3 Hz, H-5), 3.75 (3H, s, N—CH$_3$), 3.40–3.20 (5H, m, C$\underline{H}_2$CHOHC$\underline{H}_2$OH).

$^{13}$C NMR: δ 162.61 (CONH), 137.70 (s), 125.21 (s), 124.40 (d), 121.34 (d), 121.27 (d), 120.81 (s), 117.85 (s), 110.88 (d), 70.17 (CHOH), 63.75 (CH$_2$OH), 41.96 (CONHC$\underline{H}_2$), 29.95 (N—CH$_3$).

Analysis calculated for C$_{26}$H$_{30}$N$_4$O$_6$S$_2$ requires: C, 55.9; H, 5.4; N, 10.0; S, 11.5%.

Found: C, 55.4; H, 5.4; N, 9.7; S, 11.5%.

Compound 115 of Table 1

Similar reaction of 2-chloro-1-methylindole-3-carboxylic acid [XXI] with SOCl$_2$ and N,N-dimethylethylenediamine, followed by extraction into 3N HCl, neutralization with aqueous NH$_3$ and extraction with EtOAc gave N,N-dimethylaminoethyl-2-chloro-1-methylindole-3-carboxamide [XXII: $R_6$=H, $R_7$=CH$_2$CH$_2$NMe$_2$] as an oil (74% yield), which eventually solidified; mp 63° C.

$^1$H NMR (CDCl$_3$): δ 8.20 (1H, dd, J=8.1, 1.7 Hz, H-4), 7.26–7.20 (3H, m, H-5,6,7), 7.01 (1H, br, CONH), 3.69 (3H, s, N—CH$_3$), 3.58 (2H, dt, J=6.1, 5.1 Hz, CONHC$\underline{H}_2$), 2.55 (2H, t, J=6.1 Hz, C$\underline{H}_2$N(CH$_3$)$_2$, 2.30 (6H, s, N(CH$_3$)).

$^{13}$C NMR: δ 163.62 (CONH), 135.31 (s), 126.43 (s), 125.79 (s), 122.90 (d), 121.83 (d), 121.06 (d), 109.17 (d), 107.07 (s), 57.84 (CONHC$\underline{H}_2$), 45.14 (N(CH$_3$)$_2$), 36.80 C$\underline{H}_2$N(CH$_3$)$_2$), 29.96 (N—CH$_3$).

Analysis calculated for C$_{14}$H$_{18}$ClN$_3$O requires: M$^+$ 281.1109, 279.1138.

Found: M$^+$ 281.1106, 279.1118 (mass spectrum).

Following treatment of this with MeSLi as above, the reaction mixture was partitioned between CH$_2$Cl$_2$ and water. The organic portion was extracted with 3N HCl, and the extract was neutralized with aqueous NH$_3$, extracted with CH$_2$Cl$_2$, and worked up to give an oil which was dissolved in MeOH and allowed to stand at 20° C. for 48 hours. The product was adsorbed directly onto silica and chromatographed. Elution with MeOH/EtOAc (1:19 ) containing a trace of concentrated NH$_4$OH gave 2,2'-dithiobis[N-(N,N-dimethylaminoethyl) 1-methylindolyl-3-carboxamide] (115) [V: $R_1$=H, $R_2$=CONHCH$_2$CH$_2$NMe$_2$, $R_3$=Me] (54% yield); mp (CH$_2$Cl$_2$/light petroleum) 163.5°–165° C.

$^1$H NMR (CDCl$_3$): δ 8.24 (1H, d, J=8.1 Hz, H-7), 7.36 (1H, dd, J=8.2, 7.8 Hz, H-6), 7.30 (1H, d, J=8.2 Hz, H-7), 7.25 (1H, dd, J=8.1, 7.8 Hz, H-5), 7.10 (1H, br, CONH), 3.60 (3H, s, N—CH$_3$), 2.99 (2H, dt, J=6.3, 5.5 Hz, CONHC$\underline{H}_2$), 2.26 (2H, t, J=6.3 Hz, C$\underline{H}_2$N(CH$_3$)$_2$), 2.21 (6H, s, N(CH$_3$)2).

$^{13}$C NMR: δ 163.71 (CONH), 138.27 (s), 126.64 (s), 125.20 (d), 122.70 (d), 122.11 (d), 118.46 (s), 110.08 (d), 57.72 (CONHC$\underline{H}_2$), 45.19 (N(CH$_3$)$_2$), 36.81 (C$\underline{H}_2$N(CH$_3$)$_2$), 30.15 (N—CH$_3$).

Analysis calculated for C$_{28}$H$_{36}$N$_6$O$_2$S$_2$ requires: C, 60.8; H, 6.6; N, 15.2; S, 11.6%.

Found: C, 60.7; H, 6.8; N, 14.9; S, 11.4%.

Compound 116 of Table 1

Similar reaction of 2-chloro-1-methylindole- 3-carboxylic acid [XXI] with SOCl$_2$ and 4-aminopyridine gave N-(4-pyridyl)-2-chloro-1-methylindole-3-carboxamide [XXII: $R_6$=H, $R_7$=4-pyridyl] (61% yield); mp (CHCl$_3$/light petroleum) 220°–223° C.

$^1$H NMR ((CD$_3$)$_2$SO): δ 10.28 (1H, br, CONH), 8.47 (2H, d, J=6.1 Hz, H-2',6'), 7.82 (1H, d, J=7.5 Hz, H-4), 7.72 (2H, d, J=6.1 Hz, H-3',5'), 7.63 (1H, d, J=8.0 Hz, H-7), 7.33 (1H, dd, J=8.0, 7.6 Hz, H-6), 7.25 (1H, dd, J=7.6, 7.5 Hz, H-5), 3.84 (3H, s, N—CH$_3$).

$^{13}$C NMR: δ 162.03 (CONH), 150.16 (d), 145.81 (s), 134.98 (s), 127.50 (s), 124.49 (s), 122.8 (d), 121.54 (d), 119.59 (d), 113.50 (d), 110.47 (d), 107.60 (s), 30.11 (N—CH$_3$).

Analysis calculated for C$_{15}$H$_{12}$ClN$_3$O requires: C, 63.1; H, 4.2; N, 14.7%.

Found: C, 62.8; H, 3.9; N, 14.6%.

Reaction of this with MeSLi as above gave 2,2'-dithiobis[N-(4-pyridyl)-1-methylindolyl-3-carboxamide] (116) [V: $R_1$=H, $R_2$=CONH-4-pyridyl, $R_3$=Me] (53% yield); mp 226°–229° C. (dec.).

$^1$H NMR ((CD$_3$)$_2$SO): δ 14.46 (1H, s, CONH), 8.51 (2H, d, J=7.0 Hz, H-2',6') 8.13 (2H, d, J=7.0 Hz, H-3',5') 8.05 (1H, d, J=7.9 Hz, H-4), 7.16 (1H, d, J=8.1 Hz, H-7), 7.00 (2H, m, H-5,6), 3.68 (3H, s, N—CH$_3$).

$^{13}$C NMR: δ 165.13 (s), 164.33 (CONH), 153.80 (s), 141.35 (d), 137.26 (s), 128.35 (s), 120.30 (d), 119.97 (d), 118.52 (d), 112.83 (d), 107.66 (d), 104.06 (s), 29.37 (N—CH$_3$).

Analysis calculated for $C_{30}H_{24}N_6O_2S_2$ requires: C, 62.8; H, 4.4; N, 14.6; S, 11.2%.

Found: C, 62.4; H, 4.9; N, 14.5; S, 11.4%.

Compound 117 of Table 1

Similar reaction of 2-chloro-1-methylindole-3-carboxylic acid [XXI] with $SOCl_2$ and 3-aminopyridine gave N-(3-pyridyl)-2-chloro-1-methylindole-3-carboxamide [XXII: $R_7$=H, $R_8$=3-pyridyl] (86% yield); mp (EtOAc/light petroleum) 175°–177° C.

$^1$H NMR (($CD_3)_2SO$): δ 10.13 (1H, s, CONH), 8.90 (1H, d, J=2.4 Hz, H-2'), 8.30 (1H, dd, J=4.7, 1.4 Hz, H-6'), 8.18 (1H, ddd, J=4.5, 2.4, 1.4 Hz, H-4'), 7.84 (1H, d, J=7.9 Hz, H-4), 7.63 (1H, d, J=8.2 Hz, H-7), 7.40 (1H, dd, J=4.7, 4.5 Hz, H-5'), 7.32 (1H, dd, J=8.2, 7.7 Hz, H-6), 7.25 (1H, dd, J=7.9, 7.7 Hz, H-5), 3.84 (3H, s, N—$CH_3$).

$^{13}$C NMR: δ 161.71 (CONH), 144.11 (d), 141.38 (d), 135.85 (s), 134.98 (s), 127.15 (s), 126.62 (d), 124.51 (s), 123.46 (d), 122.74 (d), 121.43 (d), 119.70 (d), 110.43 (d), 107.69 (s), 30.09 (N—$CH_3$).

Analysis calculated for $C_{15}H_{12}ClN_3O$ requires: C, 63.1; H, 4.1; N, 14.3; Cl, 13.6%.

Found: C, 63.2; H, 4.2; N, 14.9; Cl, 12.4%.

Treatment of this with MeSLi as above gave 2,2'-dithiobis[N-(3-pyridyl) 1-methylindolyl-3-carboxamide] (117) [V: $R_1$=H, $R_2$=CONH-3-pyridyl, $R_3$=Me] (71% yield); mp 257°–260° C.

$^1$H NMR (($CD_3)_2SO$): δ 13.82 (1H, s, CONH), 9.53 (1H, d, J=1.6 Hz, H-2'), 8.44 (2H, m, H-4',6'), 8.05 (1H, d, J=8.0 Hz, H-4), 7.91 (1H, dd, J=4.6, 4.5 Hz, H-5'), 7.14 (1H, d, J=8.1 Hz, H-7), 6.96 (2H, m, H-5',6'), 3.67 (3H, s, N—$CH_3$).

$^{13}$C NMR: δ 164.76 (CONH), 162.70 (s), 140.01 (s), 136.97 (s), 134.17 (d), 132.51 (d), 131.06 (d), 128.44 (s), 127.08 (d), 119.90 (d), 119.45 (d), 118.39 (d), 107.50 (d), 103.89 (s), 29.25. (N—$CH_3$).

Analysis calculated for $C_{30}H_{24}N_6O_2S_2$ requires: C, 63.8; H, 4.3; N, 14.9; S, 11.4%.

Found: C, 63.5; H, 4.9; N, 14.8; S, 11.1%.

Compound 118 of Table 1

Treatment of 2-chloro-1-methylindole-3-carboxamide [XXII: $R_7$=$R_8$=H] (Andreani A, Rambaldi M, *J. Het. Chem.* 1988;25:1519–1523) with MeSLi as above gave 2,2'-dithiobis[1-methylindolyl-3-carboxamide] (118) [V: $R_1$=H, $R_2$=$CONH_2$, $R_3$=Me] (71% yield); mp 186°–188° C.

$^1$H NMR (($CD_3)_2SO$): δ 7.99 (1H, d, J=7.9 Hz, H-4), 7.52 (1H, d, J=8.3 Hz, H-7), 7.33 (1H, dd, J=8.3, 7.2 Hz, H-6), 7.25–7.11 (3H, m, H-5 and $CONH_2$), 3.48 (3H, s, N—$CH_3$).

$^{13}$C NMR: δ 164.76 ($CONH_2$), 137.56 (s), 129.35 (s), 125.51 (s), 124.37 (d), 121.58 (d), 121.23 (d), 117.77 (s), 110.74 (d), 29.82 (N—$CH_3$).

Analysis calculated for $C_{20}H_{18}N_4O_2S_2.0.5H_2O$ requires: C, 57.3; H, 4.6; N, 13.4; S, 15.3%.

Found: C, 57.7; H, 4.5; N, 13.5; S, 15.4%.

Compound 119 of Table 1

Treatment of N,N-dimethyl 2-chloro-1-methylindole-3-carboxamide [XXII: $R_7$=$R_8$=Me] (Bergman J, Carlsson R, Sjöberg B, *J. Het. Chem.* 1977;14:1123–1134) with MeSLi as above gave 2,2'-dithiobis[N,N-dimethyl- 1-methylindolyl-3-carboxamide] (119) [V: $R_1$=H, $R_2$=$CONMe_2$, $R_3$=Me]. Chromatography on silica gel, eluting with EtOAc, followed by crystallization from EtOAc/light petroleum gave pure material (54% yield); mp 96°–102° C.

$^1$H NMR ($CDCl_3$): δ 7.43 (1H, d, J=8.0 Hz, H-4), 7.31 (2H, m, H-6,7), 7.15 (1H, m, H-5), 3.64 (3H, s, N—$CH_3$), 2.91, 2.62 (2×3H, 2×br, N($CH_3)_2$).

$^{13}$C NMR: δ 165.89 ($CONMe_2$), 138.06 (s), 128.51 (s), 125.04 (s), 124.47 (d), 121.15 (d), 120.59 (d), 120.19 (s), 110.19 (d), 38.65 (N($CH_3)_2$), 34.84 (N($CH_3)_2$), 30.23 (N—$CH_3$).

Analysis calculated for $C_{24}H_{26}N_4O_2S_2.0.5H_2O$ requires: C, 60.6; H, 5.7; N, 11.7%.

Found: C, 60.3; H, 5.8; N, 11.2%.

Analysis calculated for $C_{24}H_{27}N_4S_2O_2$ requires: $[M+H]^+$ 467.1575.

Found: $[M+H]^+$ 467.1559 (FAB mass spectrum).

Compound 120 of Table 1

A mixture of 2-chloroindole-3-carboxaldehyde (7.0 g, 36 mmol) was reacted with a slight excess of hydroxylamine hydrochloride and pyridine in refluxing EtOH for 1 hour, to give the crude oxime (Latrell R, Bartmann W, Musif J, Granzer E, German Patent 2,707,268, 31 Aug. 1978, *Chem. Abstr.* 1978;89:179858y). A solution of this in $Ac_2O$ (100 mL) was heated under reflux for 1 hour, cooled, and stirred with water (700 mL). The precipitated solid was collected, washed with water, and crystallized from aqueous MeOH to give 2-chloro-1H-indole-3-carbonitrile (3.7 g, 58%); mp 177°–180°·C.

$^1$H NMR (($CD_3)_2SO$): δ 13.23 (1H, s, NH), 7.60 (1H, d, J=7.5 Hz, ArH), 7.50 (1H, d, J=7.9 Hz, ArH), 7.34 (1H, t, J=7.5 H, ArH), 7.29 (1H, t, J=7.3 Hz, ArH).

$^{13}$C NMR: δ 134.0, 131.5, 126.2, 114.1 (C), 123.8, 122.3, 117.9, 112.3 (CH), 83.8 (CN).

Analysis calculated for $C_9H_5ClN_2$ requires: C, 61.2; H, 2.9; N, 15.9%.

Found: C, 61.2; H, 2.7; N, 15.9%.

A solution of the above nitrile (2.5 g, 14 mmol) in $Me_2CO$ was treated with a slight excess of MeI and $K_2CO_3$ under reflux for 1 hour. Crystallization of the crude product from hexane gave 2-chloro-1-methylindole-3-carbonitrile (1.88 g, 70%); mp 112°–114° C.

$^1$H NMR ($CDCl_3$): δ 7.61–7.55 (1H, m, ArH), 7.34–7.21 (3H, m, ArH), 3.74 (3H, s, $CH_3$).

$^{13}$C NMR: δ 135.0, 133.4, 126.0, 114.1 (C), 123.9, 122.7, 118.8, 110.1 (CH), 85.2 (CN).

Analysis calculated for $C_{10}H_7ClN_2$ requires: C, 63.0; H, 3.7; N, 14.7%.

Found: C, 63.0; H, 3.6; N, 14.7%.

Treatment of this with MeSLi as above gave 2,2'-dithiobis(2-chloro-1-methylindole-3-carbonitrile) (120) [V: $R_1$=H, $R_2$=CN, $R_3$=Me] (53% yield); mp 205°–207° C.

$^1$H NMR (($CD_3)_2SO$): δ 7.69 (1H, d, J=8.3 Hz, H-4), 7.51 (1H, d, J=8.0 Hz, H-7), 7.42 (1H, dd, J=8.0, 7.3 Hz, H-6), 7.28 (1H, dd, J=8.3, 7.3 Hz, H-5), 3.82 (3H, s, N—$CH_3$).

Analysis calculated for $C_{20}H_{14}N_4S_2$ requires: C, 64.2; H, 3.8; N, 15.0; S, 17.1%.

Found: C, 64.2; H, 3.8; N, 15.1; S, 17.7%.

Compound 121 of Table 1

3-Acetyl -2-chloro-1-methylindole was prepared by the reported method (Coppola GM, Hardtmann GE, *J. Het. Chem.* 1977;14:117–1118). This was reacted with MeSLi as above gave 3-acetyl-1-methyl-2-indolinethione [XV: $R_5$=Me] (66% yield); mp 180° C.

$^1$H NMR ((CD$_3$)$_2$SO): δ 15.60 (1H, br, SH), 7.64 (1H, d, J=6.5 Hz, H-4), 7.39 (1H, d, J=7.6 Hz, H-7), 7.32 (1H, dd, J=7.6, 7.3 Hz, H-6), 7.24 (1H, dd, J=7.3, 6.5 Hz, H-5), 3.65 (3H, s, N—CH$_3$), 2.66 (3H, s, COCH$_3$).

$^{13}$C NMR: δ 178.29 (COCH$_3$), 140.56 (s), 125.21 (d), 124.67 (s), 123.27. (d), 120.60 (d), 111.31 (s), 109.99 (d), 29.31 (N—CH$_3$), 22.44 (COCH$_3$).

Analysis calculated for C$_9$H$_8$ClN$_2$ requires: C, 61.2; H, 2.9; N, 15.9%.

Found: C, 61.2; H, 2.7; N, 15.9%.

A solution of the above thione (0.10 g, 0.49 mmol) in MeOH/EtOAc (1:9) (10 mL) was stirred vigorously with 30% H$_2$O$_2$ (0.20 mL) for 4 hours. The solution was concentrated to a volume of 0.5 mL, and the orange precipitate was filtered off and washed well with MeOH to give 2,2'-dithiobis(3-acetyl-1-methylindole) (121) [V: $R_1$=H, $R_2$=COMe, $R_3$=Me] (100% yield); mp 178.5°–179.5° C.

$^1$H NMR ((CD$_3$)$_2$SO): δ 8.14 (1H, d, J=8.1 Hz, H-4), 7.62 (1H, d, J=8.3 Hz, H-7), 7.39 (1H, dd, J=8.3, 7.3 Hz, H-6), 7.27 (1H, dd, J=8.1, 7.3 Hz, H-5), 3.75 (3H, s, N -CH$_3$), 2.00 (3H, s, COCH$_3$).

$^{13}$C NMR: δ 192.56 (COCH$_3$), 137.65 (s), 139.73 (s), 125.41 (s), 124.79 (d), 122.73 (d), 121.95 (d), 121.43 (s), 110.92 (d), 30.34 (COCH$_3$), 29.43 (N—CH$_3$).

Analysis calculated for C$_{22}$H$_{20}$N$_2$O$_2$S$_2$.0.5H$_2$O requires: C, 63.3; H, 5.1; N, 6.7%.

Found: C, 63.7; H, 4.7; N, 6.8%.

Compound 122 of Table 1

Similar reaction of 2-chloro-1-methylindole-3-carboxylic acid [XXI] with SOCl$_2$ and 2-aminopyridine gave N-(2'-pyridyl)-2-chloro-1-methylindole-3-carboxamide [XXII: $R_6$=H, $R_7$=2-pyridyl] (42% yield); mp (light petroleum) 123° C.

$^1$H NMR (CDCl$_3$): δ 8.85 (1H, s, CONH), 8.41 (1H, d, J=8.4 Hz, H-4), 8.30 (2H, m), 7.72 (1H, m), 7.28 (3H, m), 7.02 (1H, dd, J=7.2, 4.9 Hz), 3.74 (3H, s, N—CH$_3$).

$^{13}$C NMR: δ 161.58 (CONH), 151.85 (s), 147.92 (d), 138.27 (d), 135.46 (s), 127.22 (s), 125.84 (s), 123.45 (d), 122.48 (d) 121.16 (d) 119.47 (d), 114.25 (d), 109.44 (d), 106.59 (s), 30.21 (N—CH$_3$).

Analysis calculated for C$_{15}$H$_{12}$ClN$_3$O requires: C, 63.1; H, 4.2; N, 14.7%.

Found: C, 62.9; H, 4.2; N, 14.4%.

Treatment of this with MeSLi as above gave 2,2'-dithiobis [N-(2'-pyridyl)-1-methylindole-3-carboxamide] (122) [V: $R_1$=H, $R_2$=CONH-2-pyridyl, $R_3$=Me] (68% yield); mp 270°–272° C. (dec).

$^1$H NMR ((CD$_3$)$_2$SO): δ 14.93 (1H, br, CONH), 8.32 (1H, d, J=6.0 Hz), 8.25 (1H, dd, J=8.3, 7.7 Hz), 8.02 (1H, dd, J=7.4, 3.7 Hz), 7.57 (1H, d, J=8.7 Hz), 7.35 (1H, t, J=6.6 Hz), 7.21 (1H, dd, J=5.1, 3.0 Hz), 7.04 (2H, m), 3.69 (3H, s, N—CH$_3$).

$^{13}$C NMR: δ 166.48 (s), 165.41 (CONH), 149.16 (s), 145.34 (d), 137.66 (s), 137.49 (s), 127.89 (s), 120.66 (d), 120.44. (d), 118.32 (d), 117.55 (d), 115.32 (d), 107.96 (d), 102.69 (s), 29.40 (N—CH$_3$).

Analysis calculated for C$_{30}$H$_{24}$N$_6$O$_2$S$_2$.0.25H$_2$O requires: C, 63.3; H, 4.3; N, 14.8; S, 11.3%.

Found: C, 63.2; H, 4.5; N, 14.8; S, 11.7%.

Compound 123 of Table 1

Similar treatment of 1-methyl -2-indolinethione [IV: $R_1$, $R_2$=H, $R_3$=CH$_3$] with the acyl azide derived from 2-furoic acid gave 3-(2-furoyl)-1-methyl-2-indolinethione [IV: $R_1$=H, $R_2$=CO(2-furyl); $R_3$=Me] (85% yield); mp 113.5° C.

$^1$H NMR ((CD$_3$)$_2$SO): δ 15.90 (1H, br, SH), 8.28 (1H, d, J=1.6 Hz, H-5'), 7.97 (1H, d, J=8.0 Hz, H-4), 7.56 (1H, d, J=3.6 Hz, H-3'), 7.46 (1H, d, J=8.0 Hz, H-7), 7.37 (1H, dd, J=8.0, 7.4 Hz, H-6), 7.21 (1H, dd, J=8.0, 7.4 Hz, H-5), 6.94 (1H, dd, J=3.6, 1.6 Hz, H-4'), 3.72 (3H, s, N—CH$_3$).

$^{13}$C NMR: δ 180.09 (CS), 160.65 (CO), 147.95 (d), 147.27 (s), 140.92 (s), 126.05 (d), 123.26 (s), 123.12 (d), 121.04 (d), 119.19 (d), 113.22 (d), 110.11 (d), 109.64 (s), 29.79 (N—CH$_3$).

Analysis calculated for C$_{14}$H$_{11}$NO$_2$S requires: C, 65.3; H, 4.4; N, 5.7; S, 12.7%.

Found: C, 65.4; H, 4,3; N, 5.4; S, 12.5%.

Reaction of the above compound with I$_2$ as described above gave 2,2'-dithiobis[3-(2-furoyl)-1-methylindole] (123) [V: $R_1$=H; $R_2$=CO(2-furyl); $R_3$=Me] (85% yield); mp 175°–176.5° C.

$^1$H NMR (CDCl$_3$): δ 7.47 (1H, d, J=8.1 Hz, H-4), 7.33 (1H, dd, J=1.6, 0.7 Hz, H-5'), 7.23 (1H, dd, J=8.1, 7.8 Hz, H-6), 7.21 (1H, d, J=8.1 Hz, H-7), 7.09 (1H, dd, J=8.1, 7.9 Hz, H-5), 6.63 (1H, dd, J=3.6, 0.7 Hz, H-3'), 6.23 (1H, dd, J=3.6, 1.6 Hz, H-4'), 3.73 (3H, s, NCH$_3$).

$^{13}$C NMR: δ 177.09 (CO), 152.55 (s), 145.91 (d), 138.18, 131.32, 125.80 (3×s), 124.72 (d), 123.60 (s), 121.73, 121.12, 119.16, 111.91, 110.06 (5×d), 30.54 (NCH$_3$).

Analysis calculated for C$_{28}$H$_{20}$N$_2$O$_4$S$_2$.0.5H$_2$O requires:

Found: C, 64.4; H, 4.1; N, 5.4; S, 12.3%. C, 64.7; H, 4.1; N, 5.6; S, 12.4%.

Compound 124 of Table 1

Similar treatment of 1-methyl-2-indolinethione [IV: $R_1$, $R_2$=H, $R_3$-CH$_3$] with the isocyanate derived from thiophene-2-carboxylic acid gave 2,2'-dithiobis[N-( 2-thienyl)-1-methylindole-3-carboxamide] (124) [V: $R_1$=H, $R_2$=CONHfuryl, $R_3$=Me] (21% yield; mp 183° C. (dec).

$^1$H NMR ((CD$_3$)$_2$SO): δ 11.26 (1H, s, CONH), 7.93 (1H, d, J=8.0 Hz, H-4), 7.62 (1H, d, J=8.3 Hz, H-7), 7.34 (1H, dd, J=8.3, 7.4 Hz, H-6), 7.24 (1H, dd, J=8.0, 7.4 Hz, H-5), 7.05 (1H, dd, J=5.3, 3.6 Hz, H-4'), 6.94 (1H, d, J=5.3 Hz, H-5'), 6.41 (1H, d, J=3.6 Hz, H-3'), 3.95 (3H, s, NCH$_3$).

$^{13}$C NMR: δ 160.10 (CONH), 139.86 (s), 137.81 (s), 136.86 (s), 125.19 (s), 123.96 (d), 123.69 (d), 121.28 (d), 120.54 (d), 116.85 (d), 114.73 (s), 111.20 (d), 110.77 (d), 30.54 (N—CH$_3$).

Analysis calculated for C$_{28}$H$_{22}$N$_4$O$_2$S$_4$.H$_2$O requires: C, 57.6; H, 4.0; N, 9.6%.

Found: C, 57.6; H, 4.1; N, 10.0%.

Example J

Preparation of Compound 125 of Table 1 by the Method Outlined in Scheme 9

Reaction of 3-chlorocarbonyl-1-(phenylsulfonyl) indole [XXIII] (Ketcha DM, Gribble GW, *J. Org. Chem.* 1985;50:5451–5457) with an excess of benzylamine in CH$_2$Cl$_2$) (method of Ketcha and Gribble) gave N-benzyl-1-(phenylsulfonyl)indole-3-carboxamide [XXIV: $R_8$=CH$_2$Ph]; mp (MeOH) 188°–189° C.

¹H NMR (CDCl₃): δ 8.05 (1H, s, H-2), 8.03–7.86 (4H, m, ArH), 7.56–7.26 (10H, m, ArH), 6.43 (1H, m, NH), 4.64 (2H, d, J=5.7 Hz, CH₂).

Analysis calculated for $C_{22}H_{18}N_2O_3S$ requires: C, 67.7; H, 4.5; N, 7.2; S, 8.2%.

Found: C, 67.4; H, 4.8; N, 7.1; S, 8.2%.

A solution of the above N-benzyl-1-(phenylsulfonyl)indole- 3-carboxamide [XXIV: $R_8$=CH₂Ph] (4.2 g, 11 mmol) in dry THF (200 mL) was treated at –78° C. with a solution of 2.5M n-BuLi in hexanes (9.1 mL, 23 mmol), and the stirred mixture was allowed to warm to –20° C. for 15 minutes, before being recooled to –78° C., when it was treated with methyldisulfide (2.5 mL, 28 mmol). The mixture was allowed to warm to 20° C., then quenched with water (25 mL). Volatiles were removed under reduced pressure, and the residue was extracted with EtOAc. Workup of the organic layer gave a crude product. This was dissolved in MeOH (300 mL), mixed with a solution of K₂CO₃ (6.9 g, 50 mmol) in water (125 mL), and heated under gentle reflux under N₂ for 2 hours to ensure complete hydrolysis of the phenylsulfonyl group (*J. Org. Chem.* 1985;50:5451–5457). MeOH was removed under reduced pressure, and the residue was diluted with water and extracted with CH₂Cl₂. Chromatography of the resulting oil on Al₂O₃ (eluting with CH₂Cl₂) gave N-benzyl-2-(methylthio)indole- 3-carboxamide [XXV: $R_8$=CH₂Ph] (2.8 g, 88% yield) as an oil.

¹H NMR (CDCl₃): δ 10.65 (1H, s, H-1), 8.29 (d, J=5.1 Hz, H-4), 7.87 (1H, t, J=5.6 Hz, CONH), 7.34–7.08 (8H, m, ArH), 4.73 (2H, d, J=5.6 Hz, CH₂), 2.33 (3H, s, SMe).

¹³C NMR (CDCl₃): δ 165.6 (C=O), 138.5, 136.4, 133.1 and 110.8 (C), 128.5, 127.2, 127.1, 122.9, 121.4, 126.8 and 111.2 (CH), 43.2 (CH₂), 18.5 (CH₃).

HREIMS calculated for $C_{17}H_{16}N_2OS$: 296.0983. Found: 296.0985.

A solution of the above N-benzyl-2-(methylthio)indole-3-carboxamide [XXV: R=CH₂Ph] (0.85 g, 2.87 mmol) in DMA (5 mL) was added under N₂ to a stirred suspension of MeSLi (0.93 g, 17.2 mmol) in DMA (10 mL). After warming at 80° C. for 6 hours, the mixture was acidified with 3N HCl, extracted with CH₂Cl₂, and worked up. Traces of DMA were removed under high vacuum, and the residue was dissolved in MeOH (15 mL) and treated dropwise with H₂O₂ (0.5 mL of 30% solution). After chilling at –30° C. overnight, the precipitate was filtered off to give 2,2'-dithiobis[N-benzylindolyl-3-carboxamide] (125) [V: $R_1$=$R_3$=H, $R_2$=CONHCH₂Ph], (74%); mp 203°–205° C.

¹H NMR ((CD₃)₂SO): δ 12.97 (1H, s, NH), 8.48 (1H, t, J=5.7 Hz, CONHCH₂), 7.86 (1H, d, J=8.2 Hz, H-4), 7.40 (2H, d, J=8.3 Hz, H-2',6') 7.34 (3H, dd, J=8.3, 8.2 Hz, H-7,3',5') 7.25 (1H, t, J=8.2 Hz, H-4'), 7.20–7.10 (2H, m, H-5,6), 4.56 (2H, d J=5.7 Hz, CONHCH₂).

¹³C NMR: δ 164.71 (CONH), 139.77 (s), 135.69 (s), 135.30 (s), 128.16 (d), 127.15 (d), 126.56 (d), 124.44 (s), 122.63 (d), 120.78 (d), 119.25 (d), 111.60 (d), 110.54 (s), 42.62 (CONHCH₂).

Analysis calculated for $C_{32}N_{26}N_4O_2S_2$ requires: C, 68.3; H, 4.7; N, 10.0; S, 11.4%.

Found: C, 68.0; H, 4.8; N, 9.9; S, 11.2%.

Compound 126 of Table 1

Reaction of 3-chlorocarbonyl -1-(phenylsulfonyl)indole [XXIII] with an excess of aniline as above gave N-phenyl-1-(phenylsulfonyl)indole-3-carboxamide [XXIV: $R_8$=Ph]; mp (MeOH) 220°–222.5° C.

¹H NMR: δ (CDCl₃) 8.18 (1H, s, H-2), 8.12 (1H, d, J=7.8 Hz, H-4), 7.99 (1H, d, J=8.3 Hz, H-7), 7.91 (2H, d, J=7.9 Hz, ArH), 7.90 (1H, m, NH), 7.65 (2H, d, J=8.4 Hz, ArH), 7.57 (1H, t, J=7.8 Hz, ArH), 7.45 (2H, t, J=7.8 Hz, ArH), 7.41–7.33 (4H, m, ArH), 7.15 (1H, t, J=7.4 Hz, H-5).

Analysis calculated for $C_{21}H_{18}N_2O_3S$ requires: C, 67.0; H, 4.3; N, 7.4; S, 8.5%. Found: C, 66.9; H, 4.4; N, 7.3; S, 8.5%.

Treatment of this with n-BuLi/methyldisulfide as above gave 2-(methylthio)-N-phenylindole-3-carboxamide [XXV: $R_8$=Ph] (81%) as an oil.

¹H NMR (CDCl₃): δ 10.19 (1H, s, H-1), 9.59 (1H, s, CONH), 8.47 (1H, d, J=6.8 Hz, H-4), 7.80 (2H, d, J=8.5 Hz, ArH), 7.43–7.35 (3H, m, ArH), 7.28–7.16 (3H, m, ArH), 2.51 (3H, s, SCH₃).

¹³C NMR (CDCl₃): δ 163.5 (CO), 138.2, 136.1, 132.5, 127.3, 111.2 (CH), 19.1 (CH₃).

HREIMS calculated for $C_{16}H_{14}N_2OS$: 282.0827 Found: 282.0827.

Treatment of this with MeSLi as above gave 2,2'-dithiobis [N-phenylindolyl-3-carboxamide] (126) [V: $R_1$=$R_3$=H, $R_2$=CONHPh], (67%); mp 220°–223° C.

¹H NMR ((CD₃)₂SO): δ 12.73 (1H, s, NH), 9.88 (1H, s, CONH), 7.81 (1H, d, J=7.9 Hz, H-4), 7.59 (2H, d, J=8.4 Hz, H-2',6') 7.46 (1H, d, J=7.7 Hz, H-7), 7.34 (2H, dd, J=8.4, 8.3 Hz, H-3',5'), 7.24 (1H, dd, J=7.7, 7.7 Hz, H-6), 7.17 (1H, dd, J=7.9, 7.7 Hz, H-5), 7.10 (1H, dd, J=8.3 Hz, H-4').

¹³C NMR: δ 163.27 (CONH), 138.89 (s), 136.73 (s), 133.94 (s), 128.53 (d), 125.12 (s), 123.49 (d), 123.17 (d), 120.99 (d), 120.32 (d), 119.97 (d), 112.89 (s), 111.67 (d).

Analysis calculated for $C_{30}H_{22}N_4O_2S_2$ requires: C, 67.4; H, 4.2; N, 10.5; S, 12.0%.

Found: C, 67.1; H, 4.3; N, 10.6; S, 12.0%.

Compound 127 of Table 1

Reaction of 3-chlorocarbonyl-1-(phenylsulfonyl)indole [XXIII] with an excess of methylamine as above gave N-methyl-1-(phenylsulfonyl)indole-3-carboxamide [XXIV: $R_8$=Me]; mp (MeOH) 192.5°–195° C.

¹H NMR (CDCl₃): δ 8.06 (1H, s, H-2), 8.03–7.84 (4H, m, ArH) 7.53–7.26 (5H, m, ArH), 6.37 (1H, m, NH), 2.99 (d, J=4.9 Hz, CH₃).

Analysis calculated for $C_{16}H_{14}N_2O_3S$ requires: C, 61.1, H, 4.5; N, 8.9; S, 10.2%.

Found: C, 61.1; H, 4.7; N, 8.9; S, 10.0%.

Treatment of this with n-BuLi/methyldisulfide as above gave N-methyl-2-(methylthio)indole-3-carboxamide [XXV: $R_8$=Me] (95%); mp (hexane-CH₂Cl₂) 138.5°–139.5° C.

¹H NMR (CDCl₃): δ 10.31 (1H, s, H-1), 8.35–8.26 (1H, m, H-4), 7.44 (1H, t, J=4.8 Hz, NH), 7.38–7.30 (1H, m, ArH), 7.19–7.11 (2H, m, ArH), 3.06 (3H, d, J=4.8 Hz, CH₃), 2.49 (3H, s, SCH₃).

¹³C NMR (CDCl₃): δ 166.4 (CO), 136.4, 132.4, 127.4 and 111.7 (C), 123.1, 121.5, 121.2, 111.1 (CH), 26.3 and 18.9 (CH₃).

Analysis calculated for $C_{11}H_{12}N_2OS$ requires: C, 60.0; H, 5.5; N, 12.7; S, 14.6%.

Found: C, 59.8; H, 5.7; N, 12.7; S, 14.5%.

Treatment of this with MeSLi as above gave 2,2'-dithiobis [N-methylindolinyl-3-carboxamide] (127) [V: $R_1$=$R_3$=H, $R_2$=CONHMe], (57% yield); mp 232°–236° C. (dec).

¹H NMR ((CD₃)₂SO): δ 12.94 (1H, s, NH), 7.85 (1H, br, CONH), 7.81 (1H, d, J=8.0 Hz, H-4), 7.46 (1H, d, J=8.0 Hz,

H-7), 7.20 (1H, dd, J=8.0, 7.7 Hz, H-6), 7.14 (1H, dd, J=8.0, 7.7 Hz, H-5), 2.88 (3H, d, J=4.5 Hz, CONHCH$_3$).

$^{13}$H NMR: δ 165.20 (CONH), 136.70 (s), 134.76 (s), 124.47 (s), 122.61 (d), 120.71 (d), 119.55 (d), 111.55 (d), 111.02 (s), 26.22 (CONHCH$_3$).

Analysis calculated for C$_{20}$H$_{18}$N$_4$O$_2$S$_2$ requires: C, 58.5; H, 4.4; N, 13.7; S, 15.6%.

Found: C, 58.4; H, 4.7; N, 13.6; S, 15.4%.

Compound 128 of Table 1

A solution of 2-(methylthio)-N-phenyl-1H-indole-3-carboxamide [XXV: R$_8$=H] (1.8 g, 6.4 mmol) in EtOH (400 mL) was treated with 3-(dimethylamino)propyl chloride hydrochloride (10.0 g, 64 mmol) and K$_2$CO$_3$ (13 g, 96 mmol) and heated under reflux for 3 hours. A further 10 equivalents of the reagents were then added, and the mixture was heated under reflux for a further 48 hours. EtOH was removed under reduced pressure, and the residue was diluted with water to give crude product. This was chromatographed on alumina, eluting with CH$_2$Cl$_2$ containing 0.2% MeOH, to give 1-[3-(dimethylamino)propyl]-2-(methylthio)-N-phenyl-1H-indole-3-carboxamide [XXVI: R$_8$=H, R$_9$=(CH$_2$)$_3$NMe$_2$] (0.49 g, 21%) as an oil.

$^1$H NMR (CDCl$_3$): δ 9.93 (1H, s, NH), 8.54 (1H, d, J=7.8 Hz, H-4), 7.74 (2H, d, J=8.6 Hz, H-2',6'), 7.42–7.24 (5H, m, ArH), 7.11 (1H, t, J=7.4 Hz, ArH), 4.46 (2H, t, J=7.4 Hz, 1-CH$_2$), 2.47 (3H, s, SCH$_3$), 2.37 (2H, t, J=6.9 Hz, CH$_2$N), 2.27 (6H, s, N(CH$_3$)$_2$), 1.97 (2H, dxt, J=7.4, 6.9 Hz, CH$_2$CH$_2$CH$_2$).

$^{13}$C NMR: δ 162.6 (CO), 138.8, 136.7, 131.4, 127.5, 114.1 (C), 129.0, 124.1, 123.7, 122.8, 122.1, 119.8, 110.0 (CH), 56.5, 42.0, 28.3 (CH$_2$), 45.3 (N(CH$_3$)$_2$), 21.1 (SCH$_3$).

Analysis calculated for C$_{21}$H$_{25}$N$_3$O$_8$ requires: [M+H$^+$]= 368.1797.

HRFABMS Found: [M+H$^+$]=368.1812.

This was treated with MeSLi at 80° C. for 8 hours as above. Water was added, the mixture washed washed with CH$_2$Cl$_2$, and the aqueous portion was carefully neutralized with 3N HCl and extracted with CH$_2$Cl$_2$. This extract was worked up to give an oil which was dissolved in MeOH and treated dropwise at room temperature with a saturated solution of 12 in CH$_2$Cl$_2$ until no starting material was evident on TLC analysis. The reaction mixture was absorbed directly onto silica and chromatographed. MeOH/EtOAc (1:9) eluted foreruns, while MeOH/EtOAc (1:9) containing a trace of concentrated NH$_4$OH gave 2,2'-dithiobis[1-{3-(dimethylamino)}propyl)-N-phenyl-1H-indole-3-carboxamide] (128) [V: R$_1$=H, R$_2$=CONHPh, R$_3$=(CH$_2$)$_3$NMe$_2$] (10% yield) as a yellow foam.

$^1$H NMR (CD$_3$OD): δ 8.19 (1H, d, J=7.3 Hz, H-4), 7.64 (1H, d, J=7.5 Hz, H-7), 7.30–7.20 (3H, m, ArH), 7.10–6.95 (4H, m, ArH), 4.41 (2H, t, J=6.2 Hz, CH$_2$N), 2.74 (2H, t, J=6.7 Hz, CH$_2$NMe$_2$), 2.64 (6H, s, N(CH$_3$)$_2$), 2.09 (2 H, m, CH$_2$CH$_2$CH$_2$).

Analysis calculated for C$_{40}$H$_{45}$N$_6$O$_2$S$_2$ requires: [M+H$^+$]=705.3045.

HRFABMS found: [M+H$^+$]=705.3035.

Example K

Preparation of Compound 129 of Table 1 by the Method Outlined in Scheme 10

To a stirred 25° C. solution of 41 mL (558 mmol) of DMF and 75 mL of dichloromethane was added dropwise a solution of 133.5 g (465 mmol) of POBr$_3$ in 100 mL of dichloromethane at such a rate to maintain a gentle reflux via the exothermic reaction (ca. 1 hour). The resulting thick tan suspension was stirred vigorously for 10 minutes, then treated dropwise over 20 minutes with a solution of 27.38 g (186 mmol) of 1-methyl-2-indolinone [VII: R$_1$=H, R$_3$=CH$_3$) in 55 mL of dichloromethane. The mixture was heated at reflux for 3.5 hours, cooled to 25° C., and the supernatant was decanted and concentrated to a thick reddish brown oil. This was combined with the solids above and treated very cautiously with portionwise addition of ca. 20 g of ice, then with 112 g of 50% (w/w) aqueous NaOH, all the while keeping the temperature between 30°–40° C. (pH=3). An additional 20 g of 50% NaOH, then 100 mL of ice water were added, and the precipitate was collected by filtration. The solids were washed well with water, then dried over P$_2$O$_5$ to leave 42.6 g of crude bromoaldehyde; mp 92°–97° C. The solids were dissolved in ca. 65 mL of dichloromethane and the solution filtered over 165 g of flash silica gel placed in a 600 mL sintered glass funnel. The frit was washed with dichloromethane until all the product had eluted. The combined product fractions were concentrated to leave 34.66 g (78%) of nearly pure 2-brom-1-methylindole-3-carboxaldehyde [XXVI: R$_1$=H, R$_3$=CH$_3$, X=Br]; mp 110°–112° which was used directly in the next reaction.

To a vigorously stirred solution of 2.38 g (10 mmol) of 2-bromo-1-methylindole-3-carboxaldehyde [XXVI: R$_1$=H, R$_3$=CH$_3$, X=Br], 10 mL of 2-methyl-2-butene, and 40 mL of p-dioxane at 25° C. was added dropwise over ca. 15 minutes a solution of 5 (55 mmol) of sodium chlorite and 5 g (36 mmol) of NaH$_2$PO$_4$.H$_2$O in 25 mL of water. The solution was maintained at 25° C. After 3.5 hours, the mixture was treated with an additional 2.5 g each of the chlorite and phosphate. After a total reaction time of 24 hours, the mixture was extracted 3 times with dichloromethane, then the aqueous phase was acidified to pH 2 with aqueous HCl, and extracted once more. The combined organic extracts were washed with water, dried, and evaporated to leave a solid residue that was boiled in 2-propanol. After cooling, the solids were collected by filtration, washed with a little 2-propanol, and dried to leave 2.21 g (87%) of 2-bromo-1-methyl indole-3-carboxylic acid [XXVII: R$_1$=H, R$_3$=CH$_3$, X=Br] as a beige solid; mp ca. 198° C. (dec), in 2 crops.

A suspension of 2.54 g (10 mmol) of 2-bromo-1-methylindole-3-carboxylic acid [XXVII: R$_1$=H, R$_3$=CH$_3$, X=Br], 2.54 g (10 mmol) of bis(2-oxo-3-oxazolidinyl)phosphinic chloride, 2.78 mL (20 mmol) of triethylamine, and 25 mL of 1,2-dichloroothane was heated at reflux for 1.5 hours. The mixture was cooled and poured into 150 mL 5% aqueous sodium bicarbonate solution and stirred for 30 minutes. The mixture was extracted with dichloromethane (3 times), the combined organic phase washed with water, brine, dried (MgSO$_4$), and concentrated to leave a red oil. The oil was triturated in ethyl acetate:hexanes and the solids were collected by filtration to give 0.95 g of a side product; mp 227°–228° C. (dec). The filtrate was concentrated to a viscous oil that was dissolved into chloroform and adsorbed into 9 g of flash SiO$_2$. This was introduced onto a column containing flash SiO$_2$ and the column was eluted with hexanes:ethyl acetate (95:5). Product fractions were pooled, concentrated, and triturated from isooctane to give 1.96 g (63%) of 2-bromo-1-methylindole -3-carboxylic acid, t-butyl ester [XXVIII: R$_1$=H, R$_2$=COO-t-butyl, R$_3$=CH$_3$] as a white solid; mp 87°–88° C.

Analysis calculated for C$_{14}$H$_{16}$BrNO$_2$ requires: C, 54.21; H, 5.20; N, 4.52; Br, 25.76%.

Found: C, 54.28; H, 5.20; N, 4.49, Br, 25.83%.

An ice-cold suspension of 119 mg (1.5 mmol) of elemental selenium in 2 mL of THF under N$_2$ was treated dropwise with 1.1 mL of methyl lithium:lithium bromide complex (1.5M in ether). The flask was opened to the air and with a brisk stream of $N_2$, the resultant white suspension was warmed to ca. 85° C. to distill off the ether and most of the THF. The residual semi-solid was cooled in an ice bath and diluted with 1.5 mL of DMA followed by 155 mg (0.5 mmol) of 2-bromo-1-methylindole-3-carboxylic acid, t-butyl ester. The resultant solution was stirred at room temperature for 24 hours, cooled to 0° C., then treated with 2 mL of dilute acetic acid. The mixture was diluted with water and extracted with chloroform (3×10 mL). The combined extracts were washed with water (4 times), dried ($Na_2SO_4$), and concentrated to leave a golden solid. The solid was suspended in 2.3 mL of 2:1 v/v $HOAc:H_2O$ and the suspension was treated with 154 mg of $NaBO3.4H_2O$, then stirred at 25° C. for 30 minutes. The solids were collected by filtration, washed with water, and dried to leave 119 mg (77%) of 2,2'-diselenobis[1-methyl -1H-indole-3-carboxylic acid, t-butyl ester] (129) [XXIX: $R_1$=H, $R_2$=COO-t-butyl, $R_3$=$CH_3$]; mp 187°–189° C.

$^1$H NMR ($CDCl_3$): $\partial$ 8.13 (1H, dd, J=0.7, 7.9 Hz, H-4), 7.31–7.19 (3H, m, ArH), 3.63 (3H, s, $NCH_3$), 1.44 (9H, s, $C(CH_3)_3$).

Analysis calculated for $C_{28}H_{32}N_2O_4Se_2.0.2H_2O$ requires: C, 54.06; H, 5.25; N, 4.50%.

Found: C, 54.40; H, 5.48; N, 4.11%.

Compound 130 of Table 1

To an ice-cold solution of 4 mL of trifluoroacetic acid under nitrogen was added 420 mg (0.68 mmol) of 2,2'-diselenobis [1-methyl -1H-indole -3-carboxylic acid, t-butyl ester] (101) [XXIX: $R_1$=H, $R_2$=COO-t-butyl, $R_3$=$CH_3$]. The suspension was maintained at 0° C. for 3 hours, then poured into ice water. The solids were collected by filtration, washed well with water, and dried to leave 361 mg of product; mp 165° C. (dec). The solids were suspended into 80 mL 10% aqueous $NH_4OH$ and the insolubles were removed by filtration. The filtrate was adjusted to pH 3 with 6N aqueous HCl, and the precipitated solids were collected by filtration, washed with water, and dried to leave 268 mg (78%) of 2,2 '-diselenobis[1-methyl-1H-indole-3-carboxylic acid] (130) [XXIX: $R_1$=H, $R_2$=COOH, $R_3$=$CH_3$]; mp 174° C. (dec) as an orange solid.

$^1$H NMR (($CD_3$)$_2$SO): $\partial$ 12.35 (1H, s, $CO_2\underline{H}$), 8.04 (1H, d, J=7.9 Hz, H-4), 7.56 (1H, d, J=8.4 Hz, H-7), 7.31–7.20 (2H, m, ArH), 3.63 (3H, s, $NCH_3$).

Analysis calculated for $C_{20}H_{16}N_2O_4Se_2.0.1H_2O$ requires: C, 47.28; H, 3.21; N, 5.51%.

Found: C, 47.20; H, 3.20; N, 5.12%.

Compound 131 of Table 1

A 25° C. suspension of 2.79 g (11 mmol) of 2-bromo-1-methylindole-3-carboxylic acid [XXVII: $R_1$=H, $R_3$=$CH_3$, X=Br] in 13 mL of 1,2-dichloroethane was treated dropwise with 2.41 mL (33 mmol) of thionyl chloride. The mixture was heated at 75° C. for 2 hours. The solution was concentrated to a solid which was co-evaporated once with dichloromethane. The solid was ice-cooled and treated rapidly with 26 mL of 40% aqueous methylamine. The bath was removed and the suspension was stirred at 25° C. for 2 hours. The solids were collected by filtration, washed well with water, and dried at 200 mm/70° C./12 hours over $P_2O_5$ to leave 2.2 g (75%) of product; mp 154°–157° C. Recrystallization from MeOH provided 1.91 g of pure 2-bromo-1-methylindole-3-N-methylcarboxamide [XXX: $R_1$=H, $R_3$=$CH_3$, $R_7$=H, $R_8$=$CH_3$] as a beige solid; mp 159°–160° C. in three crops.

An ice-cold solution of lithium methyl selenide in 2 mL of DMA, made up as previously described from 237 mg (3 mmol) of elemental Se and 2.2 mL of methyllithium (1.5M in ether) in 3 mL of THF, was treated with 267 mg (1.0 mmol) of 2-bromo-1-methylindole-3-N-methylcarboxamide [XXX: $R_1$=H, $R_3$=$CH_3$, $R_7$=H, $R_8$=$CH_3$]. The resultant solution was stirred at room temperature for 3.5 hours, cooled to 0° C., then treated with 5% aqueous HCl. The mixture was extracted with dichloromethane (2×10 mL), the combined extracts washed with water (2 times), then concentrated in vacuo to leave an oil that was dissolved in methanol. The solution was ice-cooled and treated with 113 µL of 30% aqueous $H_2O_2$. After stirring for 10 minutes, the resultant suspension was filtered, and the solids were washed with 2-propanol and dried to leave 183 mg (67%) of 2,2'-diselenobis [N, 1-dimethyl-1H-indole-3-carboxamide] (131) [XXIX: $R_1$=H, $R_2$=$CONHCH_3$, $R_3$=$CH_3$] as a yellow solid; mp 225°–230° C. (dec).

$^1$H NMR ($CDCl_3$+($CD_3$)$_2$SO): $\partial$ 7.97 (1H, d, J=7.9 Hz, H-4), 7.39–7.18 (3H, m, ArH), 6.84 (1H, s, $N\underline{H}CH_3$), 3.85 (3H, s, indole $NCH_3$), 2.12 (3H, d, J=4.5 Hz, $NHC\underline{H}_3$).

Analysis calculated for $C_{22}H_{22}N_4O_2Se_2.0.9H_2O$ requires: C, 48.17; H, 4.37; N, 10.21%.

Found: C, 48.20; H, 4.22; N, 10.28%.

Compound 132 of Table 1

Similar reaction of 2-chloro-1-methylindole-3-carboxylic acid [XXVII: $R_1$=H, $R_3$=$CH_3$, X=Cl] with $SOCl_2$ as described in Example I and reaction of this with 3 equivalents of N,N-diethylethylenediamine in dichloromethane at 0° C. followed by workup gave 2-chloro-1-methylindole-3-N-(2-(diethylamino)ethyl)carboxamide [XXX: $R_1$=H, $R_6$=H, $R_7$=$(CH_2)_2NEt_2$, X=Cl] as a soft solid in 68% yield, used without further purification.

Treatment of this with lithium methyl selenide as described above gave 2,2'-diselenobis [N-[2-(diethylamino)ethyl]-1-methyl-1H-indole-3-carboxamide] (132) [XXIX: $R_1$=H, $R_2$=$CONH(CH_2)_2NEt_2$, $R_3$=$CH_3$] (68% yield); mp 128°–130° C. Reaction of the free base with excess hydrogen chloride in 2-propanol followed by concentration to an oil and crystallization at 25° C. gave the compound as a dihydrochloride salt (18% yield); mp 160°–164° C.

$^1$H NMR (($CD_3$)$_2$SO): $\partial$ 10.13 (1H, s, $^+N\underline{H}(CH_2CH_3)_2$), 8.14–8.11 (1H, m, $CON\underline{H}$), 7.89 (1H, d, J=8.2 Hz, H-4), 7.57 (1H, d, J=8.4 Hz, H-7), 7.34–7.17 (2H, m, ArH), 3.63 (3H, s, $NC\underline{H}_3$), 3.17–3.14 (2H, m, $CONHC\underline{H}_2$), 3.06–3.00 (4H, m, $N(C\underline{H}_2CH_3)_2$), 2.86 (2H, t, J=6.5 Hz, $CONHCH_2C\underline{H}_2$), 1.16 (6H, t, J=7.2 Hz, $N(CH_2C\underline{H}_3)_2$), Analysis calculated for $C_{32}H_{44}N_6O_2Se_2.2.0HCl.1.7H_2O$ requires: C, 47.67; H, 6.18; N, 10.42; Cl$^-$, 8.79%.

Found: C, 47.71; H, 6.12; N, 10.35; Cl$^-$, 8.97%.

Compound 133 of Table 1

A mechanically stirred suspension of 15 g (83.5 mmol) of 2-chloroindole-3-carboxaldehyde [XXVI: $R_1$=$R_3$=H, X=Cl] (Schule, et al., *Arch. Pharm.* [Weinheim] 1972;305:523–533), 84 mL of 2-methyl-2-butene, and 200 mL of p-dioxane in an ice bath was treated with a solution of 40 g each of sodium chlorite and sodium dihydrogen phosphate monohydrate in 200 mL of water. The biphasic mixture was then stirred vigorously at 25° C. for 3.5 hours.

An additional 16 g each of solid sodium chlorite and sodium dihydrogen phosphate monohydrate was added and the mixture was stirred for another 3.5 hours. The mixture was diluted with 350 mL of ethyl acetate and 200 mL of water. The layers were separated and the aqueous phase was extracted with 300 mL of ethyl acetate. The combined organic extracts were extracted with cold 2% aqueous NaOH (3×200 mL). The basic extracts were combined and acidified to pH 4 with 6N aqueous HCl. The precipitated solids were collected by filtration, washed well with water, and air dried overnight. The solids were dissolved in 150 mL of hot acetone and the solution was treated with 65 mL of hexane. After storage at 3° C. for 20 hours, the solids were collected by filtration, washed with cold acetone, and dried to leave 7.71 g of pure 2-chloroindole-3-carboxylic acid [XXVII: $R_1=R_3=H$, X=Cl] as an off-white solid; mp 181.5° C. (dec). Further processing of the filtrate as above afforded 2.41 g of a second crop; mp 179.5° C. (dec). Total yield 10.12 g (62%).

The acid chloride of 2-chloroindole-3-carboxylic acid [XXVII: $R_1=R_3=H$, X=Cl] was made via $SOCl_2$ as described above. Reaction of this with a saturated solution of anhydrous methylamine in THF at 0° C. gave 2-chloroindole-3-N-methylcarboxamide [XXX: $R_1=R_3=H$, $R_6=H$, $R_7=CH_3$, X=Cl]; mp 234°–236° C., in 51% yield.

Reaction of this with lithium methyl selenide as described above gave 2,2'-diselenobis[N-methyl-1H-indole-3-carboxamide] (133) [XXIX: $R_1=R_3=H$, $R_3=CONHCH_3$] (20% yield), mp 272°–275° C. (decomp).

$^1$H NMR (($CD_3$)$_2$SO): ∂ 12.36 (1H, s, indole NH), 7.83 (1H, d, J=7.7 Hz, H-4), 7.79 (1H, d, J=4.1, NHCH$_3$), 7.48 (1H, d, J=7.7 Hz, H-7), 7.16–7.07 (2H, m, ArH), 2.90 (3H, d, J=4.1 Hz, NHCH$_3$).

Analysis calculated for $C_{20}H_{18}N_4O_2Se_2 \cdot 0.9H_2O$ requires: C, 46.15; H, 3.83; N, 10.76%.

Found: C, 46.08; H, 3.44; N, 10.45%.

Compound 134 of Table 1

The acid chloride of 2-chloroindole-3-carboxylic acid [XXVII: $R_1=R_3=H$, X=Cl] was made via $SOCl_2$ as described above. Reaction of this with 3 equivalents of N,N-diethylethylenediamine in ether as described above followed by workup gave 2-chloroindole-3-N-(2-(diethylamino) ethyl) carboxamide [XXX: $R_1=R_3=R_6=H$, $R_7=(CH_2)NEt_2$, X=Cl]; mp 99°–108° C. in 38% yield.

$^1$H NMR (CDCl$_3$): ∂ 11.50 (1H, s, indole NH), 8.19 (1H, d, J=6.5 Hz, H-4), 7.33 (1H, d, J=8.4 Hz, H-7), 7.21–7.15 (3H, m, ArH and CONH), 3.54 (2H, q, J=5.3 Hz, CONHCH$_2$), 2.69 (2H, t, J=6.0 Hz, CONHCH$_2$CH$_2$), 2.59 (4H, q, J=7.2 Hz, N(CH$_2$CH$_3$)$_2$), 1.05 (6H, t, J=7.2 Hz, N(CH$_2$CH$_3$)$_2$).

Reaction of this with lithium methyl selenide as described above gave 2,2'-diselenobis [N-[2-(diethylamino)ethyl]-1H-indole -3-carboxamide] (134) [XXIX: $R_1=R_3=H$, $R_2=CONH(CH_2)_2NEt_2$] (44% yield); mp 225°–226° C. (dec). Salt formation as above gave the compound as the dihydrochloride salt (85% yield); mp 257°–259° C. (dec).

$^1$H NMR (($CD_3$)$_2$SO): ∂ 12.75 (1H, s, indole NH), 10.08 (1H, s, $^+$NH(CH$_2$CH$_3$)$_2$), 8.09 (1H, t, J=5.7 Hz, CONH), 7.93 (1H, d, J=8.9 Hz, H-4), 7.51 (1H, d, J=6.8 Hz, H-7), 7.19–7.12 (2H, m, ArH), 3.78–3.73 (2H, m, CONHCH$_2$), 3.32 (2H, t, J=6.5 Hz, CONHCH$_2$CH$_2$), 3.29–3.20 (4H, m, N(CH$_2$CH$_3$)$_2$), 1.26 (6H, t, J=7.2 Hz, N(CH$_2$CH$_3$)$_2$).

Analysis calculated for $C_{30}H_{40}N_6O_2Se_2 \cdot 2.0HCl \cdot 1.0H_2O$ requires: C, 47.07; H, 5.79; N, 10.98; Cl$^-$, 9.26%.

Found: C, 47.01; H, 5.70; N, 10.56; Cl$^-$, 8.87%.

Compound 135 of Table 1

A mixture of 2.09 g (10 mmol) of 2-chloroindole-3-N-methylcarboxamide [XXX: $R_1=R_3=R_6=H$, $R_7=CH_3$, X=Cl], 1.72 g (10 mmol) of 2-diethylaminoethyl chloride hydrochloride (n=2, Q=Cl, $R_8=R_9=Et$), 7.5 g (23 mmol) of anhydrous cesium carbonate, 3 g of activated 3A molecular sieves, and 20 mL of acetone was stirred under nitrogen at 25° C. for 16 hours. The mixture was filtered over celite and the filtrate was concentrated to a solid that was partitioned between chloroform and water. The organic phase was dried (Na$_2$SO$_4$) and concentrated to a residue that was crystallized from ethyl acetate:hexanes (5:8). The solids were collected and dried to leave 1.43 g of 2-chloro-1-[2-(diethylamino)ethyl]-N-methyl-1H-indole-3-carboxamide [XXX: $R_1=R_6=H$, $R_3=(CH_2)_2NEt_2$, $R_7=CH_3$, X=Cl]; mp 103°–104° C., in 46% yield.

$^1$H NMR (CDCl$_3$); ∂ 8.24 (1H, d, J=8.0 Hz, H-4), 7.33–7.21 (3H, m, ArH), 6.35 (1H, s, CONHCH$_3$), 4.27 (2H, t, J=7.6 Hz, 1-NCH$_2$), 3.06 (3H, d, J=4.8 Hz, CONHCH$_3$), 2.73 (2H, t, J=7.5 Hz, 1-NHCH$_2$CH$_2$), 2.62–2.55 (4H, m, N(CH$_2$CH$_3$)$_2$), 1.02 (6H, t, J=7.0 Hz, N(CH$_2$CH$_3$)$_2$).

Reaction of this with lithium methyl selenide as described above gave 2,2'-diselenobis[1-[2-(diethylamino)ethyl]-N-methyl-1H-indole-3-carboxamide] (135) [XXIX: $R_1=H$, $R_2=CONHCH_3$, $R_3=(CH_2)_2NEt_2$] (63% yield); mp 156°–157° C.

Analysis calculated for $C_{32}H_{44}N_6O_2Se_2 \cdot 0.5H_2O$ requires: C, 54.01; H, 6.37; N, 11.81%.

Found: C, 54.14; H, 6.23; N, 11.54%.

Example L

Preparation of Compound 136 of Table 1 by the Method Outlined in Scheme 11.

An ice-cold solution of 15 g (50 mmol) of the N-trifluoroacetamide of D-tryptophan, synthesized by methods previously outlined (*J. Org. Chem.* 1979;44:2805–2807) in 50 mL of THF under $N_2$ was treated sequentially with 7.1 g (52.5 mmol) of 1-hydroxybenzotriazole then 10.83 g (52.5 mmol) of 1,3-dicyclohexylcarbodiimide. After 15 minutes, the solution was treated with 5.74 mL (52.6 mmol) of benzylamine. The solution was maintained at 0°–5° C. for 1 hour, then let warm to 25° C. overnight. The mixture was filtered and the collected solids were washed with ethyl acetate. The filtrate was concentrated to an oil that was dissolved in 250 mL of ethyl acetate. The solution was washed sequentially with 250 mL portions of 10% aqueous acetic acid, water, 5% aqueous sodium hydrogen carbonate, water and brine, then dried (NaSO$_4$), and concentrated to a solid. Crystallization from 170 mL of 65:35 2-propanol:petroleum ether afforded 12.81 g (66%) of (R)-N-(phenylmethyl)-α-[(trifluoroacetyl)amino]-1H-indole-3-propanamide [II: $R_1=H$, $R_2=CH_2CH(NHCOCF_3)CONHCH_2Ph$, $R_3=H$] as an off-white solid which was used directly in the next reaction; mp 186°–188° C.

To an ice-cold solution of 10 g (25.7 mmol) of (R)-N-(phenylmethyl)-α-[(trifluoroacetyl)amino] -1H-indole-3-propanamide [XXIX: $R_1=H$, $R_2=CH_2CH(NHCOCF_3)$ CONHCH$_2$Ph, $R_3=H$] in 70 mL of THF was added dropwise Se$_2$Cl$_2$. The resultant deep red suspension was stirred at 0°–5° C. for 4 hours, then quenched with 300 mL of water. The solids were collected by filtration, washed well with water, and air dried to leave 12 g of impure product as an orange solid. A portion of this material (10.7 g) was dissolved in 100 mL of methanol and the solution under $N_2$ was cooled in an ice bath. Sodium borohydride (ca 1 g) was added portionwise until there was no more color discharge. The mixture was poured immediately into a $N_2$ purged separatory funnel containing 200 mL of ether. The mixture was diluted with 200 mL of water, the mixture shaken, and the phases separated. The aqueous layer was treated with a small portion of additional sodium borohydride, extracted again with ether, ice-cooled, then acidified to pH 1 with concentrated HCl. The aqueous phase was extracted twice with ethyl acetate, then the combined extracts were dried ($MgSO_4$) and filtered through a pad of flash silica gel. The filtrate was concentrated to leave 5.91 g of a foam that was dissolved in ca 40 mL of absolute ethanol. The solution was kept at 25° C. for several hours to initiate crystallization, then stored at 5° C. The solids were collected by filtration, washed with 2-propanol, and dried to leave 4.23 g of pure [R-(R*,R*)]-2,2'-diselenobis[N-(phenylmethyl)-α-[(trifluoroacetyl)amino]-1H-indole-3-propanamide] [XXIX: $R_1$=H, $R_2$=$CH_2CH(NHCOCF_3)CONHCH_2Ph$, $R_3$=H], as a yellow powdery solid; mp 181°–185° C.

Analysis calculated for $C_{40}H_{34}N_6O_4F_6Se_2 \cdot H_2O$ requires: C, 50.43; H, 3.81; N, 8.82%.

Found: C, 50.47; H, 3.57; N, 8.71%.

Further processing of the filtrate by chromatography over flash $SiO_2$, eluting first with dichloromethane then 7% ethyl acetate in dichloromethane, provided an additional 671 mg of product following crystallization; mp 180°–183° C.

A suspension of 233.5 mg (0.25 mmol) of this diselenide in 4.5 mL of dry absolute ethanol was treated with 95 mg (2.5 mmol) of sodium borohydride. The mixture was heated at reflux for 15 minutes, then treated with 95 mg of additional borohydride. The mixture was refluxed for 1.25 hours, then treated with a third 95 mg portion of borohydride. After refluxing for 30 minutes, the mixture was cooled to 25° C., diluted with methanol, and poured into an ice-cold stirring mixture of 6N HCl and ethyl acetate. The resultant mixture was stirred vigorously for 15 minutes, filtered, the phases separated, and the aqueous layer extracted once more with ethyl acetate. The combined ethyl acetate phases were then back extracted with 5% aq HCl (five times). The acidic aqueous layers were combined and diluted with an equal volume of ethyl acetate. While carefully monitoring the pH, the stirred solution was treated carefully with 10% aqueous NaOH until pH=9.5. The resultant yellow precipitate was collected by filtration, washed well with water, and dried to leave 90 mg of [R-(R*,R*)]-2,2'-diselenobis[α-amino-N-(phenylmethyl)-1H-indole-3-propanamide] (136) [XXIX: $R_1$=H, $R_2$=$CH_2CH(NH_2)CONHCH_2Ph$, $R_3$=H], as a yellow powder; mp 172°–174° C.

$^1$H NMR (($CD_3$)$_2$SO): δ 11.62 (1H, s, NH), 8.23 (1H, t, J=5.1 Hz, NHCH$_2$), 7.61 (1H, d, J=8.0 Hz, ArH), 7.38 (1H, d, J=8.2 Hz, ArH), 7.35–6.95 (7H, m, ArH), 4.20, 4.17 (2×1H, 2×dd, J=15.2, 5.8 Hz, NHCH$_2$), 3.46–3.40 (1H, br m, Ar—CH$_2$CH), 3.04–2.98 (1H, br m, Ar—CH), 2.75–2.68 (1H, br m, Ar—CH), 1.70 (2H, br s, NH$_2$).

Analysis calculated for $C_{36}H_{36}N_6O_2Se_2 \cdot 1.5H_2O$ requires: C, 56.18; H, 5.11; N, 10.68%.

Found: C, 55.91; H, 4.72; N, 10.68%.

Processing of the ethyl acetate layer from the base treatment provided 15 mg of additional product; mp 165°–171° C. Total yield=105 mg (57%).

Compound 137 of Table 1

Starting from the N-trifluroracetamide of L-tryptophan (*J. Org. Chem.* 1979;44:2805–2807) and following the same procedures as outlined for the synthesis of compound 136 of Table 1, there was obtained [S-(R*,R*)]-2,2'-diselenobis[α-amino-N-(phenylmethyl)-1H-indole-3-propanamide] (137) [XXIX: $R_1$=H, $R_2$=$CH_2CH(NH_2)CONHCH_2Ph$, $R_3$=H] as a yellow powder; mp 171° C. (dec).

BIOLOGICAL AND BIOCHEMICAL EFFECTS

Tyrosine Kinase Inhibition Assay and Growth Inhibition Effects on Cells in Tissue Culture Table 2 provides representative data on inhibition of the epidermal growth factor receptor tyrosine kinase, and on cell growth inhibition.

In Table 2: No. is the compound number as recorded in Table 1.

IC50 (EGFR TK) is the concentration of drug necessary to reduce incorporation of $P^{32}$ in GAT by 50%.

IC$_{50}$ (PDGFR TK) is the concentration of drug necessary to reduce incorporation of $P^{32}$ in Glu-Tyr by 50%.

IC50 growth Inhibition is (cell growth inhibition) is the concentration of drug necessary to reduce the cellular growth rate by 50%.

TABLE 2

IC$_{50}$ Data for EGRF-R and PDGF-R Inhibition and Cell Growth Inhibition for Selected Compounds of Table 1

| No. | IC$_{50}$ (μM) or % Inhibition at 100 μM | | Growth Inhibition |
|---|---|---|---|
| | EGRF-R | PDGF-R | |
| 1 | 14.9 | — | |
| 2 | 26% | — | |
| 3 | 43% | 8.6% | |
| 4 | 27% | — | |
| 5 | 4% | — | |
| 6 | 25 | 8.5% | |
| 7 | 1.3 | — | 94 |
| 8 | 8.5 | — | |
| 9 | 52% | — | 16 |
| 10 | 10% | — | 34 |
| 11 | 24% | — | |
| 12 | 3% | — | |
| 13 | 43% | — | |
| 14 | 22 | — | |
| 15 | 6.8 | — | |
| 16 | 23 | — | |
| 17 | 12.5% | — | |
| 18 | 2% | 9% | |
| 19 | 10% | — | |
| 20 | 9 | — | |
| 21 | 1.0 | — | 64 |
| 22 | — | — | |
| 23 | — | — | |
| 24 | 19% | — | |
| 25 | 8.7 | — | |
| 26 | 23% | 5% | |
| 27 | 17.8 | — | 2.3 |
| 28 | 33 | — | |
| 29 | 8.3 | — | 25–100 |
| 30 | 9.3 | — | 8 |
| 31 | 35.5 | — | 1 |
| 32 | 34.5 | 4.7% | 36 |
| 33 | 39 | 16.7% | 3.0 |
| 34 | 38 | 12.8% | 2.7 |
| 35 | 16.5 | 33.9% | |
| 36 | 4.8 | — | 59 |
| 37 | 3.3 | — | |
| 38 | 36.5% | — | 1.6 |
| 39 | 20.6 | — | 7.4 |
| 40 | 16.3% | — | 5.2 |

TABLE 2-continued

IC$_{50}$ Data for EGRF-R and PDGF-R Inhibition and Cell Growth Inhibition for Selected Compounds of Table 1

| No. | IC$_{50}$ (μM) or % Inhibition at 100 μM | | Growth Inhibition |
|---|---|---|---|
| | EGRF-R | PDGF-R | |
| 41 | 8.4 | — | >25 |
| 42 | 26% | — | |
| 43 | 2.9 | — | |
| 44 | 16.6% | 5% | 2.4 |
| 45 | 1.6 | — | |
| 46 | 11.4% | — | 2.7 |
| 47 | 0.85 | — | 6 |
| 48 | 35.5 | — | |
| 49 | 84.1 | — | |
| 50 | 16.0 | 62.6% | |
| 51 | 7.0 | — | |
| 52 | 68.2 | 18.3% | |
| 53 | 4.2 | — | |
| 54 | 29 | 20.6% | |
| 55 | 44 | — | |
| 56 | 7.3 | 44.5% | |
| 57 | 46% | 14.5% | |
| 58 | 68% | — | |
| 59 | 30.5 | 11.4% | |
| 60 | 53% | — | |
| 61 | 37% | 11% | |
| 62 | 6.0 | 71% | 5.3 |
| 63 | 60 | — | |
| 64 | 29 | — | |
| 65 | 17.8 | — | |
| 66 | 8.3 | — | |
| 67 | 18% | 2% | |
| 68 | 14% | — | 1.8 |
| 69 | 55.6% | 8.9% | |
| 70 | 8.6 | 1% | 12 |
| 71 | 20% | 5% | 52 |
| 72 | 47% | 22% | |
| 73 | 4.3 | 21% | 9.3 |
| 74 | 23% | — | |
| 75 | 6% | 3% | 4 |
| 76 | 7% | 19% | 22 |
| 77 | 9% | 1% | |
| 78 | 27% | 7% | |
| 79 | 11% | 20% | 1.9 |
| 80 | 0% | 16% | |
| 81 | 3.6 | 2% | 17 |
| 82 | 6.5 | — | 24 |
| 83 | 22.3 | 57% | 10 |
| 84 | 35% | 22% | |
| 85 | 8% | 7% | |
| 86 | 4.9 | 5% | |
| 87 | 34% | 44% | |
| 88 | 54 | 51% | |
| 89 | 11.4 | 3% | |
| 90 | 26 | 36.5 | |
| 91 | 5.2 | — | |
| 92 | — | — | |
| 93 | 30% | — | |
| 94 | — | — | |
| 95 | 9.4 | — | |
| 96 | — | — | |
| 97 | 10.1 | 28.1 | 1.8 |
| 98 | 1.5 | 9% | 5–12 |
| 99 | 40 | 19% | 2.8 |
| 100 | 18% | 23% | |
| 101 | 5.5 | — | |
| 102 | 6.1 | — | |
| 103 | 7% | — | 3.8 |
| 104 | 20% | — | |
| 105 | 16.9 | 33% | |
| 106 | 34% | — | |
| 107 | 12.0 | — | |
| 108 | 20% | — | |
| 109 | 47 | 8% | |
| 110 | 13 | — | |
| 111 | 5.3 | 76% | |
| 112 | 10.0 | 69% | |
| 113 | 5% | 29% | |
| 114 | 42.9 | 7.0 | |
| 115 | 26 | 19.7 | >50 |
| 116 | 4% | 7.9 | |
| 117 | 25% | 4.2 | |
| 118 | 4.7 | 78% | |
| 119 | 21.2 | 73% | |
| 120 | 6.9 | — | |
| 121 | 5.6 | — | |
| 122 | 51% | — | |
| 123 | — | — | |
| 124 | — | — | |
| 125 | 78% | — | |
| 126 | 60% | — | |
| 127 | 6.8 | — | |
| 128 | — | — | |
| 129 | 31% | — | |
| 130 | 3.5 | — | |
| 131 | 5.8 | — | 5.5 |
| 132 | 4.7 | — | 20 |
| 133 | 13.0 | — | <5 |
| 134 | 4.6 | — | 8 |
| 135 | 6.9 | | |
| 136 | | | |
| 137 | | | |

EGF Receptor Tyrosine Kinase Assay

Membrane vesicles were prepared by the method described in Cohen S, Ushiro H, Stoscheck C, and Chinkers M. A native 170,000 epidermal growth factor receptor-kinase complex from shed plasma membrane vesicles, *J. Biol. Chem.* 1982;257:1523–1531, and kept frozen at −90° C. until use. At the time of assay, membranes were solubilized in 4% Triton X-100 and 10% glycerol. The reaction is carried out in wells of a 96-well microtiter plate in a total volume of 125 L. Buffer containing 20 mM Hepes (pH 7.4), 15 mM MgCl$_2$, 4 mM MnCl$_2$, and 0.02% BSA followed by 5 to 20 mg of membrane protein and 150 ng of epidermal growth factor. The plates are incubated for 10 minutes at room temperature to activate the receptor kinase. 20 g of GAT (random polymer of glycine, alanine, and tyrosine) and 0.2 mCi of α-[P$^{32}$] ATP plus or minus compound are added and incubated 10 minutes at room temperature. The reaction is stopped by addition of 125 mL of 30% TCA, precipitate washed twice with 200 mL of 15% TCA on 0.65 micron filters, and the filters counted by scintillation spectrometry.

PDGF Receptor Tyrosine Kinase Inhibition Assay

Recombinant baculovirus containing human PDGF β receptor intracellular tyrosine kinase domain was used to infect SF9 cells to overexpress the protein, and cell lysates were used for the assay. The ability of the tyrosine kinase to phosphorylate glutamate-tyrosine substrate in the presence of P$^{32}$-ATP and inhibitor was measured by counting the incorporation of P$^{32}$ in Glu-Tyr in TCA precipitable material.

Table 2 provides representative data on inhibition of the PDGF receptor tyrosine kinase. In Table 2, No. refers to the compound number as recorded in Table 1.

DETAILED STUDIES ON THE BIOLOGICAL EFFECTS OF COMPOUNDS 21 AND 70

Effects on Cells in Tissue Culture

Swiss 3T3 fibroblasts, that were growth arrested in serum-free media for 24 hours, were exposed to various concentrations of compound for 2hours. The cells were then exposed to individual growth factors for 5 minutes and proteins that were phosphorylated on tyrosine in response to the mitogens and were detected by Western blotting techniques using phosphotryosine antibodies. Similar techniques were used for tumor cell lines except the time in serum-free media was increased.

At concentrations of 10 to 50 mM, compound 21 suppressed: (1) EGF mediated phosphorylation of a variety of endogenous proteins; (2) PDGF mediated autophosphorylation of the PDGF receptor as well as PDGF mediated tyrosine phosphorylation of other endogenous proteins and; (3) bFGF mediated tyrosine phosphorylation. 70 was more selective and inhibited only bFGF mediated tyrosine phosphorylation and at concentrations as low as 2 mM.

Effects on Growth Factor Mediated Mitogenesis

Swiss 3T3 fibroblasts, that were growth arrested in serum-free media for 24 hours, were exposed to various concentrations of compound for 2 hours. The cells were then exposed to individual growth factors for 24 hours and mitogenesis assessed by measuring tritiated thymidine incorporation into DNA.

The concentration of 21 and 70 required to inhibit growth factor mediated mitogenesis by 50% for the following growth factors was as follows:

| Growth Factor | IC$_{50}$ (μM) for 21 | IC$_{50}$ (μM) for 70 |
| --- | --- | --- |
| EGF | 2 | 3 |
| PDGF | 8 | 4 |
| bFGF | 13 | 3 |
| serum | 19 | 3 |

Growth Inhibition Assay

Swiss 3T3 mouse fibroblasts were maintained in dMEM/F12 media containing 10% fetal calf serum. Two mL of cells at a density of 1×104/mL were placed in 24-well plates plus or minus various concentrations of the inhibitor. The cells were grown at 37° C. under 5% CO$_2$ for 72 hours and then counted by Coulter counter. The data were expressed as the concentration of inhibitor necessary to decrease the growth rate by 50%.

Compound 21 was growth inhibitory for a variety of human tumor cell lines as well as the Swiss 3T3 fibroblasts. The concentration of 21 necessary to inhibit cell growth by 50% is shown below:

| Cell Line | IC$_{50}$ (μM) |
| --- | --- |
| MDA 468 breast | 43 |
| A431 epidermoid | 62 |
| A549 lung | 30 |
| MDV-7 breast | 39 |
| MDA-231 breast | 15 |
| Swiss 3T3 fibroblasts | 64 |
| HT-29 colon | 55 |

Although the carboxyl containing structures are among the most active enzyme inhibitors, they are poorly transported into the cell, whereas the less active esters are transported efficiently and once in the cytoplasm rendered highly active by esterases. Esters may, therefore, be more favorable than carboxylic acids in this invention.

The data of Table 2 show that the 2-thioindoles of general Formula I listed in Table 1 include compounds which are active as potent inhibitors of protein tyrosine kinases and as cytotoxic agents.

The invention is not limited to the particular embodiments shown and described herein, since various changes and modifications may be made without departing from the spirit and scope of the invention as defined by the following claims.

We claim:

1. 2-Thioindole, 2-indolinethione and polysulfide compounds of the group represented by the general Formulas I and IV

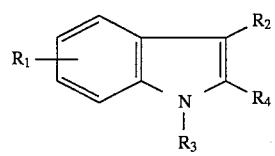

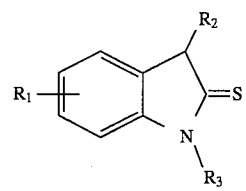

and pharmaceutically acceptable salts thereof, wherein $R_1$ is a member selected from H, halogen, R, OH, OCOR, OR, CF$_3$, NO$_2$, NH$_2$, NHR, COOH, CONHR, (CH$_2$)$_n$OH, (CH$_2$)$_n$OR, (CH$_2$)$_n$NH$_2$, (CH$_2$)$_n$NHR, and (CH$_2$)$_n$NRR, and further represents replacement in the ring of 1 or 2 ring methine (—CH=) atoms with aza (—N=) atoms;

$R_2$ is a member selected from
(CH$_2$)$_n$COOH,
(CH$_2$)$_n$COR,
(CH$_2$)$_n$SO$_2$R,
(CH$_2$)$_n$SO$_2$NRR,
(CH$_2$)$_n$SO$_2$NHR,
CH=CHCOOH,

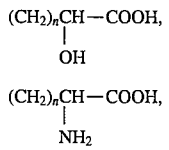

(CH$_2$)$_n$CONH$_2$,
(CH$_2$)$_n$CONHR,
(CH$_2$)$_n$CONRR,
(CH$_2$)$_n$CONHCH$_2$Ph,
CONHR,

CONRR,
CONHPh,
COY,
COPhCOOH,
COPhCOOR,
$(CH_2)_n$CONHPh,
$(CH_2)_n$CONHPhR,
$SO_2Y$;

n is an integer from 1 to 4;

R is lower alkyl;

$R_3$ is a member selected from H, lower alkyl, and benzyl;

Y represents a benzene, pyridine, thiophene, furan, thiazole, or imidazole ring optionally substituted with a lower alkyl, COOH, OH, OCOR, $NH_2$, CONHR, CONRR, OR, or NHR group; and $R_4$ represents SH, $S_oX$, and $S_oQ$ where o is 1, 2, or 3, X is a member selected from H, lower alkyl, benzyl, and benzene, pyridine, thiophene, furan, thiazole, and imidazole rings, and Q is another 2-thioindolyl moiety of Formula I provided that the group does not comprise compounds having the names
2-(2-thioxo-3-indolinyl)acetic acid,
2-(1-methyl-2-thioxo-3-indolinyl) acetic acid,
methyl 2-(2-thioxo-3-indolinyl) acetate,
ethyl 2-(1-methyl-2-thioxo-3-indolinyl)acetate,
methyl 2-(2-methylthio-3-indolyl) acetate,
bis[methylinodolinyl-3-acetate-(2)]disulfide,
bis[indolyl-3-acetic acid-(2)]disulfide,
bis[methylindolyl-3-acetate-(2)]trisulfide, and
bis[1-methylindolyl-3-acetic acid-(2)]-disulfide.

2. A thioindole compound according to claim 1 selected from
methyl 2-(1-methyl-2-thioxo-3-indolinyl)acetate,
N-benzyl(2-thioxo-3-indolinyl)acetamide,
3-(2-thioxo-3-indolinyl)propanoic acid,
3-(1-methyl-2-thioxo-3-indolinyl)propanoic acid,
methyl 3-(2-thioxo-3-indolinyl)propanoate,
ethyl 3-(2-thioxo-3-indolinyl)propanoate,
3-(1-methyl-2-thioxo-3-indolinyl)propanoate,
ethyl 3-(1-methyl-2-thioxo-3-indolinyl)propanoate,
N-benzyl 3-(2-thioxo-3-indolinyl)propanamide,
4-(2-thioxo-3-indolinyl)butanoic acid,
4-(1-methyl-2-thioxo-3-indolinyl)butanoic acid,
methyl 4-(2-thioxo-3-indolinyl)butanoate,
methyl 4-(1-methyl-2-thioxo-3-indolinyl)butanoate,
N-phenyl (1-methyl-2-thioxo-3-indolinyl)carboxamide,
N-phenyl (1-methyl-2-methylthio-3-indolinyl)carboxamide,
3-benzoyl-1-methyl-2-indolinethione,
3-(4'-carboxybenzoyl)-1-methyl-2-indolinethione,
3-(4'-carbomethoxybenzoyl)-1-methyl-2-indolinethione,
and pharmaceutically acceptable salts thereof.

3. A polysulfide compound according to claim 1 selected from
2,2'-dithiobis[methyl 2-(1-methyl-3-indolyl)acetate],
bis[indolyl-3-acetic acid-(2)]trisulfide,
bis[ethyl1-methylindolyl-3-acetate-(2)]disulfide,
2,2'-dithiobis[N-benzyl-2-(3-indolyl)acetamide],
bis[indolyl-3-propanoic acid-(2)]disulfide,
2,2'-dithiobis[3-(1-methyl-3-indolyl)propanoic acid],
bis[ethylindolyl-3-propanoate-(2)]disulfide,
2,2'-dithiobis[methyl-3-(3-indolyl)propanoate],
2,2'-dithiobis[methyl-3-(1-methyl-3-indolyl)propanoate],
bis[5-methylindolyl-3-propanoic acid-(2)]disulfide,
bis[ethyl-5-methylindolyl-3-propanoate-(2)]disulfide,
bis[6-methylindolyl-3-propanoic acid-(2)]disulfide,
bis[ethyl-6-methylindolyl-3-propanoate-(2)]disulfide,
bis[7-methylindolyl-3-propanoic acid-(2)]disulfide,
bis[ethyl-7-methylindolyl-3-propanoate-(2)]disulfide,
2,2'-dithiobis[N-benzyl-3-(3-indolyl)propanamide],
bis[indolyl-3-butanoic acid-(2)disulfide,
2,2'-dithiobis[4-(1-methyl-3-indolyl butanoic acid],
bis[methyl indolyl-3-butanoate-(2)]disulfide,
bis[methyl 1-methylindolyl-3-butanoate-(2)]disulfide,
bis[N-phenyl 1-methyl indolyl-3-carboxamide-(2)]disulfide,
bis[N-phenyl 1-ethylindolyl-3-carboxamide-(2)]disulfide,
bis[N-phenyl 4-chloro-1-methylindolyl-3-carboxamide-(2)]disulfide,
bis[N-phenyl 5-chloro-1-methylindolyl-3-carboxamide-(2)]disulfide,
bis[N-phenyl 7-chloro-1-methylindolyl-3-carboxamide-(2)]disulfide,
bis[N-phenyl 1-methyl-7-azaindolyl-3-carboxamide-(2)] disulfide,
bis[N-phenyl 1,4-dimethylindolyl-3-carboxamide-(2)] disulfide,
bis[N-phenyl 1,5-dimethylindolyl-3-carboxamide-(2)] disulfide,
bis[N-phenyl 1,6-dimethylindolyl-3-carboxamide-(2)] disulfide,
bis[N-phenyl 1,7-dimethylindolyl-3-carboxamide-(2)] disulfide,
bis[N-phenyl 4-methoxy-1-methylindolyl-3-carboxamide-(2)]disulfide,
bis[N-phenyl 5-methoxy-1-methylindolyl-3-carboxamide-(2)]disulfide,
bis[N-phenyl 6-methoxy-1-methylindolyl-3-carboxamide-(2)]disulfide,
bis[N-phenyl 7-methoxy-1-methylindolyl-3-carboxamide-(2)]disulfide,
bis[N-methyl 1-methylindolyl-3-carboxamide-(2)]disulfide,
bis[N-benzyl 1-methylindolyl-3-carboxamide-(2)]disulfide,
bis[N-methylphenylsulfonyl)-2-indolyl]disulfide,
bis[3-benzoyl-1-methylindole-(2)]disulfide,
bis[3-(4'-carboxybenzoyl)-1-methylindole-(2)]disulfide,
bis[3-(4'-carbomethoxybenzoyl)-1-methylindole (2)]disulfide,
and pharmaceutically acceptable salts thereof.

4. A pharmaceutical composition useful for inhibition of protein tyrosine kinase dependent disease in a mammal, containing in a pharmaceutically acceptable carrier a therapeutically effective amount of a compound selected from 2-thioindole, 2-indolinethione, and polysulfide compounds represented by the general Formulas I and IV

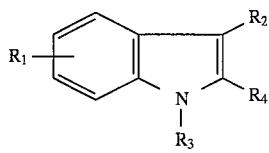

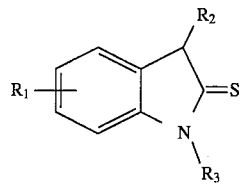

and pharmaceutically acceptable salts thereof, wherein
$R_1$ is a member selected from H, halogen, R, OH, OR, $CF_3$, $NO_2$, $NH_2$, NHR, COOH, CONHR, $(CH_2)_n$OH, $(CH_2)_n$OR, $(CH_2)_n NH_2$, $(CH_2)_n$NHR, and $(CH_2)_n$NRR, and further represents replacement in the ring of 1 or 2 ring methine (—CH=) atoms with aza(—N=) atoms;

$R_2$ is a member selected from
$(CH_2)_n$COOH,
$(CH_2)_n$COOR,
$(CH_2)_n$COR,
$(CH_2)_n SO_2 R$,
$(CH_2)_n SO_2 NRR$,
$(CH_2)_n SO_2 NHR$,
CH=CHCOOH,

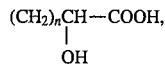

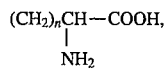

$(CH_2)_n CONH_2$,
$(CH_2)_n$CONHR,
$(CH_2)_n$CONRR,
$(CH_2)_n CONHCH_2 Ph$,
CONHR,
CONRR,
CONHPh,
COY,
COPhCOOH,
COPhCOOR,
$(CH_2)_n$CONHPh,
$(CH_2)_n$CONHPhR,
$SO_2 Y$;

n is an integer from 1 to 4;

R is lower alkyl;

$R_3$ is a member selected from H, lower alkyl, and benzyl;

Y represents a benzene, pyridine, thiophene, furan, thiazole, or imidazole ring optionally substituted with a lower alkyl, COOH, OH, OCOR, $NH_2$, CONHR, CONRR, OR, or NHR group; and $R_4$ represents SH, $S_o X$, and $S_o Q$ where o is 1, 2, or 3, X is a member selected from H, lower alkyl, benzyl, and benzene, pyridine, thiophene, furan, thiazole, and imidazole rings, and Q is another 2-thioindolyl moiety of Formula I.

5. A pharmaceutical composition useful for treating aberrant cell growth in a mammal containing in a pharmaceutically acceptable carrier a therapeutically effective amount of a compound selected from 2-thioindole, 2-indolinethione, and polysulfide compounds represented by the general Formulas I and IV

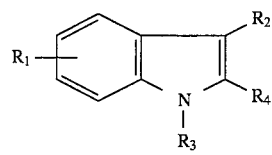

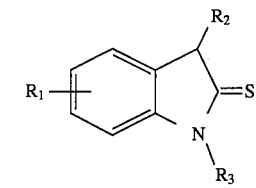

and pharmaceutically acceptable salts thereof, wherein
$R_1$ is a member selected from H, halogen, R, OH, OR, $CF_3$, $NO_2$, $NH_2$, NHR, COOH, CONHR, $(CH_2)_n$OH, $(CH_2)_n$OR, $(CH_2)_n NH_2$, $(CH_2)_n$NHR, and $(CH_2)_n$NRR, and further represents replacement in the ring of 1 or 2 ring methine (—CH=) atoms with aza (—N=) atoms;

$R_2$ is a member selected from
$(CH_2)_n$COOH,
$(CH_2)_n$COOR,
$(CH_2)_n$COR,
$(CH_2)_n SO_2 R$,
$(CH_2)_n SO_2 NRR$,
$(CH_2)_n SO_2 NHR$,
CH=CHCOOH,

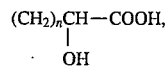

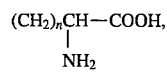

$(CH_2)_n CONH_2$,
$(CH_2)_n$CONHR,
$(CH_2)_n$CONRR,
$(CH_2)_n CONHCH_2 Ph$,
CONHR,
CONHPh,
COY,
COPhCOOH,
COPhCOOR,
$(CH_2)_n$CONHPh,
$(CH_2)_n$CONHPhR,
$SO_2 Y$;

n is an integer from 1 to 4;

R is lower alkyl;

$R_3$ is a member selected from H, lower alkyl, and benzyl;

Y represents a benzene, pyridine, thiophene, furan, thiazole, or imidazole ring optionally substituted with a lower alkyl, COOH, OH, OCOR, $NH_2$, CONHR, CONRR, OR, or NHR group; and $R_4$ represents SH, $S_o X$, and $S_o Q$ where o is 1, 2, or 3, X is a member selected from H, lower alkyl, benzyl, and benzene, pyridine, thiophene, furan, thiazole, and imidazole rings, and Q is another 2-thioindolyl moiety of Formula I.

6. The compound of claim 1 having the name 3-(2-thioxo-3-indolinyl)propanoic acid.

7. The compound of claim 1 having the name 4-(2-thioxo-3-indolinyl)butanoic acid and pharmaceutically acceptable salts thereof.

8. The compound of claim 1 having the name benzyl[N-phenyl 1-methylindolyl-3-carboxamide(2)]disulfide.

9. The compound of claim 1 having the name bis[indolyl-3-acetic acid-(2)]trisulfide.

10. The compound of claim 1 having the name N-benzyl(2-thioxo-3-indolinyl)acetamide and pharmaceutically acceptable salts thereof.

11. The compound of claim 1 having the name bis[indolyl-3-propanoic acid-(2)]disulfide and pharmaceutically acceptable salts thereof.

12. The compound of claim 1 having the name 2,2'-dithiobis[3-(1-methyl-3-indolyl)propanoic acid] and pharmaceutically acceptable salts thereof.

13. The compound of claim 1 having the name bis[ethylindolyl-3-propanoate-(2)]disulfide.

14. The compound of claim 1 having the name 2,2'-dithiobis[methyl-3-(1-methyl-3-indolyl)propanoate].

15. The compound of claim 1 having the name bis[6-methylindolyl-3-propanoic acid-(2)]disulfide and pharmaceutically acceptable salts thereof.

16. The compound of claim 1 having the name bis[ethyl-6-methylindolyl-3-propanoate(2)]disulfide.

17. The compound of claim 1 having the name bis[7-methylindolyl-3-propanoic acid-(2)]disulfide and pharmaceutically acceptable salts thereof.

18. The compound of claim 1 having the name 2,2'-dithiobis[N-benzyl-3-(3-indolyl)propanamide].

19. The compound of claim 1 having the name 2,2'-dithiobis[4-(1-methyl-3-indolyl)butanoic acid] and pharmaceutically acceptable salts thereof.

20. The compound of claim 1 having the name bis[methyl 1-methylindolyl-3-butanoate-(2)]disulfide.

21. The compound of claim 1 having the name bis[N-phenyl 1-methylindolyl-3-carboxamide(2)]disulfide.

22. The compound of claim 1 having the name bis[N-phenyl 5-chloro-1-methylindolyl-3-carboxamide-(2)]disulfide.

23. The compound of claim 1 having the name bis[N-phenyl 6-methoxy-1-methylindolyl-3-carboxamide-(2)]disulfide.

24. The compound of claim 1 having the name bis[N-phenyl 7-methoxy-1-methylindolyl-3-carboxamide-(2)]disulfide.

25. The compound of claim 1 having the name bis[N-methyl 1-methylindolyl-3-carboxamide(2)]disulfide.

26. The compound of claim 1 having the name bis[N-benzyl 1-methylindolyl-3-carboxamide(2)]disulfide.

27. The compound of claim 1 having the name bis[(N-methylphenylsulfonyl)-2-indolyl]disulfide.

28. The compound of claim 1 having the name bis[3-(4'-carboxybenzoyl)-1-methylindole-(2)]disulfide.

29. The compound of claim 1 having the name bis[3-(4'-carbomethoxybenzoyl)-1-methylindole-(2)]disulfide.

30. The compound of claim 1 having the name methyl 3-(1-methyl-2-thioxo-3-indolinyl)propanoate.

31. The compound of claim 1 having the name ethyl 3-(1-methyl-2-thioxo-3-indolinyl)propanoate.

32. The compound of claim 1 having the name N-benzyl 3-(2-thioxo-3-indolinyl)propanamide.

33. A method for inhibiting protein tyrosine kinase dependent disease in a mammal, comprising administering to said mammal a pharmaceutical composition according to claim 4.

34. A method for treating aberrant cell growth in a mammal, comprising administering to said mammal a pharmaceutical composition according to claim 5.

* * * * *

UNITED STATES PATENT AND TRADEMARK OFFICE
CERTIFICATE OF CORRECTION

PATENT NO. : 5,556,874

DATED : September 17, 1996

INVENTOR(S) : Dobrusin et al.

It is certified that error appears in the above-identified patent and that said Letters Patent is hereby corrected as shown below:

On column 32, line 3, please delete "$R_2$" and substitute therefore --$R_3$--

On column 67, line 51, please delete "CPNHPh" and substitute therefore --CONHPh--

Signed and Sealed this

Eleventh Day of February, 1997

Attest:

BRUCE LEHMAN

Attesting Officer

Commissioner of Patents and Trademarks